United States Patent
Lafleur et al.

(10) Patent No.: US 11,827,716 B2
(45) Date of Patent: Nov. 28, 2023

(54) D-DOMAIN CONTAINING POLYPEPTIDES AND USES THEREOF

(71) Applicant: Arcellx, Inc., Gaithersburg, MD (US)

(72) Inventors: David Lafleur, Gaithersburg, MD (US); Jeffrey S. Swers, Gaithersburg, MD (US); Justin Edwards, Gaithersburg, MD (US)

(73) Assignee: ARCELLX, INC., Gaithersburg, MD (US)

( * ) Notice: Subject to any disclaimer, the term of this patent is extended or adjusted under 35 U.S.C. 154(b) by 0 days.

(21) Appl. No.: 18/055,096

(22) Filed: Nov. 14, 2022

(65) Prior Publication Data

US 2023/0250185 A1    Aug. 10, 2023

Related U.S. Application Data

(60) Provisional application No. 63/279,489, filed on Nov. 15, 2021.

(51) Int. Cl.
*C07K 16/28* (2006.01)
*A61P 35/00* (2006.01)
*C12N 15/86* (2006.01)

(52) U.S. Cl.
CPC ......... *C07K 16/2896* (2013.01); *A61P 35/00* (2018.01); *C12N 15/86* (2013.01);
(Continued)

(58) Field of Classification Search
CPC ............ C07K 16/2896; C07K 2317/52; C07K 2319/02; C07K 2319/03; A61P 35/00; C12N 15/86; C12N 2740/15043
See application file for complete search history.

(56) References Cited

U.S. PATENT DOCUMENTS 10,647,775 B2    5/2020    Lafleur et al.
10,662,248 B2    5/2020    Lafleur et al.
(Continued)

FOREIGN PATENT DOCUMENTS

WO    2016164305    10/2016
WO    2016164308    10/2016
(Continued)

OTHER PUBLICATIONS

Lafleur, David W., et al., "Chimeric Antigen Receptors Incorporating Novel (non-scFv) Binding Domains Targeting CD123 Direct Potent Antitumor Activity of T Cells: Correlation Between Affinity and Activity", Arcellx, Inc., presented at the American Association for Cancer Research 2020 Virtual Annual Meeting II, Jun. 22-24, 2020, Abstract 3243, 1 page.
(Continued)

*Primary Examiner* — Scarlett Y Goon
*Assistant Examiner* — Audrey L Buttice
(74) *Attorney, Agent, or Firm* — Wilson Sonsini Goodrich & Rosati

(57) ABSTRACT

Provided herein are D domain containing polypeptides that specifically bind targets of interest, as are nucleic acids encoding the D domain containing polypeptides, vectors containing the nucleic acids and host cells containing the nucleic acids and vectors. Also provided herein are methods of making and using the D domain containing polypeptides, nucleic acids, vectors and host cells, for example, but not limited to, in diagnostic and therapeutic applications. Also provided herein are multi-functional chimeric antigen receptor (CAR)-based compositions and Adapters and their use in methods of directing immune responses to target cells. In some embodiments, the methods include the use of a CAR expressing cell in combination with an Adapter. The Adapter confers the ability to modulate, alter, and/or direct CAR
(Continued)

expressing cell-mediated immune response in vitro and in vivo.

27 Claims, 17 Drawing Sheets

Specification includes a Sequence Listing.

(52) U.S. Cl.
CPC ...... *C07K 2317/52* (2013.01); *C07K 2319/02* (2013.01); *C07K 2319/03* (2013.01); *C12N 2740/15043* (2013.01)

(56) References Cited

U.S. PATENT DOCUMENTS

| | | |
|---|---|---|
| 11,008,397 B2 | 5/2021 | Lafleur et al. |
| 11,318,165 B2 | 5/2022 | Hilbert et al. |
| 11,377,482 B2 | 7/2022 | Hilbert et al. |
| 11,464,803 B2 | 10/2022 | Hilbert et al. |
| 2018/0209983 A1 | 7/2018 | Lafleur et al. |
| 2018/0251521 A1 | 9/2018 | Lafleur et al. |
| 2020/0362046 A1 | 11/2020 | Lafleur et al. |
| 2021/0002381 A1 | 1/2021 | Lafleur et al. |
| 2021/0023133 A1 | 1/2021 | Lafleur et al. |
| 2021/0230288 A1 | 7/2021 | Lafleur et al. |

FOREIGN PATENT DOCUMENTS

| | | |
|---|---|---|
| WO | 2016164369 | 10/2016 |
| WO | 2019099433 | 5/2019 |
| WO | 2019099440 | 5/2019 |
| WO | 2022204340 | 9/2022 |
| WO | WO-2023086983 A1 | 5/2023 |

OTHER PUBLICATIONS

Buonato, Janine et al., "Novel CAR-T Cell Therapy that can be Activated, Silenced, and Reprogrammed In Vivo with Soluble Protein Adapters in a Dose Dependent Manner", Arcellx, Inc., presented at the American Society of Gene & Cell Therapy Virtual Annual Meeting, May 12-15, 2020, Abstract 788, 1 page.

Qin et al., "Chimeric Antigen Receptors Incorporating D Domains Targeting CD123 Direct Potent Mono- and Bi-specific Antitumor Activity of T Cells" Molecular Therapy vol. 27. No. 7 pp. 1262-1274, Jul. 2019.

Unpublished U.S. Appl. No. 17/936,023, filed Sep. 28, 2022, inventor: Hilbert et al.

Unpublished U.S. Appl. No. 18/145,169, filed Dec. 22, 2022, inventor: Lafleur, David William.

Unpublished U.S. Appl. No. 18/055,096, filed Nov. 14, 2022, inventor: Swers et al.

PCT/US2022/079796 International Search Report and Written Opinion dated Apr. 7, 2023.

Qin et al. Chimeric Antigen Receptors Incorporating D Domains Targeting CD123 Direct Potent Mono- and Bi-specific Antitumor Activity of T Cells. Molecular Therapy, vol. 27, No. 7, pp. 1262-1274 (Jul. 2019). With Supplemental Information. 18 pages.

UniProtKB Accession No. A0A0V017C1 "Putative poly(U)-specific endoribonuclease-B-like" Apr. 7, 2021 [online]. Retrieved Aug. 18, 2023 at URL: https://rest.uniprot.org/unisave/A0A0V0I7C1?format=txt&versions=11. 2 pages.

Walsh et al. "Solution structure and dynamics of a de novo designed three-helix bundle protein," Proceedings of the National Academy of Sciences, vol. 96, No. 10, pp. 5486-5491, May 11, 1999.

| ID | a3D | 6T1D | 3F4N | 4R8U | 0C8S | 5B1Q |
|---|---|---|---|---|---|---|
| Mutations | a3D | 6T1D | 6T1D (N50S) | 6T1D (K48E, N50S) | 6T1D (G8S, K48E, N50S, I59L) | 6T1D (G8S, L21Q, K48E, N50S, I59L) |
| IFNγ | na | 0.894 | 0.152 | 0.059 | 0.021 | 0.029 |

Figure 16.

| Model | Recipient Strain | Patient Characteristics ||||| Disease Characteristics ||||
|---|---|---|---|---|---|---|---|---|---|---|
| | | Age | Gender | Ethnicity | Diagnosis | Treatment history | FAB Classification | Cytogenetics | Mutational Status |
| 2239 | NOG | 79 | Male | African American | De novo | Naïve | NOS | Normal | IDH1/2 WT FLT3 N/A NPM mutant |
| 2229 | NCG | 53 | Male | Caucasian | Refractory | Preptreated | M1 (without maturation) | 46XY, del(2) (p13p23), t(4;13)(q31;q34), add(4)(q25), del(6)(q13q25), t(9;22)(q34;q11.2), del(10)(q24), add(16)(q24) [20] | IDH1 mutant (R132C) FLT3 WT NPM WT |
| 3438 | NOG-EXL | 62 | Female | Caucasian | Relapsed | Preptreated | M4 (myelo-monocytic) | Normal | IDH1/2 WT FLT3 WT NPM WT |
| 2227 | NOG | 59 | Female | Caucasian | Relapsed | Preptreated | M4 (myelo-monocytic) | Not available | IDH1 mutant FLT3 ITD mutant NPM mutant |
| 2240 | NOG | 75 | Male | not avail. | De novo | Naïve | AML (11q23 abnormalities) | 46, XY, t(9;11)(p22;q23), add(10)(q24) [5]/46, XY [5] | IDH1/2 WT FLT3 WT NPM WT |
| 2456 | NOG | not avail | Female | Caucasian | De novo | Preptreated | NOS | 46, XX, del(7) (q22q36) [15] | IDH1/2 WT FLT3 WT NPM WT |

SEQUENCE LISTING

```
Sequence total quantity: 119
SEQ ID NO: 1            moltype = AA  length = 287
FEATURE                 Location/Qualifiers
REGION                  1..287
                        note = Recombinant polypeptide
source                  1..287
                        mol_type = protein
                        organism = synthetic construct
SEQUENCE: 1
TKEDPNPPIT NLRMKAKAQQ LTWDLNRNVT DIECVKDADY SMPAVNNSYC QFGAISLCEV   60
TNYTVRVANP PFSTWILFPE NSGKPWAGAE NLTCWIHDVD FLSCSWAVGP GAPADVQYDL  120
YLNVANRRQQ YECLHYKTDA QGTRIGCRFD DISRLSSGSQ SSHILVRGRS AAFGIPCTDK  180
FVVFSQIEIL TPPNMTAKCN KTHSFMHWKM RSHFNRKFRY ELQIQKRMQP VITEQVRDRT  240
SFQLLNPGTY TVQIRARERV YEFLSAWSTP QRFECDQEEG ANTRAWR               287

SEQ ID NO: 2            moltype = AA  length = 73
FEATURE                 Location/Qualifiers
REGION                  1..73
                        note = Recombinant polypeptide
source                  1..73
                        mol_type = protein
                        organism = synthetic construct
SEQUENCE: 2
MGSWAEFKQR LAAIKTRLQA LGGSEAELAA FEKEIAAFES ELQAYKGKGN PEVEALRKEA   60
AAIRDELQAY RHN                                                     73

SEQ ID NO: 3            moltype = AA  length = 73
```

```
FEATURE                 Location/Qualifiers
REGION                  1..73
                        note = Recombinant polypeptide
source                  1..73
                        mol_type = protein
                        organism = synthetic construct
SEQUENCE: 3
MGSWAEFKQR LAAIKTRLEA LGGSEAELAA FEKEIAAFES ELQAYKGKGN PEVEALRKEA    60
AAIRDELQAY RHN                                                      73

SEQ ID NO: 4            moltype = AA  length = 73
FEATURE                 Location/Qualifiers
REGION                  1..73
                        note = Recombinant polypeptide
source                  1..73
                        mol_type = protein
                        organism = synthetic construct
SEQUENCE: 4
MGSWDEFGRR LYAIEWRLYA LGGSEAELAA FEKEIAAFES ELQAYKGKGN PEVEKLREIA    60
AVIRSNLQAY RHN                                                      73

SEQ ID NO: 5            moltype = AA  length = 73
FEATURE                 Location/Qualifiers
REGION                  1..73
                        note = Recombinant polypeptide
source                  1..73
                        mol_type = protein
                        organism = synthetic construct
SEQUENCE: 5
MGSWDEFGRR LYAIEWQLYA LGGTEAELAA FEKEIAAFES ELQAYKGKGN PEVEKLREIA    60
AVIRENLQAY RHN                                                      73

SEQ ID NO: 6            moltype = AA  length = 73
FEATURE                 Location/Qualifiers
REGION                  1..73
                        note = Recombinant polypeptide
source                  1..73
                        mol_type = protein
                        organism = synthetic construct
SEQUENCE: 6
MGSWDEFGRR LYAIEWRLYA LGGSEAELAA FEKEIAAFES ELQAYKGKGS PEVEKLREIA    60
AVIRSNLQAY RHN                                                      73

SEQ ID NO: 7            moltype = AA  length = 73
FEATURE                 Location/Qualifiers
REGION                  1..73
                        note = Recombinant polypeptide
source                  1..73
                        mol_type = protein
                        organism = synthetic construct
SEQUENCE: 7
MGSWDEFSRR LYAIEWRLYA LGGSEAELAA FEKEIAAFES ELQAYKGKGN PEVEKLREIA    60
AVIRSNLQAY RHN                                                      73

SEQ ID NO: 8            moltype = AA  length = 73
FEATURE                 Location/Qualifiers
REGION                  1..73
                        note = Recombinant polypeptide
source                  1..73
                        mol_type = protein
                        organism = synthetic construct
SEQUENCE: 8
MGSWDEFGRR LYAIEWQLYA LGGTEAELAA FEKEIAAFES ELQAYKGKGS PEVEKLREIA    60
AVIRENLQAY RHN                                                      73

SEQ ID NO: 9            moltype = AA  length = 73
FEATURE                 Location/Qualifiers
REGION                  1..73
                        note = Recombinant polypeptide
source                  1..73
                        mol_type = protein
                        organism = synthetic construct
SEQUENCE: 9
MGSWDEFSRR LYAIEWQLYA LGGTEAELAA FEKEIAAFES ELQAYKGKGN PEVEKLREIA    60
AVIRENLQAY RHN                                                      73

SEQ ID NO: 10           moltype = AA  length = 73
FEATURE                 Location/Qualifiers
REGION                  1..73
```

```
                       note = Recombinant polypeptide
source                 1..73
                       mol_type = protein
                       organism = synthetic construct
SEQUENCE: 10
MGSWDEFGRR LYAIEWQLYA LGGTEAELAA FEKEIAAFES ELQAYKGKGN PEVEKLRELA    60
AVIRENLQAY RHN                                                       73

SEQ ID NO: 11          moltype = AA  length = 73
FEATURE                Location/Qualifiers
REGION                 1..73
                       note = Recombinant polypeptide
source                 1..73
                       mol_type = protein
                       organism = synthetic construct
SEQUENCE: 11
MGSWDEFGRR LYAIEWQLYA LGGTEAELAA FEKEIAAFES ELQAYKGEGS PEVEKLREIA    60
AVIRENLQAY RHN                                                       73

SEQ ID NO: 12          moltype = AA  length = 73
FEATURE                Location/Qualifiers
REGION                 1..73
                       note = Recombinant polypeptide
source                 1..73
                       mol_type = protein
                       organism = synthetic construct
SEQUENCE: 12
MGSWDEFGRR LYAIEWQLYA QGGTEAELAA FEKEIAAFES ELQAYKGKGN PEVEKLRELA    60
AVIRENLQAY RHN                                                       73

SEQ ID NO: 13          moltype = AA  length = 73
FEATURE                Location/Qualifiers
REGION                 1..73
                       note = Recombinant polypeptide
source                 1..73
                       mol_type = protein
                       organism = synthetic construct
SEQUENCE: 13
MGSWDEFSRR LYAIEWQLYA LGGTEAELAA FEKEIAAFES ELQAYKGEGS PEVEKLRELA    60
AVIRENLQAY RHN                                                       73

SEQ ID NO: 14          moltype = AA  length = 73
FEATURE                Location/Qualifiers
REGION                 1..73
                       note = Recombinant polypeptide
source                 1..73
                       mol_type = protein
                       organism = synthetic construct
SEQUENCE: 14
MGSWDEFSRR LYAIEWQLYA QGGTEAELAA FEKEIAAFES ELQAYKGEGS PEVEKLRELA    60
AVIRENLQAY RHN                                                       73

SEQ ID NO: 15          moltype = AA  length = 73
FEATURE                Location/Qualifiers
REGION                 1..73
                       note = Recombinant polypeptide
source                 1..73
                       mol_type = protein
                       organism = synthetic construct
SEQUENCE: 15
MGSWSEFGRR LYAIEWQLYA LGGTEAELAA FEKEIAAFES ELQAYKGKGN PEVEKLREIA    60
AVIRENLQAY RHN                                                       73

SEQ ID NO: 16          moltype = AA  length = 73
FEATURE                Location/Qualifiers
REGION                 1..73
                       note = Recombinant polypeptide
source                 1..73
                       mol_type = protein
                       organism = synthetic construct
SEQUENCE: 16
MGSWDEFGRR LYAIEWQLYA LGGTEAELAA FEKEIAAFES ELQAYKGKGN PEVEKLREIA    60
AVIRDELQAY RHN                                                       73

SEQ ID NO: 17          moltype = AA  length = 73
FEATURE                Location/Qualifiers
REGION                 1..73
                       note = Recombinant polypeptide
source                 1..73
```

```
                        mol_type = protein
                        organism = synthetic construct
SEQUENCE: 17
MGSWDEFGRR LYAIEWQLYA LGGTEAELAA FEKEIAAFES ELQAYKGKGN PEVEKLREIA    60
AVIREELQAY RHN                                                      73

SEQ ID NO: 18           moltype = AA   length = 73
FEATURE                 Location/Qualifiers
REGION                  1..73
                        note = Recombinant polypeptide
source                  1..73
                        mol_type = protein
                        organism = synthetic construct
SEQUENCE: 18
MGSWDEFGRR LYAIEWQLYA LGGTEAELAA FEKEIAAFES ELQAYKGKGN PEVEKLREIA    60
AVIRDNLQAY RHN                                                      73

SEQ ID NO: 19           moltype = AA   length = 73
FEATURE                 Location/Qualifiers
REGION                  1..73
                        note = Recombinant polypeptide
source                  1..73
                        mol_type = protein
                        organism = synthetic construct
SEQUENCE: 19
MGSWDEFGRR LYAIEWQLYA LGGTEAELAA FEKEIAAFES ELQAYKGKGN PEVEKLREIA    60
AAIRENLQAY RHN                                                      73

SEQ ID NO: 20           moltype = AA   length = 73
FEATURE                 Location/Qualifiers
REGION                  1..73
                        note = Recombinant polypeptide
source                  1..73
                        mol_type = protein
                        organism = synthetic construct
SEQUENCE: 20
MGSWDEFGRR LYAIEWQLYA LGGTEAELAA FEKEIAAFES ELQAYKGKGN PEVEKLREEA    60
AVIRENLQAY RHN                                                      73

SEQ ID NO: 21           moltype = AA   length = 73
FEATURE                 Location/Qualifiers
REGION                  1..73
                        note = Recombinant polypeptide
source                  1..73
                        mol_type = protein
                        organism = synthetic construct
SEQUENCE: 21
MGSWDEFGRR LYAIEWQLYA LGGTEAELAA FEKEIAAFES ELQAYKGKGN PEVEKLRKIA    60
AVIRENLQAY RHN                                                      73

SEQ ID NO: 22           moltype = AA   length = 73
FEATURE                 Location/Qualifiers
REGION                  1..73
                        note = Recombinant polypeptide
source                  1..73
                        mol_type = protein
                        organism = synthetic construct
SEQUENCE: 22
MGSWDEFGRR LYAIEWQLYA LGGTEAELAA FEKEIAAFES ELQAYKGKGN PEVEALREIA    60
AVIRENLQAY RHN                                                      73

SEQ ID NO: 23           moltype = AA   length = 73
FEATURE                 Location/Qualifiers
REGION                  1..73
                        note = Recombinant polypeptide
source                  1..73
                        mol_type = protein
                        organism = synthetic construct
SEQUENCE: 23
MGSWDEFGRR LYAIEWQLEA LGGTEAELAA FEKEIAAFES ELQAYKGKGN PEVEKLREIA    60
AVIRENLQAY RHN                                                      73

SEQ ID NO: 24           moltype = AA   length = 73
FEATURE                 Location/Qualifiers
REGION                  1..73
                        note = Recombinant polypeptide
source                  1..73
                        mol_type = protein
                        organism = synthetic construct
```

```
SEQUENCE: 24
MGSWDEFGRR LYAIETQLYA LGGTEAELAA FEKEIAAFES ELQAYKGKGN PEVEKLREIA    60
AVIRENLQAY RHN                                                     73

SEQ ID NO: 25           moltype = AA   length = 73
FEATURE                 Location/Qualifiers
REGION                  1..73
                        note = Recombinant polypeptide
source                  1..73
                        mol_type = protein
                        organism = synthetic construct
SEQUENCE: 25
MGSWDEFGRR LYAIKWQLYA LGGTEAELAA FEKEIAAFES ELQAYKGKGN PEVEKLREIA    60
AVIRENLQAY RHN                                                     73

SEQ ID NO: 26           moltype = AA   length = 73
FEATURE                 Location/Qualifiers
REGION                  1..73
                        note = Recombinant polypeptide
source                  1..73
                        mol_type = protein
                        organism = synthetic construct
SEQUENCE: 26
MGSWDEFGRR LAAIEWQLYA LGGTEAELAA FEKEIAAFES ELQAYKGKGN PEVEKLREIA    60
AVIRENLQAY RHN                                                     73

SEQ ID NO: 27           moltype = AA   length = 73
FEATURE                 Location/Qualifiers
REGION                  1..73
                        note = Recombinant polypeptide
source                  1..73
                        mol_type = protein
                        organism = synthetic construct
SEQUENCE: 27
MGSWDEFGQR LYAIEWQLYA LGGTEAELAA FEKEIAAFES ELQAYKGKGN PEVEKLREIA    60
AVIRENLQAY RHN                                                     73

SEQ ID NO: 28           moltype = AA   length = 73
FEATURE                 Location/Qualifiers
REGION                  1..73
                        note = Recombinant polypeptide
source                  1..73
                        mol_type = protein
                        organism = synthetic construct
SEQUENCE: 28
MGSWDEFKRR LYAIEWQLYA LGGTEAELAA FEKEIAAFES ELQAYKGKGN PEVEKLREIA    60
AVIRENLQAY RHN                                                     73

SEQ ID NO: 29           moltype = AA   length = 73
FEATURE                 Location/Qualifiers
REGION                  1..73
                        note = Recombinant polypeptide
source                  1..73
                        mol_type = protein
                        organism = synthetic construct
SEQUENCE: 29
MGSWAEFGRR LYAIEWQLYA LGGTEAELAA FEKEIAAFES ELQAYKGKGN PEVEKLREIA    60
AVIRENLQAY RHN                                                     73

SEQ ID NO: 30           moltype = AA   length = 73
FEATURE                 Location/Qualifiers
REGION                  1..73
                        note = Recombinant polypeptide
source                  1..73
                        mol_type = protein
                        organism = synthetic construct
SEQUENCE: 30
MGSWDEFGRR LYAIEWRLYA LGGSEAELAA FEKEIAAFES ELQAYKGIGN PEVENLREIA    60
AVIRSNLQAY RHN                                                     73

SEQ ID NO: 31           moltype = AA   length = 73
FEATURE                 Location/Qualifiers
REGION                  1..73
                        note = Recombinant polypeptide
source                  1..73
                        mol_type = protein
                        organism = synthetic construct
SEQUENCE: 31
MGSWDEFGRR LYAIESQLYA LGGTEAELAA FEKEIAAFES ELQAYKGKGN PEVEKLREIA    60
```

```
AVIRENLQAY RHN                                                              73

SEQ ID NO: 32           moltype = AA  length = 73
FEATURE                 Location/Qualifiers
REGION                  1..73
                        note = Recombinant polypeptide
source                  1..73
                        mol_type = protein
                        organism = synthetic construct
SEQUENCE: 32
MGSWDEFGRR LYAIEAQLYA LGGTEAELAA FEKEIAAFES ELQAYKGKGN PEVEKLREIA           60
AVIRENLQAY RHN                                                              73

SEQ ID NO: 33           moltype = AA  length = 73
FEATURE                 Location/Qualifiers
REGION                  1..73
                        note = Recombinant polypeptide
source                  1..73
                        mol_type = protein
                        organism = synthetic construct
SEQUENCE: 33
MGSWDEFGRR LYAIEEQLYA LGGTEAELAA FEKEIAAFES ELQAYKGKGN PEVEKLREIA           60
AVIRENLQAY RHN                                                              73

SEQ ID NO: 34           moltype = AA  length = 54
FEATURE                 Location/Qualifiers
REGION                  1..54
                        note = Recombinant polypeptide
source                  1..54
                        mol_type = protein
                        organism = synthetic construct
SEQUENCE: 34
MLQMAGQCSQ NEYFDSLLHA CIPCQLRCSS NTPPLTCQRY CNASVTNSVK GTNA                 54

SEQ ID NO: 35           moltype = AA  length = 204
FEATURE                 Location/Qualifiers
REGION                  1..204
                        note = Recombinant polypeptide
source                  1..204
                        mol_type = protein
                        organism = synthetic construct
SEQUENCE: 35
SGPVKELVGS VGGAVTFPLK SKVKQVDSIV WTFNTTPLVT IQPEGGTIIV TQNRNRERVD           60
FPDGGYSLKL SKLKKNDSGI YYVGIYSSSL QQPSTQEYVL HVYEHLSKPK VTMGLQSNKN          120
GTCVTNLTCC MEHGEEDVIY TWKALGQAAN ESHNGSILPI SWRWGESDMT FICVARNPVS          180
RNFSSPILAR KLCEGAADDP DSSM                                                 204

SEQ ID NO: 36           moltype = AA  length = 591
FEATURE                 Location/Qualifiers
REGION                  1..591
                        note = Recombinant polypeptide
source                  1..591
                        mol_type = protein
                        organism = synthetic construct
SEQUENCE: 36
RTLHRNEYGI ASILDSYQCT AEISLADLAT IFFAQFVQEA TYKEVSKMVK DALTAIEKPT           60
GDEQSSGCLE NQLPAFLEEL CHEKEILEKY GHSDCCSQSE EGRHNCFLAH KKPTPASIPL          120
FQVPEPVTSC EAYEEDRETF MNKFIYEIAR RHPFLYAPTI LLWAARYDKI IPSCCKAENA          180
VECFQTKAAT VTKELRESSL LNQHACAVMK NFGTRTFQAI TVTKLSQKFT KVNFTEIQKL          240
VLDVAHVHEH CCRGDVLDCL QDGEKIMSYI CSQQDTLSNK ITECCKLTTL ERGQCIIHAE          300
NDEKPEGLSP NLNRFLGDRD FNQFSSGEKN IFLASFVHEY SRRHPQLAVS VILRVAKGYQ          360
ELLEKCFQTE NPLECQDKGE EELQKYIQES QALAKRSCGL FQKLGEYYLQ NAFLVAYTKK          420
APQLTSSELM AITRKMAATA ATCCQLSEDK LLACGEGAAD IIIGHLCIRH EMTPVNPGVG          480
QCCTSSYANR RPCFSSLVVD ETYVPPAFSD DKFIFHKDLC QAQGVALQTM KQEFLINLVK          540
QKPQITEEQL EAVIADFSGL LEKCCQGQEQ EVCFAEEGQK LISKTRAALG V                   591

SEQ ID NO: 37           moltype = AA  length = 229
FEATURE                 Location/Qualifiers
REGION                  1..229
                        note = Recombinant polypeptide
source                  1..229
                        mol_type = protein
                        organism = synthetic construct
SEQUENCE: 37
LEKCFQTENP LECQDKGEEE LQKYIQESQA LAKRSCGLFQ KLGEYYLQNA FLVAYTKKAP           60
QLTSSELMAI TRKMAATAAT CCQLSEDKLL ACGEGAADII IGHLCIRHEM TPVNPGVGQC          120
CTSSYANRRP CFSSLVVDET YVPPAFSDDK FIFHKDLCQA QGVALQTMKQ EFLINLVKQK          180
PQITEEQLEA VIADFSGLLE KCCQGQEQEV CFAEEGQKLI SKTRAALGV                      229
```

```
SEQ ID NO: 38              moltype = AA  length = 229
FEATURE                    Location/Qualifiers
REGION                     1..229
                           note = Recombinant polypeptide
source                     1..229
                           mol_type = protein
                           organism = synthetic construct
SEQUENCE: 38
LEKCFQTENP LECQDKGEEE LQKYIQESQA LAKRSCGLFQ KLGEYYLQNA FLVAYTKKAP    60
QLTSSELMAI TRKMAATAAT CCQLSEDKLL ACGEGAADII IGHLCIRHEM TPVNPGVGQC   120
CTSSYANRRP CFSSLVVDET YVPPAFSDDK FIFHKDLCQA QGVALQTMKQ EFLINLVKQK   180
PQITEEQLEA VIADFSGLLE KCCQGQEQEV CFAEEGPKLI SKTRAALGV               229

SEQ ID NO: 39              moltype = AA  length = 204
FEATURE                    Location/Qualifiers
REGION                     1..204
                           note = Recombinant polypeptide
source                     1..204
                           mol_type = protein
                           organism = synthetic construct
SEQUENCE: 39
QESQALAKRS CGLFQKLGEY YLQNAFLVAY TKKAPQLTSS ELMAITRKMA ATAATCCQLS    60
EDKLLACGEG AADIIIGHLC IRHEMTPVNP GVGQCCTSSY ANRRPCFSSL VVDETYVPPA   120
FSDDKFIFHK DLCQAQGVAL QTMKQEFLIN LVKQKPQITE EQLEAVIADF SGLLEKCCQG   180
QEQEVCFAEE GQKLISKTRA ALGV                                         204

SEQ ID NO: 40              moltype = AA  length = 204
FEATURE                    Location/Qualifiers
REGION                     1..204
                           note = Recombinant polypeptide
source                     1..204
                           mol_type = protein
                           organism = synthetic construct
SEQUENCE: 40
QESQALAKRS CGLFQKLGEY YLQNAFLVAY TKKAPQLTSS ELMAITRKMA ATAATCCQLS    60
EDKLLACGEG AADIIIGHLC IRHEMTPVNP GVGQCCTSSY ANRRPCFSSL VVDETYVPPA   120
FSDDKFIFHK DLCQAQGVAL QTMKQEFLIN LVKQKPQITE EQLEAVIADF SGLLEKCCQG   180
QEQEVCFAEE GPKLISKTRA ALGV                                         204

SEQ ID NO: 41              moltype = AA  length = 207
FEATURE                    Location/Qualifiers
REGION                     1..207
                           note = Recombinant polypeptide
source                     1..207
                           mol_type = protein
                           organism = synthetic construct
SEQUENCE: 41
KYIQESQALA KRSCGLFQKL GEYYLQNAFL VAYTKKAPQL TSSELMAITR KMAATAATCC    60
QLSEDKLLAC GEGAADIIIG HLCIRHEMTP VNPGVGQCCT SSYANRRPCF SSLVVDETYV   120
PPAFSDDKFI FHKDLCQAQG VALQTMKQEF LINLVKQKPQ ITEEQLEAVI ADFSGLLEKC   180
CQGQEQEVCF AEEGQKLISK TRAALGV                                      207

SEQ ID NO: 42              moltype = AA  length = 207
FEATURE                    Location/Qualifiers
REGION                     1..207
                           note = Recombinant polypeptide
source                     1..207
                           mol_type = protein
                           organism = synthetic construct
SEQUENCE: 42
KYIQESQALA KRSCGLFQKL GEYYLQNAFL VAYTKKAPQL TSSELMAITR KMAATAATCC    60
QLSEDKLLAC GEGAADIIIG HLCIRHEMTP VNPGVGQCCT SSYANRRPCF SSLVVDETYV   120
PPAFSDDKFI FHKDLCQAQG VALQTMKQEF LINLVKQKPQ ITEEQLEAVI ADFSGLLEKC   180
CQGQEQEVCF AEEGPKLISK TRAALGV                                      207

SEQ ID NO: 43              moltype = AA  length = 213
FEATURE                    Location/Qualifiers
REGION                     1..213
                           note = Recombinant polypeptide
source                     1..213
                           mol_type = protein
                           organism = synthetic construct
SEQUENCE: 43
GEEELQKYIQ ESQALAKRSC GLFQKLGEYY LQNAFLVAYT KKAPQLTSSE LMAITRKMAA    60
TAATCCQLSE DKLLACGEGA ADIIIGHLCI RHEMTPVNPG VGQCCTSSYA NRRPCFSSLV   120
VDETYVPPAF SDDKFIFHKD LCQAQGVALQ TMKQEFLINL VKQKPQITEE QLEAVIADFS   180
GLLEKCCQGQ EQEVCFAEEG QKLISKTRAA LGV                               213

SEQ ID NO: 44              moltype = AA  length = 213
```

```
FEATURE              Location/Qualifiers
REGION               1..213
                     note = Recombinant polypeptide
source               1..213
                     mol_type = protein
                     organism = synthetic construct
SEQUENCE: 44
GEEELQKYIQ ESQALAKRSC GLFQKLGEYY LQNAFLVAYT KKAPQLTSSE LMAITRKMAA    60
TAATCCQLSE DKLLACGEGA ADIIIGHLCI RHEMTPVNPG VGQCCTSSYA NRRPCFSSLV   120
VDETYVPPAF SDDKFIFHKD LCQAQGVALQ TMKQEFLINL VKQKPQITEE QLEAVIADFS   180
GLLEKCCQGQ EQEVCFAEEG PKLISKTRAA LGV                                213

SEQ ID NO: 45        moltype = AA  length = 5
FEATURE              Location/Qualifiers
REGION               1..5
                     note = Recombinant polypeptide
source               1..5
                     mol_type = protein
                     organism = synthetic construct
SEQUENCE: 45
GGGGG                                                                 5

SEQ ID NO: 46        moltype = AA  length = 8
FEATURE              Location/Qualifiers
REGION               1..8
                     note = Recombinant polypeptide
source               1..8
                     mol_type = protein
                     organism = synthetic construct
SEQUENCE: 46
GGGGGGGG                                                              8

SEQ ID NO: 47        moltype = AA  length = 10
FEATURE              Location/Qualifiers
REGION               1..10
                     note = Recombinant polypeptide
source               1..10
                     mol_type = protein
                     organism = synthetic construct
SEQUENCE: 47
GGGGTGGGGS                                                           10

SEQ ID NO: 48        moltype = AA  length = 10
FEATURE              Location/Qualifiers
REGION               1..10
                     note = Recombinant polypeptide
source               1..10
                     mol_type = protein
                     organism = synthetic construct
SEQUENCE: 48
GGGGDGGGGS                                                           10

SEQ ID NO: 49        moltype = AA  length = 9
FEATURE              Location/Qualifiers
REGION               1..9
                     note = Recombinant polypeptide
source               1..9
                     mol_type = protein
                     organism = synthetic construct
SEQUENCE: 49
LAAIKTRLQ                                                             9

SEQ ID NO: 50        moltype = AA  length = 293
FEATURE              Location/Qualifiers
REGION               1..293
                     note = Recombinant polypeptide
source               1..293
                     mol_type = protein
                     organism = synthetic construct
SEQUENCE: 50
MGSWDEFSRR LYAIEWQLYA QGGTEAELAA FEKEIAAFES ELQAYKGEGS PEVEKLRELA    60
AVIRENLQAY RHNGGGGDGG GGGSGGGSGQ ESQALAKRSC GLFQKLGEYY LQNAFLVAYT   120
KKAPQLTSSE LMAITRKMAA TAATCCQLSE DKLLACGEGA ADIIIGHLCI RHEMTPVNPG   180
VGQCCTSSYA NRRPCFSSLV VDETYVPPAF SDDKFIFHKD LCQAQGVALQ TMKQEFLINL   240
VKQKPQITEE QLEAVIADFS GLLEKCCQGQ EQEVCFAEEG QKLISKTRAA LGV          293

SEQ ID NO: 51        moltype = AA  length = 293
FEATURE              Location/Qualifiers
REGION               1..293
```

```
                        note = Recombinant polypeptide
source                  1..293
                        mol_type = protein
                        organism = synthetic construct
SEQUENCE: 51
MGSWDEFGRR LYAIESQLYA LGGTEAELAA FEKEIAAFES ELQAYKGKGN PEVEKLREIA    60
AVIRENLQAY RHNGGGGDGG GGGSGGGSGQ ESQALAKRSC GLFQKLGEYY LQNAFLVAYT   120
KKAPQLTSSE LMAITRKMAA TAATCCQLSE DKLLACGEGA ADIIIGHLCI RHEMTPVNPG   180
VGQCCTSSYA NRRPCFSSLV VDETYVPPAF SDDKFIFHKD LCQAQGVALQ TMKQEFLINL   240
VKQKPQITEE QLEAVIADFS GLLEKCCQGQ EQEVCFAEEG QKLISKTRAA LGV          293

SEQ ID NO: 52           moltype = AA  length = 293
FEATURE                 Location/Qualifiers
REGION                  1..293
                        note = Recombinant polypeptide
source                  1..293
                        mol_type = protein
                        organism = synthetic construct
SEQUENCE: 52
MGSWDEFGRR LYAIEAQLYA LGGTEAELAA FEKEIAAFES ELQAYKGKGN PEVEKLREIA    60
AVIRENLQAY RHNGGGGDGG GGGSGGGSGQ ESQALAKRSC GLFQKLGEYY LQNAFLVAYT   120
KKAPQLTSSE LMAITRKMAA TAATCCQLSE DKLLACGEGA ADIIIGHLCI RHEMTPVNPG   180
VGQCCTSSYA NRRPCFSSLV VDETYVPPAF SDDKFIFHKD LCQAQGVALQ TMKQEFLINL   240
VKQKPQITEE QLEAVIADFS GLLEKCCQGQ EQEVCFAEEG QKLISKTRAA LGV          293

SEQ ID NO: 53           moltype = AA  length = 293
FEATURE                 Location/Qualifiers
REGION                  1..293
                        note = Recombinant polypeptide
source                  1..293
                        mol_type = protein
                        organism = synthetic construct
SEQUENCE: 53
MGSWDEFGRR LYAIEEQLYA LGGTEAELAA FEKEIAAFES ELQAYKGKGN PEVEKLREIA    60
AVIRENLQAY RHNGGGGDGG GGGSGGGSGQ ESQALAKRSC GLFQKLGEYY LQNAFLVAYT   120
KKAPQLTSSE LMAITRKMAA TAATCCQLSE DKLLACGEGA ADIIIGHLCI RHEMTPVNPG   180
VGQCCTSSYA NRRPCFSSLV VDETYVPPAF SDDKFIFHKD LCQAQGVALQ TMKQEFLINL   240
VKQKPQITEE QLEAVIADFS GLLEKCCQGQ EQEVCFAEEG QKLISKTRAA LGV          293

SEQ ID NO: 54           moltype = AA  length = 293
FEATURE                 Location/Qualifiers
REGION                  1..293
                        note = Recombinant polypeptide
source                  1..293
                        mol_type = protein
                        organism = synthetic construct
SEQUENCE: 54
MGSWDEFGRR LYAIEWQLYA LGGTEAELAA FEKEIAAFES ELQAYKGKGS PEVEKLREIA    60
AVIRENLQAY RHNGGGGDGG GGGSGGGSGQ ESQALAKRSC GLFQKLGEYY LQNAFLVAYT   120
KKAPQLTSSE LMAITRKMAA TAATCCQLSE DKLLACGEGA ADIIIGHLCI RHEMTPVNPG   180
VGQCCTSSYA NRRPCFSSLV VDETYVPPAF SDDKFIFHKD LCQAQGVALQ TMKQEFLINL   240
VKQKPQITEE QLEAVIADFS GLLEKCCQGQ EQEVCFAEEG QKLISKTRAA LGV          293

SEQ ID NO: 55           moltype = AA  length = 293
FEATURE                 Location/Qualifiers
REGION                  1..293
                        note = Recombinant polypeptide
source                  1..293
                        mol_type = protein
                        organism = synthetic construct
SEQUENCE: 55
MGSWDEFSRR LYAIEWQLYA LGGTEAELAA FEKEIAAFES ELQAYKGEGS PEVEKLRELA    60
AVIRENLQAY RHNGGGGDGG GGGSGGGSGQ ESQALAKRSC GLFQKLGEYY LQNAFLVAYT   120
KKAPQLTSSE LMAITRKMAA TAATCCQLSE DKLLACGEGA ADIIIGHLCI RHEMTPVNPG   180
VGQCCTSSYA NRRPCFSSLV VDETYVPPAF SDDKFIFHKD LCQAQGVALQ TMKQEFLINL   240
VKQKPQITEE QLEAVIADFS GLLEKCCQGQ EQEVCFAEEG QKLISKTRAA LGV          293

SEQ ID NO: 56           moltype = AA  length = 382
FEATURE                 Location/Qualifiers
REGION                  1..382
                        note = Recombinant polypeptide
source                  1..382
                        mol_type = protein
                        organism = synthetic construct
SEQUENCE: 56
MGSWDEFGRR LYAIESQLYA LGGTEAELAA FEKEIAAFES ELQAYKGKGN PEVEKLREIA    60
AVIRENLQAY RHNGGGGDGG GGGSGGGSGQ ESQALAKRSC GLFQKLGEYY LQNAFLVAYT   120
KKAPQLTSSE LMAITRKMAA TAATCCQLSE DKLLACGEGA ADIIIGHLCI RHEMTPVNPG   180
VGQCCTSSYA NRRPCFSSLV VDETYVPPAF SDDKFIFHKD LCQAQGVALQ TMKQEFLINL   240
```

```
VKQKPQITEE QLEAVIADFS GLLEKCCQGQ EQEVCFAEEG QKLISKTRAA LGVGGGGSGG   300
GGSGGGGSGM GSWDEFGRRL YAIESQLYAL GGTEAELAAF EKEIAAFESE LQAYKGKGNP   360
EVEKLREIAA VIRENLQAYR HN                                           382

SEQ ID NO: 57          moltype = AA  length = 382
FEATURE                Location/Qualifiers
REGION                 1..382
                       note = Recombinant polypeptide
source                 1..382
                       mol_type = protein
                       organism = synthetic construct
SEQUENCE: 57
MGSWDEFGRR LYAIEAQLYA LGGTEAELAA FEKEIAAFES ELQAYKGKGN PEVEKLREIA    60
AVIRENLQAY RHNGGGDGG GGGSGGGSGQ ESQALAKRSC GLFQKLGEYY LQNAFLVAYT   120
KKAPQLTSSE LMAITRKMAA TAATCCQLSE DKLLACGEGA ADIIIGHLCI RHEMTPVNPG   180
VGQCCTSSYA NRRPCFSSLV VDETYVPPAF SDDKFIFHKD LCQAQGVALQ TMKQEFLINL   240
VKQKPQITEE QLEAVIADFS GLLEKCCQGQ EQEVCFAEEG QKLISKTRAA LGVGGGGSGG   300
GGSGGGGSGM GSWDEFGRRL YAIEAQLYAL GGTEAELAAF EKEIAAFESE LQAYKGKGNP   360
EVEKLREIAA VIRENLQAYR HN                                           382

SEQ ID NO: 58          moltype = AA  length = 382
FEATURE                Location/Qualifiers
REGION                 1..382
                       note = Recombinant polypeptide
source                 1..382
                       mol_type = protein
                       organism = synthetic construct
SEQUENCE: 58
MGSWDEFGRR LYAIEEQLYA LGGTEAELAA FEKEIAAFES ELQAYKGKGN PEVEKLREIA    60
AVIRENLQAY RHNGGGDGG GGGSGGGSGQ ESQALAKRSC GLFQKLGEYY LQNAFLVAYT   120
KKAPQLTSSE LMAITRKMAA TAATCCQLSE DKLLACGEGA ADIIIGHLCI RHEMTPVNPG   180
VGQCCTSSYA NRRPCFSSLV VDETYVPPAF SDDKFIFHKD LCQAQGVALQ TMKQEFLINL   240
VKQKPQITEE QLEAVIADFS GLLEKCCQGQ EQEVCFAEEG QKLISKTRAA LGVGGGGSGG   300
GGSGGGGSGM GSWDEFGRRL YAIEEQLYAL GGTEAELAAF EKEIAAFESE LQAYKGKGNP   360
EVEKLREIAA VIRENLQAYR HN                                           382

SEQ ID NO: 59          moltype = AA  length = 382
FEATURE                Location/Qualifiers
REGION                 1..382
                       note = Recombinant polypeptide
source                 1..382
                       mol_type = protein
                       organism = synthetic construct
SEQUENCE: 59
MGSWDEFGRR LYAIEWQLYA LGGTEAELAA FEKEIAAFES ELQAYKGKGS PEVEKLREIA    60
AVIRENLQAY RHNGGGDGG GGGSGGGSGQ ESQALAKRSC GLFQKLGEYY LQNAFLVAYT   120
KKAPQLTSSE LMAITRKMAA TAATCCQLSE DKLLACGEGA ADIIIGHLCI RHEMTPVNPG   180
VGQCCTSSYA NRRPCFSSLV VDETYVPPAF SDDKFIFHKD LCQAQGVALQ TMKQEFLINL   240
VKQKPQITEE QLEAVIADFS GLLEKCCQGQ EQEVCFAEEG QKLISKTRAA LGVGGGGSGG   300
GGSGGGGSGM GSWDEFGRRL YAIEWQLYAL GGTEAELAAF EKEIAAFESE LQAYKGKGSP   360
EVEKLREIAA VIRENLQAYR HN                                           382

SEQ ID NO: 60          moltype = AA  length = 382
FEATURE                Location/Qualifiers
REGION                 1..382
                       note = Recombinant polypeptide
source                 1..382
                       mol_type = protein
                       organism = synthetic construct
SEQUENCE: 60
MGSWDEFSRR LYAIEWQLYA LGGTEAELAA FEKEIAAFES ELQAYKGEGS PEVEKLRELA    60
AVIRENLQAY RHNGGGDGG GGGSGGGSGQ ESQALAKRSC GLFQKLGEYY LQNAFLVAYT   120
KKAPQLTSSE LMAITRKMAA TAATCCQLSE DKLLACGEGA ADIIIGHLCI RHEMTPVNPG   180
VGQCCTSSYA NRRPCFSSLV VDETYVPPAF SDDKFIFHKD LCQAQGVALQ TMKQEFLINL   240
VKQKPQITEE QLEAVIADFS GLLEKCCQGQ EQEVCFAEEG QKLISKTRAA LGVGGGGSGG   300
GGSGGGGSGM GSWDEFSRRL YAIEWQLYAL GGTEAELAAF EKEIAAFESE LQAYKGEGSP   360
EVEKLRELAA VIRENLQAYR HN                                           382

SEQ ID NO: 61          moltype = AA  length = 382
FEATURE                Location/Qualifiers
REGION                 1..382
                       note = Recombinant polypeptide
source                 1..382
                       mol_type = protein
                       organism = synthetic construct
SEQUENCE: 61
MGSWDEFSRR LYAIEWQLYA QGGTEAELAA FEKEIAAFES ELQAYKGEGS PEVEKLRELA    60
AVIRENLQAY RHNGGGDGG GGGSGGGSGQ ESQALAKRSC GLFQKLGEYY LQNAFLVAYT   120
KKAPQLTSSE LMAITRKMAA TAATCCQLSE DKLLACGEGA ADIIIGHLCI RHEMTPVNPG   180
```

```
VGQCCTSSYA NRRPCFSSLV VDETYVPPAF SDDKFIFHKD LCQAQGVALQ TMKQEFLINL    240
VKQKPQITEE QLEAVIADFS GLLEKCCQGQ EQEVCFAEEG QKLISKTRAA LGVGGGGSGG    300
GGSGGGGSGM GSWDEFSRRL YAIEWQLYAQ GGTEAELAAF EKEIAAFESE LQAYKGEGSP    360
EVEKLRELAA VIRENLQAYR HN                                            382

SEQ ID NO: 62           moltype = AA  length = 309
FEATURE                 Location/Qualifiers
REGION                  1..309
                        note = Recombinant polypeptide
source                  1..309
                        mol_type = protein
                        organism = synthetic construct
SEQUENCE: 62
DEMGSWDEFG RRLYAIESQL YALGGTEAEL AAFEKEIAAF ESELQAYKGK GNPEVEKLRE     60
IAAVIRENLQ AYRHNGGGGD GGGGSGTTTP APRPPTPAPT IASQPLSLRP EACRPAAGGA    120
VHTRGLDFAC DIYIWAPLAG TCGVLLLSLV ITLYCKRGRK KLLYIFKQPF MRPVQTTQEE    180
DGCSCRFPEE EEGGCELRVK FSRSADAPAY KQGQNQLYNE LNLGRREEYD VLDKRRGRDP    240
EMGGKPRRKN PQEGLYNELQ KDKMAEAYSE IGMKGERRRG KGHDGLYQGL STATKDTYDA    300
LHMQALPPR                                                           309

SEQ ID NO: 63           moltype = AA  length = 309
FEATURE                 Location/Qualifiers
REGION                  1..309
                        note = Recombinant polypeptide
source                  1..309
                        mol_type = protein
                        organism = synthetic construct
SEQUENCE: 63
DEMGSWDEFG RRLYAIEAQL YALGGTEAEL AAFEKEIAAF ESELQAYKGK GNPEVEKLRE     60
IAAVIRENLQ AYRHNGGGGD GGGGSGTTTP APRPPTPAPT IASQPLSLRP EACRPAAGGA    120
VHTRGLDFAC DIYIWAPLAG TCGVLLLSLV ITLYCKRGRK KLLYIFKQPF MRPVQTTQEE    180
DGCSCRFPEE EEGGCELRVK FSRSADAPAY KQGQNQLYNE LNLGRREEYD VLDKRRGRDP    240
EMGGKPRRKN PQEGLYNELQ KDKMAEAYSE IGMKGERRRG KGHDGLYQGL STATKDTYDA    300
LHMQALPPR                                                           309

SEQ ID NO: 64           moltype = AA  length = 309
FEATURE                 Location/Qualifiers
REGION                  1..309
                        note = Recombinant polypeptide
source                  1..309
                        mol_type = protein
                        organism = synthetic construct
SEQUENCE: 64
DEMGSWDEFG RRLYAIEEQL YALGGTEAEL AAFEKEIAAF ESELQAYKGK GNPEVEKLRE     60
IAAVIRENLQ AYRHNGGGGD GGGGSGTTTP APRPPTPAPT IASQPLSLRP EACRPAAGGA    120
VHTRGLDFAC DIYIWAPLAG TCGVLLLSLV ITLYCKRGRK KLLYIFKQPF MRPVQTTQEE    180
DGCSCRFPEE EEGGCELRVK FSRSADAPAY KQGQNQLYNE LNLGRREEYD VLDKRRGRDP    240
EMGGKPRRKN PQEGLYNELQ KDKMAEAYSE IGMKGERRRG KGHDGLYQGL STATKDTYDA    300
LHMQALPPR                                                           309

SEQ ID NO: 65           moltype = AA  length = 309
FEATURE                 Location/Qualifiers
REGION                  1..309
                        note = Recombinant polypeptide
source                  1..309
                        mol_type = protein
                        organism = synthetic construct
SEQUENCE: 65
DEMGSWDEFG RRLYAIEWQL YALGGTEAEL AAFEKEIAAF ESELQAYKGK GSPEVEKLRE     60
IAAVIRENLQ AYRHNGGGGD GGGGSGTTTP APRPPTPAPT IASQPLSLRP EACRPAAGGA    120
VHTRGLDFAC DIYIWAPLAG TCGVLLLSLV ITLYCKRGRK KLLYIFKQPF MRPVQTTQEE    180
DGCSCRFPEE EEGGCELRVK FSRSADAPAY KQGQNQLYNE LNLGRREEYD VLDKRRGRDP    240
EMGGKPRRKN PQEGLYNELQ KDKMAEAYSE IGMKGERRRG KGHDGLYQGL STATKDTYDA    300
LHMQALPPR                                                           309

SEQ ID NO: 66           moltype = AA  length = 309
FEATURE                 Location/Qualifiers
REGION                  1..309
                        note = Recombinant polypeptide
source                  1..309
                        mol_type = protein
                        organism = synthetic construct
SEQUENCE: 66
DEMGSWDEFS RRLYAIEWQL YALGGTEAEL AAFEKEIAAF ESELQAYKGE GSPEVEKLRE     60
LAAVIRENLQ AYRHNGGGGD GGGGSGTTTP APRPPTPAPT IASQPLSLRP EACRPAAGGA    120
VHTRGLDFAC DIYIWAPLAG TCGVLLLSLV ITLYCKRGRK KLLYIFKQPF MRPVQTTQEE    180
DGCSCRFPEE EEGGCELRVK FSRSADAPAY KQGQNQLYNE LNLGRREEYD VLDKRRGRDP    240
EMGGKPRRKN PQEGLYNELQ KDKMAEAYSE IGMKGERRRG KGHDGLYQGL STATKDTYDA    300
LHMQALPPR                                                           309
```

-continued

```
SEQ ID NO: 67            moltype = AA   length = 309
FEATURE                  Location/Qualifiers
REGION                   1..309
                         note = Recombinant polypeptide
source                   1..309
                         mol_type = protein
                         organism = synthetic construct
SEQUENCE: 67
DEMGSWDEFS RRLYAIEWQL YAQGGTEAEL AAFEKEIAAF ESELQAYKGE GSPEVEKLRE  60
LAAVIRENLQ AYRHNGGGGD GGGGSGTTTP APRPPTPAPT IASQPLSLRP EACRPAAGGA 120
VHTRGLDFAC DIYIWAPLAG TCGVLLLSLV ITLYCKRGRK KLLYIFKQPF MRPVQTTQEE 180
DGCSCRFPEE EEGGCELRVK FSRSADAPAY KQGQNQLYNE LNLGRREEYD VLDKRRGRDP 240
EMGGKPRRKN PQEGLYNELQ KDKMAEAYSE IGMKGERRRG KGHDGLYQGL STATKDTYDA 300
LHMQALPPR                                                       309

SEQ ID NO: 68            moltype = AA   length = 309
FEATURE                  Location/Qualifiers
REGION                   1..309
                         note = Recombinant polypeptide
source                   1..309
                         mol_type = protein
                         organism = synthetic construct
SEQUENCE: 68
DEMGSWSEFY DRLNAIDARL WALGGSEAEL AAFEKEIAAF ESELQAYKGK GNPEVESLRE  60
HAAAIREWLQ AYRHNGGGGD GGGGSGTTTP APRPPTPAPT IASQPLSLRP EACRPAAGGA 120
VHTRGLDFAC DIYIWAPLAG TCGVLLLSLV ITLYCKRGRK KLLYIFKQPF MRPVQTTQEE 180
DGCSCRFPEE EEGGCELRVK FSRSADAPAY KQGQNQLYNE LNLGRREEYD VLDKRRGRDP 240
EMGGKPRRKN PQEGLYNELQ KDKMAEAYSE IGMKGERRRG KGHDGLYQGL STATKDTYDA 300
LHMQALPPR                                                       309

SEQ ID NO: 69            moltype = AA   length = 309
FEATURE                  Location/Qualifiers
REGION                   1..309
                         note = Recombinant polypeptide
source                   1..309
                         mol_type = protein
                         organism = synthetic construct
SEQUENCE: 69
DEMGSWFEFY DRLNAIDARL WALGGSEAEL AAFEKEIAAF ESELQAYKGK GNPEVESLRV  60
HAAAIREWLQ AYRHNGGGGD GGGGSGTTTP APRPPTPAPT IASQPLSLRP EACRPAAGGA 120
VHTRGLDFAC DIYIWAPLAG TCGVLLLSLV ITLYCKRGRK KLLYIFKQPF MRPVQTTQEE 180
DGCSCRFPEE EEGGCELRVK FSRSADAPAY KQGQNQLYNE LNLGRREEYD VLDKRRGRDP 240
EMGGKPRRKN PQEGLYNELQ KDKMAEAYSE IGMKGERRRG KGHDGLYQGL STATKDTYDA 300
LHMQALPPR                                                       309

SEQ ID NO: 70            moltype = AA   length = 73
FEATURE                  Location/Qualifiers
REGION                   1..73
                         note = Recombinant polypeptide
source                   1..73
                         mol_type = protein
                         organism = synthetic construct
SEQUENCE: 70
MGSWFEFYDR LNAIDARLWA LGGSEAELAA FEKEIAAFES ELQAYKGKGN PEVESLRVHA  60
AAIREWLQAY RHN                                                   73

SEQ ID NO: 71            moltype = AA   length = 73
FEATURE                  Location/Qualifiers
REGION                   1..73
                         note = Recombinant polypeptide
source                   1..73
                         mol_type = protein
                         organism = synthetic construct
SEQUENCE: 71
MGSWFEFYDR LNAIDARLWA LGGSEAELAA FEKEIAAFES ELQAYKGKGN PEVESLREHA  60
AHIREWLQAY RHN                                                   73

SEQ ID NO: 72            moltype = AA   length = 73
FEATURE                  Location/Qualifiers
REGION                   1..73
                         note = Recombinant polypeptide
source                   1..73
                         mol_type = protein
                         organism = synthetic construct
SEQUENCE: 72
MGSWFEFYDR LNAIDARLWA LGGSEAELAA FEKEIAAFES ELQAYKGKGN PEVESLREHA  60
AAIREWLQAY RHN                                                   73
```

```
SEQ ID NO: 73              moltype = AA   length = 73
FEATURE                    Location/Qualifiers
REGION                     1..73
                           note = Recombinant polypeptide
source                     1..73
                           mol_type = protein
                           organism = synthetic construct
SEQUENCE: 73
MGSWSEFYDR LNAIDARLWA LGGSEAELAA FEKEIAAFES ELQAYKGKGN PEVESLREHA    60
AAIREWLQAY RHN                                                      73

SEQ ID NO: 74              moltype = AA   length = 73
FEATURE                    Location/Qualifiers
REGION                     1..73
                           note = Recombinant polypeptide
source                     1..73
                           mol_type = protein
                           organism = synthetic construct
SEQUENCE: 74
MGSWYEFYTR LDAIDARLWA LGGSEAELAA FEKEIAAFES ELQAYKGKGN PEVEKLRVHA    60
AAIRNWLQAY RHN                                                      73

SEQ ID NO: 75              moltype = AA   length = 73
FEATURE                    Location/Qualifiers
REGION                     1..73
                           note = Recombinant polypeptide
source                     1..73
                           mol_type = protein
                           organism = synthetic construct
SEQUENCE: 75
MGSWLEFWNR LEAIDQRLWA LGGSEAELAA FEKEIAAFES ELQAYKGKGN PEVEVLREHA    60
AAIRAWLQAY RHN                                                      73

SEQ ID NO: 76              moltype = AA   length = 73
FEATURE                    Location/Qualifiers
REGION                     1..73
                           note = Recombinant polypeptide
source                     1..73
                           mol_type = protein
                           organism = synthetic construct
SEQUENCE: 76
MGSWVEFWNR LQAIDTRLWA LGGSEAELAA FEKEIAAFES ELQAYKGKGN PEVESLRIHA    60
AHIRFWLQAY RHN                                                      73

SEQ ID NO: 77              moltype = AA   length = 73
FEATURE                    Location/Qualifiers
REGION                     1..73
                           note = Recombinant polypeptide
source                     1..73
                           mol_type = protein
                           organism = synthetic construct
SEQUENCE: 77
MGSWHEFWFR LDAIDTRLWA LGGSEAELAA FEKEIAAFES ELQAYKGKGN PEVESLREHA    60
AAIRYWLQAY RHN                                                      73

SEQ ID NO: 78              moltype = AA   length = 73
FEATURE                    Location/Qualifiers
REGION                     1..73
                           note = Recombinant polypeptide
source                     1..73
                           mol_type = protein
                           organism = synthetic construct
SEQUENCE: 78
MGSWIEFYVR LDAIDTRLWA LGGSEAELAA FEKEIAAFES ELQAYKGKGN PEVESLREHA    60
AYIRVWLQAY RHN                                                      73

SEQ ID NO: 79              moltype = AA   length = 73
FEATURE                    Location/Qualifiers
REGION                     1..73
                           note = Recombinant polypeptide
source                     1..73
                           mol_type = protein
                           organism = synthetic construct
SEQUENCE: 79
MGSWMEFMTR LDAIDERLWA LGGSEAELAA FEKEIAAFES ELQAYKGKGN PEVESLREHA    60
AAIRHWLQAY RHN                                                      73

SEQ ID NO: 80              moltype = AA   length = 73
FEATURE                    Location/Qualifiers
```

```
REGION                     1..73
                           note = Recombinant polypeptide
source                     1..73
                           mol_type = protein
                           organism = synthetic construct
SEQUENCE: 80
MGSWTEFWDR LQAIDNRLWA LGGSEAELAA FEKEIAAFES ELQAYKGKGN PEVEALREQA    60
ASIRIWLQAY RHN                                                      73

SEQ ID NO: 81              moltype = AA  length = 73
FEATURE                    Location/Qualifiers
REGION                     1..73
                           note = Recombinant polypeptide
source                     1..73
                           mol_type = protein
                           organism = synthetic construct
SEQUENCE: 81
MGSWVEFYHR LEAIENRLFA LGGSEAELAA FEKEIAAFES ELQAYKGKGN PEVENLRQHA    60
AHIRQWLQAY RHN                                                      73

SEQ ID NO: 82              moltype = AA  length = 73
FEATURE                    Location/Qualifiers
REGION                     1..73
                           note = Recombinant polypeptide
source                     1..73
                           mol_type = protein
                           organism = synthetic construct
SEQUENCE: 82
MGSWMEFSDR LFAIWIRLWA LGGSEAELAA FEKEIAAFES ELQAYKGKGN PEVEGLRSLA    60
AHIRGHLQAY RHN                                                      73

SEQ ID NO: 83              moltype = AA  length = 73
FEATURE                    Location/Qualifiers
REGION                     1..73
                           note = Recombinant polypeptide
source                     1..73
                           mol_type = protein
                           organism = synthetic construct
SEQUENCE: 83
MGSWTEFYDR LNAIDARLWA LGGSEAELAA FEKEIAAFES ELQAYKGKGN PEVESLRVHA    60
AAIREWLQAY RHN                                                      73

SEQ ID NO: 84              moltype = AA  length = 73
FEATURE                    Location/Qualifiers
REGION                     1..73
                           note = Recombinant polypeptide
source                     1..73
                           mol_type = protein
                           organism = synthetic construct
SEQUENCE: 84
MGSWTEFYDR LNAIDARLWA LGGSEAELAA FEKEIAAFES ELQAYKGKGN PEVESLRAHA    60
AAIREWLQAY RHN                                                      73

SEQ ID NO: 85              moltype = AA  length = 73
FEATURE                    Location/Qualifiers
REGION                     1..73
                           note = Recombinant polypeptide
source                     1..73
                           mol_type = protein
                           organism = synthetic construct
SEQUENCE: 85
MGSWTEFYDR LNAIDARLWA LGGSEAELAA FEKEIAAFES ELQAYKGKGN PEVESLKAHA    60
AAIREWLQAY RHN                                                      73

SEQ ID NO: 86              moltype = AA  length = 73
FEATURE                    Location/Qualifiers
REGION                     1..73
                           note = Recombinant polypeptide
source                     1..73
                           mol_type = protein
                           organism = synthetic construct
SEQUENCE: 86
MGSWTEFYDR LNAIDARLWA LGGSEAELAA FEKEIAAFES ELQAYKGKGN PEVESLQAHA    60
AAIREWLQAY RHN                                                      73

SEQ ID NO: 87              moltype = AA  length = 73
FEATURE                    Location/Qualifiers
REGION                     1..73
                           note = Recombinant polypeptide
```

```
source                        1..73
                              mol_type = protein
                              organism = synthetic construct
SEQUENCE: 87
MGSWTEFYDR LNAIDARLWA LGGSEAELAA FEKEIAAFES ELQAYKGKGN PEVESLRAHA   60
AGIREWLQAY RHN                                                     73

SEQ ID NO: 88                 moltype = AA   length = 73
FEATURE                       Location/Qualifiers
REGION                        1..73
                              note = Recombinant polypeptide
source                        1..73
                              mol_type = protein
                              organism = synthetic construct
SEQUENCE: 88
MGSWSEFYDR LNAIDARLWA LGGSEAELAA FEKEIAAFES ELQAYKGKGN PEVESLRSHA   60
AAIREWLQAY RHN                                                     73

SEQ ID NO: 89                 moltype = AA   length = 73
FEATURE                       Location/Qualifiers
REGION                        1..73
                              note = Recombinant polypeptide
source                        1..73
                              mol_type = protein
                              organism = synthetic construct
SEQUENCE: 89
MGSWSEFYDR LNAIDARLWA LGGSEAELAA FEKEIAAFES ELQAYKGKGN PEVESLQSHA   60
AAIREWLQAY RHN                                                     73

SEQ ID NO: 90                 moltype = AA   length = 73
FEATURE                       Location/Qualifiers
REGION                        1..73
                              note = Recombinant polypeptide
source                        1..73
                              mol_type = protein
                              organism = synthetic construct
SEQUENCE: 90
MGSWTEFYDR LNAIDARLWA LGGSEAELAA FEKEIAAFES ELQAYKGKGN PEVESLRSHA   60
AAIREWLQAY RHN                                                     73

SEQ ID NO: 91                 moltype = AA   length = 73
FEATURE                       Location/Qualifiers
REGION                        1..73
                              note = Recombinant polypeptide
source                        1..73
                              mol_type = protein
                              organism = synthetic construct
SEQUENCE: 91
MGSWTEFYDR LNAIDARLWA LGGSEAELAA FEKEIAAFES ELQAYKGKGN PEVESLQSHA   60
AAIREWLQAY RHN                                                     73

SEQ ID NO: 92                 moltype = AA   length = 73
FEATURE                       Location/Qualifiers
REGION                        1..73
                              note = Recombinant polypeptide
source                        1..73
                              mol_type = protein
                              organism = synthetic construct
SEQUENCE: 92
MGSWTEFYDR LNAIDARLWA LGGSEAELAA FEKEIAAFES ELQAYKGKGN PEVESLREHA   60
AHIREWLQAY RHN                                                     73

SEQ ID NO: 93                 moltype = AA   length = 73
FEATURE                       Location/Qualifiers
REGION                        1..73
                              note = Recombinant polypeptide
source                        1..73
                              mol_type = protein
                              organism = synthetic construct
SEQUENCE: 93
MGSWSEFYDR LNAIDARLWA LGGSEAELAA FEKEIAAFES ELQAYKGKGN PEVESLREHA   60
AHIREWLQAY RHN                                                     73

SEQ ID NO: 94                 moltype = AA   length = 73
FEATURE                       Location/Qualifiers
REGION                        1..73
                              note = Recombinant polypeptide
source                        1..73
                              mol_type = protein
```

```
                              organism = synthetic construct
SEQUENCE: 94
MGSWTEFYDR LNAIDARLWA LGGSEAELAA FEKEIAAFES ELQAYKGKGN PEVESLREHA    60
AAIREWLQAY RHN                                                      73

SEQ ID NO: 95             moltype = AA   length = 291
FEATURE                   Location/Qualifiers
REGION                    1..291
                          note = Recombinant polypeptide
source                    1..291
                          mol_type = protein
                          organism = synthetic construct
SEQUENCE: 95
MPPPRLLFFL LFLTPMEVRP EEPLVVKVEE GDNAVLQCLK GTSDGPTQQL TWSRESPLKP    60
FLKLSLGLPG LGIHMRPLAI WLFIFNVSQQ MGGFYLCQPG PPSEKAWQPG WTVNVEGSGE   120
LFRWNVSDLG GLGCGLKNRS SEGPSSPSGK LMSPKLYVWA KDRPEIWEGE PPCLPPRDSL   180
NQSLSQDLTM APGSTWLSC GVPPDSVSRG PLSWTHVHPK GPKSLLSLEL KDDRPARDMW    240
VMETGLLLPR ATAQDAGKYY CHRGNLTMSF HLEITARPVL WHWLLRTGGW K            291

SEQ ID NO: 96             moltype = AA   length = 5
FEATURE                   Location/Qualifiers
REGION                    1..5
                          note = Recombinant polypeptide
source                    1..5
                          mol_type = protein
                          organism = synthetic construct
SEQUENCE: 96
GGGGS                                                                5

SEQ ID NO: 97             moltype = AA   length = 73
FEATURE                   Location/Qualifiers
REGION                    1..73
                          note = Recombinant polypeptide
source                    1..73
                          mol_type = protein
                          organism = synthetic construct
SEQUENCE: 97
MGSWSEFNMR LDAIYERLTA LGGSEAELAA FEKEIAAFES ELQAYKGKGN PEVEWLRHSA    60
ARIRLELQAY RHN                                                      73

SEQ ID NO: 98             moltype = AA   length = 73
FEATURE                   Location/Qualifiers
REGION                    1..73
                          note = Recombinant polypeptide
source                    1..73
                          mol_type = protein
                          organism = synthetic construct
SEQUENCE: 98
MGSWIEFNMR LDAIYERLVA LGGSEAELAA FEKEIAAFES ELQAYKGKGN PEVEWLRKVA    60
ANIRLELQAY RHN                                                      73

SEQ ID NO: 99             moltype = AA   length = 73
FEATURE                   Location/Qualifiers
REGION                    1..73
                          note = Recombinant polypeptide
source                    1..73
                          mol_type = protein
                          organism = synthetic construct
SEQUENCE: 99
MGSWDEFGRR LYAIEWRLYA LGGSEAELAA FEKEIAAFES ELQAYKGKGN PEVEKLRELA    60
AVIRSNLQAY RHN                                                      73

SEQ ID NO: 100            moltype = AA   length = 73
FEATURE                   Location/Qualifiers
REGION                    1..73
                          note = Recombinant polypeptide
source                    1..73
                          mol_type = protein
                          organism = synthetic construct
SEQUENCE: 100
MGSWDEFGRR LYAIEWRLYA LGGSEAELAA FEKEIAAFES ELQAYKGEGN PEVEKLREIA    60
AVIRSNLQAY RHN                                                      73

SEQ ID NO: 101            moltype = AA   length = 438
FEATURE                   Location/Qualifiers
REGION                    1..438
                          note = Recombinant polypeptide
source                    1..438
                          mol_type = protein
```

```
                         organism = synthetic construct
SEQUENCE: 101
DEGGGGSMGS  WAEFKQRLAA  IKTRLEALGG  SEAELAAFEK  EIAAFESELQ  AYKGKGNPEV   60
EALRKEAAAI  RDELQAYRHN  GGGGSGGGGS  GGGGSGLEKC  FQTENPLECQ  DKGEEELQKY  120
IQESQALAKR  SCGLFQKLGE  YYLQNAFLVA  YTKKAPQLTS  SELMAITRKM  AATAATCCQL  180
SEDKLLACGE  GAADIIIGHL  CIRHEMTPVN  PGVGQCCTSS  YANRRPCFSS  LVVDETYVPP  240
AFSDDKFIFH  KDLCQAQGVA  LQTMKQEFLI  NLVKQKPQIT  EEQLEAVIAD  FSGLLEKCCQ  300
GQEQEVCFAE  EGQKLISKTR  AALGVGGGGS  GGGGSGGGGS  MGSWDEFGRR  LYAIEWQLYA  360
LGGTEAELAA  FEKEIAAFES  ELQAYKGKGN  PEVEKLREIA  AVIRENLQAY  RHNGGGGSGG  420
GGSGGGGSHH  HHHHHHH                                                    438

SEQ ID NO: 102         moltype = AA  length = 438
FEATURE                Location/Qualifiers
REGION                 1..438
                       note = Recombinant polypeptide
source                 1..438
                       mol_type = protein
                       organism = synthetic construct
SEQUENCE: 102
DEGGGGSMGS  WAEFKQRLAA  IKTRLEALGG  SEAELAAFEK  EIAAFESELQ  AYKGKGNPEV   60
EALRKEAAAI  RDELQAYRHN  GGGGSGGGGS  GGGGSGLEKC  FQTENPLECQ  DKGEEELQKY  120
IQESQALAKR  SCGLFQKLGE  YYLQNAFLVA  YTKKAPQLTS  SELMAITRKM  AATAATCCQL  180
SEDKLLACGE  GAADIIIGHL  CIRHEMTPVN  PGVGQCCTSS  YANRRPCFSS  LVVDETYVPP  240
AFSDDKFIFH  KDLCQAQGVA  LQTMKQEFLI  NLVKQKPQIT  EEQLEAVIAD  FSGLLEKCCQ  300
GQEQEVCFAE  EGQKLISKTR  AALGVGGGGS  GGGGSGGGGS  MGSWDEFGRR  LYAIEWQLYA  360
LGGTEAELAA  FEKEIAAFES  ELQAYKGKGS  PEVEKLREIA  AVIRENLQAY  RHNGGGGSGG  420
GGSGGGGSHH  HHHHHHH                                                    438

SEQ ID NO: 103         moltype = AA  length = 438
FEATURE                Location/Qualifiers
REGION                 1..438
                       note = Recombinant polypeptide
source                 1..438
                       mol_type = protein
                       organism = synthetic construct
SEQUENCE: 103
DEGGGGSMGS  WAEFKQRLAA  IKTRLEALGG  SEAELAAFEK  EIAAFESELQ  AYKGKGNPEV   60
EALRKEAAAI  RDELQAYRHN  GGGGSGGGGS  GGGGSGLEKC  FQTENPLECQ  DKGEEELQKY  120
IQESQALAKR  SCGLFQKLGE  YYLQNAFLVA  YTKKAPQLTS  SELMAITRKM  AATAATCCQL  180
SEDKLLACGE  GAADIIIGHL  CIRHEMTPVN  PGVGQCCTSS  YANRRPCFSS  LVVDETYVPP  240
AFSDDKFIFH  KDLCQAQGVA  LQTMKQEFLI  NLVKQKPQIT  EEQLEAVIAD  FSGLLEKCCQ  300
GQEQEVCFAE  EGQKLISKTR  AALGVGGGGS  GGGGSGGGGS  MGSWDEFGRR  LYAIEWQLYA  360
LGGTEAELAA  FEKEIAAFES  ELQAYKGEGS  PEVEKLREIA  AVIRENLQAY  RHNGGGGSGG  420
GGSGGGGSHH  HHHHHHH                                                    438

SEQ ID NO: 104         moltype = AA  length = 320
FEATURE                Location/Qualifiers
REGION                 1..320
                       note = Recombinant polypeptide
source                 1..320
                       mol_type = protein
                       organism = synthetic construct
SEQUENCE: 104
DEMGSWDEFS  RRLYAIEWQL  YAQGGTEAEL  AAFEKEIAAF  ESELQAYKGE  GSPEVEKLRE   60
LAAVIRENLQ  AYRHNGGGGD  GGGGSGGGGS  GQESQALAKR  SCGLFQKLGE  YYLQNAFLVA  120
YTKKAPQLTS  SELMAITRKM  AATAATCCQL  SEDKLLACGE  GAADIIIGHL  CIRHEMTPVN  180
PGVGQCCTSS  YANRRPCFSS  LVVDETYVPP  AFSDDKFIFH  KDLCQAQGVA  LQTMKQEFLI  240
NLVKQKPQIT  EEQLEAVIAD  FSGLLEKCCQ  GQEQEVCFAE  EGQKLISKTR  AALGVGGGGS  300
GGGGSGGGGS  HHHHHHHHHH                                                 320

SEQ ID NO: 105         moltype = AA  length = 325
FEATURE                Location/Qualifiers
REGION                 1..325
                       note = Recombinant polypeptide
source                 1..325
                       mol_type = protein
                       organism = synthetic construct
SEQUENCE: 105
DEGGGGSMGS  WAEFKQRLAA  IKTRLEALGG  SEAELAAFEK  EIAAFESELQ  AYKGKGNPEV   60
EALRKEAAAI  RDELQAYRHN  GGGDGGGGS   GGGGSGQESQ  ALAKRSCGLF  QKLGEYYLQN  120
APLVAYTKKA  PQLTSSELMA  ITRKMAATAA  TCCQLSEDKL  LACGEGAADI  IIGHLCIRHE  180
MTPVNPGVGQ  CCTSSYANRR  PCFSSLVVDE  TYVPPAFSDD  KFIFHKDLCQ  AQGVALQTMK  240
QEFLINLVKQ  KPQITEEQLE  AVIADFSGLL  EKCCQGQEQE  VCFAEEGQKL  ISKTRAALGV  300
GGGGSGGGGS  GGGGSHHHHH  HHHHH                                          325

SEQ ID NO: 106         moltype = AA  length = 325
FEATURE                Location/Qualifiers
REGION                 1..325
                       note = Recombinant polypeptide
```

```
source                     1..325
                           mol_type = protein
                           organism = synthetic construct
SEQUENCE: 106
DYKDDDDKGG GGSGGGGSMG SWDEFSRRLY AIEWQLYAQG GTEAELAAFE KEIAAFESEL    60
QAYKGEGSPE VEKLRELAAV IRENLQAYRH NGGGGSGGGG SGTTTPAPRP PTPAPTIASQ   120
PLSLRPEACR PAAGGAVHTR GLDFACDIYI WAPLAGTCGV LLLSLVITLY CKRGRKKLLY   180
IFKQPFMRPV QTTQEEDGCS CRFPEEEEGG CELRVKFSRS ADAPAYKQGQ NQLYNELNLG   240
RREEYDVLDK RRGRDPEMGG KPRRKNPQEG LYNELQKDKM AEAYSEIGMK GERRRGKGHD   300
GLYQGLSTAT KDTYDALHMQ ALPPR                                        325

SEQ ID NO: 107             moltype = AA   length = 325
FEATURE                    Location/Qualifiers
REGION                     1..325
                           note = Recombinant polypeptide
source                     1..325
                           mol_type = protein
                           organism = synthetic construct
SEQUENCE: 107
DYKDDDDKGG GGSGGGGSMG SWSEFYDRLN AIDARLWALG GSEAELAAFE KEIAAFESEL    60
QAYKGKGNPE VESLREHAAA IREWLQAYRH NGGGGSGGGG SGTTTPAPRP PTPAPTIASQ   120
PLSLRPEACR PAAGGAVHTR GLDFACDIYI WAPLAGTCGV LLLSLVITLY CKRGRKKLLY   180
IFKQPFMRPV QTTQEEDGCS CRFPEEEEGG CELRVKFSRS ADAPAYKQGQ NQLYNELNLG   240
RREEYDVLDK RRGRDPEMGG KPRRKNPQEG LYNELQKDKM AEAYSEIGMK GERRRGKGHD   300
GLYQGLSTAT KDTYDALHMQ ALPPR                                        325

SEQ ID NO: 108             moltype = AA   length = 16
FEATURE                    Location/Qualifiers
REGION                     1..16
                           note = Recombinant polypeptide
source                     1..16
                           mol_type = protein
                           organism = synthetic construct
SEQUENCE: 108
GGGGDGGGGS GGGGSG                                                   16

SEQ ID NO: 109             moltype = AA   length = 16
FEATURE                    Location/Qualifiers
REGION                     1..16
                           note = Recombinant polypeptide
source                     1..16
                           mol_type = protein
                           organism = synthetic construct
SEQUENCE: 109
GGGGDGGGGG SGGGSG                                                   16

SEQ ID NO: 110             moltype = AA   length = 16
FEATURE                    Location/Qualifiers
REGION                     1..16
                           note = Recombinant polypeptide
source                     1..16
                           mol_type = protein
                           organism = synthetic construct
SEQUENCE: 110
GGGGSGGGGS GGGGSG                                                   16

SEQ ID NO: 111             moltype = AA   length = 73
FEATURE                    Location/Qualifiers
REGION                     1..73
                           note = Recombinant polypeptide
source                     1..73
                           mol_type = protein
                           organism = synthetic construct
SEQUENCE: 111
MGSWEEFDKR LDAITRRLMA LGGSEAELAE FESTIAWFEW DLQEYKGKGN PEVEALDWEA    60
YAIDYELGAY RHN                                                      73

SEQ ID NO: 112             moltype = AA   length = 45
FEATURE                    Location/Qualifiers
REGION                     1..45
                           note = Recombinant polypeptide
source                     1..45
                           mol_type = protein
                           organism = synthetic construct
SEQUENCE: 112
TTTPAPRPPT PAPTIASQPL SLRPEACRPA AGGAVHTRGL DFACD                   45

SEQ ID NO: 113             moltype = AA   length = 24
FEATURE                    Location/Qualifiers
```

```
REGION                   1..24
                         note = Recombinant polypeptide
source                   1..24
                         mol_type = protein
                         organism = synthetic construct
SEQUENCE: 113
IYIWAPLAGT CGVLLLSLVI TLYC                                          24

SEQ ID NO: 114           moltype = AA  length = 21
FEATURE                  Location/Qualifiers
REGION                   1..21
                         note = Recombinant polypeptide
source                   1..21
                         mol_type = protein
                         organism = synthetic construct
SEQUENCE: 114
IYIWAPLAGT CGVLLLSLVI T                                             21

SEQ ID NO: 115           moltype = AA  length = 42
FEATURE                  Location/Qualifiers
source                   1..42
                         mol_type = protein
                         organism = synthetic construct
SEQUENCE: 115
KRGRKKLLYI FKQPFMRPVQ TTQEEDGCSC RFPEEEEGGC EL                      42

SEQ ID NO: 116           moltype = AA  length = 112
FEATURE                  Location/Qualifiers
source                   1..112
                         mol_type = protein
                         organism = synthetic construct
SEQUENCE: 116
RVKFSRSADA PAYKQGQNQL YNELNLGRRE EYDVLDKRRG RDPEMGGKPR RKNPQEGLYN    60
ELQKDKMAEA YSEIGMKGER RRGKGHDGLY QGLSTATKDT YDALHMQALP PR           112

SEQ ID NO: 117           moltype = AA  length = 223
FEATURE                  Location/Qualifiers
source                   1..223
                         mol_type = protein
                         organism = synthetic construct
SEQUENCE: 117
TTTPAPRPPT PAPTIASQPL SLRPEACRPA AGGAVHTRGL DFACDIYIWA PLAGTCGVLL    60
LSLVITLYCK RGRKKLLYIF KQPFMRPVQT TQEEDGCSCR FPEEEEGGCE LRVKFSRSAD   120
APAYKQGQNQ LYNELNLGRR EEYDVLDKRR GRDPEMGGKP RRKNPQEGLY NELQKDKMAE   180
AYSEIGMKGE RRRGKGHDGL YQGLSTATKD TYDALHMQAL PPR                     223

SEQ ID NO: 118           moltype = AA  length = 11
FEATURE                  Location/Qualifiers
source                   1..11
                         mol_type = protein
                         organism = synthetic construct
SEQUENCE: 118
GGGGTGGGGS G                                                        11

SEQ ID NO: 119           moltype = AA  length = 11
FEATURE                  Location/Qualifiers
source                   1..11
                         mol_type = protein
                         organism = synthetic construct
SEQUENCE: 119
GGGGTGGGGS G                                                        11
```

D-DOMAIN CONTAINING POLYPEPTIDES AND USES THEREOF

CROSS-REFERENCE TO RELATED APPLICATIONS

This application claims the benefit of U.S. application No. 63/279,489, filed Nov. 15, 2021, which is incorporated herein by reference in its entirety.

REFERENCE TO SEQUENCE LISTING SUBMITTED ELECTRONICALLY

The content of the electronically submitted sequence listing (Name: 6666_0310_Sequence_Listing.xml; Size: 163,863 bytes; and Date of Creation: Nov. 6, 2022) filed with the application is incorporated herein by reference in its entirety.

FIELD OF THE INVENTION

The field of the invention generally relates to D domain containing polypeptides, including multi-functional chimeric antigen receptors and Adapters comprising the D domains, and their use in methods of treatment, for example, by directing immune responses to target cells.

BACKGROUND

The adoptive transfer of genetically modified T cells is a rapidly evolving innovative treatment for cancer. Chimeric antigen receptor (CAR) engineered T cells are renewable drugs with the capacity to provide sustained functional immunity. Clinical efficacy has been demonstrated with CD19 CAR T in a range of hematological cancers and encouraging early clinical data has been reported for other genetically modified CAR T in solid tumors. However, significant challenges must be met before CAR technology can more fully realize its substantial potential.

SUMMARY

In one aspect, provided herein are proteins comprising a D Domain (DD) target binding domain (DDpp) wherein the DD specifically binds a target of interest. In some embodiments, the target of interest is human CD123 (SEQ ID NO: 1), or a fragment thereof. In some embodiments, the DDpp are monovalent or multivalent. In some embodiments, the DDpp are monospecific or multispecific. In further embodiments, the DDpp are monospecific and multivalent. In other embodiments, the DDpp are multispecific and multivalent. Fusion proteins comprising one or more DD are also provided, as are methods of making and using the fusion proteins. Nucleic acids encoding the DDpps and vectors and host cells containing the nucleic acids are also provided. Non-limiting examples of such uses include, but are not limited to target analysis, and diagnostic and therapeutic applications. In some embodiments, the DDpp comprises a CD123-binding DD comprising an amino acid sequence selected from the group consisting of SEQ ID NO: 8-33, 99 and 100. In some embodiments, the DDpp comprises a DD comprising an amino acid sequence selected from the group consisting of SEQ ID NO: 8, 13, 14, 31, 32, and 33. In some embodiments, the DDpp comprises a DD comprising the amino acid sequence of SEQ ID NO: 14.

In one aspect, the disclosure provides a chimeric antigen receptor (CAR) which comprises a target binding domain comprising a DD disclosed. In some embodiments, the DD binds CD123 and comprises an amino acid sequence selected from the group consisting of SEQ ID NO: 8-33, 99 and 100. In some embodiments, the CD123-specific DD comprises an amino acid sequence selected from the group consisting of SEQ ID NO: 8, 13, 14, 31, 32, and 33. In some embodiments, the CD123-specific DD comprises the amino acid sequence of SEQ ID NO: 14. In some embodiments, the DD binds AFP p26 (SEQ ID NO: 37) and comprises an amino acid sequence selected from the group consisting of SEQ ID NO: 74-93 and 94. In some embodiments, the CAR comprises, a target binding domain, a transmembrane domain, and an intracellular signaling domain. In some embodiments the CAR further comprises a second target binding domain having the same or a different target than the DD target binding domain. In some embodiments, the CAR is expressed in an immune cell. In some embodiments, the CAR is expressed in an immune effector cell. In some embodiments, the immune cell is a T cell (CAR-T cell) or a natural killer (NK) cell (CAR-NK cell). In some embodiments, the cell is an autologous immune cell. In some embodiments the cell is an autologous T cell (CAR-T cell) or an autologous natural killer (NK) cell. In some embodiments, the cell is an allogenic immune cell. In some embodiments the cell is an allogenic T cell (CAR-T cell) or an allogenic natural killer (NK) cell. In some embodiments, the CAR is expressed in an immune cell derived from human embryonic stem cells (CAR-hESCs) or induced pluripotent stem cells (CAR-iPSC cell).

Nucleic acids encoding the disclosed DDpp (e.g., DDpp fusion protein, CAR, or Adapter) are also provided. Additionally provided are vectors (e.g., plasmids, viral vectors, and non-viral vectors) containing nucleic acids encoding the DDpp (e.g., DDpp fusion protein, CAR, or Adapter) and host cells containing the nucleic acids and vectors. In some embodiments, the vector comprises a nucleotide sequence which regulates the expression of the polypeptide encoded by the nucleic acid molecule. In further embodiments, the vector comprises an inducible promoter sequence. In additional embodiments, the vector includes one or more additional standard components for expression of a protein encoded a nucleic acid (e.g., promoters, packaging components, etc.). In some embodiments, the vector is a lentiviral vector.

In one aspect, the disclosure also provides host cells that comprise the nucleic acid molecules encoding a target-binding DDpp disclosed herein. In some embodiments, the host cells (e.g., cells of a cell line) are engineered to express a protein containing a DD disclosed herein (e.g., a DD having the amino acid sequence of SEQ ID NO: 8-33). In some embodiments, the expression of the DDpp (e.g., DDpp fusion protein, or Adapter) by the host cells allows production and isolation of the DDpp. In some embodiments, the expression results in the DDpp (e.g., CAR) being expressed on the surface and/or integral to the membrane of the host cells. In some embodiments, the host cell is a bacterial, yeast, fungal, or plant cell. In other embodiments, the host cell is a mammalian cell. In a further embodiment, the mammalian cell is an immune cell. In one embodiment, the host cell is a human immune cell. In some embodiments, the human immune cell is a T cell. In other embodiments, the human immune cell is a natural killer (NK) cell. In some embodiments, the human immune cell displays the DDpp (e.g., CAR) on its cell surface.

In one aspect, the disclosure further provides a host cell expressing a protein comprising a DD disclosed herein. In some embodiments, the host cell expresses a chimeric antigen receptor (CAR) comprising a DD disclosed herein. In some embodiments, the CAR comprises a target binding domain that comprises a DD comprising an amino acid sequence selected from SEQ ID NO: 8-33 and a transmembrane domain. In some embodiments, the CD123-specific DD comprises an amino acid sequence selected from the group consisting of SEQ ID NO: 8, 13, 14, 31, 32, and 33. In some embodiments, the CD123-specific DD comprises the amino acid sequence of SEQ ID NO: 14. In some embodiments, the CAR further comprise an intracellular domain (comprising a signaling domain) In some embodiments, the CAR immune cell is a T cell. In some embodiments, the CAR immune effector cell is a NK cell. In some embodiments, the CAR immune effector cell is not a T cell or an NK cell. In some embodiments, the CAR immune cell is an autologous immune cell. In some embodiments, the CAR immune cell is an allogenic immune cell. In some embodiments, the host cell is an immune effector cell that further comprises a second CAR polypeptide having a DD or other binding domain (e.g., scFv) that specifically binds the same or a different target (e.g., a different epitope of the same target, or a second target of interest) expressed by the cancer cell) as the first CAR expressed by the host immune cell.

Pharmaceutical compositions containing a protein comprising a DD disclosed herein, nucleic acids disclosed herein encoding the proteins, vectors disclosed herein containing the nucleic acids, viruses encoding the proteins, and host cells disclosed herein containing the nucleic acids and or vectors are also provided. As are kits containing one or more of the disclosed target-binding DDpps (e.g., DDpp fusion proteins such as DD-Fc and DD-CAR, or Adapter), nucleic acid molecules, vectors, and host cells (e.g., a therapeutic kit, a diagnostic kit, a kit for research use, etc.).

DDpp provided herein possess activities that include but are not limited to the ability to specifically bind a target of interest (e.g., CD123) in vitro or in vivo and the ability to serve as a reactive site for linking or associating a protein such as a DDpp fusion protein with one or more additional moieties (e.g., a solid support), and/or other modifications. The DDpp provided herein can also possess additional desirable properties and/or functionalities useful in manufacturing, formulation and biological, diagnostic, and therapeutic applications.

Methods of using DDpp in diagnostic and therapeutic applications are also provided. In one embodiment, the disclosure provides a method of treating a disease or disorder comprising administering a therapeutically effective amount of a DDpp (e.g., a DDpp fusion protein, CAR and/or Adapter) that specifically binds a therapeutic target of interest (e.g., CD123) to a subject in need thereof. In some embodiments, the disease or disorder is cancer, a B cell malignancy, a disease or disorder of the immune system, or an infection. Methods of treating a disease or disorder that comprises co-administering an additional therapeutic agent along with a disclosed DDpp are also provided. In some embodiments, the disease or disorder is acute myeloid leukemia (AML), myelodysplastic syndrome (e.g., high-risk myelodysplastic syndrome), B-cell acute lymphoblastic leukemia, hairy cell leukemia, Hodgkin's lymphoma or blastic plasmacytoid dendritic neoplasm (BPDCN). In some embodiments, the disease or disorder is acute myeloid leukemia.

In some embodiments, the disclosure provides:

[1.] A protein comprising a D Domain target binding domain that specifically binds CD123 and comprises the amino acid sequence of SEQ ID NO: 8-32 or 33.

[2.] The protein of [1], wherein the D domain comprises the amino acid sequence of SEQ ID NO: 8, 13, 14, or 31-33.

[3.] The protein of [1], wherein the D domain comprises the amino acid sequence of SEQ ID NO: 14.

[4.] The protein of any one of [1] to [3], wherein the D domain is fused to a heterologous polypeptide.

[5.] The protein of [4], wherein the heterologous polypeptide comprises a full-length antibody or an antibody fragment.

[6.] The protein of [4], wherein the D domain is fused to the amino terminus of a full-length antibody heavy chain; the amino terminus of a full-length antibody light chain; the carboxyl terminus of a full-length antibody heavy chain; or the carboxyl terminus of a full-length antibody light chain.

[7.] The protein of [4], wherein the heterologous polypeptide is an Fc domain.

[8.] The protein of [4], wherein the heterologous polypeptide comprises a member selected from the group consisting of.

(a) a transmembrane domain;
(b) a membrane associating domain;
(c) human serum albumin or a fragment thereof;
(d) AFP or a fragment thereof;
(e) AFP p26 or a fragment thereof; and
(f) the extracellular domain of a receptor or a fragment thereof.

[9.] The protein of [4], wherein the heterologous polypeptide comprises the extracellular domain, or a fragment of an extracellular domain, of a receptor selected from the group consisting of: BCMA, CD123, CS1, and CD19.

[10.] The protein of any one of [2] to [9] further comprising a peptide linker.

[11.] The protein of any one of [1] to [10], which is labeled.

[12.] The protein of [11], wherein the label is selected from the group consisting of an enzymatic label, a fluorescent label, a luminescent label, a bioluminescent label and a biotin moiety.

[13.] A protein of any one of [1] to [12], which is conjugated to a therapeutic or cytotoxic agent.

[14.] A chimeric antigen receptor (CAR) which comprises a target binding domain comprising the protein according to any one of [1] to [3].

[15.] The CAR of [14], which comprises, a target binding domain, a transmembrane domain, and an intracellular signaling domain.

[16.] The CAR of [14] or [15], wherein transmembrane domain comprises a CD8a, 41BB, or CD28 transmembrane domain.

[17.] The CAR of any one of [14] to [16], wherein the intracellular signaling domain is selected from the group consisting of a domain of a human T cell receptor alpha, beta, or zeta chain; a human 41BB domain; a human CD28 domain; and any combination thereof.

[18.] The CAR of any one of [14] to [17], wherein the intracellular signaling domain comprises the intracellular domain of a costimulatory molecule selected from the group consisting of CD27, CD28, 41BB, OX40, CD30, CD40, PD1, lymphocyte function-associated antigen-1 (LFA-1), CD2, CD7, LIGHT, NKG2C, NKG2D, B7-H3, a ligand that specifically binds with CD83, and any combination thereof.

[19.] The CAR of any one of [14] to [18], further comprising a peptide linker.

[20.] The CAR of [14] comprising the amino acid sequence of SEQ ID NO: 62-66 or 67.

[21.] The CAR of [14] comprising the amino acid sequence of SEQ ID NO: 67.

[22.] A protein of any one of [1] to [13] or the CAR of any one of [14] to [21], which further comprises a second target binding domain having the same or a different target than the D domain target binding domain.

[23.] An Adapter comprising (a) a D domain target binding domain that specifically binds CD123 and comprises the amino acid sequence of SEQ ID NO: 8-32 or 33, and (b) an antigenic determinant (AD).

[24.] The Adapter of [23], wherein the D domain comprises the amino acid sequence of SEQ ID NO: 8, 13, 14, or 31-33.

[25.] The Adapter of [23], wherein the D domain comprises the amino acid sequence of SEQ ID NO: 14.

[26.] The Adapter of any one of [23] to [25], wherein the AD comprises AFP p26 or a fragment thereof.

[27.] The Adapter of [26], wherein AFP p26 comprises an amino acid sequence selected from the group consisting of SEQ ID NO: 37-43 and 44.

[28.] The Adapter of [26], wherein AFP p26 comprises the amino acid sequence of SEQ ID NO: 37.

[29.] The Adapter of [26], wherein AFP p26 comprises the amino acid sequence of SEQ ID NO: 39.

[30.] The Adapter of any one of [23] to [25], wherein the AD comprises BCMA (SEQ ID NO: 34) or a fragment thereof.

[31.] The Adapter of any one of [23] to [30] further comprising a peptide linker.

[32.] The Adapter of any one of [23] to [31], wherein the Adapter comprises a single D domain that specifically binds CD123.

[33.] The Adapter of [32], which comprises the amino acid sequence of SEQ ID NO: 50-54 or 55.

[34.] The Adapter of [32], which comprises the amino acid sequence of SEQ ID NO: 50.

[35.] The Adapter of any one of [23] to [31], wherein the Adapter comprises two D domains that specifically bind CD123.

[36.] The Adapter of [35], which comprises the amino acid sequence of SEQ ID NO: 56-60 or 61.

[37.] The Adapter of [35], which comprises the amino acid sequence of SEQ ID NO: 61.

[38.] An isolated polynucleotide encoding the protein of any one of [1] to [10] or [22] or the Adapter of any one of [23] to [37].

[39.] A vector comprising the polynucleotide of [38].

[40.] The vector of [39], wherein polynucleotide is operably linked with a nucleotide sequence which regulates the expression of the protein encoded by the polynucleotide.

[41.] A host cell comprising the polynucleotide of [38] or the vector of [39] or [40].

[42.] A method of producing the protein of any one of [1 o 10 or 22 or the Adapter of any one of [23] to [37], comprising culturing the host cell of [41] under suitable conditions to produce the protein or Adapter.

[43.] An isolated polynucleotide encoding the CAR of any one of [14] to [22].

[44.] A vector comprising the polynucleotide of [43].

[45.] The vector of [44], wherein the polynucleotide is operably linked with a nucleotide sequence which regulates the expression of the protein encoded by the polynucleotide.

[46.] The vector of [45] which is a lentiviral vector.

[47.] A host cell comprising the polynucleotide of [43] or the vector of any one of [44] to [46].

[48.] A cell engineered to express the CAR of any one of [14] to [22].

[49.] A cell of [47] or [48], wherein the cell is a T cell or a natural killer (NK) cell.

[50.] A pharmaceutical composition comprising the protein according to any one of [1] to [13] or [22] and a pharmaceutically acceptable excipient.

[51.] A pharmaceutical composition comprising the vector of [44] and a pharmaceutically acceptable excipient.

[52.] The pharmaceutical composition of [51], wherein the vector is a lentiviral vector.

[53.] A pharmaceutical composition comprising a cell expressing the CAR of any one of [14] to [22] and a pharmaceutically acceptable excipient.

[54.] The pharmaceutical composition of [53], wherein the cell is a T cell or a natural killer (NK) cell.

[55.] A kit comprising the Adapter of any one of [23] to [37].

[56.] A kit comprising the vector of [44].

[57.] A kit comprising a cell expressing the CAR of any one of [14] to [22].

[58.] The kit of [57], wherein the cell is a T cell or a natural killer (NK) cell.

[59.] A method of delivering an immune response to one or more target cells comprising contacting a composition comprising the target cell with a cell expressing a chimeric antigen receptor (CAR) comprising (i) a D domain that binds to CD123, (ii) a transmembrane domain, and (iii) an intracellular domain.

[60.] A method of killing a target cell comprising contacting a composition comprising the target cell with a cell expressing a chimeric antigen receptor (CAR) comprising (i) a D domain that binds to CD123, (ii) a transmembrane domain, and (iii) an intracellular domain.

[61.] The method of [59] or [60], wherein the target cell expresses CD123.

[62.] The method of any one of [59] to [61], wherein the D domain that binds to CD123 comprises an amino acid sequence selected from the group consisting of SEQ ID NO: 8-32 and 338-33, 99 and 100.

[63.] The method of any one of [59] to [61], wherein the D domain that binds to CD123 comprises an amino acid sequence selected from the group consisting of SEQ ID NO: 8, 13, 14, 31, 32, and 33.

[64.] The method of any one of [59] to [61], wherein the D domain that binds to CD123 comprises the amino acid sequence of SEQ ID NO: 14.

[65.] The method of any one of [59] to [64], wherein the transmembrane domain comprises a CD8a, 41BB or CD28 transmembrane domain.

[66.] The method of any one of [59] to [65], wherein the intracellular signaling domain is selected from the group consisting of a domain of a human T cell receptor alpha, beta, or zeta chain; a human 41BB domain; a human CD28 domain; and any combination thereof.

[67.] The method of any one of [59] to [66], wherein the intracellular signaling domain comprises the intracellular domain of a costimulatory molecule selected from the group consisting of CD27, CD28, 41BB, OX40, CD30, CD40, PD1, lymphocyte function-associated antigen-1 (LFA-1), CD2, CD7, LIGHT, NKG2C, NKG2D, B7-H3, a ligand that specifically binds with CD83, and any combination thereof.

[68.] The method of any one of [59] to [61], wherein the CAR comprising a D domain that binds to CD123 comprises the amino acid sequence of SEQ ID NO: 62-66 or 67.

[69.] The method of any one of [59] to [61], wherein the CAR comprising a D domain that binds to CD123 comprises the amino acid sequence of SEQ ID NO: 67.

[70.] The method of any one of [59] to [61], wherein the cell expressing the CAR is an immune cell.

[71.] The method of [70], wherein the cell expressing the CAR is an immune effector cell.

[72.] The method of [70], wherein the cell expressing the CAR is a T cell.

[73.] The method of [70], wherein the cell expressing the CAR is a natural killer (NK) cell.

[74.] The method of any one of [58] to [73], wherein the target cell is a cancer cell.

[75.] The method of [74], wherein the target cell is an acute myeloid leukemia (AML) cell, myelodysplasia cell, B-cell acute lymphoblastic leukemia cell, hairy cell leukemia cell, Hodgkin's lymphoma cell or blastic plasmacytoid dendritic neoplasm (BPDCN) cell, preferably an acute myeloid leukemia (AML) cell.

[76.] The method of any one of [58] to [73], wherein the contacting occurs in a human patient.

[77.] A method of delivering an immune response to a target cell comprising: contacting a composition comprising the target cell with an Adapter, wherein (a) the composition comprising the target cell further comprises a cell expressing a CAR, wherein the CAR comprises (i) an antigenic determinant binding domain (ADBD) that binds to an AFP p26 antigenic determinant (AD), (ii) a transmembrane domain, and (iii) an intracellular domain; and (b) the Adapter comprises (i) a D domain that binds to CD123 and (ii) AFP p26 AD.

[78.] A method of delivering an immune response to a target cell comprising: contacting a composition comprising the target cell with an Adapter, wherein (a) the composition comprising the target cell further comprises a cell expressing a CAR, wherein the CAR comprises (i) AFP p26 antigenic determinant (AD), (ii) a transmembrane domain, and (iii) an intracellular domain; and (b) the Adapter comprises (i) a D domain that binds to CD123 and (ii) an antigenic determinant binding domain (ADBD) that binds to the AFP p26 antigenic determinant (AD).

[79.] A method of delivering an immune response to a target cell comprising: contacting a composition comprising the target cell with an Adapter, wherein (a) the composition comprising the target cell further comprises a cell expressing a CAR, wherein the CAR comprises (i) an antigenic determinant binding domain (ADBD) that binds to an antigenic determinant (AD) other than CD123, (ii) a transmembrane domain, and (iii) an intracellular domain; and (b) the Adapter comprises (i) a D domain that binds to CD123 and (ii) an the AD bound by the CAR.

[80.] A method of delivering an immune response to a target cell comprising: contacting a composition comprising the target cell with an Adapter, wherein (a) the composition comprising the target cell further comprises a cell expressing a CAR, wherein the CAR comprises (i) AFP p26 antigenic determinant (AD), (ii) a transmembrane domain, and (iii) an intracellular domain; and (b) the Adapter comprises (i) a first antigenic determinant binding domain (ADBD) that binds to a target AD and (ii) an second antigenic determinant binding domain (ADBD) that binds to the AFP p26 antigenic determinant (AD).

[81.] A method of delivering an immune response to a target cell comprising: contacting a composition comprising the target cell with a cell expressing a CAR, wherein (a) the CAR comprises (i) an antigenic determinant binding domain (ADBD) that binds to an AFP p26 antigenic determinant (AD), (ii) a transmembrane domain, and (iii) an intracellular domain; and (b) the composition comprising the target cell further comprises an Adapter comprising (i) a D domain that binds to CD123 and (ii) an AFP p26 AD.

[82.] A method of delivering an immune response to a target cell comprising: contacting a composition comprising the target cell with a cell expressing a CAR, wherein (a) the CAR comprises (i) an AFP p26 antigenic determinant (AD), (ii) a transmembrane domain, and (iii) an intracellular domain; and (b) the composition comprising the target cell further comprises an Adapter comprising (i) a D domain that binds to CD123 and (ii) an antigenic determinant binding domain (ADBD) that binds to the AFP p26 antigenic determinant (AD).

[83.] A method of delivering an immune response to a target cell comprising: contacting a composition comprising the target cell with a cell expressing a CAR, wherein (a) the CAR comprises (i) an antigenic determinant binding domain (ADBD) that binds to an antigenic determinant (AD) other than CD123, (ii) a transmembrane domain, and (iii) an intracellular domain; and (b) the composition comprising the target cell further comprises an Adapter comprising (i) a D domain that binds to CD123 and (ii) the AD bound by the CAR.

[84.] A method of delivering an immune response to a target cell comprising: contacting a composition comprising the target cell with a cell expressing a CAR, wherein (a) the CAR comprises (i) an AFP p26 antigenic determinant (AD), (ii) a transmembrane domain, and (iii) an intracellular domain; and (b) the composition comprising the target cell further comprises an Adapter comprising (i) a first antigenic determinant binding domain (ADBD) that binds to a target AD and (ii) a second antigenic determinant binding domain (ADBD) that binds to the AFP p26 antigenic determinant (AD).

[85.] A method of killing a target cell comprising: contacting a composition comprising the target cell with an Adapter, wherein (a) the composition comprising the target cell further comprises a cell expressing a CAR, wherein the CAR comprises (i) an antigenic determinant binding domain (ADBD) that binds to an AFP p26 antigenic determinant (AD), (ii) a transmembrane domain, and (iii) an intracellular domain; and (b) the Adapter comprises (i) a D domain that binds to CD123 and (ii) an AFP p26 AD.

[86.] A method of killing a target cell comprising: contacting a composition comprising the target cell with an Adapter, wherein (a) the composition comprising the target cell further comprises a cell expressing a CAR, wherein the CAR comprises (i) an AFP p26 antigenic determinant (AD), (ii) a transmembrane domain, and (iii) an intracellular domain; and (b) the Adapter comprises (i) a D domain that binds to CD123 and (ii) an antigenic determinant binding domain (ADBD) that binds to the AFP p26 antigenic determinant (AD).

[87.] A method of killing a target cell comprising: contacting a composition comprising the target cell with an Adapter, wherein (a) the composition comprising the target cell further comprises a cell expressing a CAR, wherein the CAR comprises (i) an antigenic determinant binding domain (ADBD) that binds to an antigenic determinant (AD) other than CD123, (ii) a transmembrane domain, and (iii) an intracellular domain; and (b) the Adapter comprises (i) a D domain that binds to CD123 and (ii) an the AD bound by the CAR.

[88.] A method of killing a target cell comprising: contacting a composition comprising the target cell with an Adapter, wherein (a) the composition comprising the target cell further comprises a cell expressing a CAR, wherein the CAR comprises (i) an AFP p26 antigenic determinant (AD), (ii) a transmembrane domain, and (iii) an intracellular domain; and (b) the Adapter comprises (i) a first antigenic determinant binding domain (ADBD) that binds to a target AD and (ii) an second antigenic determinant binding domain (ADBD) that binds to the AFP p26 antigenic determinant (AD).

[89.] A method of killing a target cell comprising: contacting a composition comprising the target cell with a cell expressing a CAR, wherein (a) the CAR comprises (i) an antigenic determinant binding domain (ADBD) that binds to an AFP p26 antigenic determinant (AD), (ii) a transmembrane domain, and (iii) an intracellular domain; and (b) the composition comprising the target cell further comprises an Adapter comprising (i) a D domain that binds to CD123 and (ii) an AFP p26 AD.

[90.] A method of killing a target cell comprising: contacting a composition comprising the target cell with a cell expressing a CAR, wherein (a) the CAR comprises (i) an AFP p26 antigenic determinant (AD), (ii) a transmembrane domain, and (iii) an intracellular domain; and (b) the composition comprising the target cell further comprises an Adapter comprising (i) a D domain that binds to CD123 and (ii) an antigenic determinant binding domain (ADBD) that binds to the AFP p26 antigenic determinant (AD).

[91.] A method of killing a target cell comprising: contacting a composition comprising the target cell with a cell expressing a CAR, wherein (a) the CAR comprises (i) an antigenic determinant binding domain (ADBD) that binds to an antigenic determinant (AD) other than CD123, (ii) a transmembrane domain, and (iii) an intracellular domain; and (b) the composition comprising the target cell further comprises an Adapter comprising (i) a D domain that binds to CD123 and (ii) the AD bound by the CAR.

[92.] A method of killing a target cell comprising: contacting a composition comprising the target cell with a cell expressing a CAR, wherein (a) the CAR comprises (i) an AFP p26 antigenic determinant (AD), (ii) a transmembrane domain, and (iii) an intracellular domain; and (b) the composition comprising the target cell further comprises an Adapter comprising (i) a first antigenic determinant binding domain (ADBD) that binds to a target AD and (ii) a second antigenic determinant binding domain (ADBD) that binds to the AFP p26 antigenic determinant (AD).

[93.] The method of any one of [77] to [79], [81] to [83], [85] to [87] or [89] to [91], wherein the target cell expresses CD123.

[94.] The method of any one of [80], [84], [88] or [92], wherein the target cell expresses the target AD.

[95.] The method of any one of [77] to [94], wherein the D domain that binds to CD123 comprises an amino acid sequence selected from the group consisting of SEQ ID NO: 8-32 and 338-33, 99 and 100.

[96.] The method of any one of [77] to [94], wherein the D domain that binds to CD123 comprises an amino acid sequence selected from the group consisting of SEQ ID NO: 8, 13, 14, 31, 32, and 33.

[97.] The method of any one of [77] to [94], wherein the D domain that binds to CD123 comprises the amino acid sequence of SEQ ID NO: 14.

[98.] The method of any one of [77] to [97], wherein the transmembrane domain comprises a CD8a, 41BB or CD28 transmembrane domain.

[99.] The method of any one of [77] to [98], wherein the intracellular signaling domain is selected from the group consisting of a domain of a human T cell receptor alpha, beta, or zeta chain; a human 41BB domain; a human CD28 domain; and any combination thereof.

[100.] The method of any one of [77] to [99], wherein the intracellular signaling domain comprises the intracellular domain of a costimulatory molecule selected from the group consisting of CD27, CD28, 41BB, OX40, CD30, CD40, PD1, lymphocyte function-associated antigen-1 (LFA-1), CD2, CD7, LIGHT, NKG2C, NKG2D, B7-H3, a ligand that specifically binds with CD83, and any combination thereof.

[101.] The method of any one of [77] to [94], wherein the CAR comprising a D domain that binds to CD123 comprises the amino acid sequence of SEQ ID NO: 62-66 or 67.

[102.] The method of any one of [77] to [94], wherein the CAR comprising a D domain that binds to CD123 comprises the amino acid sequence of SEQ ID NO: 67.

[103.] The method of any one of [77] to [102], wherein the AFP p26 AD comprises an amino acid sequence selected from the group consisting of SEQ ID NO: 37-43 and 44.

[104.] The method of any one of [77] to [103], wherein the AFP p26 AD comprises the amino acid sequence of SEQ ID NO: 37.

[105.] The method of any one of [77] to [103], wherein the AFP p26 AD comprises the amino acid sequence of SEQ ID NO: 39.

[106.] The method of any one of [77] to [105], wherein the ADBD that binds to AFP p26 AD comprises an scFv that binds to AFP p26 AD.

[107.] The method of any one of [77] to [105], wherein the ADBD that binds to AFP p26 AD comprises a D domain that binds to AFP p26 AD.

[108.] The method of [107], wherein the D domain that binds to AFP p26 AD comprises an amino acid sequence selected from the group consisting of SEQ ID NO: 74-93 and 94.

[109.] The method of [107], wherein the D domain that binds to AFP p26 AD comprises the amino acid sequence of SEQ ID NO: 70-73 or 92-94.

[110.] The method of [107], wherein the D domain that binds to AFP p26 AD comprises the amino acid sequence of SEQ ID NO: 73.

[111.] The method of [107], wherein the CAR comprising a D domain that binds to AFP p26 AD comprises the amino acid sequence of SEQ ID NO: 68.

[112.] The method of [107], wherein the CAR comprising a D domain that binds to AFP p26 AD comprises the amino acid sequence of SEQ ID NO: 69.

[113.] The method of any one of [77] to [112], wherein the CAR comprises an ADBD that binds to an AD other than CD123, the ADBD binds to a tumor antigen.

[114.] The method of [113], wherein the tumor antigen is selected from the group: BCMA, CD19, CD22, CS1, HER2, TACI, BAFFR, and PDL1.

[115.] The method of [113], wherein the tumor antigen is BCMA.

[116.] The method of [113], wherein the tumor antigen is CD19.

[117.] The method of [113], wherein the tumor antigen is selected from the group: CD45, CD26, CD30, CD33, and CD38.

[118.] The method of any one of [77] to [117], wherein the Adapter comprising (i) a D domain that binds to CD123 and (ii) an AFP p26 AD comprises the amino acid sequence of SEQ ID NO: 50-54 or 55.

[119.] The method of any one of [77] to [117], wherein the Adapter comprising (i) a D domain that binds to CD123 and (ii) an AFP p26 AD comprises the amino acid sequence of SEQ ID NO: 50.

[120.] The method of any one of [77] to [117], wherein the Adapter comprising (i) a D domain that binds to CD123 and (ii) an AFP p26 AD comprises the amino acid sequence of SEQ ID NO: 56-60 or 61.

[121.] The method of any one of [77] to [117], wherein the Adapter comprising (i) a D domain that binds to CD123 and (ii) an AFP p26 AD comprises the amino acid sequence of SEQ ID NO: 61.

[122.] The method of any one of [77] to [121], wherein the target AD is selected from: CD45, CD26, CD30, CD33, and CD38.

[123.] The method of any one of [77] to [121], wherein the target AD is selected from: CD19, CD22, CD123, BCMA, CS1, HER2, TACI, BAFFR, and PDL1.

[124.] The method of any one of [77] to [121], wherein the target AD is BCMA.

[125.] The method of any one of [77] to [121], wherein the target AD is CD19.

[126.] The method of any one of [77] to [125], wherein the cell expressing the CAR is an immune cell.

[127.] The method of [126], wherein the cell expressing the CAR is an immune effector cell.

[128.] The method of [126], wherein the cell expressing the CAR is a T cell.

[129.] The method of [126], wherein the cell expressing the CAR is a natural killer (NK) cell.

[130.] The method of any one of [77] to [129], wherein the target cell is a cancer cell.

[131.] The method of [130], wherein the target cell is an acute myeloid leukemia (AML) cell, myelodysplasia cell, B-cell acute lymphoblastic leukemia cell, hairy cell leukemia cell, Hodgkin's lymphoma cell or blastic plasmacytoid dendritic neoplasm (BPDCN) cell.

[132.] The method of [130], wherein the target cell is an acute myeloid leukemia (AML) cell.

[133.] The method of any one of [77] to [132], wherein the contacting occurs in a human patient.

[134.] The method of [133], comprising administering to the human patient the cell expressing the CAR and the Adapter in any order.

[135.] The method of [133], comprising administering to the human patient the Adapter wherein the human patient has been administered the cell expressing the CAR.

[136.] The method of [133], comprising administering to the human patient the Adapter wherein the human patient comprises the cell expressing the CAR.

[137.] A method of delivering an immune response to a target cell in a patient comprising: administering to the patient a cell expressing a chimeric antigen receptor (CAR) comprising (i) a D domain that binds to CD123, (ii) a transmembrane domain, and (iii) an intracellular domain

[138.] A method of killing a target cell in a patient in need thereof comprising: administering to the patient a cell expressing a chimeric antigen receptor (CAR) comprising (i) a D domain that binds to CD123, (ii) a transmembrane domain, and (iii) an intracellular domain.

[139.] The method of [137] or [138], wherein the target cell expresses CD123.

[140.] The method of any one of [137] to [139], wherein the target cell is a cancer cell.

[141.] The method of [140], wherein the target cell is an acute myeloid leukemia (AML) cell, myelodysplasia cell, B-cell acute lymphoblastic leukemia cell, hairy cell leukemia cell, Hodgkin's lymphoma cell or blastic plasmacytoid dendritic neoplasm (BPDCN) cell, preferably an acute myeloid leukemia (AML) cell.

[142.] A method of depleting lymphocytes in a patient in need thereof comprising: administering to the patient a cell expressing a chimeric antigen receptor (CAR) comprising (i) a D domain that binds to CD123, (ii) a transmembrane domain, and (iii) an intracellular domain.

[143.] The method of [142], wherein the lymphocytes express CD123.

[144.] The method of [142] or [143], wherein the lymphocytes are B lymphocytes.

[145.] A method of treating cancer comprising: administering to a patient in need thereof a cell expressing a chimeric antigen receptor (CAR) comprising (i) a D domain that binds to CD123, (ii) a transmembrane domain, and (iii) an intracellular domain.

[146.] The method of [145], wherein the cancer is hematological cancer.

[147.] The method of [146], wherein the hematological cancer is acute leukemia, chronic leukemia, polycythemia vera, lymphoma, Hodgkin's disease, non-Hodgkin's lymphoma, multiple myeloma, Waldenstrom's macroglobulinemia, heavy chain disease, myelodysplastic syndrome (e.g., high-risk myelodysplastic syndrome), hairy cell leukemia, or myelodysplasia.

[148.] The method of [146], wherein the hematological cancer is is acute myeloid leukemia (AML), myelodysplastic syndrome (e.g., high-risk myelodysplastic syndrome), B-cell acute lymphoblastic leukemia, hairy cell leukemia, Hodgkin's lymphoma or blastic plasmacytoid dendritic neoplasm (BPDCN).

[149.] The method of [146], wherein the hematological cancer is AML.

[150.] The method of [146], wherein the hematological cancer is BPDCN.

[151.] A method of treating an autoimmune disease or disorder comprising: administering to a patient in need thereof a cell expressing a chimeric antigen receptor (CAR) comprising (i) a D domain that binds to CD123, (ii) a transmembrane domain, and (iii) an intracellular domain.

[152.] The method of [146], wherein the autoimmune disease or disorder is lupus erythematosus.

[153.] The method of any one of [137] to [152], wherein the D domain that binds to CD123 comprises an amino acid sequence selected from the group consisting of SEQ ID NO: 8-32 and 338-33, 99 and 100.

[154.] The method of any one of [137] to [152], wherein the D domain that binds to CD123 comprises an amino acid sequence selected from the group consisting of SEQ ID NO: 8, 13, 14, 31, 32, and 33.

[155.] The method of any one of [137] to [152], wherein the D domain that binds to CD123 comprises the amino acid sequence of SEQ ID NO: 14.

[156.] The method of any one of [137] to [155], wherein the transmembrane domain comprises a CD8a, 41BB or CD28 transmembrane domain.

[157.] The method of any one of [137] to [156], wherein the intracellular signaling domain is selected from the group consisting of a domain of a human T cell receptor alpha, beta, or zeta chain; a human 41BB domain; a human CD28 domain; and any combination thereof.

[158.] The method of any one of [137] to [157], wherein the intracellular signaling domain comprises the intracellular domain of a costimulatory molecule selected from the group consisting of CD27, CD28, 41BB, OX40, CD30, CD40, PD1, lymphocyte function-associated antigen-1 (LFA-1), CD2, CD7, LIGHT, NKG2C, NKG2D, B7-H3, a ligand that specifically binds with CD83, and any combination thereof.

[159.] The method of any one of [137] to [152], wherein the CAR comprising a D domain that binds to CD123 comprises the amino acid sequence of SEQ ID NO: 62-66 or 67.

[160.] The method of any one of [137] to [152], wherein the CAR comprising a D domain that binds to CD123 comprises the amino acid sequence of SEQ ID NO: 67.

[161.] The method of any one of [137] to [160], wherein the cell expressing the CAR is an immune cell.

[162.] The method of [161], wherein the cell expressing the CAR is an immune effector cell.

[163.] The method of [161], wherein the cell expressing the CAR is a T cell.

[164.] The method of [161], wherein the cell expressing the CAR is a natural killer (NK) cell.

[165.] The method of any one of [137] to [164], wherein administering the cell expressing the CAR comprises administering a pharmaceutical composition comprising the cell expressing the CAR.

[166.] A method of delivering an immune response to a target cell in a patient comprising: administering to the patient an Adapter comprising (i) a D domain that binds to CD123 and (ii) an AFP p26 AD.

[167.] A method of killing a target cell in a patient in need thereof comprising: administering to the patient an Adapter comprising (i) a D domain that binds to CD123 and (ii) an AFP p26 AD.

[168.] The method of [166] or [167], wherein the target cell expresses CD123.

[169.] The method of any one of [166] to [168], wherein the target cell is a cancer cell.

[170.] The method of [168], wherein the target cell is an acute myeloid leukemia (AML) cell, myelodysplasia cell, B-cell acute lymphoblastic leukemia cell, hairy cell leukemia cell, Hodgkin's lymphoma cell or blastic plasmacytoid dendritic neoplasm (BPDCN) cell, preferably an acute myeloid leukemia (AML) cell.

[171.] A method of depleting lymphocytes in a patient in need thereof comprising: administering to the patient an Adapter comprising (i) a D domain that binds to CD123 and (ii) an AFP p26 AD.

[172.] The method of [171], wherein the lymphocytes express CD123.

[173.] The method of [171] or [172], wherein the lymphocytes are B lymphocytes.

[174.] A method of treating cancer comprising: administering to a patient in need thereof an Adapter comprising (i) a D domain that binds to CD123 and (ii) an AFP p26 AD.

[175.] The method of [174], wherein the cancer is hematological cancer.

[176.] The method of [175], wherein the hematological cancer is acute leukemia, chronic leukemia, polycythemia vera, lymphoma, Hodgkin's disease, non-Hodgkin's lymphoma, multiple myeloma, Waldenstrom's macroglobulinemia, heavy chain disease, myelodysplastic syndrome (e.g., high-risk myelodysplastic syndrome), hairy cell leukemia, or myelodysplasia.

[177.] The method of [175], wherein the hematological cancer is is acute myeloid leukemia (AML), myelodysplastic syndrome (e.g., high-risk myelodysplastic syndrome), B-cell acute lymphoblastic leukemia, hairy cell leukemia, Hodgkin's lymphoma or blastic plasmacytoid dendritic neoplasm (BPDCN)

[178.] The method of [175], wherein the hematological cancer is AML.

[179.] The method of [175], wherein the hematological cancer is BPDCN.

[180.] A method of treating an autoimmune disease or disorder comprising: administering to a patient in need thereof an Adapter comprising (i) a D domain that binds to CD123 and (ii) an AFP p26 AD.

[181.] The method of [180], wherein the autoimmune disease or disorder is lupus erythematosus.

[182.] The method of any one of [166] to [181], wherein the patient has been administered a cell expressing a CAR], wherein the CAR comprises (i) an antigenic determinant binding domain (ADBD) that binds to an AFP p26 antigenic determinant (AD), (ii) a transmembrane domain, and (iii) an intracellular domain.

[183.] The method of any one of [166] to [181], wherein the patient comprises a cell expressing a CAR], wherein the CAR comprises (i) an antigenic determinant binding domain (ADBD) that binds to an AFP p26 antigenic determinant (AD), (ii) a transmembrane domain, and (iii) an intracellular domain

[184.] The method of any one of [166] to [181], further comprising administering a cell expressing a CAR], wherein the CAR comprises (i) an antigenic determinant binding domain (ADBD) that binds to an AFP p26 antigenic determinant (AD), (ii) a transmembrane domain, and (iii) an intracellular domain.

[185.] A method of delivering an immune response to a target cell in a patient comprising: administering to the patient an Adapter comprising (i) a D domain that binds to CD123 and (ii) an antigenic determinant binding domain (ADBD) that binds to the AFP p26 antigenic determinant (AD).

[186.] A method of killing a target cell in a patient in need thereof comprising: administering to the patient an Adapter comprising (i) a D domain that binds to CD123 and (ii) an antigenic determinant binding domain (ADBD) that binds to the AFP p26 antigenic determinant (AD).

[187.] The method of [185] or [186], wherein the target cell expresses CD123.

[188.] The method of any one of [185] to [187], wherein the target cell is a cancer cell.

[189.] The method of [187], wherein the target cell is an acute myeloid leukemia (AML) cell, myelodysplasia cell, B-cell acute lymphoblastic leukemia cell, hairy cell leukemia cell, Hodgkin's lymphoma cell or blastic plasmacytoid dendritic neoplasm (BPDCN) cell, preferably an acute myeloid leukemia (AML) cell.

[190.] A method of depleting lymphocytes in a patient in need thereof comprising: administering to the patient an Adapter comprising (i) a D domain that binds to CD123 and (ii) an antigenic determinant binding domain (ADBD) that binds to the AFP p26 antigenic determinant (AD).

[191.] The method of [190], wherein the lymphocytes express CD123.

[192.] The method of [190] or [191], wherein the lymphocytes are B lymphocytes.

[193.] A method of treating cancer comprising: administering to a patient in need thereof an Adapter comprising (i) a D domain that binds to CD123 and (ii) an antigenic determinant binding domain (ADBD) that binds to the AFP p26 antigenic determinant (AD).

[194.] The method of [193], wherein the cancer is hematological cancer.

[195.] The method of [194], wherein the hematological cancer is acute leukemia, chronic leukemia, polycythemia vera, lymphoma, Hodgkin's disease, non-Hodgkin's lymphoma, multiple myeloma, Waldenstrom's macroglobulinemia, heavy chain disease, myelodysplastic syndrome (e.g., high-risk myelodysplastic syndrome), hairy cell leukemia, or myelodysplasia.

[196.] The method of [194], wherein the hematological cancer is is acute myeloid leukemia (AML), myelodysplastic syndrome (e.g., high-risk myelodysplastic syndrome), B-cell acute lymphoblastic leukemia, hairy cell leukemia, Hodgkin's lymphoma or blastic plasmacytoid dendritic neoplasm (BPDCN).

[197.] The method of [194], wherein the hematological cancer is AML.

[198.] The method of [194], wherein the hematological cancer is BPDCN.

[199.] A method of treating an autoimmune disease or disorder comprising: administering to a patient in need thereof an Adapter comprising (i) a D domain that binds to CD123 and (ii) an antigenic determinant binding domain (ADBD) that binds to the AFP p26 antigenic determinant (AD).

[200.] The method of [199], wherein the autoimmune disease or disorder is lupus erythematosus.

[201.] The method of any one of [185] to [200], wherein the patient has been administered a cell expressing a CAR, wherein (a) the CAR comprises (i) an AFP p26 antigenic determinant (AD), (ii) a transmembrane domain, and (iii) an intracellular domain.

[202.] The method of any one of [185] to [200] wherein the patient comprises a cell expressing a CAR, wherein (a) the CAR comprises (i) an AFP p26 antigenic determinant (AD), (ii) a transmembrane domain, and (iii) an intracellular domain.

[203.] The method of any one of [185] to [200] further comprising administering a cell expressing a CAR, wherein (a) the CAR comprises (i) an AFP p26 antigenic determinant (AD), (ii) a transmembrane domain, and (iii) an intracellular domain.

[204.] A method of delivering an immune response to a target cell in a patient comprising: administering to the patient an Adapter comprising (i) a D domain that binds to CD123 and (ii) the AD bound by a CAR, wherein the patient has been administered a cell expressing the CAR, wherein (a) the CAR comprises (i) an antigenic determinant binding domain (ADBD) that binds to an antigenic determinant (AD) other than CD123, (ii) a transmembrane domain, and (iii) an intracellular domain.

[205.] A method of killing a target cell in a patient in need thereof comprising: administering to the patient an Adapter comprising (i) a D domain that binds to CD123 and (ii) the AD bound by a CAR, wherein the patient has been administered a cell expressing the CAR, wherein (a) the CAR comprises (i) an antigenic determinant binding domain (ADBD) that binds to an antigenic determinant (AD) other than CD123, (ii) a transmembrane domain, and (iii) an intracellular domain, wherein the patient has been administered a cell expressing a CAR, wherein (a) the CAR comprises (i) an antigenic determinant binding domain (ADBD) that binds to an antigenic determinant (AD) other than CD123, (ii) a transmembrane domain, and (iii) an intracellular domain.

[206.] The method of [204] or [205], wherein the target cell expresses CD123.

[207.] The method of any one of [204] to [206], wherein the target cell is a cancer cell.

[208.] The method of [206], wherein the target cell is an acute myeloid leukemia (AML) cell, myelodysplasia cell, B-cell acute lymphoblastic leukemia cell, hairy cell leukemia cell, Hodgkin's lymphoma cell or blastic plasmacytoid dendritic neoplasm (BPDCN) cell, preferably an acute myeloid leukemia (AML) cell.

[209.] A method of depleting lymphocytes in a patient in need thereof comprising: administering to the patient an Adapter comprising (i) a D domain that binds to CD123 and (ii) the AD bound by a CAR, wherein the patient has been administered a cell expressing the CAR, wherein (a) the CAR comprises (i) an antigenic determinant binding domain (ADBD) that binds to an antigenic determinant (AD) other than CD123, (ii) a transmembrane domain, and (iii) an intracellular domain.

[210.] The method of [209], wherein the lymphocytes express CD123.

[211.] The method of [209] or [210], wherein the lymphocytes are B lymphocytes.

[212.] A method of treating cancer comprising: administering to a patient in need thereof an Adapter comprising (i) a D domain that binds to CD123 and (ii) the AD bound by a CAR, wherein the patient has been administered a cell expressing the CAR, wherein (a) the CAR comprises (i) an antigenic determinant binding domain (ADBD) that binds to an antigenic determinant (AD) other than CD123, (ii) a transmembrane domain, and (iii) an intracellular domain.

[213.] The method of [212], wherein the cancer is hematological cancer.

[214.] The method of [213], wherein the hematological cancer is acute leukemia, chronic leukemia, polycythemia vera, lymphoma, Hodgkin's disease, non-Hodgkin's lymphoma, multiple myeloma, Waldenstrom's macroglobulinemia, heavy chain disease, myelodysplastic syndrome (e.g., high-risk myelodysplastic syndrome), hairy cell leukemia, or myelodysplasia.

[215.] The method of [213], wherein the hematological cancer is is acute myeloid leukemia (AML), myelodysplastic syndrome (e.g., high-risk myelodysplastic syndrome), B-cell acute lymphoblastic leukemia, hairy cell leukemia, Hodgkin's lymphoma or blastic plasmacytoid dendritic neoplasm (BPDCN).

[216.] The method of [213], wherein the hematological cancer is AML.

[217.] The method of [213], wherein the hematological cancer is BPDCN.

[218.] A method of treating an autoimmune disease or disorder comprising: administering to a patient in need thereof an Adapter comprising (i) a D domain that binds to CD123 and (ii) the AD bound by a CAR, wherein the patient has been administered a cell expressing the CAR, wherein (a) the CAR comprises (i) an antigenic determinant binding domain (ADBD) that binds to an antigenic determinant (AD) other than CD123, (ii) a transmembrane domain, and (iii) an intracellular domain.

[219.] The method of [218], wherein the autoimmune disease or disorder is lupus erythematosus.

[220.] A method of delivering an immune response to a target cell in a patient comprising: administering to the patient an Adapter comprising (i) a D domain that binds to CD123 and (ii) the AD bound by a CAR, wherein the patient comprise a cell expressing the CAR, wherein (a) the CAR comprises (i) an antigenic determinant binding domain (ADBD) that binds to an antigenic determinant (AD) other than CD123, (ii) a transmembrane domain, and (iii) an intracellular domain.

[221.] A method of killing a target cell in a patient in need thereof comprising: administering to the patient an Adapter comprising (i) a D domain that binds to CD123 and (ii) the AD bound by a CAR, wherein the patient comprise a cell expressing the CAR, wherein (a) the CAR comprises (i) an antigenic determinant binding domain (ADBD) that binds to an antigenic determinant (AD) other than CD123, (ii) a transmembrane domain, and (iii) an intracellular domain.

[222.] The method of [220] or [221], wherein the target cell expresses CD123. Can we include a method of any one of [220] to [222], wherein the target cell is an endothelial cell?

[223.] The method of any one of [220] to [222], wherein the target cell is a cancer cell or wherein the target cell is an endothelial cell.

[224.] The method of [222], wherein the target cell is an acute myeloid leukemia (AML) cell, myelodysplasia cell, B-cell acute lymphoblastic leukemia cell, hairy cell leukemia cell, Hodgkin's lymphoma cell or blastic plasmacytoid dendritic neoplasm (BPDCN) cell, preferably an acute myeloid leukemia (AML) cell.

[225.] A method of depleting lymphocytes in a patient in need thereof comprising: administering to the patient an Adapter comprising (i) a D domain that binds to CD123 and (ii) the AD bound by a CAR, wherein the patient comprise a cell expressing the CAR, wherein (a) the CAR comprises (i) an antigenic determinant binding domain (ADBD) that binds to an antigenic determinant (AD) other than CD123, (ii) a transmembrane domain, and (iii) an intracellular domain.

[226.] The method of [225], wherein the lymphocytes express CD123.

[227.] The method of [225] or [226], wherein the lymphocytes are B lymphocytes.

[228.] A method of treating cancer comprising: administering to a patient in need thereof an Adapter comprising (i) a D domain that binds to CD123 and (ii) the AD bound by a CAR, wherein the patient comprise a cell expressing the CAR, wherein (a) the CAR comprises (i) an antigenic determinant binding domain (ADBD) that binds to an antigenic determinant (AD) other than CD123, (ii) a transmembrane domain, and (iii) an intracellular domain.

[229.] The method of [228], wherein the cancer is hematological cancer.

[230.] The method of [229], wherein the hematological cancer is acute leukemia, chronic leukemia, polycythemia vera, lymphoma, Hodgkin's disease, non-Hodgkin's lymphoma, multiple myeloma, Waldenstrom's macroglobulinemia, heavy chain disease, myelodysplastic syndrome (e.g., high-risk myelodysplastic syndrome), hairy cell leukemia, or myelodysplasia.

[231.] The method of [229], wherein the hematological cancer is is acute myeloid leukemia (AML), myelodysplastic syndrome (e.g., high-risk myelodysplastic syndrome), B-cell acute lymphoblastic leukemia, hairy cell leukemia, Hodgkin's lymphoma or blastic plasmacytoid dendritic neoplasm (BPDCN).

[232.] The method of [229], wherein the hematological cancer is AML.

[233.] The method of [229], wherein the hematological cancer is BPDCN.

[234.] A method of treating an autoimmune disease or disorder comprising: administering to a patient in need thereof an Adapter comprising (i) a D domain that binds to CD123 and (ii) the AD bound by a CAR, wherein the patient comprise a cell expressing the CAR, wherein (a) the CAR comprises (i) an antigenic determinant binding domain (ADBD) that binds to an antigenic determinant (AD) other than CD123, (ii) a transmembrane domain, and (iii) an intracellular domain.

[235.] The method of [234], wherein the autoimmune disease or disorder is lupus erythematosus.

[236.] A method of delivering an immune response to a target cell in a patient comprising: administering to the patient an Adapter comprising (i) a first antigenic determinant binding domain (ADBD) that binds to a target AD and (ii) a second antigenic determinant binding domain (ADBD) that binds to the AFP p26 antigenic determinant (AD).

[237.] A method of killing a target cell in a patient in need thereof comprising: administering to the patient an Adapter comprising (i) a first antigenic determinant binding domain (ADBD) that binds to a target AD and (ii) an second antigenic determinant binding domain (ADBD) that binds to the AFP p26 antigenic determinant (AD).

[238.] The method of [236] or [237], wherein the target cell expresses the target AD.

[239.] The method of any one of [236] to [238], wherein the target cell is a cancer cell.

[240.] A method of depleting lymphocytes in a patient in need thereof comprising: administering to the patient an Adapter comprising (i) a first antigenic determinant binding domain (ADBD) that binds to a target AD and (ii) an second antigenic determinant binding domain (ADBD) that binds to the AFP p26 antigenic determinant (AD).

[241.] The method of [240], wherein the lymphocytes express the target AD.

[242.] The method of [240] or [241], wherein the lymphocytes are B lymphocytes or T lymphocytes.

[243.] A method of treating cancer comprising: administering to a patient in need thereof an Adapter comprising (i) a first antigenic determinant binding domain (ADBD) that binds to a target AD and (ii) an second antigenic determinant binding domain (ADBD) that binds to the AFP p26 antigenic determinant (AD).

[244.] The method of [243], wherein the cancer is hematological cancer.

[245.] The method of [244], wherein the hematological cancer is acute leukemia, chronic leukemia, polycythemia vera, lymphoma, Hodgkin's disease, non-Hodgkin's lymphoma, multiple myeloma, Waldenstrom's macroglobulinemia, heavy chain disease, myelodysplastic syndrome (e.g., high-risk myelodysplastic syndrome), hairy cell leukemia, or myelodysplasia.

[246.] The method of [244], wherein the hematological cancer is is acute myeloid leukemia (AML), myelodysplastic syndrome (e.g., high-risk myelodysplastic syndrome), B-cell acute lymphoblastic leukemia, hairy cell leukemia, Hodgkin's lymphoma or blastic plasmacytoid dendritic neoplasm (BPDCN).

[247.] The method of [244], wherein the hematological cancer is AML.

[248.] The method of [244], wherein the hematological cancer is BPDCN.

[249.] A method of treating an autoimmune disease or disorder comprising: administering to a patient in need thereof an Adapter comprising (i) a first antigenic determinant binding domain (ADBD) that binds to a target AD and (ii) an second antigenic determinant binding domain (ADBD) that binds to the AFP p26 antigenic determinant (AD).

[250.] The method of [249], wherein the autoimmune disease or disorder is rheumatoid arthritis.

[251.] The method of any one of [236] to [250], wherein the patient has been administered a cell expressing a CAR, wherein the CAR comprises (i) AFP p26 antigenic determinant (AD), (ii) a transmembrane domain, and (iii) an intracellular domain.

[252.] The method of any one of [236] to [250], wherein the patient comprises a cell expressing a CAR, wherein the CAR comprises (i) AFP p26 antigenic determinant (AD), (ii) a transmembrane domain, and (iii) an intracellular domain.

[253.] The method of any one of [236] to [250, further comprising administering a cell expressing a CAR, wherein the CAR comprises (i) AFP p26 antigenic determinant (AD), (ii) a transmembrane domain, and (iii) an intracellular domain.

[254.] The method of any one of [166] to [253], wherein the D domain that binds to CD123 comprises an amino acid sequence selected from the group consisting of SEQ ID NO: 8-32 and 338-33, 99 and 100.

[255.] The method of any one of [166] to [253], wherein the D domain that binds to CD123 comprises an amino acid sequence selected from the group consisting of SEQ ID NO: 8, 13, 14, 31, 32, and 33.

[256.] The method of any one of [166] to [253], wherein the D domain that binds to CD123 comprises the amino acid sequence of SEQ ID NO: 14.

[257.] The method of any one of [166] to [256], wherein the transmembrane domain comprises a CD8a, 41BB or CD28 transmembrane domain

[258.] The method of any one of [166] to [257], wherein the intracellular signaling domain is selected from the group consisting of a domain of a human T cell receptor alpha, beta, or zeta chain; a human 41BB domain; a human CD28 domain; and any combination thereof.

[259.] The method of any one of [166] to [258], wherein the intracellular signaling domain comprises the intracellular domain of a costimulatory molecule selected from the group consisting of CD27, CD28, 41BB, OX40, CD30, CD40, PD1, lymphocyte function-associated antigen-1 (LFA-1), CD2, CD7, LIGHT, NKG2C, NKG2D, B7-H3, a ligand that specifically binds with CD83, and any combination thereof.

[260.] The method of any one of [166] to [259], wherein the AFP p26 AD comprises an amino acid sequence selected from the group consisting of SEQ ID NO: 37-43 and 44.

[261.] The method of any one of [166] to [260], wherein the AFP p26 AD comprises the amino acid sequence of SEQ ID NO: 37.

[262.] The method of any one of [166] to [260], wherein the AFP p26 AD comprises the amino acid sequence of SEQ ID NO: 39.

[263.] The method of any one of [166] to [262], wherein the ADBD that binds to AFP p26 AD comprises an scFv that binds to AFP p26 AD.

[264.] The method of any one of [166] to [262], wherein the ADBD that binds to AFP p26 AD comprises a D domain that binds to AFP p26 AD.

[265.] The method of [264], wherein the D domain that binds to AFP p26 AD comprises an amino acid sequence selected from the group consisting of SEQ ID NO: 74-93 and 94.

[266.] The method of [264], wherein the D domain that binds to AFP p26 AD comprises the amino acid sequence of SEQ ID NO: 70-73 or 92-94.

[267.] The method of [264], wherein the D domain that binds to AFP p26 AD comprises the amino acid sequence of SEQ ID NO: 73.

[268.] The method of [264], wherein the CAR comprising a D domain that binds to AFP p26 AD comprises the amino acid sequence of SEQ ID NO: 68.

[269.] The method of [264], wherein the CAR comprising a D domain that binds to AFP p26 AD comprises the amino acid sequence of SEQ ID NO: 69.

[270.] The method of any one of [166] to [269], wherein the CAR comprises an ADBD that binds to an AD other than CD123, the ADBD binds to a tumor antigen.

[271.] The method of [270], wherein the tumor antigen is selected from the group: BCMA, CD19, CD22, CS1, HER2, TACI, BAFFR, and PDL1.

[272.] The method of [270], wherein the tumor antigen is BCMA.

[273.] The method of [270], wherein the tumor antigen is CD19.

[274.] The method of [270], wherein the tumor antigen is selected from the group: CD45, CD26, CD30, CD33, and CD38.

[275.] The method of any one of [166] to [274], wherein the Adapter comprising (i) a D domain that binds to CD123 and (ii) an AFP p26 AD comprises the amino acid sequence of SEQ ID NO: 50-54 or 55.

[276.] The method of any one of [166] to [274], wherein the Adapter comprising (i) a D domain that binds to CD123 and (ii) an AFP p26 AD comprises the amino acid sequence of SEQ ID NO: 50.

[277.] The method of any one of [166] to [274], wherein the Adapter comprising (i) a D domain that binds to CD123 and (ii) an AFP p26 AD comprises the amino acid sequence of SEQ ID NO: 56-60 or 61.

[278.] The method of any one of [166] to [274], wherein the Adapter comprising (i) a D domain that binds to CD123 and (ii) an AFP p26 AD comprises the amino acid sequence of SEQ ID NO: 61.

[279.] The method of any one of [166] to [278], wherein the target AD is selected from: CD45, CD26, CD30, CD33, and CD38.

[280.] The method of any one of [166] to [278], wherein the target AD is selected from: CD19, CD22, CD123, BCMA, CS1, HER2, TACI, BAFFR, and PDL1.

[281.] The method of any one of [166] to [278], wherein the target AD is BCMA.

[282.] The method of any one of [166] to [278], wherein the target AD is CD19.

[283.] The method of any one of [166] to [278], wherein the target AD is CD45.

[284.] The method of any one of [166] to [278], wherein the cell expressing the CAR is an immune cell.

[285.] The method of [284], wherein the cell expressing the CAR is an immune effector cell.

[286.] The method of [284], wherein the cell expressing the CAR is a T cell.

[287.] The method of [284], wherein the cell expressing the CAR is a natural killer (NK) cell.

[288.] The method of any one of [166] to [287], wherein the target cell is a cancer cell.

[289.] The method of [288], wherein the target cell is an acute myeloid leukemia (AML) cell, myelodysplasia cell, B-cell acute lymphoblastic leukemia cell, hairy cell leukemia cell, Hodgkin's lymphoma cell or blastic plasmacytoid dendritic neoplasm (BPDCN) cell.

[290.] The method of [288], wherein the target cell is acute myeloid leukemia (AML) cell.

[291.] The method of any one of [166] to [290], wherein the cell expressing the CAR and the Adapter is administered separately in any order.

[292.] The method of any one of [166] to [291], wherein administering the Adapter comprises administering a pharmaceutical composition comprising the Adapter.

[293.] The method of any one of [166] to [291], wherein administering the Adapter and cell expressing the CAR comprises administering a pharmaceutical composition comprising the Adapter and a pharmaceutical composition comprising the cell expressing the CAR.

BRIEF DESCRIPTION OF THE DRAWINGS

FIG. 16. Patient-derived AML xenograft models.

DETAILED DESCRIPTION

Figure 1:
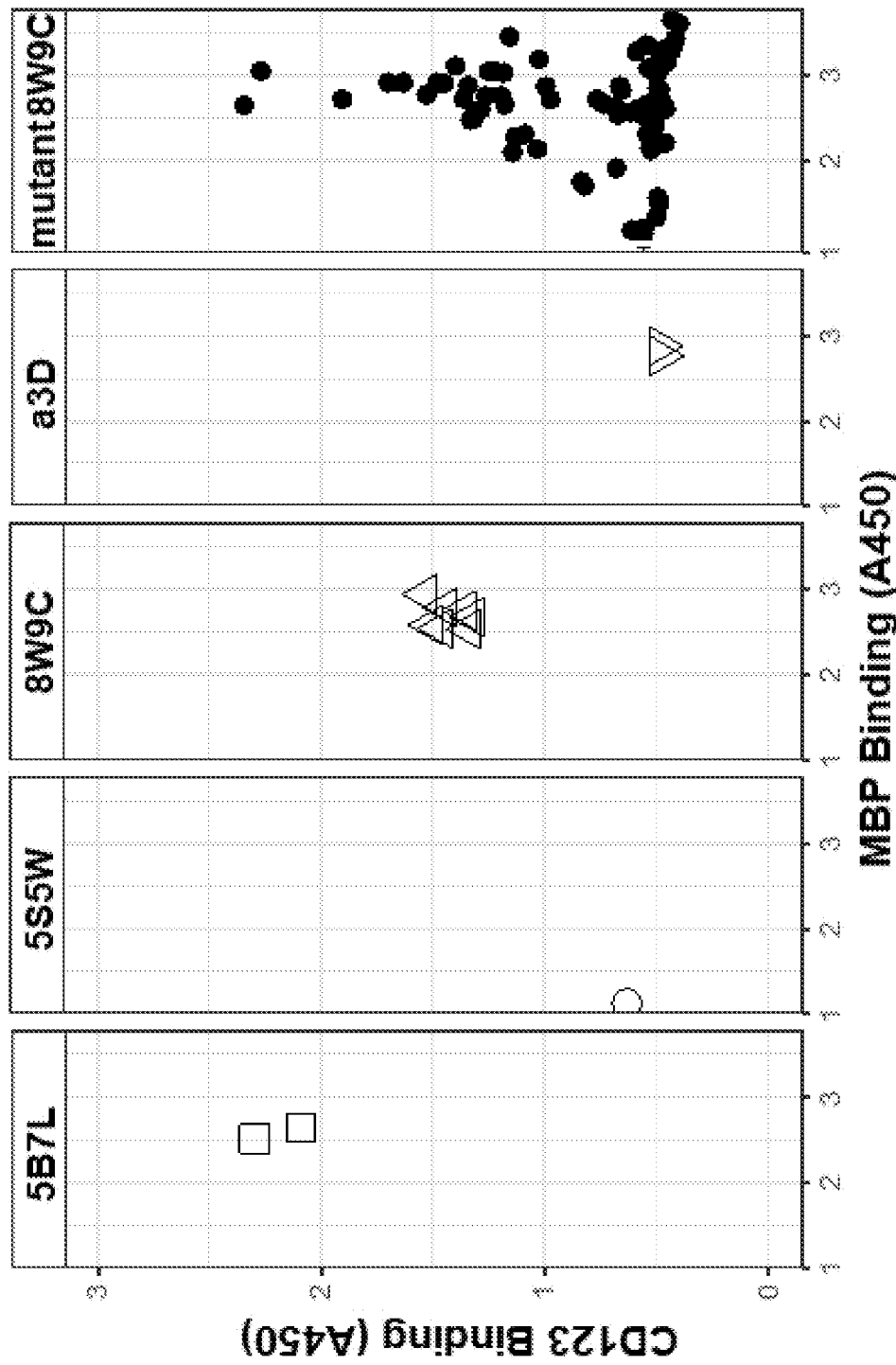
FIG. 1. Screen of 8W9C mutants as MBP fusions. Assorted clones of 8W9C mutants (mutant 8W9C) were screened by ELISA for binding to CD123 (CD123 Binding) and expression (MBP Binding). One or more replicates of wild-type (8W9C), high-affinity (5B7L), low-affinity (5S5W) and non-binding (a3D) controls were assayed for comparison.

The section headings used herein are for organizational purposes only and are not to be construed as in any way limiting of the subject matter described.

Definition of Terms

It is understood that wherever embodiments, are described herein with the language "comprising" otherwise analogous embodiments, described in terms of "consisting of" and/or "consisting essentially of" are also provided. However, when used in the claims as transitional phrases, each should be interpreted separately and in the appropriate legal and factual context (e.g., "comprising" is considered more of an open-ended phrase while "consisting of" is more exclusive and "consisting essentially of" achieves a middle ground).

As used herein, the singular form "a", "an", and "the" includes plural references unless indicated otherwise.

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

"About" as the term is used herein, when referring to a measurable value such as an amount, a temporal duration, and other measurable values known in the art, is meant to encompass variations of ±20% or in some embodiments ±10%, or in some embodiments ±5%, or in some embodiments ±1%, or in some embodiments ±0.1% from the specified value, as such variations are appropriate to perform the disclosed methods.

Chimeric antigen receptor" or "CAR" or "CARs" as used herein refers to an engineered receptor, which grafts an antigen or target specificity onto a cell (for example T cells such as naive T cells, central memory T cells, effector memory T cells, NK cells, NKT cells or combination thereof). CARs are also known as artificial T cell receptors, chimeric T cell receptors or chimeric immunoreceptors.

The term "Adapter" as used herein refers to a multi-domain soluble protein that comprises an antigenic determinant (AD) and an antigenic determinant binding domain (ADBD), wherein the ADBD binds to a second AD. In addition to the AD and the ADBD, an Adapter can comprise additional AD, additional ADBD, and/or other additional domains.

The term "antigenic determinant binding domain" or "ADBD" as the term is used herein, refers to a sequence of a polypeptide (e.g., an Adapter or CAR) that is sufficient to confer recognition and specific binding to a target antigenic determinant (AD). In some embodiments, the ADBD is an antigen-binding antibody fragment, a scFv, or an antigen-binding peptide that is not based on an antibody or antibody fragment sequence (e.g., a D domain or an affibody). In some embodiments, the ADBD comprises a non antibody-based binding scaffold (e.g., a D domain, affibody, fibronectin domain, nanobody, lipocalin domain, ankyrin domain, maxybody, Protein A domain, or affilin domain) In some embodiments the ADBD is a D domain. In some embodiments, the ADBD is an antibody-based binding sequence. In some embodiments the ADBD is a scFv or a domain antibody (dAb). In some embodiments, the ADBD has the ability to bind to a target antigen on the surface of a cell. In some embodiments, the ADBD has the ability to bind to a target antigen on the surface of an immune effector cell. In some embodiments, the ADBD has the ability to bind a growth factor receptor, an immunoregulatory receptor, or a hormone receptor.

In particular embodiments, the ADBD is a non antibody-scaffold based polypeptide sequence that is sufficient to confer recognition and specific binding to a target antigenic determinant. In some embodiments, non-antibody based ADBD is a polypeptide that has the ability to bind to target antigen on the surface of a cell. In some embodiments, the non-antibody based ADBD has the ability to bind a growth factor receptor, an immunoregulatory receptor, or a hormone receptor. In some embodiments, the ADBD is a D domain-based polypeptide. In particular embodiments, the ADBD is a D domain-based polypeptide that is sufficient to confer recognition and specific binding to a target antigenic determinant. In some embodiments, the ADBD is a D domain-based polypeptide that has the ability to bind to target antigen on the surface of a cell. In some embodiments, the ADBD is a D domain-based polypeptide that has the ability to bind a growth factor receptor, an immunoregulatory receptor, or a hormone receptor. In some embodiments, the ADBD is a D domain-based polypeptide that has the ability to bind a target antigen on a serum protein.

The term "D domain" refers to a target binding polypeptide sharing certain sequence and certain structural features of the reference scaffold sequence: MGSWAEFKQRLAAIK TRLQALGGSEAELAAFEKEIAAF-ESELQAYKGKGNPEVEALRK EAAAIRDELQAYRHN (SEQ ID NO: 2) (see WO 2016/164305 and WO 2016/164308, each of which is incorporated by reference herein in its entirety). The reference scaffold is a variant of a non-naturally occurring and targetless antiparallel three helical bundle reference polypeptide originally engineered as an exercise in protein folding (see, Walsh et al., PNAS 96: 5486-5491 (1999) incorporated by reference herein in its entirety). Although the reference scaffold has no known target binding activity, it has been discovered that polypeptides containing modifications of the reference scaffold having the amino acid sequence of SEQ ID NO: 1 are able to specifically bind targets of interest. Thus, a D domain, or a molecule comprising a D domain, can specifically (non-randomly) bind to a target molecule. While not wishing to be bound by theory, it is believed that in designing the D domain, the structural constraints of surface-exposed residues (that can be modified) confer the ability of the surface exposed residues to specifically bind a target of interest. In some embodiments, a D domain generally consists of 70-75 amino acid residues. In some embodiment, a D domain comprises an amino acid sequence that differs (e.g., due to amino acid modifications) from that of a reference scaffold having the sequence of SEQ ID NO: 2 by up to 20 substitutions. In particular embodiments, the D domain does not contain the sequence LAAIKTRLQ (SEQ ID NO: 49).

The terms "protein" and "polypeptide" are used interchangeably herein to refer to a biological polymer comprising units derived from amino acids linked via peptide bonds; a protein can be composed of two or more polypeptide chains.

The terms "antibody" or "immunoglobulin," as used interchangeably herein, include full-length antibodies and antibody fragments including any functional domain of an antibody such as an antigen-binding fragment or single chains thereof, an effector domain, salvage receptor binding epitope, or portion thereof. A typical antibody comprises at least two heavy (H) chains and two light (L) chains interconnected by disulfide bonds. Each heavy chain is comprised of a heavy chain variable region (abbreviated herein as VH) and a heavy chain constant region. The heavy chain constant region is comprised of three domains, CH1, CH2, and CH3. Each light chain is comprised of a light chain variable region (abbreviated herein as VL) and a light chain constant region. The light chain constant region is comprised of one domain, Cl. The VH and VL regions can be further subdivided into regions of hypervariability, termed Complementarity Determining Regions (CDRs), interspersed with regions that are more conserved, termed framework regions (FW). Each VH and VL is composed of three CDRs and four FWs, arranged from amino-terminus to carboxyl-terminus in the following order: FW1, CDR1, FW2, CDR2, FW3, CDR3, FW4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system. Examples of antibodies of the present disclosure include typical antibodies, scFvs, and combinations thereof where, for example, a DDpp is covalently linked (e.g., via peptide bonds or via a chemical linker) to the N-terminus of either the heavy chain and/or the light chain of a typical whole (full-length) antibody, or intercalated in the H chain and/or the L chain of a full-length antibody.

The term "antibody fragment" refers to a portion of an intact antibody and refers to any functional domain of an antibody such as an antigen-binding fragment or single chains thereof, an effector domain or a portion thereof, and a salvage receptor binding epitope or a portion thereof. Examples of antibody fragments include, but are not limited to, Fab, Fab', F(ab')2, and Fv fragments, linear antibodies, single chain antibodies, and multi-specific antibodies formed from antibody fragments. "Antibody fragment" as used herein comprises an antigen-binding site or epitope binding site. In one embodiment, the DDpp fusion protein comprises an effector domain or portion thereof. In one embodiment, the DDpp fusion protein comprises a salvage receptor binding epitope, or portion thereof.

The terms "single chain variable fragment(s)," or "scFv" antibodies as used herein refer to forms of antibodies (e.g., antibody fragments) comprising the variable regions of only the heavy and light chains, connected by a linker peptide. The scFv may comprise VL-linker-VH or may comprise VH-linker-VL. ScFv antibodies are generally 220-250 amino acids in length and contain linkers 10-25 amino acids in length. In one embodiment, a DDpp fusion protein comprises a DDpp and a scFv.

As used herein, the term, "Fc region" or simply "Fc" is understood to mean the carboxyl-terminal portion of an immunoglobulin chain constant region, preferably an immunoglobulin heavy chain constant region, or a portion thereof. For example, an immunoglobulin Fc region may comprise (1) a CH1 domain, a CH2 domain, and a CH3 domain, (2) a CH1 domain and a CH2 domain, (3) a CH1 domain and a CH3 domain, 4) a CH2 domain and a CH3 domain, or (5) a combination of two or more domains and an immunoglobulin hinge region. Thus, in various embodiments, Fc refers to the last two constant region immunoglobulin domains of IgA, IgD, and IgG, and the last three constant region immunoglobulin domains of IgE and IgM, and the flexible hinge N-terminal to these domains. For IgA and IgM Fc may include the J chain. For IgG, Fc comprises immunoglobulin domains Cγ2 and Cγ3 and the hinge between Cγ1 and Cγ2. In a preferred embodiment the immunoglobulin Fc region comprises at least an immunoglobulin hinge region a CH2 domain and a CH3 domain, and preferably lacks the CH1 domain. In one embodiment, the class of immunoglobulin from which the heavy chain constant region is derived is IgG (Igγ) (γ subclasses 1, 2, 3, or 4). Other classes of immunoglobulin, IgA (Igα), IgD (Igδ), IgE (Igε) and IgM (Igμ), may be used. Although the boundaries of the Fc region may vary, the human IgG heavy chain Fc region is usually defined to comprise residues C226 or p260 to its carboxyl-terminus, wherein the numbering is according to the EU index as set forth in Kabat (Kabat et al., Sequences of Proteins of Immunological Interest, 5th Ed. Public Health Service, NIH, Bethesda, Md. (1991)). Fc may refer to this region in isolation, or this region in the context of a full-length antibody, antibody fragment, or Fc fusion protein. Polymorphisms have been observed at a number of different Fc positions, including but not limited to positions 270, 272, 312, 315, 356, and 358 as numbered by the EU index, and thus slight differences between the presented sequence and sequences in the prior art may exist. The choice of appropriate immunoglobulin heavy chain constant region is discussed in detail in U.S. Pat. Nos. 5,541,087, and 5,726,044, each of which is herein incorporated by reference in its entirety. The choice of particular immunoglobulin heavy chain constant region sequences from certain immunoglobulin classes and subclasses to achieve a particular result is considered to be within the level of skill in the art. The portion of the DNA construct encoding the immunoglobulin Fc region preferably comprises at least a portion of a hinge domain, and preferably at least a portion of a CH3 domain of Fc gamma or the homologous domains in any of IgA, IgD, IgE, or IgM. Furthermore, it is contemplated that substitution or deletion of amino acids within the immunoglobulin heavy chain constant regions may be useful in the practice of the methods and compositions disclosed herein. One example would be to introduce amino acid substitutions in the upper CH2 region to create an Fc variant with reduced affinity for Fc receptors (Cole, J. Immunol. 159: 3613 (1997)).

"Antibody-dependent cell-mediated cytotoxicity" or "ADCC" refer to a cell-mediated reaction in which nonspecific cytotoxic cells that express Fc receptors (FcRs) (e.g., Natural Killer (NK) cells, neutrophils, and macrophages) recognize bound antibody on a target cell and subsequently cause lysis (or other cytotoxic effects) of the target cell. To assess ADCC activity of a molecule of interest, any in vitro ADCC assay known in the art can be used, such as that described in U.S. Pat. No. 5,500,362 or 5,821,337. Useful effector cells for such assays include, but are not limited to, peripheral blood mononuclear cells (PBMC) and Natural Killer (NK) cells. Alternatively, or additionally, ADCC activity of the molecule of interest can be assessed in vivo, e.g., in an animal model such as that disclosed in Clynes et al. PNAS 95: 652-656 (1998).

The terms "linker," "spacer," and "hinge" are used interchangeably herein to refer to a peptide or other chemical linkage located between two or more otherwise independent functional domains of a DDpp fusion protein, Adapter or CAR. For example, a linker may be located between an antigenic determinant (AD) domain and an antigenic determinant binding domain (ADBD) of an Adapter. Similarly, a linker may be located between two antigenic determinant binding domains or an antigenic binding domain and a transmembrane domain of a CAR. In some embodiments, a linker is a peptide or other chemical linkage located between a DDpp and another polypeptide of a DDpp fusion protein. Suitable linkers for coupling the two or more domains of an Adapter are described herein and/or will otherwise be clear to a person skilled in the art.

The term "operably linked," as used herein, indicates that two molecules are attached so as to each retain at least some level of functional activity that each molecule had alone (assuming that each molecule had a function activity). In embodiments, when one molecule was without functional activity, it is operably linked with another molecule if the other molecule retains at least some level of its functional activity. Operably linked can also refer to linkage of two non-functional molecules. Two molecules can be "operably linked" whether they are attached directly or indirectly (e.g., via a linker).

The terms "specifically binds," "having selective affinity for," "binds," or "binding" are used interchangeably to mean that a binding agent such as a DDpp reacts or associates more frequently, more rapidly, with greater duration, with greater affinity, or with some combination of the above, to the epitope, protein, or target molecule than with alternative substances, including proteins unrelated to the target epitope, protein, or target molecule. Because of the sequence identity between homologous proteins in different species, specific binding can, in some embodiments, include a binding agent that recognizes a protein or target in more than one species. Likewise, because of homology within certain regions of polypeptide sequences of different proteins, specific binding can include a binding agent that recognizes more than one protein or target. It is understood that, in certain embodiments, a binding agent that specifically binds a first target may or may not specifically bind a second target. As such, "specific binding" does not necessarily require (although it can include) exclusive binding, e.g., binding to a single target. Thus, a binding agent may, in certain embodiments, specifically bind more than one target. In certain embodiments, multiple targets may be bound by the same antigen-binding site on the binding agent.

"Target" refers to any molecule or combination of molecules that can be bound by a DDpp such as a DDpp fusion protein, by other component of the DDpp fusion protein such as an antibody or antibody variable domain fragment, by an Adapter or CAR, or by a component of the DDpp fusion protein, Adapter or CAR such as antigenic determinant binding domain.

The terms "epitope" and "antigenic determinant" are used interchangeably herein and refer to that portion of any molecule (e.g., a target of interest such as CD123, or AFP p26) capable of being recognized and specifically bound by a particular binding agent (e.g., an DDpp or antibody). When the recognized molecule is a polypeptide, epitopes can be formed from contiguous amino acids and noncontiguous amino acids and/or other chemically active surface groups of molecules (such as carbohydrates) juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3 amino acids, and more usually, at least 5 or 8-10 amino acids in a unique spatial conformation.

A "peptide tag" as used herein refers to a peptide sequence that is part of or attached (for instance through genetic engineering) to another protein, to provide a function to the resultant fusion. Peptide tags are usually relatively short in comparison to a protein to which they are fused; by way of example, peptide tags are, in some embodiments, four or more amino acids in length, such as, 5, 6, 7, 8, 9, 10, 15, 20, or 25 or more amino acids. In some embodiments, the DDpp is a fusion protein that contains a peptide tag. In other embodiments, the DDpp specifically binds a peptide tag. Numerous peptide tags that have uses as provided herein are known in the art. Examples of peptide tags that may be a component of a DDpp fusion protein or a target bound by a DDpp (e.g., a DDpp fusion protein) include but are not limited to HA (hemagglutinin), c-myc, the Herpes Simplex virus glycoprotein D (gD), T7, GST, GFP, MBP, Strep-tags, His-tags, Myc-tags, TAP-tags and FLAG® tag (Eastman Kodak, Rochester, N.Y.) Likewise, antibodies to the tag epitope allow detection and localization of the fusion protein using techniques known in the art, such as, Western blots, ELISA assays, and immunostaining of cells.

"Derived from" as that term is used herein, indicates a relationship between a first and a second molecule. It generally refers to structural similarity between the first molecule and a second molecule and does not connote or include a process or source limitation on a first molecule that is derived from a second molecule. For example, in the case of an intracellular signaling domain that is derived from a CD3zeta molecule, the intracellular signaling domain retains sufficient CD3zeta structure such that is has the required function, namely, the ability to generate a signal under the appropriate conditions. It does not connote or include a limitation to a particular process of producing the intracellular signaling domain, e.g., it does not mean that, to provide the intracellular signaling domain, one must start with a CD3zeta sequence and delete unwanted sequence, or impose mutations, to arrive at the intracellular signaling domain.

The term "naturally occurring" when used in connection with biological materials such as a nucleic acid molecules, polypeptides, antigenic determinants, and host cells, refers to those which are found in nature and not modified by a human being. Conversely, "non-natural" or "synthetic" when used in connection with biological materials refers to those which are not found in nature and have been modified by a human being.

As used herein "modifications" with respect to the sequence of a reference sequence includes substitutions, deletions insertions and/or additions of the sequence of the corresponding amino acid position of the reference sequence (e.g., a DD disclosed herein).

A "substitution" with respect to the sequence of a reference sequence refers to a replacement of a particular amino acid residue with a different amino acid residue at a corresponding amino acid position of the reference sequence.

A "conservative" amino acid substitution is one in which one amino acid residue is replaced with another amino acid residue having a similar side chain Families of amino acid residues having similar side chains have been defined in the art, including basic side chains (e.g., lysine (K), arginine (R), histidine (H)), acidic side chains (e.g., aspartic acid (D), glutamic acid (E)), uncharged polar side chains (e.g., glycine (G), asparagine (N), glutamine (Q), serine (S), threonine (T), tyrosine (Y), cysteine (C)), nonpolar side chains (e.g., alanine (A), valine (V), leucine (L), isoleucine (I), proline (P), phenylalanine (F), methionine (M), tryptophan (W), beta-branched side chains (e.g., threonine (T), valine (V), isoleucine (I)) and aromatic side chains (e.g., tyrosine (Y), phenylalanine (F), tryptophan (W), histidine (H)). For example, substitution of a phenylalanine for a tyrosine is a conservative substitution. In particular embodiments, conservative substitutions in the sequences of the DDpp result in the altered or unaltered specific binding of the DDpp containing the substitution to the target of interest (e.g., CD123, or AFP p26) to which it binds. In one embodiment, conservative substitutions in the sequences of the DDpp do not abrogate the binding of the DDpp containing the substitution to the target of interest to which it binds. Methods of identifying nucleotide and amino acid conservative substitutions and non-conservative substitutions which confer, alter or maintain selective binding affinity are known in the art (see, e.g., Brummell, Biochem. 32: 1180-1187 (1993); Kobayashi, Protein Eng. 12(10): 879-884 (1999); and Burks, PNAS 94: 412-417 (1997)).

A "non-conservative" amino acid substitution is one in which one amino acid residue is replaced with another amino acid residue having a dissimilar side chain. In one embodiment, non-conservative substitutions in the sequences of the DDpp result in the specific binding of the DDpp containing the substitution to the target of interest (e.g., CD123 or AFP p26) to which it binds. In one embodiment, non-conservative substitutions in the sequences of the DDpp do not abrogate the binding of the DDpp containing the substitution to the target of interest to which it binds. In one embodiment, non-conservative substitutions in the sequences of the DDpp, Adapter or CAR result in a retained specific binding of the DDpp, Adapter or CAR containing the substitution to the target of interest to which it binds.

"Non-natural amino acids," "amino acid analogs" and "non-standard amino acid residues" are used interchangeably herein. Non-natural amino acids that can be substituted in a DDpp as provided herein are known in the art. In one embodiment the non-natural amino acid is 4-hydroxyproline which can be substituted for proline; 5-hydroxylysine which can be substituted for lysine; 3-methylhistidine which can be substituted for histidine; homoserine which can be substituted for serine; and ornithine which can be substituted for lysine. Additional examples of non-natural amino acids that can be substituted in a DDpp disclosed herein include, but are not limited to molecules such as: D-isomers of the common amino acids, 2,4-diaminobutyric acid, alpha-amino isobutyric acid, A-aminobutyric acid, Abu, 2-amino butyric acid, gamma-Abu, epsilon-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, beta-alanine, lanthionine, dehydroalanine, γ-aminobutyric acid, selenocysteine and pyrrolysine fluoro-amino acids, designer amino acids such as beta-methyl amino acids, C alpha-methyl amino acids, and N alpha-methyl amino acids, or combinations of non-natural amino acids. Additional non-natural amino acids can include for example, 4-amino butyric acid, 4-amino-3-hydroxy-5-phenylpentanoic acid, 4-amino-3-hydroxy-6-methylheptanoic acid, 2-thienyl alanine, and/or D-isomers of amino acids. As discussed herein, in some embodiments, non-natural amino acids or amino acid analogs can include deletion of one or more amino acids from a sequence.

The terms "polynucleotide" and "nucleic acid," used interchangeably herein, refer to a polymeric form of nucleotides of any length, either ribonucleotides or deoxyribonucleotides. These terms include, but are not limited to, DNA, RNA, cDNA (complementary DNA), mRNA (messenger RNA), rRNA (ribosomal RNA), shRNA (small hairpin RNA), snRNA (small nuclear RNA), snoRNA (short nucleolar RNA), miRNA (microRNA), genomic DNA, synthetic DNA, synthetic RNA, and/or tRNA. In some embodiments, an isolated polynucleotide is a modified mRNA comprising non-naturally occurring nucleosides or nucleotides. In some embodiments, a modified mRNA comprises 2-thiouridine, pseudouridine, or 1-methylpseudouridine.

The terms "vector", "cloning vector" and "expression vector" as used herein refer to the vehicle by which a nucleic acid sequence (e.g., a disclosed DDpp, Adapter or CAR coding sequence) can be maintained or amplified in a host cell (e.g., cloning vector) or introduced into a host cell, so as to transform the host and promote expression (e.g., transcription and translation) of the introduced sequence. Vectors include plasmids, phages, viruses, etc.

A "host cell" includes an individual cell or cell culture which can be or has been a recipient of nucleic acids encoding a disclosed DDpp, Adapter or CAR. Host cells includes but are not limited to bacteria, yeast plant, animal, and mammalian cells. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo, in vitro, or ex vivo with nucleic acids encoding a disclosed DDpp, Adapter or CAR. In some examples, the host cell is capable of expressing and displaying a disclosed DDpp or CAR on its surface, such as for example, in phage display or a CAR T cell. In some embodiments, the host cell is capable of expressing an Adapter. In some embodiments, the host cell is capable of expressing and secreting an Adapter. In some embodiments, the host cell is capable of expressing a CAR. In some embodiments, the host cell is capable of expressing and displaying a CAR on its surface. "Expression" includes transcription and/or translation.

As used herein, the terms "solid support," "support," "matrices," and "resins" are used interchangeably and refer to, without limitation, any column (or column material), bead, test tube, microtiter dish, solid particle (for example, agarose or sepharose), microchip (for example, silicon, silicon-glass, or gold chip), or membrane (e.g., biologic or filter membrane) to which a DDpp, antibody, or other protein may be attached (e.g., coupled, linked, or adhered), either directly or indirectly (for example, through other binding partner intermediates such as other antibodies or Protein A), or in which a DDpp or antibody may be embedded (for example, through a receptor or channel). Reagents and techniques for attaching polypeptides to solid supports (e.g., matrices, resins, plastic, etc.) are well known in the art. Suitable solid supports include, but are not limited to, a chromatographic resin or matrix (e.g., SEPHAROSE-4 FF agarose beads), the wall or floor of a well in a plastic microtiter dish, a silica based biochip, polyacrylamide, agarose, silica, nitrocellulose, paper, plastic, nylon, metal, and combinations thereof. DDpp and other compositions may be attached on a support material by a non-covalent association or by covalent bonding, using reagents and techniques known in the art. In one embodiment, the DDpp is coupled to a chromatography material using a linker.

As used herein, the terms "pharmaceutically acceptable," or "physiologically tolerable" and grammatical variations thereof, as they refer to compositions, carriers, diluents and reagents, are used interchangeably and represent that the materials are capable of administration to or upon a human without the production of therapeutically prohibitive undesirable physiological effects such as nausea, dizziness, gastric upset and the like.

"Parenteral" administration of an immunogenic composition includes, e.g., subcutaneous (s.c.), intravenous (i.v.), intramuscular (i.m.), or intrasternal injection, or infusion techniques.

"Modulate," means adjustment or regulation of amplitude, frequency, degree, or activity. In another related aspect, such modulation may be positively modulated (e.g., an increase in frequency, degree, or activity) or negatively modulated (e.g., a decrease in frequency, degree, or activity). In some embodiments, modulation in a positive or negative direction is referenced as compared to the cell, tissue, or organ function prior to administration of a therapeutic. In additional embodiments, modulation in a positive or negative direction is referenced with respect to a normal, healthy cell, tissue or organ.

An "effective amount" of a DDpp (such as a DDpp fusion protein), CAR cell, Adapter, and/or CAR cell/Adapter composition as provided herein, is an amount sufficient to carry out a specifically stated purpose such as to bring about an observable change in the level of one or more biological activities related to the target to which the DDpp (e.g., a DDpp fusion protein), CAR cell and/or Adapter binds. In certain embodiments, the change increases the level of target activity. In other embodiments, the change decreases the level of target activity. An "effective amount" can be determined empirically and in a routine manner, in relation to the stated purpose. The term "therapeutically effective amount" refers to an amount of a DDpp (such as a DDpp fusion protein), a CAR cell and/or Adapter, or other therapeutic agent effective to "treat" (e.g., reduce symptoms of) a disease or disorder in a subject (mammal) The term "therapeutically effective amount" also refers to an amount effective, at dosages and for periods of time necessary, to achieve a desired prophylactic result.

"Patient," "subject," "animal" and "mammal" are used interchangeably and refer to mammals such as human patients and non-human primates, as well as experimental animals such as rabbits, rats, and mice, and other animals Animals include all vertebrates, e.g., mammals and non-mammals, such as chickens, amphibians, and reptiles. "Mammal" as used herein refers to any member of the class Mammalia, including, without limitation, humans and non-human primates such as chimpanzees and other apes and monkey species; farm animals such as cattle, sheep, pigs, goats and horses; domestic mammals such as dogs and cats; laboratory animals including rodents such as mice, rats and guinea pigs, and the like. In a particular embodiment, the patient is a human. The term does not denote a particular age or sex. Thus, adult and newborn subjects, as well as embryos and fetuses, whether male or female, are intended to be included within the scope of this term.

The terms "treat," "treatment," and "treating," as used herein refer to both therapeutic treatment and prophylactic or preventative measures, wherein the object is to prevent or slow down (lessen or delay) the symptoms, complications, or biochemical indicia of a disease, condition, or disorder, alleviating the symptoms or arresting or inhibiting further development of the disease, condition, or disorder. Treatment can be prophylactic (to prevent or delay the onset of the disease, or to prevent the manifestation of clinical or subclinical symptoms thereof) or therapeutic suppression or alleviation of symptoms after the manifestation of the disease, condition, or disorder targeted pathologic condition, prevent the pathologic condition, pursue or obtain beneficial results, or lower the chances of the individual developing the condition even if the treatment is ultimately unsuccessful. Those in need of treatment include those already with the condition as well as those prone to have the condition or those in whom the condition is to be prevented. Treatment can be with a DDpp fusion protein, CAR cell, Adapter, and/or CAR cell/Adapter composition, alone or in combination with an additional therapeutic agent. In some embodiments, the terms "treat," "treatment," and "treating," are used herein to refer to therapeutic treatment and prophylactic or preventative measures, wherein the object is to prevent or slow down (lessen or delay) the symptoms, complications, or biochemical indicia of a proliferative disorder, or the amelioration of one or more symptoms (preferably, one or more discernible symptoms) of a proliferative disorder. In specific embodiments, the terms "treat", "treatment" and "treating" refer to the amelioration of at least one measurable physical parameter of a proliferative disorder, such as growth of a tumor, not necessarily discernible by the patient. In other embodiments the terms "treat", "treatment" and "treating" refer to the inhibition of the progression of a proliferative disorder, either physically by, e.g., stabilization of a discernible symptom, physiologically by, e.g., stabilization of a physical parameter, or both. In other embodiments the terms "treat", "treatment" and "treating" refer to the reduction or stabilization of tumor size, tumor cell proliferation or survival, or cancerous cell count.

"Cancer," "tumor," or "malignancy" are used as synonymous terms and refer to any of a number of diseases that are characterized by uncontrolled, abnormal proliferation of cells, the ability of affected cells to spread locally or through the bloodstream and lymphatic system to other parts of the body (metastasize) as well as any of a number of characteristic structural and/or molecular features. "Tumor," as used herein refers to all neoplastic cell growth and proliferation, whether malignant or benign, and all pre-cancerous and cancerous cells and tissues. A "cancerous tumor," or "malignant cell" is understood as a cell having specific structural properties, lacking differentiation and being capable of invasion and metastasis. Cancers that can be treated using a DDpp fusion protein, CAR cell, Adapter, and/or CAR cell/Adapter composition provided herein include without limitation, breast, lung, brain, cervical, skin, bone, liver, pancreatic, colorectal, renal, head and neck, ovarian, hematopoietic (e.g., leukemia), and prostate cancer, and lymphoma. Other types of cancer and tumors that may be treated using a DDpp fusion protein, CAR cell, Adapter, and/or CAR cell/Adapter composition are described herein or otherwise known in the art. A reference to cancers, tumors, or tumor cells of a particular "type" is understood to mean cancer, tumors, or tumor cells characterized by a specific disease. For example, in some embodiments a first and second cancer of the same type is mixed cellularity Hodgkin's lymphoma and lymphocyte rich Hodgkin's lymphoma. In other embodiments a first and second cancer of the same type is precursor B cell acute lymphoblastic leukemia (ALL) and mature B cell ALL. Examples of a first and second cancer of a different type include, for example, Hodgkin's lymphoma and ALL.

The term "tumor antigen" refers to an antigen that is common to a specific hyperproliferative disorder such as cancer. The terms "tumor antigen" or "cancer antigen" are used interchangeably herein. In certain aspects, antigens are derived from cancers including but not limited to primary or metastatic melanoma, thymoma, lymphoma, sarcoma, lung cancer (e.g., NSCLC or SCLC), liver cancer, non-Hodgkin's lymphoma, Hodgkin's lymphoma, leukemias, multiple myeloma, glioblastoma, neuroblastoma, uterine cancer, cervical cancer, renal cancer, thyroid cancer, bladder cancer, kidney cancer, mesothelioma, and adenocarcinomas such as breast cancer, prostate cancer, ovarian cancer, pancreatic cancer, colon cancer and other cancers known in the art. In some embodiments, the cancer is acute myeloid leukemia (AML), B-cell acute lymphoblastic leukemia, hairy cell leukemia, Hodgkin's lymphoma or blastic plasmacytoid dendritic neoplasm (BPDCN). In some embodiments, the cancer is B-cell acute lymphoid leukemia ("BALL"), T cell acute lymphoid leukemia ("TALL"), acute lymphoid leukemia (ALL), acute myeloid leukemia (AML); one or more chronic leukemias including but not limited to chronic myelogenous leukemia (CML), chronic lymphocytic leukemia (CLL); additional hematologic cancers or hematologic conditions including, but not limited to B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, Marginal zone lymphoma, multiple myeloma, myelodysplasia and myelodysplastic syndrome (e.g., high-risk myelodysplastic syndrome), non-Hodgkin's lymphoma, plasmablastic lymphoma, plasmacytoid dendritic cell neoplasm, Waldenstrom macroglobulinemia.

Tumor and cancer antigens may be further defined as "tumor-specific antigens (TSA)", "cancer-specific antigens (CSA)", "tumor-associated antigens (TAA)", or "cancer-associated antigens (CAA)". A TSA is an antigen that is unique to tumor cells and does not occur on other cells in the body. A TAA is an antigen that is found on both tumor and some normal cells. A TAA may be expressed on normal cells under conditions that fail to induce a state of immunologic tolerance to the antigen. The expression of the TAAs on the tumor may occur under conditions that enable the immune system to respond to the antigen. TAAs may be expressed on normal cells during fetal development when the immune system is immature and unable to respond or may be normally present at extremely low levels on normal cells but which are expressed at much higher levels on tumor cells. Because of the dynamic nature of tumors, in some instances, tumor cells may express unique antigens at certain stages, and at others also express antigens that are also expressed on non-tumor cells. Thus, inclusion of a certain marker as a TAA does not preclude it being considered a TSA. In some embodiments, the TAA and/or TSA that contains an antigenic determinant specifically bound by a CAR cell, Adapter, and/or CAR cell/Adapter composition provided herein, is selected from: BCMA, CD19, CD20, CD22, CD30, CD33/IL3Ra, CD70, CD123, CD171 (L1-CAM), CS1, EGFRvIII, GD2, Lewis$^Y$, ROR 1, mesothelin, IL13Ra2, cMet, PSMA, folate receptor alpha (FR-alpha), CEA, ErbB2 (HER-2/neu); EGFR (HER), PSCA, PSA, MUC1, MUC16, CD44v6, CD44v6/7, CD44v7/8, CD55, IL11Ra, EphA2, EGP40, TAG72, CAIX, HMW-MAA (CSPG4), MAGEA4, NKG2D ligands, beta-HCG, Glycolipid F77, HLA-A2 (NY-ESO-1), HMW-MAA, GD3, TCR, MAGE A3, MARTI, WT1, thyroglobulin, gp100 (Pmel 17), tyrosinase, TRP1, TRP2, HLA-A1, MAGE1, MAGE3, BAGE, GAGE1, GAGE2, pi5, p53, Ras, BCR-ABL, E2A-PRL, H4-RET, IGH-IGK, MYL-RAR; VEGFR2, FAP, FAR, EBVA, HPV antigen E6, HPV antigen E7, TSP-180, MAGE4, MAGES, MAGE6, RAGE, p185erbB2, p180erbB3, nm-23H1, CA 19-9, CA72-4, CAM 17.1, NuMa, K-ras, beta-Catenin, CDK4, Mum-1, p15, p16, 43-9F, alpha-fetoprotein, BCA225, BTAA, CA125, CA 15-3, CA 27.29(BCAA), CA195, CA242, CA50, CAM43, CD68, CO-029, FGF5, G250, HTgp-175, M344, MA50, MG7-Ag, NB/70K, NY-CO-1, RCAS1, SDCCAG16, M2BP, TAAL6, TLP, TPS, FcRH5, GPCR5d, LILBR4, CLL1, and FLT3.

The term "autoimmune disease" as used herein is defined as a disorder that results from an autoimmune response. An autoimmune disease is the result of an inappropriate and excessive response to a self-antigen. Examples of autoimmune diseases include but are not limited to, Addison's disease, alopecia areata, ankylosing spondylitis, autoimmune hepatitis, autoimmune parotitis, Crohn's disease, diabetes (Type I), dystrophic epidermolysis bullosa, epididymitis, glomerulonephritis, Graves' disease, Guillain-Barr syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjogren's syndrome, spondyloarthropathies, thyroiditis, vasculitis, vitiligo, myxedema, pernicious anemia, ulcerative colitis, among others.

The term "target cell" as used herein refers to a cell or cells which are involved in a disease and can be targeted by DDpp containing compositions or by a CAR, an Adapter, and/or CAR/Adapter composition provided herein. Target cells include any cell in a subject (e.g., a human or animal) that can be targeted by a DDPP, a CAR, an Adapter, and/or CAR/Adapter composition. The target cell can be a cell expressing or overexpressing a target specifically bound by a CAR, Adapter, and/or CAR/Adapter composition. The target cell can be a cell expressing or overexpressing a target specifically bound by a DDpp fusion protein, a CAR, Adapter, and/or CAR/Adapter composition.

"Autologous" as the term is used herein refers to any material derived from the same individual to whom it is later to be re-introduced.

"Allogeneic" as the term is used herein refers to any material derived from a different animal of the same species as the individual to whom the material is introduced. Two or more individuals are said to be allogeneic to one another when the genes at one or more loci are not identical. In some aspects, allogeneic material from individuals of the same species may be sufficiently unlike genetically to interact antigenically.

The term "effector cells" as used herein refers to leukocytes which express one or more FcRs and perform effector functions. Preferably, the cells express at least Fc(RIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred in certain embodiments. The effector cells can be isolated from native source thereof, e.g., from blood or PBMCs as described herein or otherwise known in the art. In a specific embodiment, the effector cells are human effector cells.

The term "effector function" refers to the specialized immune function of a differentiated cell. Effector function of a T cell, for example, may be cytolytic activity or helper activity including the secretion of cytokines.

The term "immune cell" as used herein refers to the cells of the mammalian immune system including but not limited to antigen presenting cells, B cells, basophils, cytotoxic T cells, dendritic cells, eosinophils, granulocytes, helper T cells, leukocytes, lymphocytes, macrophages, mast cells, memory cells, monocytes, natural killer cells, neutrophils, phagocytes, plasma cells and T cells.

The terms "T cell" and "T lymphocyte" are interchangeable and used synonymously herein. Examples include but are not limited to naive T cells, central memory T cells, effector memory T cells or combinations thereof.

The term "immune response" as used herein refers to immunities including but not limited to innate immunity, humoral immunity, cellular immunity, immunity, inflammatory response, acquired (adaptive) immunity, autoimmunity and/or overactive immunity.

The term "transduction" as used herein refers to the introduction of a foreign nucleic acid into a cell using a viral vector. "Transfection" as used herein refers to the introduction of a foreign nucleic acid into a cell using recombinant DNA technology. The term "transformation" means the introduction of a "foreign" (e.g., extrinsic, extracellular, or otherwise non-endogenous) nucleic acid (DNA or RNA) sequence to a host cell, so that the host cell will express the introduced nucleic acid to produce a desired substance, such as a protein or enzyme coded by the introduced coding sequence. The introduced nucleic acid sequence can also be called a "cloned" or "foreign" gene or sequence, can include regulatory or control sequences, such as start, stop, promoter, signal, secretion, or other sequences used by a cell's genetic machinery. The nucleic acid sequence can include nonfunctional sequences or sequences with no known function. A host cell that receives and expresses introduced nucleic acid (e.g., DNA or RNA) has been "transformed" and is a "transformant" or a "clone." The DNA or RNA introduced to a host cell can come from any source, including cells of the same genus or species as the host cell, or cells of a different genus or species or may be non-naturally occurring.

"Co-express" as used herein refers to expression of two or more protein coding sequences by the same cell or cell population. The coding sequences may be for example, nucleic acids that each encode a single protein or a chimeric protein as a single polypeptide chain.

"Cell surface receptor" refers to molecules and complexes of molecules capable of receiving a signal and the transmission of such a signal across the plasma membrane of a cell. An example of a cell surface receptor provided herein is an activated integrin receptor, for example, an activated αvβ3 integrin receptor on a metastatic cell. As used herein, "cell surface receptor" also includes a molecule expressed on a cell surface that contains a DDpp capable of binding a target of interest (e.g., CD123, or AFP p26). The term "receptor" denotes a cell-associated protein that binds to, or otherwise interacts with, a molecule (e.g., a ligand) and mediates the effect of the ligand on the cell. In some embodiment, the molecule that interacts with a receptor is a bioactive molecule. Membrane-bound cell-surface receptors are typically characterized by a multi-domain structure comprising an extracellular ligand-binding domain, a membrane spanning domain, and an intracellular effector domain that is typically involved in signal transduction.

"Antigen loss escape variants" as used herein refer to cells which exhibit reduced or loss of expression of the target antigen, which antigens are targeted by a CAR provided herein.

A. Antigenic Determinants (ADs).

Antigenic determinants (ADs) are epitopes that are capable of being recognized and specifically bound by an antigenic determinant binding regions (ADBDs) (e.g., antigen-binding fragments of an antibody or alternative scaffold binding domains (ASBDs) (e.g., D domains)). The ADs in the Adapters and on the target cells provided herein can be bound by the CARs discussed below.

In some embodiments, the AD (e.g., in an Adapter and/or on a target cell) is an AD that is present in a naturally occurring protein or other molecule. In some embodiments, the AD is an AD that is endogenous to humans.

In some embodiments, the AD in the Adapter is an AD that is present on a target cell.

In some embodiments, the AD (e.g., in an Adapter and/or on a target cell) is an AD that is present in a transmembrane protein, e.g., an AD that is present in the extracellular portion of a transmembrane protein. In some embodiments, the AD is a tumor antigen. In some embodiments, the AD is a tumor-associated antigen. In some embodiments, the AD is a tumor-specific antigen.

In some embodiments, the AD (e.g., in an Adapter and/or on a target cell) is a cancer antigen. In some embodiments, the AD is a cancer-associated antigen. In some embodiments, the AD is a cancer-specific antigen.

In some embodiments, the AD (e.g., in an Adapter and/or on a target cell) is an epitope of BCMA. In some embodiments, the AD is an epitope of CD19. In some embodiments, the AD is an epitope of CD20. In some embodiments, the AD is an epitope of CD22. In some embodiments, the AD is an epitope of CD123. In some embodiments, the AD is an epitope of CD37. In some embodiments, the AD is an epitope of CS1. In further embodiments, the AD is an epitope of CS1 that is bound by elotuzumab. In some embodiments, the AD is an epitope of HER2. In some embodiments, the AD is an epitope of AFP. In some embodiments, the AD is an epitope of AFP p26. In some embodiments, the AD is an epitope of CD45. In some embodiments, the AD is an epitope of human CD45 that is bound by the UCHL-1, A6, or ODP4 antibody. In some embodiments, the AD is an epitope of human CD45 that is bound by the 4KB5, MB1, KiB3, 2H4, or MT2 antibody. In some embodiments, the AD is an epitope of CD26. In some embodiments, the AD is an epitope of CD30. In some embodiments, the AD is an epitope of CD33. In some embodiments, the AD is an epitope of CD38.

In some embodiments, the AD is an epitope of CD123. In further embodiments, the AD comprises 5-25, 5-50, 5-75, 5-100, 5-125, or 5-150 amino acid residues, more than 150 amino acid residues, or all of the amino acid residues of SEQ ID NO: 1.

In some embodiments, the AD is an epitope of AFP p26. In further embodiments, the AD comprises 5-25, 5-50, 5-75, 5-100, 5-125, or 5-150 amino acid residues, more than 150 amino acid residues, or all of the amino acid residues of SEQ ID NO: 37. In further embodiments, the AD comprises the amino acid residues of SEQ ID NO: 37. In further embodiments, the AD comprises 5-25, 5-50, 5-75, 5-100, 5-125, or 5-150 amino acid residues, more than 150 amino acid residues, or all of the amino acid residues of SEQ ID NO: 39. In further embodiments, the AD comprises the amino acid residues of SEQ ID NO: 39. In further embodiments, the AD comprises the amino acid residues of SEQ ID NO: 37-43 or 44.

In some embodiments, the AD (e.g., in an Adapter and/or on a target cell) is bound by a chimeric antigen receptor (CAR). In some embodiments, the AD is bound by a cell expressing a chimeric antigen receptor. In some embodiments, the AD (e.g., on a target cell) is bound by an Adapter. In some embodiments, the AD is bound by a scFv. In some embodiments, the AD is bound by an alternative scaffold binding domain (ASBD). In some embodiments, the AD is bound by a D domain. In some embodiments, the AD is bound by an antibody or an antigen-binding fragment thereof.

ADs suitable for use in connection with the DDpp (e.g., Adapter and CAR) disclosed herein have been disclosed in Int'l. Appl. Pub. Nos. WO 2016164305, WO 2016164308A1, WO 2019099440, and WO 2019099433, U.S. Pat. Nos. 10,662,248, and 10,647,775, and US Pat. Appl. Nos. 20200223934, and 20210002381, each of which is incorporated herein by reference for all purposes.

B. Antigenic Determinant Binding Domains (ADBDs)

A protein domain that binds to an antigenic determinant (AD) is referred to herein as an "antigenic-determinant binding domain" or "ADBD." In some embodiments, the ADBD is sufficient to confer recognition and specific binding to a target of interest. The ADBD described herein can be present in a DDpp fusion protein, Adapter and/or a chimeric antigen receptor (CAR)).

In some embodiments, the ADBD (e.g., of a DDpp fusion protein, Adapter and/or CAR) is an antibody or an antigen-binding fragment thereof. In some embodiments, the ADBD is a scFv. In some embodiments, the ADBD is an alternative scaffold binding domain. In some embodiments, the ADBD is a D domain.

ADBDs suitable for use in connection with the DDpp (e.g., Adapter and CAR) disclosed herein have been disclosed in Int'l. Appl. Pub. Nos. WO 2016164305, WO 2016164308A1, WO 2019099440, and WO 2019099433, U.S. Pat. Nos. 10,662,248, and 10,647,775, and US Pat. Appl. Nos. 20200223934, and 20210002381, each of which is incorporated herein by reference for all purposes.

i. Antibody-Derived Antigenic Determinant Binding Domains (ADBD)

In some embodiments, one or more ADBDs (e.g., of a DDpp fusion protein, Adapter and/or CAR) can be derived from an antibody molecule, e.g., one or more of monoclonal antibodies, polyclonal antibodies, recombinant antibodies, human antibodies, humanized antibodies, single-domain antibodies e.g., a heavy chain variable domain (VH), a light chain variable domain (VL) and a variable domain (VHH) from, e.g., human or camelid origin. In some embodiments, the ADBD is derived from the same species in which the Adapter or CAR will ultimately be used, e.g., for use in humans. It may be beneficial for Adapter and/or CAR to comprise a human or a humanized ADBD. Compositions and techniques for routinely generating such ADBDs are known in the art.

In some embodiments, the ADBD (e.g., of a DDpp fusion protein, Adapter and/or CAR) comprises a fragment of an antibody that is sufficient to confer recognition and specific binding to the target antigen. Examples of an antibody fragment include, but are not limited to, an Fab, Fab', F(ab')$_2$, or Fv fragment, an scFv antibody fragment, a linear antibody, single domain antibody such as an sdAb (either VL or VH), a camelid VHH domain, and multi-specific antibodies formed from antibody fragments.

In some embodiments, the ADBD (e.g., of a DDpp fusion protein, Adapter and/or CAR) is a "scFv," which can comprise a fusion protein comprising a VL chain and a VH chain of an antibody, wherein the VH and VL are, e.g., linked via a short flexible polypeptide linker, e.g., a linker described herein. scFvs can routinely be prepared according to methods known in the art (see, e.g., Bird et al., Science 242: 423-426 (1988) and Huston et al., Proc. Natl. Acad. Sci. USA 85: 5879-5883 (1988)).

In some embodiments, the ADBD (e.g., of a DDpp fusion protein, Adapter and/or CAR) is a single domain antigen binding (SDAB) molecule. A SDAB molecule includes molecules containing complementary determining regions that are part of a single domain polypeptide. Examples include, but are not limited to, heavy chain variable domains, binding molecules naturally devoid of light chains, single domains derived from conventional 4-chain antibodies, engineered domains and single domain scaffolds other than those derived from antibodies. SDAB molecules can be derived from any species including, but not limited to mouse, human, camel, llama, fish, shark, goat, rabbit, and bovine. This term also includes naturally occurring single domain antibody molecules from species other than Camelidae and sharks.

In some embodiments, the ADBD (e.g., of a DDpp fusion protein, Adapter and/or CAR) comprises a human antibody or a fragment thereof. In some embodiments, the ADBD (e.g., of a DDpp fusion protein, Adapter and/or CAR) comprises a humanized antibody or a fragment thereof.

Humanization of antibodies is well-known in the art and can essentially be performed following the method of Winter and co-workers (Jones et al., Nature 321: 522-525 (1986); Riechmann et al., Nature 332: 323-327 (1988); Verhoeyen et al., Science 239: 1534-1536 (1988)), by substituting rodent CDRs or CDR sequences for the corresponding sequences of a human antibody, i.e., CDR-grafting (EP 239,400; Intl. Appl. Publ. No. WO 91/09967; and U.S. Pat. Nos. 4,816, 567; 6,331,415; 5,225,539; 5,530,101; 5,585,089; and 6,548,640; the contents of which are incorporated herein by reference herein in their entirety). Humanization of antibodies can also be achieved by veneering or resurfacing (EP 592,106; EP 519,596; Padlan, 1991, Molecular Immunology, 28(4/5): 489-498; Studnicka et al., Protein Engineering 7(6): 805-814 (1994); and Roguska et al., PNAS 91: 969-973 (1994)) or chain shuffling (U.S. Pat. No. 5,565,332), the contents of which are incorporated herein by reference herein in their entirety.

ii. Alternative Scaffold Binding Domains

In some embodiments, the ADBD(s) (e.g., of a DDpp fusion protein, Adapter and/or CAR) is an alternative scaffold binding domain (ASBD). An "alternative scaffold binding domain" or "ASBD" as used herein, is an antigenic determinant binding domain that is derived from, or corresponds to, a non-antibody-based binding scaffold.

In some embodiments, the disclosure provides a CAR comprising an ADBD that is an ASBD. In some embodiments, the disclosure provides a cell comprising a CAR that comprises an ADBD that is an ASBD. In further embodiments, an immune effector cell that comprises a CAR comprising and ASBD is provided. In some embodiments, the disclosure provides an Adapter comprising an ADBD that is an ASBD.

In further embodiments, the disclosure provides a composition comprising an Adapter and a CAR that each comprise an ASBD.

In some embodiments, the binding of the ASBD (e.g., of a DDpp fusion protein, Adapter and/or CAR) to the target AD is mediated by secondary structures of the binding scaffold, such as alpha helices or beta sheets. In some embodiments, the ASBD is a three-helix bundle-based binding domain. In some embodiments, the ASBD is a D domain-based binding domain. In other embodiments, the ASBD is a Z-domain (Affibody)-based binding domain.

In some embodiments, the ASBD (e.g., of a DDpp fusion protein, Adapter and/or CAR) is a D domain (de novo binding domain)-based AD binding domain. In some embodiments, the D domain comprises a sequence selected from the group: SEQ ID NO: 8-33, 99 and 100. In some embodiments, the D domain comprises a sequence selected from the group: SEQ ID NO: 8, 13, 14, 31, 32, and 33. In some embodiments, the D domain comprises the sequence of SEQ ID NO: 14. In some embodiments, the D domain comprises a sequence selected from the group: SEQ ID NO: 74-93 and 94. In some embodiments, the D domain comprises a sequence selected from the group: SEQ ID NO: 70-73 and 92-94. In some embodiments, the D domain comprises the sequence of SEQ ID NO: 73.

In some embodiments the ASBD (e.g., of a DDpp fusion protein, Adapter and/or CAR) is a Z-domain scaffold (Affibody)-based AD binding domain Z-domain scaffold-based binding domains generally consist of 58 amino acid residues in which substitutions of up to 13 positions located in the first and second of three alpha helices, confer binding confer target (AD) recognition and binding specificity for the target (AD) of interest. Z-domain (Affibody) scaffold-based binding domains are further described in U.S. Pat. No. 5,831,012, the entire contents of which are herein incorporated by reference in their entirety.

Additional examples of ASBDs that display secondary structure-mediated target binding include DARPins, affilins, and armadillo repeat-based binding scaffolds.

In some embodiments, the ASBD (e.g., of a DDpp fusion protein, Adapter and/or CAR) is a DARPin-based AD binding domain.

In some embodiments, the ASBD is an adnectin-based AD binding domain. The adnectin-based binding domain is derived from the tenth domain of fibronectin type III (10Fn3). This ADBD is generally a 94 amino acid binding domain that adopts a beta sandwich fold containing seven strands that are connected by six loops. Substitutions in three surface-exposed loops on one side of the adnectin domain generate target (AD) specific binding moieties.

In some embodiments, the ASBD (e.g., of a DDpp fusion protein, Adapter and/or CAR) is a lipocalin-, affilin-, or anticalin-based AD-binding domain. The anticalin scaffold displays a conserved β-barrel structure made up of eight anti-parallel β-strands and generally consists of 160-180 amino acids. The ligand binding pocket of the anticallin-based binding scaffold is composed of four loops, each containing up to 24 substitutions, that collectively confer target (AD) recognition and binding specificity.

In some embodiments, the ASBD (e.g., of a DDpp fusion protein, Adapter and/or CAR) is an Avimer scaffold-based AD-binding domain Avimer scaffold-based binding domains are derived from the A-domain of cell surface receptors and are generally 35 amino acids in length. Avimer scaffold-based binding domains are further described in U.S. Appl. Publ. Nos. 20040175756, 20050053973, 20050048512, and 20060008844, the entire contents of each of which are herein incorporated by reference in their entireties.

In some embodiments, the ASBD (e.g., of a DDpp fusion protein, Adapter and/or CAR) is a fynomer scaffold-based AD binding domain. The fynomer binding domain is generally 60-75 amino acids in length and is composed of a pair of anti-parallel beta sheets joined by two flexible loops. Substitutions/insertions in the loops confer AD target recognition and binding specificity.

In some embodiments the ASBD (e.g., of a DDpp fusion protein, Adapter and/or CAR) is a knottin scaffold-based AD binding domain Knottin scaffold-based binding domains correspond to a 30-amino-acid protein fold composed of three anti-parallel β-strands connected by loops of variable length and multiple disulfide bonds.

In some embodiments the ASBD (e.g., of a DDpp fusion protein, Adapter and/or CAR) is a Kunitz domain-based AD binding domain Kunitz domain-based binding domains are derived from the active motif of Kunitz-type protease inhibitors and are generally about 60 amino acids in length. The hydrophobic core of this ADBD is composed of a twisted two-stranded antiparallel β-sheet and two α-helices stabilized by three pairs of disulfide bonds. Substitutions and insertions in the three loops confer AD target recognition and binding specificity. Kunitz scaffold-based binding domains are further described in Intl. Appl. Publ. No. WO 2004063337, the entire contents of which are herein incorporated by reference in their entirety.

In some embodiments the ASBD (e.g., of a DDpp fusion protein, Adapter and/or CAR) is a WW domain-based AD-binding domain.

C. Linkers

Linkers are peptide or other chemical linkages located between two or more otherwise independent functional domains of the DDpp fusion protein, Adapter or CAR.

Suitable linkers for operably linking a DDpp and an additional component of a DDpp fusion protein or two or more functional domains of the Adapter in a single-chain amino acid sequence include but are not limited to, polypeptide linkers such as glycine linkers, serine linkers, mixed glycine/serine linkers, glycine- and serine-rich linkers or linkers composed of largely polar polypeptide fragments.

In one embodiment, the linker is made up of a majority of amino acids selected from glycine, alanine, proline, asparagine, glutamine, and lysine. In one embodiment, one or more linkers in the DDpp fusion protein, Adapter or CAR is made up of a majority of amino acids selected from glycine, alanine, proline, asparagine, aspartic acid, threonine, glutamine, and lysine. In one embodiment, one or more linkers in the DDpp fusion protein, Adapter or CAR is made up of one or more amino acids selected from glycine, alanine, proline, asparagine, aspartic acid, threonine, glutamine, and lysine. In another embodiment, one or more linkers in the DDpp fusion protein, Adapter or CAR is made up of a majority of amino acids that are sterically unhindered. In another embodiment, a linker in which the majority of amino acids are glycine, serine, and/or alanine. In some embodiments, the peptide linker is selected from polyglycines (such as $(Gly)_5$ (SEQ ID NO: 45), and $(Gly)_8$ (SEQ ID NO: 46), poly(Gly-Ala), and polyalanines. In some embodiments, the peptide linker contains the sequence of Gly-Gly-Gly-Gly-Thr-Gly-Gly-Gly-Gly-Ser (SEQ ID NO: 47). In some embodiments, the peptide linker contains the sequence of Gly-Gly-Gly-Gly-Asp-Gly-Gly-Gly-Gly-Ser (SEQ ID NO: 48). In some embodiments, the peptide linker contains the sequence of SEQ ID NO: 118 or 119.

In one embodiment, the DDpp fusion protein, Adapter or CAR comprises an ADBD (e.g., a D domain) directly attached (i.e., without a linker) to another component of the DDpp fusion protein, Adapter or CAR, respectively. In one embodiment, the DDpp fusion protein, Adapter or CAR contains at least 2, at least 3, at least 4, or at least 5 ADBDs (e.g., D domains) directly attached to another domain of the DDpp fusion protein, Adapter or CAR, respectively.

In another embodiment, an ADBD (e.g., D domain) can be operably linked to another component of the DDpp fusion protein, Adapter or CAR through a linker. DDpp fusion proteins, Adapters or CARs can contain a single linker, multiple linkers, or no linkers. In one embodiment, the DDpp fusion protein, Adapter or CAR comprises an ADBD (e.g., D domain) operably linked to another component of the DDpp fusion protein, Adapter or CAR, respectively, through a linker peptide. In one embodiment, the DDpp fusion protein, Adapter or CAR contains at least 2, at least 3, at least 4, or at least 5 ADBDs (e.g., D domains) operably linked to another domain of the DDpp fusion protein, Adapter or CAR, respectively, through the same or different linkers.

Linkers can be of any size or composition so long as they are able to operably link a functional domain of the DDpp fusion protein, Adapter or CAR in a manner that enables the functional domain to function (e.g., the ability of an antigenic determinant binding domain to bind a target of interest). In some embodiments, linker(s) are about 1 to about 100 amino acids, about 1 to 50 amino acids, about 1 to 20 amino acids, about 1 to 15 amino acids, about 1 to 10 amino acids, about 1 to 5 amino acids, about 2 to 20 amino acids, about 2 to 15 amino acids, about 2 to 10 amino acids, or about 2 to 5 amino acids. It should be clear that the length, the degree of flexibility and/or other properties of the linker(s) may have some influence on the properties of the final polypeptide of the invention, including but not limited to the affinity, specificity or avidity for a target of interest, or for one or more other target proteins of interest. When two or more linkers are used in the DDpp fusion protein, Adapter or CAR, these linkers may be the same or different. In the context and disclosure provided herein, a person skilled in the art will be able to routinely determine the optimal linker composition and length for the purpose of operably linking the functional domains of a DDpp fusion protein, Adapter or CAR.

The linker can also be a non-peptide linker such as an alkyl linker, or a PEG linker. For example, alkyl linkers such as —NH—(CH2)s-C(O)—, wherein s=2-20 can be used. These alkyl linkers may further be substituted by any non-sterically hindering group such as lower alkyl e.g., C1-C6) lower acyl, halogen (e.g., CI, Br), CN, NH2, phenyl, etc. An exemplary non-peptide linker is a PEG linker. In certain embodiments, the PEG linker has a molecular weight of about 100 to 5000 kDa, or about 100 to 500 kDa.

Suitable linkers for coupling DDpp fusion protein, Adapter or CAR functional domains by chemical cross-linking include, but are not limited to, homo-bifunctional chemical cross-linking compounds such as glutaraldehyde, imidoesters such as dimethyl adipimidate (DMA), dimethyl suberimidate (DMS) and dimethyl pimelimidate (DMP) or N-hydroxysuccinimide (NHS) esters such as dithiobis(succinimidylpropionate)(DSP) and dithiobis (sulfosuccinimidylpropionate)(DTSSP). Examples of suitable linkers for coupling DDpp fusion protein, Adapter or CAR functional domains include but are not limited to cross-linkers with one amine-reactive end and a sulfhydryl-reactive moiety at the other end, or with a NHS ester at one end and an SH-reactive group (e.g., a maleimide or pyridyl).

In additional embodiments, one or more of the linkers in the DDpp fusion protein, Adapter or CAR is cleavable. Examples of cleavable linkers include, include but are not limited to a peptide sequence recognized by proteases (in vitro or in vivo) of varying type, such as Tev, thrombin, factor Xa, plasmin (blood proteases), metalloproteases, cathepsins (e.g., GFLG, etc.), and proteases found in other corporeal compartments.

In some embodiments, the linker is a "cleavable linker" that facilitates the release of a DDpp fusion protein functional domain, Adapter functional domain or cytotoxic agent in a cell or at the cell surface. For example, an acid-labile linker (e.g., hydrazone), protease-sensitive (e.g., peptidase-sensitive) linker, photolabile linker, dimethyl linker or disulfide-containing linker (see, e.g., Chari, Can. Res. 52: 127-131 (1992); U.S. Pat. No. 5,208,020; and U.S. Appl. Pub. No. 20090110753; the contents of each of which is herein incorporated by reference in its entirety) can be used wherein it is desirable that the covalent attachment between a DDpp or a cytotoxic agent and the fusion partner is intracellularly cleaved when the composition is internalized into the cell. The terms "intracellularly cleaved" and "intracellular cleavage" refer to a metabolic process or reaction inside a cell on an DDpp drug conjugate whereby the covalent attachment, i.e., linked via a linker between the DDpp and cytotoxic agent, DDpp and fusion partner, or between two DDpp is broken, resulting in the free DDpp and/or cytotoxic agent dissociated inside the cell.

In additional embodiments, one or more of the linkers in the CAR is cleavable. Examples of cleavable linkers include, include but are not limited to a peptide sequence recognized by proteases (in vitro or in vivo) of varying type, such as Tev, thrombin, factor Xa, plasmin (blood proteases), metalloproteases, cathepsins (e.g., GFLG, etc.), and proteases found in other corporeal compartments.

In some embodiments, a short oligo- or polypeptide linker, from about 1 to 100 amino acids in length, is used to link together any of the domains of a CAR. Linkers can be composed of flexible residues like glycine and serine (or any other amino acid) so that the adjacent protein domains are free to move relative to one another. The amino acids sequence composition of the linker may be selected to minimize potential immunogenicity of the CAR. Longer linkers can be used when it is desirable to ensure that two adjacent domains do not sterically interfere with one another.

In some embodiments, preferably between 2 and 10 amino acids in length forms the linkage between the transmembrane domain and the cytoplasmic signaling domain of the CAR. In further embodiments, the linker is between 10 and 15 amino acids in length, or between 15 and 20, or between 20 and 30, or between 30 and 60, or between 60 and 100 amino acids in length (or any range in between those listed). In further embodiments, the linker is a glycine-serine doublet sequence. In some embodiments, the Extracellular Spacer Domain (ESD) corresponds to the human T cell surface glycoprotein CD8 alpha-chain ESD region (e.g., amino acid residues 138 to 182 CD8 alpha chain; Swiss-Prot Acc. No. P01732). In some embodiments, the ESD corresponds to the CD8 ESD region that has been further modified, through amino acid substitution, to improve expression function or immunogenicity. In further embodiments, the ESD corresponds to the CD28 ESD or sequences containing modifications of the CD28 ESD that confer improved expression function or immunogenicity.

Linker optimization can be evaluated using techniques described herein and/or otherwise known in the art. In some embodiments, linkers do not disrupt the ability of a DDpp fusion protein, Adapter or CAR to bind a target antigenic determinant and/or another Adapter or CAR functional domain to function appropriately (e.g., the ability of an effector functional domain in the Adapter to elicit an effector function or the ability of an FcRn binding domain in the Adapter to bind FcRn).

D Domain Polypeptides (DDpp)

According to various embodiments, the disclosure provides a DDpp that specifically binds to CD123. In some embodiments, the DDpp comprises a D Domain (DD) that specifically binds CD123 and comprises the amino acid sequence of SEQ ID NO: 8-32 or 33. In some embodiments, the D domain that binds to CD123 comprises an amino acid sequence selected from the group consisting of SEQ ID NO: 8, 13, 14, 31, 32, and 33. In some embodiments, the D domain that binds to CD123 comprises the amino acid sequence of SEQ ID NO: 14. Proteins comprising variants of the D domains that retain the ability to specifically bind their respective targets are also provided.

In some embodiments, the DDpp comprises a D Domain (DD) that specifically binds AFP p26 and comprises the amino acid sequence of SEQ ID NO: 74-93 or 94. Proteins comprising variants of the D domains that retain the ability to specifically bind their respective targets are also provided.

In some embodiments, the DDpp is fused to a heterologous polypeptide. In some embodiments, the heterologous polypeptide comprises a full-length antibody or an antibody fragment. In some embodiments, the DD is fused to: the amino terminus of a full-length antibody heavy chain; the amino terminus of a full-length antibody light chain; the carboxyl terminus of a full-length antibody heavy chain; or the carboxyl terminus of a full-length antibody light chain. In other embodiments, the DD is fused to an antibody fragment which is an Fc. In additional embodiments, the heterologous polypeptide comprises a member selected from the group consisting of: (i) a transmembrane domain; (ii) a membrane associating domain; (iii) human serum albumin or a fragment thereof; (iv) AFP or a fragment thereof; (v) AFP p26 or a fragment thereof; (vi) the extracellular domain of a receptor or a fragment thereof; and (vii) the extracellular domain of an intracellular receptor (e.g., a nuclear protein) or a fragment thereof. In some embodiments, the protein contains a heterologous polypeptide that comprises the extracellular domain, or a fragment of an extracellular domain of BCMA (SEQ ID NO: 34) or CD123 (SEQ ID NO: 1) or CD19 (SEQ ID NO: 95) or CS1 (SEQ ID NO: 35). In some embodiments, the protein contains a heterologous polypeptide that comprises the extracellular domain, or a fragment of an extracellular domain, of a receptor selected from the group consisting of: CD19, CD20, CD22, HVEM, BTLA, DR3, CD37; TSLPR, IL7R, and gp96. In some embodiments, the protein contains a heterologous polypeptide that comprises an antigenic portion of a serum protein (e.g., AFP, and AFP p26). In some embodiments, the protein contains a heterologous polypeptide that comprises an antigenic portion of an intracellular protein (e.g., a nuclear protein). In some embodiments, the protein is labeled. In further embodiments, the label is selected from the group consisting of an enzymatic label, a fluorescent label, a luminescent label, a bioluminescent label, and a biotin moiety. In additional embodiments, the protein is conjugated to a therapeutic or cytotoxic agent. In some embodiments, the protein contains a heterologous polypeptide that binds to one or more with major histocompatibility complex (MHC) class I or class II complexes.

In some embodiments, a DD of the DDpp is a variant of a CD123-binding DD reference sequence selected from the group consisting of SEQ ID NO: 8-33, 99 and 100, that retains the ability to specifically bind CD123. In some embodiments, the sequence of the variant DD comprises the amino acid sequence of a variant that has at least 75%, 80%, 85%, 87%, 89%, 90%, 92%, 94%, 96% or 98% sequence identity to a reference DD sequence selected from the group consisting of SEQ ID NO: 8-33, 99 and 100, and the variant DD retains the ability to specifically bind CD123.

In some embodiments, a DD of the DDpp is a variant of a AFP p26-binding DD reference sequence selected from the group consisting of SEQ ID NO: 74-93 and 94, that retains the ability to specifically bind AFP p26. In some embodiments, the sequence of the variant DD comprises the amino acid sequence of a variant that has at least 75%, 80%, 85%, 87%, 89%, 90%, 92%, 94%, 96% or 98% sequence identity to a reference DD sequence selected from the group consisting of SEQ ID NO: 74-93 and 94, and the variant DD retains the ability to specifically bind AFP p26.

In particular embodiments, the identity between a variant DD (query) sequence and a reference DD sequence, also referred to as a global sequence alignment, is determined using the FASTDB computer program based on the algorithm of Brutlag et al. Comp. App. Biosci. 6: 237-245 (1990). Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter. According to this embodiment, if the reference DD sequence is shorter than the variant DD query sequence due to N- or C-terminal deletions, not because of internal deletions, a manual correction is made to the results to take into consideration the fact that the FASTDB program does not account for N- and C-terminal truncations of the reference DD sequence when calculating global percent identity. For reference sequences truncated at the N- and C-termini, relative to the query sequence, the percent identity is corrected by calculating the number of residues of the query sequence that are N- and C-terminal of the reference sequence, which are not matched/aligned with a corresponding subject residue, as a percent of the total bases of the query sequence. A determination of whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of this embodiment.

In some embodiments, the disclosed DDpp (e.g., a DDpp fusion protein) is labeled. Labels that can be used to label the DDpp include but are not limited to an enzymatic label, a fluorescent label, a luminescent label, and a bioluminescent label. In some embodiments, the label is a biotin moiety. In some embodiments, the label is a streptavidin moiety. In some embodiments, the label is a His-tag or a FLAG tag. In some embodiments, the label is luciferase, green fluorescent protein, red fluorescent protein, or other similar agent. In some embodiments, the DDpp comprises a CD123-binding DD comprising an amino acid sequence selected from the group consisting of SEQ ID NO: 8-33, 99 and 100. In some embodiments, the DDpp comprises a DD comprising an amino acid sequence selected from the group consisting of SEQ ID NO: 8, 13, 14, 31, 32, and 33. In some embodiments, the DDpp comprises a DD comprising the amino acid sequence of SEQ ID NO: 14. In some embodiments, the DDpp comprises a p26-binding DD comprising an amino acid sequence selected from the group consisting of SEQ ID NO: 74-93 and 94.

In other embodiments, the DDpp fusion protein is attached to a solid support. In some embodiments, the solid support is selected from the group consisting of: a bead, a glass slide, a chip, a gelatin, and an agarose. In some embodiments, the DDpp comprises a CD123-binding DD comprising an amino acid sequence selected from the group consisting of SEQ ID NO: 8-33, 99 and 100. In some embodiments, the DDpp comprises a DD comprising an amino acid sequence selected from the group consisting of SEQ ID NO: 8, 13, 14, 31, 32, and 33. In some embodiments, the DDpp comprises a DD comprising the amino acid sequence of SEQ ID NO: 14. In some embodiments, the DDpp comprises a p26-binding DD comprising an amino acid sequence selected from the group consisting of SEQ ID NO: 74-93 and 94.

In some embodiments, the DDpp (e.g., a DDpp fusion protein) is associated with a liposome. In some embodiments, the DDpp is associated with the liposome through covalent binding. In some embodiments, DDpp is a fusion protein. In further embodiments, the DDpp is a CAR. In additional embodiments, the DDpp is associated with the liposome through ionic binding but not covalent binding. In some embodiments, the DDpp comprises a CD123-binding DD comprising an amino acid sequence selected from the group consisting of SEQ ID NO: 8-33, 99 and 100. In some embodiments, the DDpp comprises a DD comprising an amino acid sequence selected from the group consisting of SEQ ID NO: 8, 13, 14, 31, 32, and 33. In some embodiments, the DDpp comprises a DD comprising the amino acid sequence of SEQ ID NO: 14. In some embodiments, the DDpp comprises a p26-binding DD comprising an amino acid sequence selected from the group consisting of SEQ ID NO: 74-93 and 94.

In some embodiments, the target-binding DDpp is conjugated to a therapeutic or cytotoxic agent (e.g., a chemotherapeutic agent or a radiotherapeutic agent). In some embodiments, the DDpp comprises a CD123-binding DD comprising an amino acid sequence selected from the group consisting of SEQ ID NO: 8-33, 99 and 100. In some embodiments, the DDpp comprises a DD comprising an amino acid sequence selected from the group consisting of SEQ ID NO: 8, 13, 14, 31, 32, and 33. In some embodiments, the DDpp comprises a DD comprising the amino acid sequence of SEQ ID NO: 14. In some embodiments, the DDpp comprises a p26-binding DD comprising an amino acid sequence selected from the group consisting of SEQ ID NO: 74-93 and 94.

TABLE 1

Exemplary target-specific binding DDs

| SEQ ID NO: | D-Domain Sequence | Target |
|---|---|---|
| 4 | MGSWDEFGRRLYAIEWRLYALGGSEAELAAFEKEIAAFESELQAYKGKGNPEVEKLREIAAVIRSNLQAYRHN | CD123 |
| 5 | MGSWDEFGRRLYAIEWQLYALGGTEAELAAFEKEIAAFESELQAYKGKGNPEVEKLREIAAVIRENLQAYRHN | CD123 |
| 6 | MGSWDEFGRRLYAIEWRLYALGGSEAELAAFEKEIAAFESELQAYKGKGSPEVEKLREIAAVIRSNLQAYRHN | CD123 |
| 7 | MGSWDEFSRRLYAIEWRLYALGGSEAELAAFEKEIAAFESELQAYKGKGNPEVEKLREIAAVIRSNLQAYRHN | CD123 |
| 8 | MGSWDEFGRRLYAIEWQLYALGGTEAELAAFEKEIAAFESELQAYKGKGSPEVEKLREIAAVIRENLQAYRHN | CD123 |
| 9 | MGSWDEFSRRLYAIEWQLYALGGTEAELAAFEKEIAAFESELQAYKGKGNPEVEKLREIAAVIRENLQAYRHN | CD123 |
| 10 | MGSWDEFGRRLYAIEWQLYALGGTEAELAAFEKEIAAFESELQAYKGKGNPEVEKLRELAAVIRENLQAYRHN | CD123 |
| 11 | MGSWDEFGRRLYAIEWQLYALGGTEAELAAFEKEIAAFESELQAYKGEGSPEVEKLREIAAVIRENLQAYRHN | CD123 |
| 12 | MGSWDEFGRRLYAIEWQLYAQGGTEAELAAFEKEIAAFESELQAYKGKGNPEVEKLRELAAVIRENLQAYRHN | CD123 |
| 13 | MGSWDEFSRRLYAIEWQLYALGGTEAELAAFEKEIAAFESELQAYKGEGSPEVEKLRELAAVIRENLQAYRHN | CD123 |
| 14 | MGSWDEFSRRLYAIEWQLYAQGGTEAELAAFEKEIAAFESELQAYKGEGSPEVEKLRELAAVIRENLQAYRHN | CD123 |
| 15 | MGSWSEFGRRLYAIEWQLYALGGTEAELAAFEKEIAAFESELQAYKGKGNPEVEKLREIAAVIRENLQAYRHN | CD123 |
| 16 | MGSWDEFGRRLYAIEWQLYALGGTEAELAAFEKEIAAFESELQAYKGKGNPEVEKLREIAAVIRDELQAYRHN | CD123 |
| 17 | MGSWDEFGRRLYAIEWQLYALGGTEAELAAFEKEIAAFESELQAYKGKGNPEVEKLREIAAVIREELQAYRHN | CD123 |
| 18 | MGSWDEFGRRLYAIEWQLYALGGTEAELAAFEKEIAAFESELQAYKGKGNPEVEKLREIAAVIRDNLQAYRHN | CD123 |
| 19 | MGSWDEFGRRLYAIEWQLYALGGTEAELAAFEKEIAAFESELQAYKGKGNPEVEKLREIAAAIRENLQAYRHN | CD123 |
| 20 | MGSWDEFGRRLYAIEWQLYALGGTEAELAAFEKEIAAFESELQAYKGKGNPEVEKLREEAAVIRENLQAYRHN | CD123 |
| 21 | MGSWDEFGRRLYAIEWQLYALGGTEAELAAFEKEIAAFESELQAYKGKGNPEVEKLRKIAAVIRENLQAYRHN | CD123 |
| 22 | MGSWDEFGRRLYAIEWQLYALGGTEAELAAFEKEIAAFESELQAYKGKGNPEVEALREIAAVIRENLQAYRHN | CD123 |
| 23 | MGSWDEFGRRLYAIEWQLEALGGTEAELAAFEKEIAAFESELQAYKGKGNPEVEKLREIAAVIRENLQAYRHN | CD123 |
| 24 | MGSWDEFGRRLYAIETQLYALGGTEAELAAFEKEIAAFESELQAYKGKGNPEVEKLREIAAVIRENLQAYRHN | CD123 |

TABLE 1-continued

Exemplary target-specific binding DDs

| SEQ ID NO: | D-Domain Sequence | Target |
|---|---|---|
| 25 | MGSWDEFGRRLYAIKWQLYALGGTEA ELAAFEKEIAAFESELQAYKGKGNPE VEKLREIAAVIRENLQAYRHN | CD123 |
| 26 | MGSWDEFGRRLAAIEWQLYALGGTEA ELAAFEKEIAAFESELQAYKGKGNPE VEKLREIAAVIRENLQAYRHN | CD123 |
| 27 | MGSWDEFGQRLYAIEWQLYALGGTEA ELAAFEKEIAAFESELQAYKGKGNPE VEKLREIAAVIRENLQAYRHN | CD123 |
| 28 | MGSWDEFKRRLYAIEWQLYALGGTEA ELAAFEKEIAAFESELQAYKGKGNPE VEKLREIAAVIRENLQAYRHN | CD123 |
| 29 | MGSWAEFGRRLYAIEWQLYALGGTEA ELAAFEKEIAAFESELQAYKGKGNPE VEKLREIAAVIRENLQAYRHN | CD123 |
| 30 | MGSWDEFGRRLYAIEWRLYALGGSEA ELAAFEKEIAAFESELQAYKGIGNPE VENLREIAAVIRSNLQAYRHN | CD123 |
| 31 | MGSWDEFGRRLYAIESQLYALGGTEA ELAAFEKEIAAFESELQAYKGKGNPE VEKLREIAAVIRENLQAYRHN | CD123 |
| 32 | MGSWDEFGRRLYAIEAQLYALGGTEA ELAAFEKEIAAFESELQAYKGKGNPE VEKLREIAAVIRENLQAYRHN | CD123 |
| 33 | MGSWDEFGRRLYAIEEQLYALGGTEA ELAAFEKEIAAFESELQAYKGKGNPE VEKLREIAAVIRENLQAYRHN | CD123 |
| 97 | MGSWSEFNMRLDAIYERLTALGGSEA ELAAFEKEIAAFESELQAYKGKGNPE VEWLRHSAARIRLELQAYRHN | CD123 |
| 98 | MGSWIEFNMRLDAIYERLVALGGSEA ELAAFEKEIAAFESELQAYKGKGNPE VEWLRKVAANIRLELQAYRHN | CD123 |
| 99 | MGSWDEFGRRLYAIEWRLYALGGSEA ELAAFEKEIAAFESELQAYKGKGNPE VEKLRELAAVIRSNLQAYRHN | CD123 |
| 100 | MGSWDEFGRRLYAIEWRLYALGGSEA ELAAFEKEIAAFESELQAYKGEGNPE VEKLREIAAVIRSNLQAYRHN | CD123 |
| 111 | MGSWEEFDKRLDAITRRLMALGGSEA ELAEFESTIAWFEWDLQEYKGKGNPE VEALDWEAYAIDYELGAYRHN | CD123 |
| 70 | MGSWFEFYDRLNAIDARLWALGGSEA ELAAFEKEIAAFESELQAYKGKGNPE VESLRVHAAAIREWLQAYRHN | AFP p26 |
| 71 | MGSWFEFYDRLNAIDARLWALGGSEA ELAAFEKEIAAFESELQAYKGKGNPE VESLREHAAHIREWLQAYRHN | AFP p26 |
| 72 | MGSWFEFYDRLNAIDARLWALGGSEA ELAAFEKEIAAFESELQAYKGKGNPE VESLREHAAAIREWLQAYRHN | AFP p26 |
| 73 | MGSWSEFYDRLNAIDARLWALGGSEA ELAAFEKEIAAFESELQAYKGKGNPE VESLREHAAAIREWLQAYRHN | AFP p26 |
| 74 | MGSWYEFYTRLDAIDARLWALGGSEA ELAAFEKEIAAFESELQAYKGKGNPE VEKLRVHAAAIRNWLQAYRHN | AFP p26 |

TABLE 1-continued

Exemplary target-specific binding DDs

| SEQ ID NO: | D-Domain Sequence | Target |
|---|---|---|
| 75 | MGSWLEFWNRLEAIDQRLWALGGSEA ELAAFEKEIAAFESELQAYKGKGNPE VEVLREHAAAIRAWLQAYRHN | AFP p26 |
| 76 | MGSWVEFWNRLQAIDTRLWALGGSEA ELAAFEKEIAAFESELQAYKGKGNPE VESLRIHAAHIRFWLQAYRHN | AFP p26 |
| 77 | MGSWHEFWFRLDAIDTRLWALGGSEA ELAAFEKEIAAFESELQAYKGKGNPE VESLREHAAAIRYWLQAYRHN | AFP p26 |
| 78 | MGSWIEFYVRLDAIDTRLWALGGSEA ELAAFEKEIAAFESELQAYKGKGNPE VESLREHAAYIRVWLQAYRHN | AFP p26 |
| 79 | MGSWMEFMTRLDAIDERLWALGGSEA ELAAFEKEIAAFESELQAYKGKGNPE VESLREHAAAIRHWLQAYRHN | AFP p26 |
| 80 | MGSWTEFWDRLQAIDNRLWALGGSEA ELAAFEKEIAAFESELQAYKGKGNPE VEALREQAASIRIWLQAYRHN | AFP p26 |
| 81 | MGSWVEFYHRLEAIENRLFALGGSEA ELAAFEKEIAAFESELQAYKGKGNPE VENLRQHAAHIRWLQAYRHN | AFP p26 |
| 82 | MGSWMEFSDRLFAIWIRLWALGGSEA ELAAFEKEIAAFESELQAYKGKGNPE VEGLRSLAAHIRGHLQAYRHN | AFP p26 |
| 83 | MGSWTEFYDRLNAIDARLWALGGSEA ELAAFEKEIAAFESELQAYKGKGNPE VESLRVHAAAIREWLQAYRHN | AFP p26 |
| 84 | MGSWTEFYDRLNAIDARLWALGGSEA ELAAFEKEIAAFESELQAYKGKGNPE VESLRAHAAAIREWLQAYRHN | AFP p26 |
| 85 | MGSWTEFYDRLNAIDARLWALGGSEA ELAAFEKEIAAFESELQAYKGKGNPE VESLKAHAAAIREWLQAYRHN | AFP p26 |
| 86 | MGSWTEFYDRLNAIDARLWALGGSEA ELAAFEKEIAAFESELQAYKGKGNPE VESLQAHAAAIREWLQAYRHN | AFP p26 |
| 87 | MGSWTEFYDRLNAIDARLWALGGSEA ELAAFEKEIAAFESELQAYKGKGNPE VESLRAHAAGIREWLQAYRHN | AFP p26 |
| 88 | MGSWSEFYDRLNAIDARLWALGGSEA ELAAFEKEIAAFESELQAYKGKGNPE VESLRSHAAAIREWLQAYRHN | AFP p26 |
| 89 | MGSWSEFYDRLNAIDARLWALGGSEA ELAAFEKEIAAFESELQAYKGKGNPE VESLQSHAAAIREWLQAYRHN | AFP p26 |
| 90 | MGSWTEFYDRLNAIDARLWALGGSEA ELAAFEKEIAAFESELQAYKGKGNPE VESLRSHAAAIREWLQAYRHN | AFP p26 |
| 91 | MGSWTEFYDRLNAIDARLWALGGSEA ELAAFEKEIAAFESELQAYKGKGNPE VESLQSHAAAIREWLQAYRHN | AFP p26 |
| 92 | MGSWTEFYDRLNAIDARLWALGGSEA ELAAFEKEIAAFESELQAYKGKGNPE VESLREHAAHIREWLQAYRHN | AFP p26 |
| 93 | MGSWSEFYDRLNAIDARLWALGGSEA ELAAFEKEIAAFESELQAYKGKGNPE VESLREHAAHIREWLQAYRHN | AFP p26 |

TABLE 1-continued

Exemplary target-specific binding DDs

| SEQ ID NO: | D-Domain Sequence | Target |
|---|---|---|
| 94 | MGSWTEFYDRLNAIDARLWALGGSEA ELAAFEKEIAAFESELQAYKGKGNPE VESLREHAAAIREWLQAYRHN | AFP p26 |

In some embodiments, the disclosure provides compositions comprising one or more of the DD sequences disclosed on Table 1. In other embodiments, the disclosure provides compositions comprising one or more DDs comprising a sequence with 60-70%, 70-75%, 75-80%, 80-85%, 85-90%, 95-99% homology (and overlapping ranges therein) with a sequence disclosed in Table 1. In some embodiments, the DD(s) having such homology are functionally similar or identical as compared to the respective reference sequence in Table 1. In some embodiments, the disclosure provides a polypeptide that comprises one or more DD that compete with (wholly or partially) one or more of the DD sequences disclosed in Table 1 (reference sequence) for its respective target. The ability of one polypeptide to compete with a reference polypeptide for binding to a respective target can routinely be determined using a standard competition assay known in the art. In some embodiments, competition does not require that the polypeptide competes for the same epitope as a polypeptide (DD) of Table 1, rather the polypeptide can compete by binding a sterically inhibiting epitope, an overlapping epitope, etc.

A. CD123-Binding DDpp

In some embodiments, the disclosure provides a protein comprising a D Domain (DD) target binding domain (DDpp) that specifically binds CD123 (SEQ ID NO: 1) and comprises the amino acid sequence of SEQ ID NO: 8-32 or 33. In some embodiments, the DDpp comprises a DD comprising an amino acid sequence selected from the group consisting of SEQ ID NO: 8, 13, 14, 31, 32, and 33. In some embodiments, the DDpp comprises a DD comprising the amino acid sequence of SEQ ID NO: 14.

In some embodiments, a DD of the DDpp specifically binds CD123. In further embodiments, the DD specifically binds CD123 having an amino acid sequence consisting of SEQ ID NO: 8. In some embodiments, the DDpp comprises an amino acid sequence selected from the group consisting of SEQ ID NO: SEQ ID NO: 8-33, 99 and 100. In other embodiments, the DDpp comprises a variant of an amino acid sequence selected from the group consisting of SEQ ID NO: SEQ ID NO: 8-33, 99 and 100. In some embodiments, the DDpp specifically binds CD123 (SEQ ID NO: 1) and comprises the amino acid sequence of SEQ ID NO: 8, 13, 14, 31, 32, or 33. In some embodiments, the DDpp comprises the amino acid sequence of SEQ ID NO: 8. In some embodiments, the DDpp comprises the amino acid sequence of SEQ ID NO: 13. In some embodiments, the DDpp comprises the amino acid sequence of SEQ ID NO: 14. In some embodiments, the DDpp comprises the amino acid sequence of SEQ ID NO: 31. In some embodiments, the DDpp comprises the amino acid sequence of SEQ ID NO: 32. In some embodiments, the DDpp comprises the amino acid sequence of SEQ ID NO: 33.

In other embodiments, the CD123-binding DDpp comprises a variant of an amino acid sequence selected from the group consisting of SEQ ID NO: 8-32, and 33. In some embodiments, the CD123-binding DDpp comprises multiple target-binding domains that bind a single target (e.g., dimers, trimers, etc.). In some embodiments, the DDpp comprises 2, 3, 4, 5, or more than 5, DD that specifically bind CD123 and that have an amino acid sequence selected from the group consisting of SEQ ID NO: 8-33, 99 and 100. In some embodiments, the DDpp comprises 2, 3, 4, 5, or more than 5, DD that have the same sequence. In some embodiments, the DDpp comprises 2, 3, 4, 5 or more than 5, DD that specifically bind to different epitopes of CD123 and that have an amino acid sequence selected from the group consisting of SEQ ID NO: 8-33, 99 and 100. In some embodiments, the DDpp comprises a DD that specifically binds CD123 and further comprises 2, 3, 4, 5 or more than 5, additional different DDs or target-binding binding domains (e.g., scFvs) that specifically bind to CD123 or a different target antigen. In some embodiments, the DDpp comprises a DD that specifically binds CD123 (e.g., a DD having an amino acid sequence selected from the group consisting of SEQ ID NO: 8-33, 99 and 100) and further comprises one or more additional DDs or other target-binding binding domains that bind one or more antigens expressed on the surface of a B-lineage cell. In some embodiments, the DDpp comprises a DD that specifically binds CD123 e.g., a DD having an amino acid sequence selected from the group consisting of SEQ ID NO: 8-33, 99 and 100) and further comprises one or more additional DDs or other target-binding binding domains that bind one or more cancer antigens. In some embodiments, the DDpp comprises a DD that specifically binds CD123 (e.g., a DD having an amino acid sequence selected from the group consisting of SEQ ID NO: 8-33, 99 and 100) and specifically binds 2, 3, 4, 5, or more than 5, different targets. In further embodiments, the DDpp comprises a DD that specifically binds CD123 (e.g., a DD having an amino acid sequence selected from the group consisting of SEQ ID NO: 8-33, 99 and 100) and specifically binds 2, 3, 4, 5, or more than 5, different cancer antigens. In some embodiments, the DDpp comprises a DD that specifically binds CD123 (e.g., a DD having an amino acid sequence selected from the group consisting of SEQ ID NO: 8-33, 99 and 100) and specifically binds 2, 3, 4, 5, or more than 5, different cancer antigens expressed on the surface of a cancer cell. In some embodiments, the DDpp comprises a DD that specifically binds CD123 (e.g., a DD having an amino acid sequence selected from the group consisting of SEQ ID NO: 8-33, 99 and 100) and specifically binds 2, 3, 4, 5, or more than 5, cancer antigens expressed on the surface of different cancer cells. In some embodiments, the CD123-specific DD comprises an amino acid sequence selected from the group consisting of SEQ ID NO: 8, 13, 14, 31, 32, and 33. In some embodiments, the CD123-specific DD comprises the amino acid sequence of SEQ ID NO: 14.

In some embodiments, the DDpp comprises a variant of a CD123-binding DD disclosed herein (reference DD) that retains the ability to specifically bind CD123. In some embodiments, the sequence of the CD123-binding DD variant contains 1, 2, 3, 4, 5, 6, 7, 8, 9, or 10, 1-3, 1-5, or 1-10, conservative or non-conservative substitutions compared to a reference CD123-binding DD having an amino acid sequence selected from the group consisting of SEQ ID NO: 8-33, 99 and 100. In some embodiments, the sequence of the CD123-binding DD variant contains 1, 2, 3, 4, 5, 6, 7, 8, 9, or 10, 1-3, 1-5, or 1-10, conservative substitutions compared to a reference CD123-binding DD having an amino acid sequence selected from the group consisting of SEQ ID NO: 8-33, 99 and 100. In some embodiments, the sequence of the CD123-binding DD variant contains 1, 2, 3, 4, 5, 6, 7, 8, 9, or 10, 1-3, 1-5, or 1-10, non-conservative substitutions compared to a reference CD123-binding DD having an amino acid sequence selected from the group consisting of SEQ ID NO: 8-33, 99 and 100. In some embodiments, the reference CD123-binding DD comprises an amino acid sequence selected from the group consisting of SEQ ID NO: 8, 13, 14, 31, 32, and 33. In some embodiments, the reference CD123-binding DD comprises the amino acid sequence of SEQ ID NO: 14.

In some embodiments, the sequence of the CD123-binding DD variant contains a total of 1, 2, 3, 4, 5, 6, 7, 8, 9, or 10, 1-3, 1-5, or 1-10, conservative or non-conservative substitutions in positions corresponding to amino acid residues 1-22, 29-46, and 52-72, of a reference CD123-binding DD having an amino acid sequence selected from the group consisting of SEQ ID NO: 8-33, 99 and 100. In some embodiments, the sequence of the CD123-binding DD variant contains a total of 1, 2, 3, 4, 5, 6, 7, 8, 9, or 10, 1-3, 1-5, or 1-10, conservative substitutions in positions corresponding to amino acid residues 1-22, 29-46, and 52-72, of a reference CD123-DD having an amino acid sequence selected from the group consisting of SEQ ID NO: 8-33, 99 and 100. In some embodiments, the sequence of the CD123-binding DD variant contains a total of 1, 2, 3, 4, 5, 6, 7, 8, 9, or 10, 1-3, 1-5, or 1-10, non-conservative substitutions in positions corresponding to amino acid residues 1-22, 29-46, and 52-72, of a reference CD123-binding DD having an amino acid sequence selected from the group consisting of SEQ ID NO: 8-33, 99 and 100. In some embodiments, the reference CD123-binding DD comprises an amino acid sequence selected from the group consisting of SEQ ID NO: 8, 13, 14, 31, 32, and 33. In some embodiments, the reference CD123-binding DD comprises the amino acid sequence of SEQ ID NO: 14.

In some embodiments, the sequence of the CD123-binding DD variant contains a total of 1, 2, 3, 4, 5, 6, 7, 8, 9, or 10, 1-3, 1-5, or 1-10, conservative or non-conservative substitutions in positions corresponding to amino acid residues: 2-6, 8-10, 12, 13, 15-17, 19, 20, 29, 30, 32-34, 36, 37, 39-41, 43, 44, 52-55, 57-59, 61, 62, 64-66, and 68-70, of a reference CD123-binding DD having an amino acid sequence selected from the group consisting of SEQ ID NO: 8-33, 99 and 100. In some embodiments, the sequence of the CD123-binding DD variant contains a total of 1, 2, 3, 4, 5, 6, 7, 8, 9, or 10, 1-3, 1-5, or 1-10, conservative substitutions in positions corresponding to amino acid residues: 2-6, 8-10, 12, 13, 15-17, 19, 20, 29, 30, 32-34, 36, 37, 39-41, 43, 44, 52-55, 57-59, 61, 62, 64-66, and 68-70, of a reference DD having an amino acid sequence selected from the group consisting of SEQ ID NO: 8-33, 99 and 100. In some embodiments, the sequence of the CD123-binding DD variant contains a total of 1, 2, 3, 4, 5, 6, 7, 8, 9, or 10, 1-3, 1-5, or 1-10, non-conservative substitutions in positions corresponding to amino acid residues: 2-6, 8-10, 12, 13, 15-17, 19, 20, 29, 30, 32-34, 36, 37, 39-41, 43, 44, 52-55, 57-59, 61, 62, 64-66, and 68-70, of a reference DD having an amino acid sequence selected from the group consisting of SEQ ID NO: 8-33, 99 and 100. In some embodiments, the reference CD123-binding DD comprises an amino acid sequence selected from the group consisting of SEQ ID NO: 8, 13, 14, 31, 32, and 33. In some embodiments, the reference CD123-binding DD comprises the amino acid sequence of SEQ ID NO: 14.

In some embodiments, the sequence of the CD123-binding DD variant contains a total of 1, 2, 3, 4, 5, 6, 7, 8, 9, or 10, 1-3, 1-5, or 1-10, conservative or non-conservative substitutions in positions corresponding to amino acid residues: 7, 11, 14, 18, 21, 28, 31, 35, 38, 42, 45, 53, 56, 60, 63, and 67, of a reference CD123-binding DD having an amino acid sequence selected from the group consisting of SEQ ID NO: 8-33, 99 and 100. In some embodiments, the sequence of the CD123-binding DD variant contains a total of 1, 2, 3, 4, 5, 6, 7, 8, 9, or 10, 1-3, 1-5, or 1-10, conservative substitutions in positions corresponding to amino acid residues: 7, 11, 14, 18, 21, 28, 31, 35, 38, 42, 45, 53, 56, 60, 63, and 67, of a reference DD having an amino acid sequence selected from the group consisting of SEQ ID NO: 8-33, 99 and 100. In some embodiments, the sequence of the CD123-binding DD variant contains a total of 1, 2, 3, 4, 5, 6, 7, 8, 9, or 10, 1-3, 1-5, or 1-10, non-conservative substitutions in positions corresponding to amino acid residues: 7, 11, 14, 18, 21, 28, 31, 35, 38, 42, 45, 53, 56, 60, 63, and 67, of a reference DD having an amino acid sequence selected from the group consisting of SEQ ID NO: 8-33, 99 and 100. In some embodiments, the reference CD123-binding DD comprises an amino acid sequence selected from the group consisting of SEQ ID NO: 8, 13, 14, 31, 32, and 33. In some embodiments, the reference CD123-binding DD comprises the amino acid sequence of SEQ ID NO: 14.

In some embodiments, the disclosure provides CD123-binding DDpp that completely or partially (e.g., overlap with an epitope) block binding of a reference DD to CD123, wherein the reference DD has an amino acid sequence selected from SEQ ID NO: 8-33, 99 and 100. In other embodiments, the disclosure provides CD123-binding DDpp that bind to the same epitope of CD123as a a reference DD consisting of an amino acid sequence selected from SEQ ID NO: 8-33, 99 and 100. In some embodiments, the reference CD123-binding DD comprises an amino acid sequence selected from the group consisting of SEQ ID NO: 8, 13, 14, 31, 32, and 33. In some embodiments, the reference CD123-binding DD comprises the amino acid sequence of SEQ ID NO: 14.

In some embodiments, the DDpp is a fusion protein comprising a DD that specifically binds CD123. In some embodiments, a DD of the DDpp fusion protein specifically binds CD123 having an amino acid sequence consisting of of SEQ ID NO: 1. In some embodiments, the DDpp comprises an amino acid sequence selected from the group consisting of SEQ ID NO: 8-33, 99 and 100. In other embodiments, the DDpp comprises a variant of an amino acid sequence selected from the group consisting of SEQ ID NO: 8-33, 99 and 100. In some embodiments, the DDpp comprises an amino acid sequence selected from the group consisting of SEQ ID NO: 8, 13, 14, 31, 32, and 33. In some embodiments, the DDpp comprises the amino acid sequence of SEQ ID NO: 8. In some embodiments, the DDpp comprises the amino acid sequence of SEQ ID NO: 13. In some embodiments, the DDpp comprises the amino acid sequence of SEQ ID NO: 14. In some embodiments, the DDpp comprises the amino acid sequence of SEQ ID NO: 31. In some embodiments, the DDpp comprises the amino acid sequence of SEQ ID NO: 32. In some embodiments, the DDpp comprises the amino acid sequence of SEQ ID NO: 33. In some embodiments, the DDpp fusion protein comprises a full-length antibody or a portion (fragment) of an antibody. In some embodiments, the DDpp fusion protein comprises a full length IgG antibody (e.g., IgG1, IgG2, IgG2, or IgG4). In further embodiments, the DDpp fusion protein comprises a full length antibody that specifically binds a cancer antigen. In further embodiments, the DDpp comprises a commercially approved therapeutic antibody (e.g., rituximab, ofatumumab, ocrelizumab, veltuzumab, MEDI-551, epratuzumab, belimumab, tabalumab, AMG-557, MEDI-570, and NN882). In other embodiments, the CD123-binding DDpp is an Fc fusion protein.

In some embodiments, the DDpp is a fusion protein comprising a CD123-binding DD operably linked to a serum protein. In some embodiments, the CD123-binding DDpp fusion protein comprises an amino acid sequence selected from the group consisting of SEQ ID NO: 8-33, 99 and 100. In some embodiments, the DDpp comprises an amino acid sequence selected from the group consisting of SEQ ID NO: 8, 13, 14, 31, 32, and 33. In some embodiments, the DDpp comprises the amino acid sequence of SEQ ID NO: 8. In some embodiments, the DDpp comprises the amino acid sequence of SEQ ID NO: 13. In some embodiments, the DDpp comprises the amino acid sequence of SEQ ID NO: 14. In some embodiments, the DDpp comprises the amino acid sequence of SEQ ID NO: 31. In some embodiments, the DDpp comprises the amino acid sequence of SEQ ID NO: 32. In some embodiments, the DDpp comprises the amino acid sequence of SEQ ID NO: 33. In other embodiments, the CD123-binding DDpp fusion protein comprises a variant of an amino acid sequence selected from the group consisting of SEQ ID NO: 8-33, 99 and 100. In some embodiments, the CD123-binding DDpp fusion protein comprises all or a portion of human serum albumin. In some embodiments, the DDpp fusion protein comprises AFP (SEQ ID NO: 36), or a fragment thereof. In some embodiments, the CD123-binding DDpp fusion protein comprises AFP p26 (SEQ ID NO: 37), or a fragment thereof. In some embodiments, the CD123-binding DDpp fusion protein comprises a polypeptide having the sequence of SEQ ID NO: 37-43 or 44. In some embodiments, the DDpp fusion protein contains a fragment of a serum protein or an antigenic fragment of a serum protein (e.g., AFP, and AFP p26). In some embodiments, the DDpp fusion protein comprises a fragment consisting of 5-500, 5-400, 5-300, 5-200, 5-100, 5-50, 10-500, 10-400, 10-300, 10-200, 10-100, or 10-50 amino acids of a serum protein. In some embodiments, the CD123-specific DD comprises an amino acid sequence selected from the group consisting of SEQ ID NO: 8, 13, 14, 31, 32, and 33. In some embodiments, the CD123-specific DD comprises the amino acid sequence of SEQ ID NO: 14.

In some embodiments, the CD123-binding DDpp fusion protein comprises the extracellular domain of a receptor or a fragment thereof. In some embodiments, the DDpp fusion protein comprises a DD that comprises an amino acid sequence selected from the group consisting of SEQ ID NO: 8-33, 99 and 100. In some embodiments, the CD123-binding DDpp comprises an amino acid sequence selected from the group consisting of SEQ ID NO: 8, 13, 14, 31, 32, and 33. In some embodiments, the CD123-binding DDpp comprises the amino acid sequence of SEQ ID NO: 8. In some embodiments, the CD123-binding DDpp comprises the amino acid sequence of SEQ ID NO: 13. In some embodiments, the CD123-binding DDpp comprises the amino acid sequence of SEQ ID NO: 14. In some embodiments, the CD123-binding DDpp comprises the amino acid sequence of SEQ ID NO: 31. In some embodiments, the CD123-binding DDpp comprises the amino acid sequence of SEQ ID NO: 32. In some embodiments, the CD123-binding DDpp comprises the amino acid sequence of SEQ ID NO: 33. In other embodiments, the CD123-binding DDpp fusion protein comprises a variant of an amino acid sequence selected from the group consisting of SEQ ID NO: 8-33, 99 and 100. In further embodiments, the CD123-binding DDpp fusion protein comprises the extracellular domain of CD123 (SEQ ID NO: 1), or a fragment thereof. In some embodiments, the CD123-binding DDpp fusion protein comprises the extracellular domain of a receptor selected from the group consisting of: CD19, CD20, CD22, HVEM, BTLA, DR3, CD37; TSLPR, IL7R, NKG2D and gp96, or a fragment thereof.

In some embodiments, the CD123-binding DDpp fusion protein contains a fragment consisting of 5-500, 5-400, 5-300, 5-200, 5-100, 5-50, 10-500, 10-400, 10-300, 10-200, 10-100, or 10-50 amino acids of an extracellular domain, of a cell surface receptor. In some embodiments, the DDpp fusion protein contains a fragment of an extracellular domain of BCMA (SEQ ID NO: 34). In some embodiments, the DDpp fusion protein contains a fragment of an extracellular domain of CD123 (SEQ ID NO: 1). In some embodiments, the DDpp fusion protein contains a fragment of an extracellular domain of CS1 (SEQ ID NO: 35). In some embodiments, the DDpp contains a fragment of an extracellular domain, of a receptor selected from the group consisting of: CD19, CD20, CD22, HVEM, BTLA, DR3, CD37; TSLPR, IL7R, and gp96.

In additional embodiments, the CD123-binding DDpp fusion protein comprises an intracellular protein (e.g., a nuclear protein) or a fragment thereof. In some embodiments, the DDpp fusion protein comprises a DD that comprises an amino acid sequence selected from the group consisting of SEQ ID NO: 8-33, 99 and 100. In some embodiments, the CD123-binding DDpp comprises an amino acid sequence selected from the group consisting of SEQ ID NO: 8, 13, 14, 31, 32, and 33. In some embodiments, the CD123-binding DDpp comprises the amino acid sequence of SEQ ID NO: 8. In some embodiments, the CD123-binding DDpp comprises the amino acid sequence of SEQ ID NO: 13. In some embodiments, the CD123-binding DDpp comprises the amino acid sequence of SEQ ID NO: 14. In some embodiments, the CD123-binding DDpp comprises the amino acid sequence of SEQ ID NO: 31. In some embodiments, the CD123-binding DDpp comprises the amino acid sequence of SEQ ID NO: 32. In some embodiments, the CD123-binding DDpp comprises the amino acid sequence of SEQ ID NO: 33. In other embodiments, the CD123-binding DDpp fusion protein comprises a variant of an amino acid sequence selected from the group consisting of SEQ ID NO: 8-33, 99 and 100. In some embodiments, the CD123-binding DDpp fusion protein comprises a fragment consisting of 5-500, 5-400, 5-300, 5-200, 5-100, 5-50, 10-500, 10-400, 10-300, 10-200, 10-100, or 10-50 amino acid residues of an intracellular protein (e.g., a nuclear protein).

B. AFP p26-Binding DDpp

In some embodiments, the disclosure provides a protein comprising a D Domain (DD) target binding domain (DDpp) that specifically binds AFP p26 (SEQ ID NO: 37) and comprises the amino acid sequence of SEQ ID NO: 74-93 or 94.

In some embodiments, a DD of the DDpp specifically binds AFP p26. In further embodiments, a DD of the DDpp specifically binds AFP p26 having an amino acid sequence consisting of SEQ ID NO: 37. In some embodiments, the DDpp comprises an amino acid sequence selected from the group consisting of SEQ ID NO: 74-93 and 94. In additional embodiments, the AFP p26-binding DDpp comprises a variant of an amino acid sequence selected from the group consisting of SEQ ID NO: 74-93 and 94. In some embodiments, the DDpp comprises an amino acid sequence selected from the group consisting of SEQ ID NO: 92, 93 and 94. In some embodiments, the DDpp comprises an amino acid sequence selected from the group consisting of SEQ ID NO: 70-73, 92, 93 and 94. In some embodiments, the DDpp comprises an amino acid sequence selected from the group consisting of SEQ ID NO: 73.

In further embodiments, the DDpp comprises a variant of an amino acid sequence selected from the group consisting of SEQ ID NO: 74-93 and 94. In further embodiments, the DD specifically binds AFP p26 having an amino acid sequence consisting of SEQ ID NO: 37, but does not specifically bind AFP having an amino acid sequence consisting of SEQ ID NO: 36. In some embodiments, the AFP p26-binding DDpp comprises multiple target-binding domains that bind a single target (e.g., dimers, trimers, etc.). In some embodiments, the DDpp comprises 2, 3, 4, 5, or more than 5, DD that specifically bind AFP p26 and that have an amino acid sequence selected from the group consisting of SEQ ID NO: 74-93 and 94. In some embodiments, the DDpp comprises 2, 3, 4, 5, or more than 5, DD that have the same sequence. In some embodiments, the DDpp comprises 2, 3, 4, 5 or more than 5, DD that specifically bind to different epitopes of AFP p26 and that have an amino acid sequence selected from the group consisting of SEQ ID NO: 74-93 and 94. In some embodiments, the DDpp comprises a DD that specifically binds AFP p26 and further comprises 2, 3, 4, 5 or more than 5, additional different DDs or target-binding binding domains (e.g., scFvs) that specifically bind to AFP p26 or a different target antigen. In some embodiments, the DDpp comprises a DD that specifically binds AFP p26 (e.g., a DD having an amino acid sequence selected from the group consisting of SEQ ID NO: 74-93 and 94) and further comprises one or more additional DDs or other target-binding binding domains that bind one or more antigens expressed on the surface of a B cell. In some embodiments, the DDpp comprises a DD that specifically binds AFP p26 e.g., a DD having an amino acid sequence selected from the group consisting of SEQ ID NO: 74-93 and 94) and further comprises one or more additional DDs or other target-binding binding domains that bind one or more cancer antigens. In some embodiments, the DDpp comprises a DD that specifically binds AFP p26 (e.g., a DD having an amino acid sequence selected from the group consisting of SEQ ID NO: 74-93 and 94) and specifically binds 2, 3, 4, 5, or more than 5, different targets. In further embodiments, the DDpp comprises a DD that specifically binds AFP p26 (e.g., a DD having an amino acid sequence selected from the group consisting of SEQ ID NO: 74-93 and 94) and specifically binds 2, 3, 4, 5, or more than 5, different cancer antigens. In some embodiments, the DDpp comprises a DD that specifically binds AFP p26 (e.g., a DD having an amino acid sequence selected from the group consisting of SEQ ID NO: 74-93 and 94) and specifically binds 2, 3, 4, 5, or more than 5, different cancer antigens expressed on the surface of a cancer cell. In some embodiments, the DDpp comprises a DD that specifically binds AFP p26 (e.g., a DD having an amino acid sequence selected from the group consisting of SEQ ID NO: 74-93 and 94) and specifically binds 2, 3, 4, 5, or more than 5, cancer antigens expressed on the surface of different cancer cells.

In some embodiments, the DDpp comprises a variant of a AFP p26-binding DD disclosed herein (reference DD) that retains the ability to specifically bind AFP p26. In some embodiments, the sequence of the AFP p26-binding DD variant contains 1, 2, 3, 4, 5, 6, 7, 8, 9, or 10, 1-3, 1-5, or 1-10, conservative or non-conservative substitutions compared to a reference AFP p26-binding DD having an amino acid sequence selected from the group consisting of SEQ ID NO: 74-93 and 94. In some embodiments, the sequence of the AFP p26-binding DD variant contains 1, 2, 3, 4, 5, 6, 7, 8, 9, or 10, 1-3, 1-5, or 1-10, conservative substitutions compared to a reference AFP p26-binding DD having an amino acid sequence selected from the group consisting of SEQ ID NO: 74-93 and 94. In some embodiments, the sequence of the AFP p26-binding DD variant contains 1, 2, 3, 4, 5, 6, 7, 8, 9, or 10, 1-3, 1-5, or 1-10, non-conservative substitutions compared to a reference AFP p26-binding DD having an amino acid sequence selected from the group consisting of SEQ ID NO: 74-93 and 94.

In some embodiments, the sequence of the AFP p26-binding DD variant contains a total of 1, 2, 3, 4, 5, 6, 7, 8, 9, or 10, 1-3, 1-5, or 1-10, conservative or non-conservative substitutions in positions corresponding to amino acid residues 1-22, 29-46, and 52-72, of a reference AFP p26-binding DD having an amino acid sequence selected from the group consisting of SEQ ID NO: 74-93 and 94. In some embodiments, the sequence of the AFP p26-binding DD variant contains a total of 1, 2, 3, 4, 5, 6, 7, 8, 9, or 10, 1-3, 1-5, or 1-10, conservative substitutions in positions corresponding to amino acid residues 1-22, 29-46, and 52-72, of a reference AFP p26-DD having an amino acid sequence selected from the group consisting of SEQ ID NO: 74-93 and 94. In some embodiments, the sequence of the AFP p26-binding DD variant contains a total of 1, 2, 3, 4, 5, 6, 7, 8, 9, or 10, 1-3, 1-5, or 1-10, non-conservative substitutions in positions corresponding to amino acid residues 1-22, 29-46, and 52-72, of a reference AFP p26-binding DD having an amino acid sequence selected from the group consisting of SEQ ID NO: 74-93 and 94. In some embodiments, the reference p26-binding DD comprises an amino acid sequence selected from the group consisting of SEQ ID NO: 70-73 and 92-94. In some embodiments, the reference p26-binding DD comprises the amino acid sequence of SEQ ID NO: 14.

In some embodiments, the sequence of the AFP p26-binding DD variant contains a total of 1, 2, 3, 4, 5, 6, 7, 8, 9, or 10, 1-3, 1-5, or 1-10, conservative or non-conservative substitutions in positions corresponding to amino acid residues: 2-6, 8-10, 12, 13, 15-17, 19, 20, 29, 30, 32-34, 36, 37, 39-41, 43, 44, 52-55, 57-59, 61, 62, 64-66, and 68-70, of a reference AFP p26-binding DD having an amino acid sequence selected from the group consisting of SEQ ID NO: 74-93 and 94. In some embodiments, the sequence of the AFP p26-binding DD variant contains a total of 1, 2, 3, 4, 5, 6, 7, 8, 9, or 10, 1-3, 1-5, or 1-10, conservative substitutions in positions corresponding to amino acid residues: 2-6, 8-10, 12, 13, 15-17, 19, 20, 29, 30, 32-34, 36, 37, 39-41, 43, 44, 52-55, 57-59, 61, 62, 64-66, and 68-70, of a reference DD having an amino acid sequence selected from the group consisting of SEQ ID NO: 74-93 and 94. In some embodiments, the sequence of the AFP p26-binding DD variant contains a total of 1, 2, 3, 4, 5, 6, 7, 8, 9, or 10, 1-3, 1-5, or 1-10, non-conservative substitutions in positions corresponding to amino acid residues: 2-6, 8-10, 12, 13, 15-17, 19, 20, 29, 30, 32-34, 36, 37, 39-41, 43, 44, 52-55, 57-59, 61, 62, 64-66, and 68-70, of a reference DD having an amino acid sequence selected from the group consisting of SEQ ID NO: 74-93 and 94. In some embodiments, the reference AFP p26-binding DD comprises an amino acid sequence selected from the group consisting of SEQ ID NO: 70-73 and 92-94. In some embodiments, the reference AFP p26-binding DD comprises the amino acid sequence of SEQ ID NO: 73.

In some embodiments, the sequence of the AFP p26-binding DD variant contains a total of 1, 2, 3, 4, 5, 6, 7, 8, 9, or 10, 1-3, 1-5, or 1-10, conservative or non-conservative substitutions in positions corresponding to amino acid residues: 7, 11, 14, 18, 21, 28, 31, 35, 38, 42, 45, 53, 56, 60, 63, and 67, of a reference AFP p26-binding DD having an amino acid sequence selected from the group consisting of SEQ ID NO: 74-93 and 94. In some embodiments, the sequence of the AFP p26-binding DD variant contains a total of 1, 2, 3, 4, 5, 6, 7, 8, 9, or 10, 1-3, 1-5, or 1-10, conservative substitutions in positions corresponding to amino acid residues: 7, 11, 14, 18, 21, 28, 31, 35, 38, 42, 45, 53, 56, 60, 63, and 67, of a reference DD having an amino acid sequence selected from the group consisting of SEQ ID NO: 74-93 and 94. In some embodiments, the sequence of the AFP p26-binding DD variant contains a total of 1, 2, 3, 4, 5, 6, 7, 8, 9, or 10, 1-3, 1-5, or 1-10, non-conservative substitutions in positions corresponding to amino acid residues: 7, 11, 14, 18, 21, 28, 31, 35, 38, 42, 45, 53, 56, 60, 63, and 67, of a reference DD having an amino acid sequence selected from the group consisting of SEQ ID NO: 74-93 and 94. In some embodiments, the reference AFP p26-binding DD comprises an amino acid sequence selected from the group consisting of SEQ ID NO: 70-73 and 92-94. In some embodiments, the reference AFP p26-binding DD comprises the amino acid sequence of SEQ ID NO: 73.

In some embodiments, the disclosure provides an AFP p26-binding DDpp that completely or partially (e.g., overlap with an epitope) block binding of a reference DD to AFP p26, wherein the reference DD has an amino acid sequence selected from SEQ ID NO: 74-93, and 94. In other embodiments, the disclosure provides AFP p26-binding DDpp that bind to the same epitope of AFP p26 as a a reference DD consisting of an amino acid sequence selected from SEQ ID NO: 74-93, and 94. In some embodiments, the reference p26-binding DD comprises an amino acid sequence selected from the group consisting of SEQ ID NO: 70-73 and 92-94. In some embodiments, the reference p26-binding DD comprises the amino acid sequence of SEQ ID NO: 73.

In some embodiments, the DDpp is a fusion protein comprising a DD that specifically binds AFP p26. In some embodiments, the DD specifically binds AFP p26 having an amino acid sequence consisting of SEQ ID NO: 37. In some embodiments, the DDpp fusion protein comprises an amino acid sequence selected from the group consisting of SEQ ID NO: 74-93 and 94. In some embodiments, a DD of the DDpp fusion protein specifically binds AFP p26 but does not specifically bind AFP having an amino acid sequence consisting of SEQ ID NO: 36. In other embodiments, the DDpp comprises a variant of an amino acid sequence selected from the group consisting of SEQ ID NO: 74-93 and 94. In other embodiments, the AFP p26-binding DDpp is an Fc fusion protein.

In some embodiments, the DDpp is a fusion protein comprising a DD that specifically binds AFP p26. In some embodiments, the DDpp is a fusion protein comprising a DD that specifically binds AFP p26 having an amino acid sequence consisting of SEQ ID NO: 37. In further embodiments, the DDpp comprises an amino acid sequence selected from the group consisting of SEQ ID NO: 74-93 and 94. In other embodiments, the DDpp is a fusion protein comprising a AFP p26-binding DD that is a variant of a DD comprising an amino acid sequence selected from the group consisting of SEQ ID NO: 74-93 and 94. In some embodiments, the DDpp is a fusion protein comprising a DD that specifically binds AFP p26 operably linked to a full-length antibody or a portion (fragment) of an antibody. In some embodiments, the DDpp is an Fc fusion protein. In some embodiment, the DDpp fusion protein comprises a full length IgG antibody (e.g., IgG1, IgG2, IgG2, or IgG4). In further embodiments, the DDpp fusion protein comprises a full length antibody that specifically binds a cancer antigen. In further embodiments, the DDpp comprises a commercially approved therapeutic antibody (e.g., rituximab, ofatumumab, ocrelizumab, veltuzumab, MEDI-551, epratuzumab, belimumab, tabalumab, AMG-557, MEDI-570, NN882, elotuzumab, and daratumumab). In other embodiments, the AFP p26-binding DDpp is an Fc fusion protein. In further embodiments, the Fc fusion protein comprises a variant human Fc domain.

In some embodiments, the DDpp is a fusion protein comprising an AFP p26-binding DD operably linked to a serum protein. In some embodiments, the DDpp fusion protein comprises an amino acid sequence selected from the group consisting of SEQ ID NO: 74-93 and 94. In other embodiments, the AFP p26-binding DDpp fusion protein comprises a variant of an amino acid sequence selected from the group consisting of SEQ ID NO: 74-93 and 94. In further embodiments, the DDpp fusion protein comprises human serum albumin or a fragment thereof. In some embodiments, the DDpp fusion protein contains a fragment of a serum protein or an antigenic fragment of a serum protein. In some embodiments, the DDpp fusion protein comprises a fragment consisting of 5-500, 5-400, 5-300, 5-200, 5-100, 5-50, 10-500, 10-400, 10-300, 10-200, 10-100, or 10-50 amino acids of a serum protein.

In some embodiments, the AFP p26-binding DDpp fusion protein comprises the extracellular domain of a receptor or a fragment thereof. In some embodiments, the DDpp fusion protein comprises a DD that comprises an amino acid sequence selected from the group consisting of SEQ ID NO: 74-93 and 94. In other embodiments, the AFP p26-binding DDpp fusion protein comprises a variant of an amino acid sequence selected from the group consisting of SEQ ID NO: 74-93 and 94. In further embodiments, the AFP p26-binding DDpp fusion protein comprises the extracellular domain of BCMA (SEQ ID NO: 34) or CD123 (SEQ ID NO: 1), or a fragment thereof. In further embodiments, the AFP p26-binding DDpp fusion protein comprises the extracellular domain of BCMA (SEQ ID NO: 34), or CD123 (SEQ ID NO: 1), or CS1 (SEQ ID NO: 35), or a fragment thereof. In some embodiments, the AFP p26-binding DDpp fusion protein comprises the extracellular domain of of a receptor selected from the group consisting of: CD19, CD20, CD22, HVEM, BTLA, DR3, CD37; TSLPR, IL7R, and gp96, or a fragment thereof.

In some embodiments, the AFP p26-binding DDpp fusion protein contains a fragment consisting of 5-500, 5-400, 5-300, 5-200, 5-100, 5-50, 10-500, 10-400, 10-300, 10-200, 10-100, or 10-50 amino acids of an extracellular domain, of a cell surface receptor. In some embodiments, the DDpp fusion protein contains a fragment of an extracellular domain of BCMA (SEQ ID NO: 34) or CD123 (SEQ ID NO: 1). In some embodiments, the DDpp fusion protein contains a fragment of an extracellular domain of BCMA (SEQ ID NO: 34), or CD123 (SEQ ID NO: 1), or CS1 (SEQ ID NO: 35). In some embodiments, the DDpp contains a fragment of an extracellular domain, of a receptor selected from the group consisting of: CD19, CD20, CD22, HVEM, BTLA, DR3, CD37; TSLPR, IL7R, and gp96.

In additional embodiments, the AFP p26-binding DDpp fusion protein comprises an intracellular protein (e.g., a nuclear protein) or a fragment thereof. In some embodiments, the DDpp fusion protein comprises a DD that comprises an amino acid sequence selected from the group consisting of SEQ ID NO: 74-93 and 94. In other embodiments, the AFP p26-binding DDpp fusion protein comprises a variant of an amino acid sequence selected from the group consisting of SEQ ID NO: 74-93 and 94. In some embodiments, the AFP p26-binding DDpp fusion protein comprises a fragment consisting of 5-500, 5-400, 5-300, 5-200, 5-100, 5-50, 10-500, 10-400, 10-300, 10-200, 10-100, or 10-50 amino acid residues of an intracellular protein (e.g., a nuclear protein). In some embodiments, the AFP p26-binding DDpp fusion protein comprises a fragment of a serum protein (e.g., HSA), an extracellular domain of a receptor (e.g., BCMA, CS1, CD123, and CD19), or an intracellular protein (e.g., a nuclear protein), consisting of 5-500, 5-400, 5-300, 5-200, 5-100, 5-50, 10-500, 10-400, 10-300, 10-200, 10-100, or 10-50 amino acid residues.

Nucleic acids encoding the DDpp and vectors containing the nucleic acids are also provided. Host cells containing the nucleic acids and vectors containing the nucleic acids (including viral particles) are also provided. In some embodiments, the host cell is a prokaryote or a eukaryote that display the variant DD on its surface. In some embodiments, the host cell displays the variant DD on its surface. In a further embodiment, the host cell is a phage that displays the variant DD on its surface. In a further embodiment, the host cell is a human immune cell that expresses a variant DD fusion protein on its surface.

A DDpp agonist refers to a DDpp that in some way increases or enhances the biological activity of the DDpp target (e.g., CD123) or has biological activity comparable to a known agonist of the DDpp target. In another embodiment, the DDpp is an antagonist of the target it binds (e.g., CD123). A DDpp antagonist refers to a DDpp that completely or partially blocks or in some way interferes with the biological activity of the DDpp target protein or has biological activity comparable to a known antagonist or inhibitor of the DDpp target protein.

DDpp Fusion Proteins

Provided herein are DDpp fusion proteins. A "fusion protein," "chimeric polypeptide," "chimeric protein," "chimeric antigen," and a DDpp that comprises/contains a heterologous polypeptide, is a polypeptide comprised of at least two polypeptides and optionally a linker to operatively link the two polypeptides into one continuous polypeptide produced, e.g., by recombinant processes. The two polypeptides may be operably attached directly or indirectly.

A "DDpp fusion protein" provided herein comprises at least one DDpp disclosed herein that specifically binds a target of interest (e.g., BCMA (SEQ ID NO: 34), CD123 (SEQ ID NO: 1), CS1 (SEQ ID NO: 35), HER2, AFP (SEQ ID NO: 36), AFP p26 (SEQ ID NO: 37), or a fragment thereof). In one embodiment, the DDpp fusion protein contains one DDpp.

In some embodiments, the DDpp fusion protein is a soluble protein comprising one or more target-binding DDpp and a p26 protein (e.g., having the sequence of SEQ ID NO: 37-43 or 44). In some embodiments, the soluble DDpp fusion protein has a plasma half-life in vivo of at least 1 hour, at least 2 hours, at least 4 hours, at least 8 hours, at least 16 hours, at least 32 hours, at least 64 hours, or more. In some embodiments, the soluble fusion protein has an in vivo plasma half-life of at least 1 hour, at least 2 hours, at least 4 hours, at least 8 hours, at least 16 hours, at least 32 hours, at least 64 hours, or more than 65 hours, or 1-10 hours, 2-10 hours, 4-10 hours, 6-10 hours, or 6-9 hours in a mouse. In some embodiments, the soluble DDpp fusion protein has an in vivo plasma half-life of at least 1 hour, at least 2 hours, at least 4 hours, at least 8 hours, at least 16 hours, at least 32 hours, at least 64 hours, or more than 65 hours, or 1-10 hours, 2-10 hours, 4-10 hours, 6-10 hours, or 6-9 hours, in a human.

In some embodiments, the disclosure provides a method for modifying the in vivo half-life (e.g., in a mouse or human) of a soluble fusion protein comprising a p26 protein (e.g., having the sequence of SEQ ID NO: 37-43 or 44). In some embodiments, the soluble p26 fusion protein comprises one or more target-binding DDpp. In some embodiments, the half-life of the p26 soluble fusion protein is increased or decreased by substituting or deleting one or more amino acid residues normally found in the human p26 protein, or by inserting one or more amino acid residues not normally found in the human p26 protein. In another embodiment, the p26 sequence of the soluble fusion protein is modified through 1, 2, 3, 4, 5, 10, or 1-20, 1-10, 3-10, or 3-5, amino acid substitutions (conservative and/or nonconservative substitutions), deletions, and/or insertions so as to increase or decrease the in vivo half-life of the soluble fusion protein. In a particular embodiment, the amino acid residue corresponding to the glutamine (Gln, Q) at position 217 of SEQ ID NO: 37 of p26 is substituted with another amino acid residues. In a further embodiment the substitution is Gln217Pro. In another embodiment, the p26 sequence of the soluble fusion protein is modified through deletion of 1-150, 1-100, 1-50, 1-25 or 1-10 amino acid residues so as to increase or decrease the in vivo half-life of the soluble fusion protein. In additional embodiments, the p26 sequence of the soluble fusion protein is modified through 1, 2, 3, 4, 5, 10 or 1-20, 1-10, 3-10, or 3-5, amino acid substitutions (conservative and/or nonconservative substitutions), deletions, and/or insertions so as to increase or decrease the interaction of the soluble fusion protein with FcRn.

A. Multimeric DDpp Fusion Proteins

In one embodiment, the DDpp fusion protein comprises more than one DDpp, wherein two or more DDpp have the same or different specificities. In additional embodiments, the DDpp fusion protein comprises a tandem repeat of the same or different DD that allow a DDpp fusion protein to bind multiple targets and/or repeating epitopes or different epitopes on the same target. In some embodiments, the DDpp fusion protein comprises at least 2, 3, 4, or 5, or more than 5, DDpp. In some embodiments, the DDpp fusion protein contains 1-3, 1-4, 1-5, or more than 5, different DDpp. In some embodiments, the DDpp fusion protein contains at least 2, 3, 4, or 5, or more than 5, different DDpp. Thus, a DDpp fusion protein can be a monomeric DDpp (i.e., containing one DDpp) or multimeric DDpp (i.e., containing more than one DDpp in tandem optionally operably connected by a linker). In some embodiments, the use of multimeric DDpp provides enhanced (e.g., synergistic) target binding. In additional embodiments, multimeric DDpp allows targeting of more than one target using a single DDpp construct (e.g., bi-, tri-specific, etc.). The linkage of two or more identical DDpp results in a multivalent molecule that provides distinct advantages (e.g., increased binding avidity, target clustering and receptor activation) over monovalent compositions. The linkage of two or more different DDpp results in a multivalent and multi-specific molecule that has the potential to bind more than one target antigen, either independently or simultaneously.

The multimeric DDpp fusion protein can be a DDpp homo-multimeric (i.e., containing more than one of the same DDpp in tandem optionally connected by linker(s) (e.g., homodimers, homotrimers, homotetramers etc.) or DDpp hetero-multimeric (i.e., containing two or more DDpp in which there are at least two different DDpp proteins. The number of monomeric DDpp included within a multimeric composition may vary, depending on the embodiment, and may be defined, at least in part, by the expression system in which the DDpp is produced. In some embodiments, however, the fusion proteins may comprises multimers of about 5 to about 10 DDpp subunits, about 10 to about 15 subunits, about 15 to about 20 subunits, about 20 to about 25 subunits, or about 25 to about 30 subunits (including numbers in between those listed as well as endpoints). Moreover, multiple tandem components of a DDpp fusion protein can contain the same or different DDpp. In some DDpp fusions, the DDpp are present as a monomer, or in homomultimers or heteromers such as, homodimers or heterodimers, homotrimers or heterotrimers, homotetramers or heterotetramers.

A DDpp fusion protein can be "monospecific" or "multi-specific." A DDpp fusion protein that is "multi-specific" (e.g., bispecific, trispecific or of greater multi-specificity) recognizes and binds to two or more different epitopes present on one or more different molecules (e.g., proteins, solid support structures, etc.).

In some embodiments, two or more DDs are fused together as a multivalent DDpp. The DD of the multivalent DDpp may be the same or different. Thus, the disclosure provides a DDpp homo-dimer (i.e., a DDpp comprising two identical DD), a DDpp homo-multimer (i.e., a DDpp comprising three or more identical DD), a DDpp hetero-dimer (i.e., a DDpp comprising two different DD), and DDpp hetero-multimer (i.e., a DDpp comprising three or more DD, wherein at least two of the DD are different) comprising any of the DD described herein, optionally attached by one or more linkers.

In some embodiments, two or more DDs are linked by a multimerization domain or attached via chemical linkage, to generate a multivalent DD complex. The DD of the multivalent DD complex may be the same or different. Thus, the disclosure provides a DD homo-dimer complex (i.e., a DD complex comprising two identical DD), a DD homo-multimer complex (i.e., a DD complex comprising three or more identical DD), a DD hetero-dimer complex (i.e., a DD complex comprising two different DD), and DD hetero-multimer complex (i.e., a DD complex comprising three or more DD, wherein at least two of the DD are different) comprising any of the DD described herein, optionally attached by one or more linkers.

In one embodiment, a multi-specific DDpp fusion protein contains at least two DDpp that bind to at least two different epitopes on a single target of interest (e.g., CD123, CD33, LeY, CD38, BCMA, or CS1, preferably CD123, CD33, LeY, or CD38). In a further embodiment, the DDpp fusion is bispecific and specifically binds to two different targets expressed on the surface of two different cell types. In one embodiment the bispecific DDpp fusion protein specifically binds to a target on a cancer cell and a target on an immune effector cell. In one embodiment the bispecific DDpp fusion protein specifically binds a target expressed on a cancer cell (e.g., CD123) and a target expressed on the surface of a T lymphocyte (e.g., CD3). In one embodiment the bispecific DDpp fusion protein specifically binds CD123 and CD33. In one embodiment the bispecific DDpp fusion protein specifically binds CD123 and CD38. In one embodiment the bispecific DDpp fusion protein specifically binds CD123 and LeY.

In additional embodiments, a multi-specific DDpp fusion protein comprises at least one DDpp that specifically binds one epitope on a target of interest and at least one other domain or sequence conferring function (e.g., an antibody fragment or domain such as an scFv) that specifically binds to a different epitope on the same target of interest. In one embodiment, a multi-specific DDpp fusion protein comprises at least one DDpp that specifically binds to an epitope on a target of interest and at least one domain or sequence conferring function e.g., an antibody fragment or domain (e.g., scFv), that specifically binds to an epitope on a different target of interest. In one embodiment, the multi-specific DDpp fusion protein comprises at least one DDpp that specifically binds to an epitope on a target of interest and at least one domain or sequence that specifically binds to an epitope on a different target on the same cell. In other embodiments, a DDpp fusion protein comprises at least one DDpp and at least one other DDpp or domain sequence conferring function, e.g., an antibody fragment or domain that specifically binds to a solid support.

In a further embodiment, the multimeric DDpp fusion comprising 2 or more DDpp are in turn fused with other heterologous proteins (or their subdomains) and in so doing, impart the multivalent and multi-specific properties to the fusion partner. Examples of fusion partners of a DDpp include but are not limited to, antibodies, antibody subdomains (e.g., scFv or Fc domains), serum albumin, serum albumin subdomains, cell surface receptors, an alpha chain of a T cell receptor (TCR), a beta chain of a T cell receptor, cell surface receptor subdomains, peptides, peptide tags (e.g., FLAG or myc), fibronectin type III repeats, z-domains, elastin-like polypeptides. The number and location of DDpp and their respective positions within the fusion protein can vary. For example, DDpp(s) can be located at one or all termini of a fusion partner and/or interspersed within heterologous subunits within the DDpp fusion partner.

In additional embodiments, a DDpp fusion protein comprises a DDpp and a polypeptide sequence containing an additional domain. In some embodiments, the DDpp fusion protein comprises a DDpp and a member selected from: an antibody, an antibody fragment (e.g., an antigen binding domain or portion thereof (e.g., an scFv), an effector domain or portion thereof, an FcRn binding domain or portion thereof, and an Fc or a portion thereof), a serum protein (e.g., albumin or a portion thereof), a cytokine, a growth factor, a hormone, an imaging agent, a labeling agent, and a peptide tag. In some embodiments, the DDpp fusion protein comprises an Fc domain of an immunoglobulin (e.g., a human Fc domain) or a portion thereof. In further embodiments, the Fc domain is a variant human Fc domain.

In some embodiments, the DDpp is fused to a heterologous polypeptide. In some embodiments, the heterologous polypeptide comprises a full-length antibody or an antibody fragment. In some embodiments, the DD is fused to: the amino terminus of a full-length antibody heavy chain; the amino terminus of a full-length antibody light chain; the carboxyl terminus of a full-length antibody heavy chain; or the carboxyl terminus of a full-length antibody light chain. In other embodiments, the DD is fused to an antibody fragment which is an Fc. In additional embodiments, the heterologous polypeptide comprises a member selected from the group consisting of: (i) a transmembrane domain; (ii) a membrane associating domain; (iii) human serum albumin or a fragment thereof; (iv) AFP or a fragment thereof; (v) AFP p26 or a fragment thereof; (vi) the extracellular domain of a receptor or a fragment thereof; and (vii) the extracellular domain of an intracellular receptor (e.g., a nuclear protein) or a fragment thereof. In some embodiments, the DDpp contains a heterologous polypeptide comprising the extracellular domain, or a fragment of an extracellular domain, of a cell surface receptor.

In some embodiments, the DDpp of a DDpp fusion protein is incorporated into a larger, multi-domain molecular complex (e.g., a monomeric or multimeric DDpp fusion protein) and in so doing, imparts the functional attributes of the incorporated DDpp to the resultant fusion protein. In some embodiments, the DDpp fusion protein comprises a DDpp and a polypeptide sequence from an antibody, an antibody fragment, a serum protein (e.g., human serum albumin) or serum protein fragment, or a cell surface receptor, an alpha chain of a T cell receptor (TCR), a beta chain of a T cell receptor, cytokine, growth factor, hormone, or enzyme, or fragment thereof. Incorporation of DD into multidomain and/or multifunctional complexes can routinely be achieved by way of recombinant fusion to another polypeptide, binding to another chemical moiety, and covalent chemical linkage to another polypeptide (or other desirable chemical compound) using techniques known in the art. DDpp fusion proteins can additionally contain other optional components such as linkers and other components described herein.

B. Adapters

In some embodiments, a DDpp fusion protein described herein is an Adapter protein. The Adapter comprises an antigenic determinant (AD) and an antigenic determinant binding domain (ADBD). The Adapter can further comprise additional ADs, additional ADBDs, and/or other additional domains. In some embodiments, an Adapter provided herein comprises at least one ADBD comprising a D domain.

In some embodiments, an Adapter provided herein comprises (a) a D domain (DD) that binds to CD123 and (b) an antigenic determinant (AD). In some embodiments, the D domain that binds to CD123 comprises an amino acid sequence selected from the group consisting of SEQ ID NO: 8-33, 99 and 100. In some embodiments, the D domain that binds to CD123 comprises an amino acid sequence selected from the group consisting of SEQ ID NO: 8, 13, 14, 31, 32, and 33. In some embodiments, the D domain that binds to CD123 comprises the amino acid sequence of SEQ ID NO: 14. In some embodiments, the Adapter is a monovalent Adapter comprising a single D domain that binds CD123. In some embodiments, the Adapter is a bivalent Adapter comprising two D domains that bind CD123. In some embodiments, the two D domains that bind CD123 are the same. In some embodiments, the two D domains that bind CD123 are different. In some embodiments, the Adapter is a bivalent Adapter comprising a first D domain that binds CD123 and a second D domain that binds a second AD. In some embodiments, the second AD is CD33 or LeY. In some embodiments, a monovalent Adapter comprises a D domain comprising an amino acid sequence selected from the group consisting of SEQ ID NO: 8, 13, 14, 31, 32, and 33. In some embodiments, the monovalent Adapter comprises the D domain comprising the amino acid sequence of SEQ ID NO: 14. In some embodiments, a bivalent Adapter comprises a DD comprising an amino acid sequence selected from the group consisting of SEQ ID NO: 8, 13, 14, 31, 32, and 33. In some embodiments, the bivalent Adapter comprises the D domain comprising the amino acid sequence of SEQ ID NO: 14. In some embodiments, a bivalent Adapter comprises two identical D domains comprising an amino acid sequence selected from the group consisting of SEQ ID NO: 8, 13, 14, 31, 32, and 33. In some embodiments, the bivalent Adapter comprises two identical D domains comprising the amino acid sequence of SEQ ID NO: 14. In some embodiments, the Adapter comprises an AFP p26 antigenic determinant (AD). In some embodiments, the AFP p26 AD comprises an amino acid sequence selected from the group consisting of SEQ ID NO: 37-43 and 44. In some embodiments, the AFP p26 AD comprises the amino acid sequence of SEQ ID NO: 37. In some embodiments, the AFP p26 AD comprises the amino acid sequence of SEQ ID NO: 38. In some embodiments, the AFP p26 AD comprises the amino acid sequence of SEQ ID NO: 39. In some embodiments, the AFP p26 AD comprises the amino acid sequence of SEQ ID NO: 40. In some embodiments, the monovalent Adapter comprises the amino acid sequence of SEQ ID NO: 50-54 or 55. In some embodiments, the monovalent Adapter comprises the amino acid sequence of SEQ ID NO: 50. In some embodiments, the bivalent Adapter comprises the amino acid sequence of SEQ ID NO: 56-60 or 61. In some embodiments, the monovalent Adapter comprises the amino acid sequence of SEQ ID NO: 61. In some embodiments, the Adapter comprises one or more linkers. In some embodiments, the Adapter is capable of directing an immune response to a cell expressing CD123 in an in vitro assay comprising the Adapter, a cell expressing CD123 and an immune effector cell expressing a CAR comprising an ADBD that binds the AD comprised by the Adapter, e.g., a CAR comprising a D domain that binds AFP p26.

In some embodiments, an Adapter provided herein comprising (a) a D domain that binds to CD123 and (b) an antigenic determinant binding domain (ADBD) that binds an AFP p26 AD. In some embodiments, the AFP p26 AD comprises an amino acid sequence selected from the group consisting of SEQ ID NO: 37-43 and 44. In some embodiments, the AFP p26 AD comprises the amino acid sequence of SEQ ID NO: 37. In some embodiments, the AFP p26 AD comprises the amino acid sequence of SEQ ID NO: 39. In some embodiments, the D domain that binds to CD123 comprises an amino acid sequence selected from the group consisting of SEQ ID NO: 8-33, 99 and 100. In some embodiments, the D domain that binds to CD123 comprises an amino acid sequence selected from the group consisting of SEQ ID NO: 8, 13, 14, 31, 32, and 33. In some embodiments, the D domain that binds to CD123 comprises the amino acid sequence of SEQ ID NO: 14. In some embodiments, the ADBD that binds to an AFP p26 AD comprises a D domain that binds to the AFP p26 AD. In some embodiments, the D domain that binds to an AFP p26 AD comprises an amino acid sequence selected from the group consisting of SEQ ID NO: 70-73 and 92-94. In some embodiments, the D domain that binds to an AFP p26 AD comprises the amino acid sequence of SEQ ID NO: 73. In some embodiments, the Adapter comprises one or more linkers. In some embodiments, the Adapter is capable of directing an immune response to a cell expressing CD123 in an in vitro assay comprising the Adapter, a cell expressing CD123 and an immune effector cell expressing a CAR comprising an AFP p26 AD.

In an Adapter provided herein, the AD can be N-terminal to ADBD. Alternatively, the ADBD can be N-terminal to the AD. In some embodiments, the AD and ADBD are directly fused. In some embodiments, the AD and the ADBD are fused via a linker (a protein linker or chemical linker) or another protein domain (e.g., a functional domain) In some embodiments, an Adapter provided herein comprises at least one ADBD comprising a D domain.

In some embodiments, the Adapter comprises a linker located between an ADBD and another functional domain of the Adapter. In some embodiments, the linker is located between two ADBDs of the Adapter. In some embodiments, the linker is located between the AD and an ADBD of the Adapter. Suitable linkers for coupling the two or more functional domains of the Adapter will be clear to persons skilled in the art and may generally be any linker used in the art to link peptides, proteins or other organic molecules. Exemplary linkers are provided herein. In particular embodiments, the linker(s) is suitable for constructing proteins or polypeptides that are intended for pharmaceutical use. In some embodiments, an Adapter provided herein comprises at least one ADBD comprising a D domain.

In addition to the AD (or multiple ADs) and the ADBD (or multiple ADBDs), an Adapter provided herein can further comprise an additional domain or additional domains, e.g., a domain that confers an extended half-life.

In some embodiments, the Adapter, or the ADBD in the Adapter, is deimmunized.

The Adapters provided herein have uses that include but are not limited to diagnostic, analytic, and therapeutic applications. In particular embodiments, the Adapters are used in combination with chimeric antigen receptors (CARs) provided herein expressed on the surface of cells, e.g., to kill a target cell.

Adapters suitable for use in connection with the DDpp (e.g., Adapter and CAR) disclosed herein have been disclosed in Int'l. Appl. Pub. Nos. WO 2016164305, WO 2016164308A1, WO 2019099440, and WO 2019099433, U.S. Pat. Nos. 10,662,248, and 10,647,775, and US Pat. Appl. Nos. 20200223934, and 20210002381, each of which is incorporated herein by reference for all purposes.

i. Antigenic Determinants (ADs)

An Adapter provided herein comprises at least one antigenic determinant (AD). In some embodiments, the Adapter comprises a single AD. In some embodiments, the Adapter comprises two or more ADs. Where an Adapter comprises two or more ADs, the ADs can be the same or different.

In some embodiments, the AD is an epitope of AFP p26. In further embodiments, the AD comprises 5-25, 5-50, 5-75, 5-100, 5-125, or 5-150 amino acid residues, more than 150 amino acid residues, or all of the amino acid residues of SEQ ID NO: 37. In further embodiments, the AD comprises the amino acid sequence of SEQ ID NO: 37. In further embodiments, the AD comprises 5-25, 5-50, 5-75, 5-100, 5-125, or 5-150 amino acid residues, more than 150 amino acid residues, or all of the amino acid residues of SEQ ID NO: 39. In further embodiments, the AD comprises the amino acid sequence of SEQ ID NO: 39. In further embodiments, the AD comprises the amino acid residues of SEQ ID NO: 37-43 or 44.

In some embodiments, the Adapter comprises the extracellular domain of BCMA (e.g., a polypeptide comprising the sequence of SEQ ID NO: 34. In some embodiments, the Adapter comprises 5-25, 5-50, 5-75, 5-100, 5-125, or 5-150 amino acid residues, more than 150 amino acid residues, or all of the amino acid residues of SEQ ID NO: 34.

In some embodiments, Adapter comprises the extracellular domain of CD123 (e.g., a polypeptide comprising the sequence of SEQ ID NO: 1. In some embodiments, the Adapter comprises 5-25, 5-50, 5-75, 5-100, 5-125, or 5-150 amino acid residues, more than 150 amino acid residues, or all of the amino acid residues of SEQ ID NO: 1.

In some embodiments, the Adapter comprises the extracellular domain of CD19 (e.g., a polypeptide comprising the sequence of SEQ ID NO: 95. In some embodiments, the Adapter comprises 5-25, 5-50, 5-75, 5-100, 5-125, or 5-150 amino acid residues, more than 150 amino acid residues, or all of the amino acid residues of SEQ ID NO: 95.

In some embodiments, the Adapter comprises the extracellular domain of CS1 (e.g., a polypeptide comprising the sequence of SEQ ID NO: 35). In some embodiments, the Adapter comprises 5-25, 5-50, 5-75, 5-100, 5-125, or 5-150 amino acid residues, more than 150 amino acid residues, or all of the amino acid residues of SEQ ID NO: 35. In some embodiments, the Adapter comprises the extracellular domain of CD20. In some embodiments, the Adapter comprises the extracellular domain of CD22. In some embodiments, the Adapter comprises the extracellular domain of CD37. In some embodiments, the Adapter comprises the extracellular domain of HER2. In some embodiments, the Adapter comprises the extracellular domain of CD45. In some embodiments, the Adapter comprises the extracellular domain of CD26, CD30, CD33, or CD38.

In some embodiments, the AD is an epitope of AFP. In further embodiments, the AD comprises 5-25, 5-50, 5-75, 5-100, 5-125, or 5-150 amino acid residues, more than 150 amino acid residues, or all of the amino acid residues of SEQ ID NO: 36.

In some embodiments, Adapter comprises a p26 protein (e.g., having the sequence of SEQ ID NO: 37-43 or 44). In some embodiments, the Adapter has a plasma half-life in vivo of at least 1 hour, at least 2 hours, at least 4 hours, at least 8 hours, at least 16 hours, at least 32 hours, at least 64 hours, or more. In some embodiments, the Adapter has an in vivo plasma half-life of at least 1 hour, at least 2 hours, at least 4 hours, at least 8 hours, at least 16 hours, at least 32 hours, at least 64 hours, or more than 65 hours, or 1-10 hours, 2-10 hours, 4-10 hours, 6-10 hours, or 6-9 hours in a mouse. In some embodiments, the Adapter has an in vivo plasma half-life of at least 1 hour, at least 2 hours, at least 4 hours, at least 8 hours, at least 16 hours, at least 32 hours, at least 64 hours, or more than 65 hours, or 1-10 hours, 2-10 hours, 4-10 hours, 6-10 hours, or 6-9 hours, in a human.

In some embodiments, the disclosure provides a method for modifying the in vivo half-life (e.g., in a mouse or human) of an Adapter comprising a p26 protein (e.g., having the sequence of SEQ ID NO: 37-43 or 44). In some embodiments, the Adapter comprises one or more target-binding DDpp. In some embodiments, the half-life of the Adapter is increased or decreased by substituting or deleting one or more amino acid residues normally found in the human p26 protein, or by inserting one or more amino acid residues not normally found in the human p26 protein. In another embodiment, the p26 sequence of the Adapter is modified through 1, 2, 3, 4, 5, 10, or 1-20, 1-10, 3-10, or 3-5, amino acid substitutions (conservative and/or nonconservative substitutions), deletions, and/or insertions so as to increase or decrease the in vivo half-life of the Adapter. In a particular embodiment, the amino acid residue corresponding to the glutamine (Gln, Q) at position 217 of p26 (SEQ ID NO: 37) is substituted with another amino acid residues. In a further embodiment, the substitution is Gln217Pro. In another embodiment, the p26 sequence of the Adapter is modified through deletion of 1-150, 1-100, 1-50, 1-25 or 1-10 amino acid residues so as to increase or decrease the in vivo half-life of the Adapter. In additional embodiments, the p26 sequence of the Adapter is modified through 1, 2, 3, 4, 5, 10 or 1-20, 1-10, 3-10, or 3-5, amino acid substitutions (conservative and/or nonconservative substitutions), deletions, and/or insertions so as to increase or decrease the interaction of the Adapter with FcRn.

In some embodiments, the AD (e.g., in an Adapter and/or on a target cell) is an AD that is present in a naturally occurring protein or other molecule. In some embodiments, the AD is an AD that is endogenous to humans.

In some embodiments, the AD is an epitope of a human intracellular protein. In further embodiments, the AD is an epitope of a human intracellular protein selected from: Tyk2, Jak1, Jak2, Jak3, LCK, ZAP-70, and GRB2. In further embodiments, the AD comprises 5-25, 5-50, 5-75, 5-100, 5-125, or 5-150 amino acid residues, more than 150 amino acid residues, or all of the amino acid residues of the intracellular protein.

In some embodiments, the target of interest specifically bound by the ADBD of an Adapter is itself an AD of another Adapter, having a different sequence.

ii. Antigenic Determinant Binding Domains (ADBDs)

An Adapter provided herein comprises at least one antigenic determinant binding domain (ADBD). In some embodiments, the Adapter contains one ADBD. In some embodiments, the Adapter contains at least 2, 3, 4, or 5, or more than 5 ADBDs. In some embodiments, the Adapter contains 1-3, 1-4, 1-5, or more than 5 different ADBDs. In some embodiments, the Adapter contains at least 2, 3, 4, or 5, or more than 5 different ADBDs. Thus, an Adapter can comprise a monomeric ADBD (i.e., containing one antigenic determinant binding domain) or multimeric ADBDs (i.e., containing more than one antigenic determinant binding domains in tandem optionally operably connected by a linker). In some embodiments, the use of a multimeric Adapter provides enhanced (e.g., synergistic) target binding. In additional embodiments, the use of a multimeric Adapter allows for targeting of more than one target using a single Adapter construct (e.g., bi-, tri-specific, etc.). In some embodiments, an Adapter provided herein comprises at least one ADBD comprising a D domain. In some embodiments, an Adapter provided herein comprises more than one ADBD comprising a D domain. In some embodiments, all ADBDs of an Adapter provided herein comprise a D domain.

The multimeric Adapter is homo-multimeric (i.e., containing more than one of the same ADBD optionally connected by linker(s)(e.g., homodimers, homotrimers, homotetramers etc.) or Adapter hetero-multimeric (i.e., containing two or more antigenic determinant binding domains in which there are at least two different antigenic determinant binding domains). The number of ADBDs included in any particular Adapter may vary, depending on the embodiment, and may be defined, at least in part, by the expression system in which the Adapter is produced. In several embodiments, however, the fusion proteins may comprise multimers of about 5 to about 10 ADBDs, about 10 to about 15 ADBDs, about 15 to about 20 ADBDs, about 20 to about 25 ADBDs, or about 25 to about 30 ADBDs (including numbers in between those listed as well as endpoints). Moreover, multiple domains of an Adapter can contain the same or different ADBD(s). In some embodiments, 2, 3, 4, 5, or more than 5 domains are in tandem. In some embodiments, an Adapter provided herein comprises at least one ADBD comprising a D domain. In some embodiments, an Adapter provided herein comprises more than one ADBD comprising a D domain. In some embodiments, all ADBDs of an Adapter provided herein comprise a D domain.

In one embodiment, the Adapter comprises two or more ADBDs that are operably linked. In one embodiment, the Adapter comprises two ADBDs that bind to the same or different ADs on a target antigen. The linkage of two or more identical ADBDs that bind to the same target antigen results in a multivalent molecule that provides distinct advantages (e.g., increased binding avidity, target clustering and receptor activation) over compositions that only contain one ADBD for a target antigen. In another embodiment the Adapter comprises two ADBDs that bind to different antigens. In some embodiments the Adapter comprises two ADBDs that bind to different antigens on the same cell. In some embodiments the Adapter comprises two ADBDs that bind to different antigens on different cells. The linkage of two or more ADBDs results in a multivalent and multi-specific Adapter that has the potential to bind more than one target antigen, either independently or simultaneously. In some embodiments, the multivalent Adapter is able to bind the same target antigen simultaneously. In some embodiments, the multivalent Adapter is able to bind different target antigens simultaneously. In some embodiments, the Adapter comprises two or more operably linked ADBDs that are separated by an Antigenic Determinant. In some embodiments, the Antigenic Determinant is at least 50, 75, 100, 150, 200, 250, 300, 350, 400, 450, or 500 amino acids in length. In some embodiments, the Antigenic Determinant is 5-500, 5-400, 10-300, 5-200, 50-100, 5-50, 10-500, 10-400, 10-300, 10-200, 10-100, 10-50, 50-500, 50-400, 50-300, 50-200, 50-100 50-75, 100-500, 100-400, 100-300, 100-200, or 100-150 amino acids in length. In further embodiments, the Adapter comprises two or more operably linked ADBDs that are separated by a BCMA Antigenic Determinant. In further embodiments, the Adapter comprises two or more operably linked ADBDs that are separated by an AFP P26 Antigenic Determinant. In some embodiments, an Adapter provided herein comprises at least one ADBD comprising a D domain. In some embodiments, an Adapter provided herein comprises more than one ADBD comprising a D domain. In some embodiments, all ADBDs of an Adapter provided herein comprise a D domain.

An ADBD in the Adapter provided herein can bind to any AD. In some embodiments, the ADBD binds to CD123 (e.g., a polypeptide comprising the sequence of SEQ ID NO: 1). In some embodiments, the ADBD binds to AFP p26 (e.g., a polypeptide comprising the sequence of SEQ ID NO: 37-43 or 44, preferably SEQ ID NO: 37 or 39). In some embodiments, the ADBD binds to BCMA (e.g., a polypeptide comprising the sequence of SEQ ID NO: 34). In some embodiments, the ADBD binds to CD22. In some embodiments, the ADBD binds to CD19. In some embodiments, the ADBD binds to CD20. In some embodiments, the ADBD binds to CD37. In some embodiments, the ADBD binds to CS1. In some embodiments, the ADBD binds to HER2. In some embodiments, the ADBD binds to CD45. In some embodiments, the ADBD in the Adapter provided herein specifically binds to an AD of human CD26, CD30, CD33, or CD38. An Adapter can be "monospecific" or "multi-specific." An Adapter that is "multi-specific" (e.g., bispecific, trispecific or of greater multi-specificity) recognizes and binds to two or more different epitopes present on one or more different molecules. In some embodiments, an Adapter provided herein comprises at least one ADBD comprising a D domain. In some embodiments, an Adapter provided herein comprises more than one ADBD comprising a D domain. In some embodiments, all ADBDs of an Adapter provided herein comprise a D domain.

In some embodiments, Adapter comprises a domain (e.g., the extracellular domain) of CD123 (e.g., a polypeptide comprising the sequence of SEQ ID NO: 1). In some embodiments, the Adapter comprises a domain (e.g., the extracellular domain) of BCMA (e.g., a polypeptide comprising the sequence of SEQ ID NO 34). In some embodiments, the Adapter comprises a domain (e.g., the extracellular domain) of CD22. In some embodiments, the Adapter comprises a domain (e.g., the extracellular domain) of CD19. In some embodiments, the Adapter comprises a domain (e.g., the extracellular domain) of CS1. In some embodiments, the Adapter comprises a domain (e.g., the extracellular domain) of HER2. In some embodiments, the Adapter comprises a domain (e.g., the extracellular domain) of CD45. In some embodiments, the Adapter comprises a domain (e.g., the extracellular domain) of CD26, CD30, CD33, or CD38. In some embodiments, the Adapter comprises a fragment of a domain. In some embodiments, the Adapter comprises a fragment of a domain that is at least 50, 75, 100, 150, 200, 250, 300, 350, 400, 450, or 500 amino acids in length. In some embodiments, the Antigenic Determinant is 5-500, 5-400, 10-300, 5-200, 50-100, 5-50, 10-500, 10-400, 10-300, 10-200, 10-100, 10-50, 50-500, 50-400, 50-300, 50-200, 50-100 50-75, 100-500, 100-400, 100-300, 100-200, or 100-150, amino acids in length. In some embodiments, an Adapter provided herein comprises at least one ADBD comprising a D domain. In some embodiments, an Adapter provided herein comprises more than one ADBD comprising a D domain. In some embodiments, all ADBDs of an Adapter provided herein comprise a D domain.

In some embodiments, the Adapter contains at least two ADBDs that bind and cross-link one or more target antigens bound by the ADBDs and/or complexes containing the target antigen(s). In some embodiments, the cross-linked antigen(s) is on the same cell. In some embodiments, the cross-linked antigen(s) is on different cells. In some embodiments, the Adapter comprises two or more operably linked ADBDs that are separated by an Antigenic Determinant (e.g., a domain described above). In some embodiments, the Antigenic Determinant is at least 50, 75, 100, 150, 200, 250, 300, 350, 400, 450, or 500 amino acids in length. In some embodiments, the Antigenic Determinant is 5-500, 5-400, 10-300, 5-200, 50-100, 5-50, 10-500, 10-400, 10-300, 10-200, 10-100, 10-50, 50-500, 50-400, 50-300, 50-200, 50-100 50-75, 100-500, 100-400, 100-300, 100-200, or 100-150 amino acids in length. In further embodiments, the Adapter comprises two or more operably linked ADBDs that are separated by a BCMA Antigenic Determinant. In further embodiments, the Adapter comprises two or more operably linked ADBDs that are separated by a CD123 Antigenic Determinant. In further embodiments, the Adapter comprises two or more operably linked ADBDs that are separated by a CD26, CD30, CD33, or CD38 Antigenic Determinant. In further embodiments, the Adapter comprises two or more operably linked ADBDs that are separated by an AFP p26 Antigenic Determinant. In some embodiments, an Adapter provided herein comprises at least one ADBD comprising a D domain. In some embodiments, an Adapter provided herein comprises more than one ADBD comprising a D domain. In some embodiments, all ADBDs of an Adapter provided herein comprise a D domain.

In some embodiments, the Adapter contains at least two of the same ADBDs (i.e., is multivalent). In some embodiments, the multivalent Adapter is able to bind two or more of the same target antigens simultaneously. In some embodiments, the Adapter is multivalent and is able to bind the same target antigen simultaneously. In some embodiments, the multi-multivalent Adapter comprises two or more operably linked ADBDs that are separated by an Antigenic Determinant. In some embodiments, the Antigenic Determinant is at least 50, 75, 100, 150, 200, 250, 300, 350, 400, 450, or 500 amino acids in length. In some embodiments, the Antigenic Determinant is 5-500, 5-400, 10-300, 5-200, 50-100, 5-50, 10-500, 10-400, 10-300, 10-200, 10-100, 10-50, 50-500, 50-400, 50-300, 50-200, 50-100 50-75, 100-500, 100-400, 100-300, 100-200, or 100-150 amino acids in length. In further embodiments, the Adapter comprises two or more operably linked ADBDs that are separated by a CD123 Antigenic Determinant. In further embodiments, the multivalent Adapter comprises two or more operably linked ADBDs that are separated by a BCMA Antigenic Determinant. In further embodiments, the multivalent Adapter comprises two or more operably linked ADBDs that are separated by an AFP p26 Antigenic Determinant. In some embodiments, an Adapter provided herein comprises at least one ADBD comprising a D domain. In some embodiments, an Adapter provided herein comprises more than one ADBD comprising a D domain. In some embodiments, all ADBDs of an Adapter provided herein comprise a D domain.

In some embodiments, the Adapter contains at least two ADBDs that bind to different antigens (i.e., is multispecific). In some embodiments, the multi-specific Adapter is able to bind the different target antigens simultaneously. In some embodiments, the Adapter is also multivalent and is able to bind the same target antigen simultaneously. In some embodiments, the multi-specific Adapter comprises two or more operably linked ADBDs that are separated by an Antigenic Determinant. In some embodiments, the Antigenic Determinant is at least 50, 75, 100, 150, 200, 250, 300, 350, 400, 450, or 500 amino acids in length. In some embodiments, the Antigenic Determinant is 5-500, 5-400, 10-300, 5-200, 50-100, 5-50, 10-500, 10-400, 10-300, 10-200, 10-100, 10-50, 50-500, 50-400, 50-300, 50-200, 50-100 50-75, 100-500, 100-400, 100-300, 100-200, or 100-150 amino acids in length. In further embodiments, the Adapter comprises two or more operably linked ADBDs that are separated by a CD123 Antigenic Determinant. In further embodiments, the Adapter comprises two or more operably linked ADBDs that are separated by a BCMA Antigenic Determinant. In further embodiments, the Adapter comprises two or more operably linked ADBDs that are separated by an AFP p26 Antigenic Determinant. In some embodiments, an Adapter provided herein comprises at least one ADBD comprising a D domain. In some embodiments, an Adapter provided herein comprises more than one ADBD comprising a D domain. In some embodiments, all ADBDs of an Adapter provided herein comprise a D domain.

In one embodiment, a multi-specific Adapter contains at least two ADBDs that bind to at least two different epitopes on a single target of interest (e.g., CD123). In additional embodiments, a multi-specific Adapter comprises at least one ADBD that specifically binds one epitope on a target of interest and at least one other ADBD that specifically binds to a different epitope on the same target antigen. In one embodiment, a multi-specific Adapter comprises at least one ADBD that specifically binds to an epitope on a first target antigen and at least one ADBD that specifically binds to an epitope on a second antigen. In some embodiments, the Adapter comprises at least one ADBD that specifically binds to an epitope on a first target antigen on a cell and at least one ADBD that specifically binds to an epitope on a second antigen on the same cell. In some embodiments, the Adapter comprises at least one ADBD that specifically binds to an epitope on a first target antigen on a cell and at least one ADBD that specifically binds to an epitope on a second antigen on a different cell. In some embodiments, an Adapter provided herein comprises at least one ADBD comprising a D domain. In some embodiments, an Adapter provided herein comprises more than one ADBD comprising a D domain. In some embodiments, all ADBDs of an Adapter provided herein comprise a D domain.

In a further embodiment, the Adapter comprises 2 or more ADBDs that are operably linked with other heterologous proteins (or their subdomains) and in so doing, impart the multivalent, multi-specific, and/or functional properties (e.g., pharmacokinetics such as increased half-life or pharmacodynamics such as increased function) of the fusion partner to the Adapter fusion protein. Examples of fusion partners of an Adapter include but are not limited to, antibodies, antibody subdomains (e.g., scFv or Fc domains), serum albumin, serum albumin subdomains, cell surface receptors, an alpha chain of a T cell receptor (TCR), a beta chain of a T cell receptor, cell surface receptor subdomains, peptides, peptide tags (e.g., FLAG or myc). The number and location of ADBDs and their respective positions within the Adapter can vary. For example, ADBDs can be located at one or all termini of a fusion partner and/or interspersed within heterologous subunits within the Adapter fusion partner. In some embodiments the Adapter comprises 2 or more ADBDs that are separated by a heterologous protein (e.g., Antigenic Determinant). In some embodiments, the heterologous protein is at least 50, 75, 100, 150, 200, 250, 300, 350, 400, 450, or 500 amino acids in length. In some embodiments, the heterologous protein is 5-500, 5-400, 10-300, 5-200, 50-100, 5-50, 10-500, 10-400, 10-300, 10-200, 10-100, 10-50, 50-500, 50-400, 50-300, 50-200, 50-100 50-75, 100-500, 100-400, 100-300, 100-200, or 100-150 amino acids in length. In some embodiments, an Adapter provided herein comprises at least one ADBD comprising a D domain. In some embodiments, an Adapter provided herein comprises more than one ADBD comprising a D domain. In some embodiments, all ADBDs of an Adapter provided herein comprise a D domain.

In one embodiment, the Adapter is bispecific and contains ADBDs that specifically bind to two different target antigens. In further embodiments, the bispecific Adapter specifically binds to two different target antigens expressed on the surface of two different cell types. In further embodiments, the bispecific Adapter specifically binds to two different target antigens expressed on the surface of a tumor cell. In further embodiments, the bispecific Adapter specifically binds to two different target antigens expressed on the surface of an AML cell (e.g., CD123 and CD33 or LeY). In one embodiment, the bispecific Adapter binds to target antigens expressed on different cells. In a further embodiment, the bispecific Adapter binds to target antigens expressed on different cells of a tumor. In another embodiment, the bispecific Adapter binds to target antigens expressed on different cells within a tumor vasculature or tumor microenvironment. In one embodiment, the bispecific Adapter specifically binds to a cancer cell target and an immune effector cell target. In one embodiment the bispecific Adapter specifically binds a target expressed on a cancer cell (e.g. CD123) and a target expressed on the surface of a T lymphocyte (e.g., CD3). In some embodiments, the bispecific Adapter is able to bind the different target antigens simultaneously. In some embodiments, the bispecific Adapter comprises two or more operably linked ADBDs that are separated by an Antigenic Determinant. In some embodiments, the Antigenic Determinant is at least 50, 75, 100, 150, 200, 250, 300, 350, 400, 450, or 500 amino acids in length. In some embodiments, the Antigenic Determinant is 5-500, 5-400, 10-300, 5-200, 50-100, 5-50, 10-500, 10-400, 10-300, 10-200, 10-100, 10-50, 50-500, 50-400, 50-300, 50-200, 50-100 50-75, 100-500, 100-400, 100-300, 100-200, or 100-150 amino acids in length. In further embodiments, the Adapter comprises two or more operably linked ADBDs that are separated by a CD123 Antigenic Determinant. In further embodiments, the Adapter comprises two or more operably linked ADBDs that are separated by a BCMA Antigenic Determinant. In further embodiments, the Adapter comprises two or more operably linked ADBDs that are separated by an AFP P26 Antigenic Determinant. In some embodiments, an Adapter provided herein comprises at least one ADBD comprising a D domain. In some embodiments, an Adapter provided herein comprises more than one ADBD comprising a D domain. In some embodiments, all ADBDs of an Adapter provided herein comprise a D domain.

In some embodiments where the Adapter comprises more than one ADBD, the ADBD can be any of the types of ADBD discussed herein. For example, an ADBD can be an antibody, an antigen-binding fragment thereof, a ScFv, an alternative scaffold binding domain, a D domain, a T cell receptor, or an antigen-binding fragment thereof. In some embodiments, an Adapter provided herein comprises at least one ADBD comprising a D domain. In some embodiments, an Adapter provided herein comprises more than one ADBD comprising a D domain. In some embodiments, all ADBDs of an Adapter provided herein comprise a D domain.

In some embodiments, where an Adapter comprises more than one ADBD, those ADBD can be the same types of antigen-binding molecules or can be different. For example, an Adapter can comprise two ADBD that are D domains. The two ADBD that are D domains can be the same or different. An Adapter can also comprise an ADBD that is a D domain and an ADBD that is a scFv. An Adapter can also comprise an ADBD that is a T cell receptor or antigen-binding fragment thereof and an ADBD that is a scFv. In some embodiments, the Adapter comprises two or more operably linked ADBDs that are separated by an Antigenic Determinant. In some embodiments, the Antigenic Determinant is at least 50, 75, 100, 150, 200, 250, 300, 350, 400, 450, or 500 amino acids in length. In some embodiments, the Antigenic Determinant is 5-500, 5-400, 10-300, 5-200, 50-100, 5-50, 10-500, 10-400, 10-300, 10-200, 10-100, 10-50, 50-500, 50-400, 50-300, 50-200, 50-100 50-75, 100-500, 100-400, 100-300, 100-200, or 100-150 amino acids in length. In further embodiments, the Adapter comprises two or more operably linked ADBDs that are separated by a CD123 Antigenic Determinant. In further embodiments, the Adapter comprises two or more operably linked ADBDs that are separated by a BCMA Antigenic Determinant. In further embodiments, the Adapter comprises two or more operably linked ADBDs that are separated by an AFP P26 Antigenic Determinant. In some embodiments, an Adapter provided herein comprises at least one ADBD comprising a D domain. In some embodiments, an Adapter provided herein comprises more than one ADBD comprising a D domain. In some embodiments, all ADBDs of an Adapter provided herein comprise a D domain.

In some embodiments, the ADBD of the Adapter is deimmunized. In some embodiments, the ADBD of the Adapter is deimmunized by replacing one or more amino acid residues in predicted T cell epitopes to decrease binding to host MHC molecules.

In some embodiments, the Adapter comprises an ADBD that binds to an antigen target containing an AD of interest, and has no discernable impact on the function of the target. Alternatively, in some embodiments, the Adapter comprises an ADBD that binds to an antigen target containing an AD of interest and completely or partially inhibits, antagonizes, agonizes, blocks, increases, stimulates, or interferes with the biological activity of the target. Binding can be identified as agonistic or antagonistic and determined using or routinely modifying assays, bioassays, and/or animal models known in the art for evaluating such activity.

An Adapter agonist refers to an Adapter that in some way increases or enhances the biological activity of the Adapter target or has biological activity comparable to a known agonist of the Adapter target. In another embodiment, the Adapter is an antagonist of the target it binds. An Adapter antagonist refers to an Adapter that completely or partially blocks or in some way interferes with the biological activity of the Adapter target or has biological activity comparable to a known antagonist or inhibitor of the Adapter target.

In one embodiment an Adapter specifically binds a target of interest that is a serum protein. In one embodiment, an Adapter specifically binds a serum protein selected from: serum albumin (e.g., human serum albumin (HSA)), thyroxin-binding protein, transferrin, fibrinogen, and an immunoglobulin (e.g., IgG, IgE and IgM). Without being bound by theory, the binding of an Adapter to a carrier protein is believed to confer upon the Adapter an improved pharmacodynamic profile that includes, but is not limited to, improved tumor targeting, tumor penetration, diffusion within the tumor, and enhanced therapeutic activity compared to the Adapter in which the carrier protein binding sequence is missing (see, e.g., WO 01/45746, the contents of which are herein incorporated by reference in its entirety).

iii. Adapter Functional Domain(s)

In some embodiments, the Adapter comprises a first antigenic determinant (an AD), a domain that binds to a second antigenic determinant (an ADBD), and further comprises a functional domain that confers one or more additional desirable properties (e.g., improved manufacturing) and/or pharmacokinetic or pharmacodynamic properties (e.g., improved half-life). The functional domain of the Adapter can be located between the AD and the ADBD. The Adapter can also be located N-terminal to both the AD and ADBD or C-terminal to both the AD and ADBD. In some embodiments, where the Adapter comprises two or more ADs, the functional domain of the Adapter can be located between two or more ADs, N-terminal to two or more ADs, or C-terminal to two or more ADs. In some embodiments, where the Adapter comprises two or more ADBDs, the functional domain of the Adapter can be located between two or more ADBDs, N-terminal to two or more ADBDs, or C-terminal to two or more ADBDs.

In some embodiments, the Adapter comprises a functional domain selected from: an Fc or variant Fc (e.g., a human Fc or variant Fc domain) or a fragment thereof, a serum protein (e.g., human serum albumin) or a fragment thereof; an FcRn binding domain; a serum protein binding domain; a cytokine, growth factor, hormone, or enzyme; an imaging agent; a labeling agent; and a peptide tag.

The functional domain(s) of the Adapter can be naturally derived or the result of recombinant engineering (e.g., phage display, xenomouse, or synthetic). In certain embodiments, the functional domain of the Adapter enhances half-life, increases or decreases antibody dependent cellular cytotoxicity (ADCC), and/or increases or decreases complement dependent cytotoxicity (CDC) activity.

In some embodiments, the Adapter comprises a functional domain selected from: an Fc or variant Fc (e.g., a human Fc or variant human Fc domain) or a fragment or derivative thereof, a serum protein (e.g., human serum albumin) or a fragment or derivative thereof (e.g., a serum protein binding domain); an FcRn binding domain; and a serum protein binding domain.

In one embodiment, an Adapter comprises a functional domain that comprises an antibody effector domain or derivative of an antibody effector domain that confers one or more effector functions to the Adapter, such as the ability to bind to one or more Fc receptors. In some embodiments, the functional domain comprises one or more CH2 and or CH3 domains of an antibody having effector function provided by the CH2 and CH3 domains. In some embodiments, the functional domain comprises one or more derivatives of CH2 and/or CH3 domains of an antibody having effector function provided by the CH2 and CH3 domains. Other sequences that can be included in the Adapter to provide an effector function and that are encompassed by the invention will be clear to those skilled in the art and can routinely be chosen and designed into an Adapter encompassed herein on the basis of the desired effector function(s).

In one embodiment, the Adapter comprises a functional domain that increases the antibody dependent cellular cytotoxicity (ADCC) conferred by the Adapter (see, e.g., Bruhns et al., Blood 113: 3716-3725 (2009); Shields et al., J. Biol. Chem. 276: 6591-6604 (2001); Lazar et al., PNAS 103: 4005-4010 (2006); Stavenhagen et al., Cancer Res. 67: 8882-8890 (2007); Horton et al., Cancer Res. 68: 8049-8057 (2008); Zalevsky et al., Blood 113: 3735-3743 (2009); Bruckheimer, Neoplasia 11: 509-517 (2009); WO2006/020114; Strohl, Curr. Op. Biotechnol. 20: 685-691 (2009); and WO2004/074455, each of which is herein incorporated by reference in its entirety). Examples of fragment engineering modifications of effector function conferring portions of an Fc contained in the functional domain of an Adapter that increases ADCC include one or more modifications corresponding to: IgG1-S298A, E333A, K334A; IgG1-S239D, I332E; IgG1-S239D, A330L, I332E; IgG1-P247I, A339D or Q; IgG1-D280H, K290S with or without S298D or V; IgG1-F243L, R292P, Y300L; IgG1-F243L, R292P, Y300L, P396L; and IgG1-F243L, R292P, Y300L, V305I, P396L; wherein the numbering of the residues in the Fc region is that of the EU index of Kabat et al. (Kabat et al., Sequences of proteins of Immunological Interest, 1991 Fifth edition).

Accordingly, in some embodiments, the Adapter comprises a functional domain that comprises an antibody fragment that confers upon the Adapter a biological or biochemical characteristic of an immunoglobulin. In some embodiments, the antibody fragment confers a characteristic selected from: the ability to non-covalently dimerize, the ability to localize at the site of a tumor, and an increased serum half-life when compared to an Adapter without the antibody fragment. In certain embodiments, the Adapter is at least as stable as the corresponding antibody fragment without the Adapter. In certain embodiments, the Adapter is more stable than the corresponding antibody fragment without the Adapter. Adapter protein stability can be measured using established methods, including, for example, ELISA techniques. In some embodiments, the Adapter is stable in whole blood (in vivo or ex vivo) at 37° C. for at least about 10 hours, at least about 15 hours, at least about 20 hours, at least about 24 hours, at least about 25 hours, at least about 30 hours, at least about 35 hours, at least about 40 hours, at least about 45 hours, at least about 48 hours, at least about 50 hours, at least about 55 hours, at least about 60 hours, at least about 65 hours, at least about 70 hours, at least about 72 hours, at least about 75 hours, at least about 80 hours, at least about 85 hours, at least about 90 hours, at least about 95 hours, or at least about 100 hours (including any time between those listed). In one embodiment, the Adapter contains an immunoglobulin effector domain or half-life influencing domain that corresponds to an immunoglobulin domain or fragment in which at least a fraction of one or more of the constant region domains has been altered so as to provide desired biochemical characteristics such as reduced or increased effector functions, the ability to non-covalently dimerize, increased ability to localize at the site of a tumor, reduced serum half-life, or increased serum half-life when compared with an immunoglobulin fragment having the corresponding unaltered immunoglobulin sequence. These alterations of the constant region domains can be amino acid substitutions, insertions, or deletions.

In one embodiment, the Adapter comprises a functional domain that comprises an amino acid sequence of an immunoglobulin effector domain or a derivative of an immunoglobulin effector domain that confers antibody dependent cellular cytotoxicity (ADCC) to the Adapter. In additional embodiments, the Adapter comprises a sequence of an immunoglobulin effector domain that has been modified to increase ADCC (see, e.g., Bruhns, Blood 113: 3716-3725 (2009); Shields, J. Biol. Chem. 276: 6591-6604 (2001); Lazar, PNAS 103: 4005-4010 (2006); Stavenhagen, Cancer Res. 67: 8882-8890 (2007); Horton, Cancer Res. 68: 8049-8057 (2008); Zalevsky, Blood 113: 3735-3743 (2009); Bruckheimer, Neoplasia 11: 509-517 (2009); WO 06/020114; Strohl, Curr. Op. Biotechnol. 20: 685-691 (2009); and WO 04/074455, the contents of each of which is herein incorporated by reference in its entirety). Examples of immunoglobulin fragment engineering modifications contained in an amino acid sequence in the Adapter that increases ADCC include immunoglobulin effector domain sequences having one or more modifications corresponding to: IgG1-S298A, E333A, K334A; IgG1-S239D, I332E; IgG1-S239D, A330L, I332E; IgG1-P247I, A339D or Q; IgG1-D280H, K290S with or without S298D or V; IgG1-F243L, R292P, Y300L; IgG1-F243L, R292P, Y300L, P396L; and IgG1-F243L, R292P, Y300L, V305I, P396L; wherein the numbering of the residues is that of the EU index of Kabat et al. (Kabat et al., Sequences of proteins of Immunological Interest, 1991 Fifth edition, herein incorporated by reference).

In additional embodiments, the Adapter comprises a functional domain that comprises the amino acid sequence of an immunoglobulin effector domain, or a derivative of an immunoglobulin effector domain, that confers antibody-dependent cell phagocytosis (ADCP) to the Adapter. In additional embodiments, the Adapter comprises a sequence of an immunoglobulin effector domain that has been modified to increase antibody-dependent cell phagocytosis (ADCP); (see, e.g., Shields et al., J. Biol. Chem. 276: 6591-6604 (2001); Lazar et al., PNAS 103: 4005-4010 (2006); Stavenhagen et al., Cancer Res. 67: 8882-8890 (2007); Richards et al., Mol. Cancer Ther. 7: 2517-2527 (2008); Horton et al., Cancer Res. 68: 8049-8057 (2008); Zalevsky et al., Blood 113: 3735-3743 (2009); Bruckheimer et al., Neoplasia 11: 509-517 (2009); WO 06/020114; Strohl, Curr. Op. Biotechnol. 20: 685-691 (2009); and WO 04/074455, the contents of each of which is herein incorporated by reference in its entirety). Examples of immunoglobulin fragment engineering modifications contained in an amino acid sequence in the Adapter that increases ADCP include immunoglobulin effector domain sequences having one or more modifications corresponding to: IgG1-S298A, E333A, K334A; IgG1-S239D, I332E; IgG1-S239D, A330L, I332E; IgG1-P247I, A339D or Q; IgG1-D280H, K290S with or without S298D or V; IgG1-F243L, R292P, Y300L; IgG1-F243L, R292P, Y300L, P396L; IgG1-F243L, R292P, Y300L, V305I, P396L; and IgG1-G236A, S239D, I332E; wherein the numbering of the residues is that of the EU index of Kabat et al. (Kabat et al., Sequences of proteins of Immunological Interest, 1991 Fifth edition, herein incorporated by reference).

In additional embodiments, the Adapter comprises a functional domain that comprises an amino acid sequence of an immunoglobulin effector domain, or a derivative of an immunoglobulin effector domain, that confers complement-dependent cytotoxicity (CDC) to the Adapter. In additional embodiments, the Adapter comprises a sequence of an immunoglobulin effector domain that has been modified to increase complement-dependent cytotoxicity (CDC) (see, e.g., Idusogie et al., J. Immunol. 166: 2571-2575 (2001); Strohl, Curr. Op. Biotechnol. 20: 685-691 (2009); and Natsume et al., Cancer Res. 68: 3863-3872 (2008), the contents of each of which is herein incorporated by reference in its entirety). By way of example, Adapters can contain an antibody fragment or domain that contains one or more of the following modifications that increase CDC: IgG1-K326A, E333A; IgG1-K326W, E333S, IgG2-E333S; wherein the numbering of the residues is that of the EU index of Kabat et al. (Sequences of proteins of Immunological Interest, 1991 Fifth edition, herein incorporated by reference).

In additional embodiments, the Adapter comprises a functional domain that comprises an amino acid sequence of an immunoglobulin effector domain, or a derivative of an immunoglobulin effector domain, that confers the ability to bind FcgammaRIIb receptor to the Adapter. In additional embodiments, the Adapter comprises a sequence of an immunoglobulin effector domain that has been modified to increase inhibitory binding to FcgammaRIIb receptor (see, e.g., Chu et al., Mol. Immunol. 45: 3926-3933 (2008)). An example of an immunoglobulin fragment engineering modification contained in an amino acid sequence in the Adapter that increases binding to inhibitory FcgammaRIIb receptor is IgG1-S267E, L328F.

The half-life of an IgG is mediated by its pH-dependent binding to the neonatal receptor FcRn. In certain embodiments the Adapter contains a functional domain that comprises an amino acid sequence of an immunoglobulin effector domain, or a derivative of an immunoglobulin effector domain, that confers the ability to bind neonatal receptor FcRn to the Adapter. In certain embodiments the Adapter contains a functional domain that comprises a sequence of an immunoglobulin FcRn binding domain that has been modified to enhance binding to FcRn (see, e.g., Petkova et al., Int. Immunol. 18: 1759-1769 (2006); Dall'Acqua et al., J. Immunol. 169: 5171-5180 (2002); Oganesyan et al., Mol. Immunol. 46: 1750-1755 (2009); Dall'Acqua et al., J. Biol. Chem. 281: 23514-23524 (2006), Hinton et al., J. Immunol. 176: 346-356 (2006); Datta-Mannan et al., Drug Metab. Dispos. 35: 86-94 (2007); Datta-Mannan et al., J. Biol. Chem. 282: 1709-1717 (2007); WO 06/130834; Strohl, Curr. Op. Biotechnol. 20: 685-691 (2009); and Yeung et al., J. Immunol. 182: 7663-7671 (2009), the contents of each of which is herein incorporated by reference in its entirety).

In additional embodiments, the Adapter comprises a functional domain that comprises a sequence of an immunoglobulin effector domain that has been modified to have a selective affinity for FcRn at pH 6.0, but not pH 7.4. By way of example, the Adapter functional domain can contain an antibody fragment or domain that contains one or more of the following modifications that increase half-life: IgG1-M252Y, S254T, T256E; IgG1-T250Q, M428L; IgG1-H433K, N434Y; IgG1-N434A; and IgG1-T307A, E380A, N434A; wherein the numbering of the residues is that of the EU index of Kabat et al. (Kabat et al., Sequences of Proteins of Immunological Interest, 1991 Fifth edition, herein incorporated by reference).

According to another embodiment, the Adapter comprises a functional domain that comprises an amino acid sequence corresponding to a immunoglobulin effector domain that has been modified to contain at least one substitution in its sequence corresponding to the Fc region (e.g., Fc gamma) position selected from: 238, 239, 246, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 332, 333, 334, 335, 337, 338, 340, 360, 373, 376, 378, 382, 388, 389, 398, 414, 416, 419, 430, 434, 435, 437, 438, and 439, wherein the numbering of the residues in the Fc region is according to the EU numbering system; of Kabat et al. (Sequences of proteins of Immunological Interest, 1991 Fifth edition, herein incorporated by reference). In a specific embodiment, the Adapter contains a functional domain that comprises a sequence of an immunoglobulin effector domain derivative wherein at least one residue corresponding to position 434 is a residue selected from: A, W, Y, F and H. According to another embodiment, the Adapter comprises a sequence of an immunoglobulin effector fragment derivative having the following respective substitutions S298A/E333A/K334A. In an additional embodiment, the Adapter comprises an immunoglobulin effector domain derivative having a substitution corresponding to K322A. In another embodiment, the Adapter comprises a sequence of an immunoglobulin effector domain derivative having one or any combination of the following substitutions K246H, H268D, E283L, S324G, S239D and 1332E. According to yet another embodiment, the Adapter comprises a sequence of an immunoglobulin effector domain derivative having substitutions corresponding to D265A/N297A.

In certain embodiments, the Adapter comprises a functional domain that comprises a sequence of an immunoglobulin effector domain that has been glycoengineered or mutated to increase effector function using techniques known in the art. For example, the inactivation (through point mutations or other means) of a constant region domain sequence contained in the Adapter may reduce Fc receptor binding of the circulating Adapter thereby increasing tumor localization. In other cases it may be that constant region modifications consistent with certain embodiments of the instant invention moderate complement binding and thus reduce the serum half-life and nonspecific association of a conjugated cytotoxin. Yet other modifications of the constant region may be used to modify disulfide linkages or oligosaccharide moieties that allow for enhanced localization due to increased antigen specificity or antibody flexibility. The resulting physiological profile, bioavailability and other biochemical effects of the modifications, such as tumor localization, biodistribution and serum half-life, can easily be measured and quantified using well know immunological techniques without undue experimentation.

The production of the Adapter, useful in practicing the provided methods, may be carried out using a variety of standard techniques for chemical synthesis, semi-synthetic methods, and recombinant DNA methodologies known in the art. In several embodiments, the overall production scheme for producing the Adapter comprises obtaining a reference protein scaffold and identifying a plurality of residues within the scaffold for modification. Depending on the embodiment, the reference scaffold may comprise a protein structure with one or more alpha-helical regions, or other tertiary structure. Once identified, the plurality of residues can be modified, for example by substitution of an amino acid. In some embodiments substitution is conservative, while in other embodiments non-conservative substitutions are made. In some embodiments a natural amino acid (e.g., one of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, or valine) is substituted into the reference scaffold at the targeted position for modification. In certain embodiments, the modifications do not include substituting in either a cysteine or a proline. After modifications have been made at all the identified positions desired in a particular embodiment, the resulting modified polypeptides (e.g., candidate Adapter) can be recombinantly expressed, for example in a plasmid, bacteria, phage, or other vector (e.g. to increase the number of each of the modified polypeptides). The modified polypeptides can then be purified and screened to identify those modified polypeptides that have specific binding to a particular target of interest. In several embodiments, certain modified polypeptides will show enhanced binding specificity for a target of interest vis-à-vis the reference scaffold, which in some embodiments may exhibit little or no binding to a given target of interest. In additional embodiments, depending on the target of interest the reference scaffold may show some interaction (e.g. nonspecific interaction) with a target of interest, while certain modified polypeptides will exhibit at least about two fold, at least about five fold, at least about 10 fold, at least about 20 fold, at least about 50 fold, or at least about 100 fold (or more) increased binding specificity for the target of interest. Optionally, the reference sequence and/or the modified polypeptides (e.g., Adapter) can be de-immunized. For example, residues or motifs that are potentially immunogenic can be identified and modified in order to reduce or eliminate potential immune responses to the Adapter. Additional details regarding various embodiments of the production, selection, and isolation of Adapter are provided in more detail below.

TABLE 2

Exemplary AFP p26 containing Adapters

| SEQ ID NO: | Adapter Sequence | Target |
|---|---|---|
| 50 | MGSWDEFSRRLYAIEWQLYAQGGTEAELAAFEK EIAAFESELQAYKGEGSPEVEKLRELAAVIREN LQAYRHNGGGDGGGGGSGGGSGQESQALAKRS CGLFQKLGEYYLQNAFLVAYTKKAPQLTSSELM AITRKMAATAATCCQLSEDKLLACGEGAADIII GHLCIRHEMTPVNPGVGQCCTSSYANRRPCFSS LVVDETYVPPAFSDDKFIFHKDLCQAQGVALQT MKQEFLINLVKQKPQITEEQLEAVIADFSGLLE KCCQGQEQEVCFAEEGQKLISKTRAALGV | CD123 |
| 51 | MGSWDEFGRRLYAIESQLYALGGTEAELAAFEK EIAAFESELQAYKGKGNPEVEKLREIAAVIREN LQAYRHNGGGDGGGGGSGGGSGQESQALAKRS CGLFQKLGEYYLQNAFLVAYTKKAPQLTSSELM AITRKMAATAATCCQLSEDKLLACGEGAADIII GHLCIRHEMTPVNPGVGQCCTSSYANRRPCFSS LVVDETYVPPAFSDDKFIFHKDLCQAQGVALQT MKQEFLINLVKQKPQITEEQLEAVIADFSGLLE KCCQGQEQEVCFAEEGQKLISKTRAALGV | CD123 |
| 52 | MGSWDEFGRRLYAIEAQLYALGGTEAELAAFEK EIAAFESELQAYKGKGNPEVEKLREIAAVIREN LQAYRHNGGGDGGGGGSGGGSGQESQALAKRS CGLFQKLGEYYLQNAFLVAYTKKAPQLTSSELM AITRKMAATAATCCQLSEDKLLACGEGAADIII GHLCIRHEMTPVNPGVGQCCTSSYANRRPCFSS LVVDETYVPPAFSDDKFIFHKDLCQAQGVALQT MKQEFLINLVKQKPQITEEQLEAVIADFSGLLE KCCQGQEQEVCFAEEGQKLISKTRAALGV | CD123 |
| 53 | MGSWDEFGRRLYAIEEQLYALGGTEAELAAFEK EIAAFESELQAYKGKGNPEVEKLREIAAVIREN LQAYRHNGGGDGGGGGSGGGSGQESQALAKRS CGLFQKLGEYYLQNAFLVAYTKKAPQLTSSELM AITRKMAATAATCCQLSEDKLLACGEGAADIII GHLCIRHEMTPVNPGVGQCCTSSYANRRPCFSS LVVDETYVPPAFSDDKFIFHKDLCQAQGVALQT MKQEFLINLVKQKPQITEEQLEAVIADFSGLLE KCCQGQEQEVCFAEEGQKLISKTRAALGV | CD123 |

TABLE 2-continued

Exemplary AFP p26 containing Adapters

| SEQ ID NO: | Adapter Sequence | Target |
|---|---|---|
| 54 | MGSWDEFGRRLYAIEWQLYALGGTEAELAAFEK EIAAFESELQAYKGKGSPEVEKLRELAAVIREN LQAYRHNGGGGDGGGGSGGGGSGQESQALAKRS CGLFQKLGEYYLQNAFLVAYTKKAPQLTSSELM AITRKMAATAATCCQLSEDKLLACGEGAADIII GHLCIRHEMTPVNPGVGQCCTSSYANRRPCFSS LVVDETYVPPAFSDDKFIFHKDLCQAQGVALQT MKQEFLINLVKQKPQITEEQLEAVIADFSGLLE KCCQGQEQEVCFAEEGQKLISKTRAALGV | CD123 |
| 55 | MGSWDEFSRRLYAIEWQLYALGGTEAELAAFEKE IAAFESELQAYKGEGSPEVEKLRELAAVIRENLQ AYRHNGGGGDGGGGSGGGGSGQESQALAKRSCGL FQKLGEYYLQNAFLVAYTKKAPQLTSSELMAITR KMAATAATCCQLSEDKLLACGEGAADIIIGHLCI RHEMTPVNPGVGQCCTSSYANRRPCFSSLVVDET YVPPAFSDDKFIFHKDLCQAQGVALQTMKQEFLI NLVKQKPQITEEQLEAVIADFSGLLEKCCQGQEQ EVCFAEEGQKLISKTRAALGV | CD123 |
| 56 | MGSWDEFGRRLYAIESQLYALGGTEAELAAFEKE IAAFESELQAYKGKGNPEVEKLREIAAVIRENLQ AYRHNGGGDGGGGSGGGGSGQESQALAKRSCGL FQKLGEYYLQNAFLVAYTKKAPQLTSSELMAITR KMAATAATCCQLSEDKLLACGEGAADIIIGHLCI RHEMTPVNPGVGQCCTSSYANRRPCFSSLVVDET YVPPAFSDDKFIFHKDLCQAQGVALQTMKQEFLI NLVKQKPQITEEQLEAVIADFSGLLEKCCQGQEQ EVCFAEEGQKLISKTRAALGVGGGGSGGGGSGGG GSGMGSWDEFGRRLYAIESQLYALGGTEAELAAF EKEIAAFESELQAYKGKGNPEVEKLREIAAVIRE NLQAYRHN | CD123 |
| 57 | MGSWDEFGRRLYAIEAQLYALGGTEAELAAFEKE IAAFESELQAYKGKGNPEVEKLREIAAVIRENLQ AYRHNGGGDGGGGSGGGGSGQESQALAKRSCGL FQKLGEYYLQNAFLVAYTKKAPQLTSSELMAITR KMAATAATCCQLSEDKLLACGEGAADIIIGHLCI RHEMTPVNPGVGQCCTSSYANRRPCFSSLVVDET YVPPAFSDDKFIFHKDLCQAQGVALQTMKQEFLI NLVKQKPQITEEQLEAVIADFSGLLEKCCQGQEQ EVCFAEEGQKLISKTRAALGVGGGGSGGGGSGGG GSGMGSWDEFGRRLYAIEAQLYALGGTEAELAAF EKEIAAFESELQAYKGKGNPEVEKLREIAAVIRE NLQAYRHN | CD123 |
| 58 | MGSWDEFGRRLYAIEEQLYALGGTEAELAAFEKE IAAFESELQAYKGKGNPEVEKLREIAAVIRENLQ AYRHNGGGDGGGGSGGGGSGQESQALAKRSCGL FQKLGEYYLQNAFLVAYTKKAPQLTSSELMAITR KMAATAATCCQLSEDKLLACGEGAADIIIGHLCI RHEMTPVNPGVGQCCTSSYANRRPCFSSLVVDET YVPPAFSDDKFIFHKDLCQAQGVALQTMKQEFLI NLVKQKPQITEEQLEAVIADFSGLLEKCCQGQEQ EVCFAEEGQKLISKTRAALGVGGGGSGGGGSGGG GSGMGSWDEFGRRLYAIEEQLYALGGTEAELAAF EKEIAAFESELQAYKGKGNPEVEKLREIAAVIRE NLQAYRHN | CD123 |
| 59 | MGSWDEFGRRLYAIEWQLYALGGTEAELAAFEKE IAAFESELQAYKGKGSPEVEKLRELAAVIRENLQ AYRHNGGGGDGGGGSGGGGSGQESQALAKRSCGL FQKLGEYYLQNAFLVAYTKKAPQLTSSELMAITR KMAATAATCCQLSEDKLLACGEGAADIIIGHLCI RHEMTPVNPGVGQCCTSSYANRRPCFSSLVVDET YVPPAFSDDKFIFHKDLCQAQGVALQTMKQEFLI NLVKQKPQITEEQLEAVIADFSGLLEKCCQGQEQ EVCFAEEGQKLISKTRAALGVGGGGSGGGGSGGG GSGMGSWDEFGRRLYAIEWQLYALGGTEAELAAF EKEIAAFESELQAYKGKGSPEVEKLREIAAVIRE NLQAYRHN | CD123 |
| 60 | MGSWDEFSRRLYAIEWQLYALGGTEAELAAFEKE IAAFESELQAYKGEGSPEVEKLRELAAVIRENLQ AYRHNGGGGDGGGGSGGGGSGQESQALAKRSCGL FQKLGEYYLQNAFLVAYTKKAPQLTSSELMAITR KMAATAATCCQLSEDKLLACGEGAADIIIGHLCI RHEMTPVNPGVGQCCTSSYANRRPCFSSLVVDET YVPPAFSDDKFIFHKDLCQAQGVALQTMKQEFLI NLVKQKPQITEEQLEAVIADFSGLLEKCCQGQEQ EVCFAEEGQKLISKTRAALGVGGGGSGGGGSGGG GSGMGSWDEFSRRLYAIEWQLYALGGTEAELAAF EKEIAAFESELQAYKGEGSPEVEKLRELAAVIRE NLQAYRHN | CD123 |
| 61 | MGSWDEFSRRLYAIEWQLYAQGGTEAELAAFEKE IAAFESELQAYKGEGSPEVEKLRELAAVIRENLQ AYRHNGGGGDGGGGSGGGGSGQESQALAKRSCGL FQKLGEYYLQNAFLVAYTKKAPQLTSSELMAITR KMAATAATCCQLSEDKLLACGEGAADIIIGHLCI RHEMTPVNPGVGQCCTSSYANRRPCFSSLVVDET YVPPAFSDDKFIFHKDLCQAQGVALQTMKQEFLI NLVKQKPQITEEQLEAVIADFSGLLEKCCQGQEQ EVCFAEEGQKLISKTRAALGVGGGGSGGGGSGGG GSGMGSWDEFSRRLYAIEWQLYAQGGTEAELAAF EKEIAAFESELQAYKGEGSPEVEKLRELAAVIRE NLQAYRHN | CD123 |
| 101 | DEGGGGSMGSWAEFKQRLAAIKTRLEALGGSEAE LAAFEKEIAAFESELQAYKGKGNPEVEALRKEAA AIRDELQAYRHNGGGGSGGGGSGGGGSGLEKCFQ TENPLECQDKGEEELQKYIQESQALAKRSCGLFQ KLGEYYLQNAFLVAYTKKAPQLTSSELMAITRKM AATAATCCQLSEDKLLACGEGAADIIIGHLCIRH EMTPVNPGVGQCCTSSYANRRPCFSSLVVDETYV PPAFSDDKFIFHKDLCQAQGVALQTMKQEFLINL VKQKPQITEEQLEAVIADFSGLLEKCCQGQEQEV CFAEEGQKLISKTRAALGVGGGGSGGGGSGGGGS MGSWDEFGRRLYAIEWQLYALGGTEAELAAFEKE IAAFESELQAYKGKGNPEVEKLREIAAVIRENLQ AYRHNGGGSGGGGSGGGGSHHHHHHHHHH | CD123 |
| 102 | DEGGGGSMGSWAEFKQRLAAIKTRLEALGGSEAE LAAFEKEIAAFESELQAYKGKGNPEVEALRKEAA AIRDELQAYRHNGGGGSGGGGSGGGGSGLEKCFQ TENPLECQDKGEEELQKYIQESQALAKRSCGLFQ KLGEYYLQNAFLVAYTKKAPQLTSSELMAITRKM AATAATCCQLSEDKLLACGEGAADIIIGHLCIRH EMTPVNPGVGQCCTSSYANRRPCFSSLVVDETYV PPAFSDDKFIFHKDLCQAQGVALQTMKQEFLINL VKQKPQITEEQLEAVIADFSGLLEKCCQGQEQEV CFAEEGQKLISKTRAALGVGGGGSGGGGSGGGGS MGSWDEFGRRLYAIEWQLYALGGTEAELAAFEKE IAAFESELQAYKGKGSPEVEKLREIAAVIRENLQ AYRHNGGGSGGGGSGGGGSHHHHHHHHHH | CD123 |
| 103 | DEGGGGSMGSWAEFKQRLAAIKTRLEALGGSEAE LAAFEKEIAAFESELQAYKGKGNPEVEALRKEAA AIRDELQAYRHNGGGGSGGGGSGGGGSGLEKCFQ TENPLECQDKGEEELQKYIQESQALAKRSCGLFQ KLGEYYLQNAFLVAYTKKAPQLTSSELMAITRKM AATAATCCQLSEDKLLACGEGAADIIIGHLCIRH EMTPVNPGVGQCCTSSYANRRPCFSSLVVDETYV PPAFSDDKFIFHKDLCQAQGVALQTMKQEFLINL VKQKPQITEEQLEAVIADFSGLLEKCCQGQEQEV CFAEEGQKLISKTRAALGVGGGGSGGGGSGGGGS MGSWDEFGRRLYAIEWQLYALGGTEAELAAFEKE IAAFESELQAYKGEGSPEVEKLREIAAVIRENLQ AYRHNGGGSGGGGSGGGGSHHHHHHHHHH | CD123 |
| 104 | DEMGSWDEFSRRLYAIEWQLYAQGGTEAELAAFE KEIAAFESELQAYKGEGSPEVEKLRELAAVIREN LQAYRHNGGGDGGGGSGGGGSGQESQALAKRSC GLFQKLGEYYLQNAFLVAYTKKAPQLTSSELMAI TRKMAATAATCCQLSEDKLLACGEGAADIIIGHL CIRHEMTPVNPGVGQCCTSSYANRRPCFSSLVVD ETYVPPAFSDDKFIFHKDLCQAQGVALQTMKQEF LINLVKQKPQITEEQLEAVIADFSGLLEKCCQGQ | CD123 |

TABLE 2-continued

Exemplary AFP p26 containing Adapters

| SEQ ID NO: | Adapter Sequence | Target |
|---|---|---|
| | EQEVCFAEEGQKLISKTRAALGVGGGGSGGGGSG GGGSHHHHHHHHHH | |

In some embodiments, the disclosure provides compositions comprising one or more of the Adapters disclosed on Table 2. In other embodiments, the disclosure provides compositions comprising one or more Adapters comprising a sequence with 60-70%, 70-75%, 75-80%, 80-85%, 85-90%, 95-99% homology (and overlapping ranges therein) with a sequence disclosed in Table 2. In some embodiments, the Adapters having such homology are functionally similar or identical as compared to the respective reference sequence in Table 2. In some embodiments, the disclosure provides a polypeptide that comprises one or more Adapters that compete with (wholly or partially) one or more of the Adapters disclosed in Table 2 (reference sequence) for CD123 binding. The ability of one polypeptide to compete with a reference polypeptide for binding to a respective target can routinely be determined using a standard competition assay known in the art. In some embodiments, competition does not require that the Adapter competes for the same epitope as an Adapters of Table 2, rather the polypeptide can compete by binding a sterically inhibiting epitope, an overlapping epitope, etc.

C. Chimeric Antigen Receptors

Also provided herein are chimeric antigen receptors (CAR) comprising an extracellular domain, a transmembrane domain, and an intracellular signaling domain. In some embodiments, a CAR disclosed herein comprises an extracellular domain comprising an Antigenic Determinant (AD). In some embodiments, a CAR disclosed herein comprises an extracellular domain comprising at least one D domain (DD) disclosed herein to impart binding specificity. In some embodiments, a CAR disclosed herein comprises an extracellular domain comprising an ADBD. CARs may be expressed by any cell type.

In some embodiments, a chimeric antigen receptor (CAR) disclosed herein comprises comprises a D domain that binds to CD123, (ii) a transmembrane domain, and (iii) an intracellular domain. In some embodiments, the D domain that binds to CD123 comprises an amino acid sequence selected from the group consisting of SEQ ID NO: 8-33, 99 and 100. In some embodiments, the D domain that binds to CD123 comprises an amino acid sequence selected from the group consisting of SEQ ID NO: 8, 13, 14, 31, 32, and 33. In some embodiments, the D domain that binds to CD123 comprises the amino acid sequence of SEQ ID NO: 14. In some embodiments, the CAR comprises the amino acid sequence of SEQ ID NO: 62-66 or 67. In some embodiments, the CAR comprises the amino acid sequence of SEQ ID NO: 67.

In some embodiments, a chimeric antigen receptor (CAR) disclosed herein comprises comprises an antigenic determinant binding domain (ADBD) that binds to an AFP p26 AD, (ii) a transmembrane domain, and (iii) an intracellular domain. In some embodiments, the ADBD that binds to AFP p26 AD comprises an scFv that binds to AFP p26 AD. In some embodiments, the ADBD that binds to AFP p26 AD comprises a D domain that binds to AFP p26 AD. In some embodiments, the AFP p26 AD comprises an amino acid sequence selected from the group consisting of SEQ ID NO: 37-43 and 44. In some embodiments, the AFP p26 AD comprises the amino acid sequence of SEQ ID NO: 37. In some embodiments, the AFP p26 AD comprises the amino acid sequence of SEQ ID NO: 39. In some embodiments, the DD that binds to an AFP p26 AD comprises an amino acid sequence selected from the group consisting of SEQ ID NO: 74-93 and 94. In some embodiments, the DD that binds to an AFP p26 AD comprises the amino acid sequence of SEQ ID NO: 70-73 or 92-94. In some embodiments, the DD that binds to an AFP p26 AD comprises the amino acid sequence of SEQ ID NO: 73. In some embodiments, the CAR comprises the amino acid sequence of SEQ ID NO: 68. In some embodiments, the CAR comprises the amino acid sequence of SEQ ID NO: 69.

In some embodiments, a chimeric antigen receptor (CAR) disclosed herein comprises comprises an AFP p26 antigenic determinant (AD), (ii) a transmembrane domain, and (iii) an intracellular domain. In some embodiments, the AFP p26 AD comprises an amino acid sequence selected from the group consisting of SEQ ID NO: 37-43 and 44. In some embodiments, the AFP p26 AD comprises the amino acid sequence of SEQ ID NO: 37. In some embodiments, the AFP p26 AD comprises the amino acid sequence of SEQ ID NO: 39.

In some embodiments, a CAR disclosed herein comprises an extracellular domain comprising an Antigenic Determinant (AD). Such CARs can be expressed on the surface of cells (e.g., immune cell or immune effector cell) and used in combination with Adapters comprising a first ADBD (e.g., a D domain) that binds the AD and a second ADBD (e.g., a D domain) that binds a target on a target cell, for example, to kill a target cell. In some embodiments, the AD comprises AFP or a fragment thereof. In some embodiments, the AD comprises p26 or a fragment thereof. In some embodiments, the AD comprises an amino acid sequence of SEQ ID NO: 37-43 or 44. In some embodiments, the AD comprises the amino acid sequence of SEQ ID NO: 39. In some embodiments, the AD comprises the amino acid sequence of SEQ ID NO: 40.

In some embodiments, a CAR disclosed herein comprises an extracellular domain comprising at least one D domain (DD). In some embodiments, the D domain can recognize an Antigenic Determinant (AD) (e.g., CD123) on a target cell or an AD (e.g., p26) comprised by an Adapter. In some embodiments, CARs comprising a DD capable of binding an AD on a target cell can be expressed on the surface of cells (e.g., immune cell or immune effector cell) and used, for example, to kill a target cell expressing the AD. In some embodiments, a CAR disclosed herein comprises an extracellular domain comprising at least one CD123-binding D domain comprising an amino acid sequence selected from the group consisting of SEQ ID NO: 8-33, 99 and 100. In some embodiments, the CD123-binding DD comprises an amino acid sequence selected from the group consisting of SEQ ID NO: 8, 13, 14, 31, 32, and 33. In some embodiments, the CD123-binding DD comprises the amino acid sequence of SEQ ID NO: 14. In some embodiments, CARs comprising a DD capable of binding a first AD (e.g., p26) can be expressed on the surface of cells (e.g., immune cell or immune effector cell) and used in combination with an Adapter comprising the first AD and an ADBD (e.g., a D domain) that binds a second AD on a target cell, for example, to kill the target cell. In some embodiments, a CAR disclosed herein comprises an extracellular domain comprising at least one p26-binding D domain comprising an amino acid sequence selected from the group consisting of SEQ ID NO: 74-93 and 94. In some embodiments, a CAR disclosed herein comprises an extracellular domain comprising at least one p26-binding D domain comprising an amino acid sequence selected from the group consisting of SEQ ID NO: 70-73 and 92-94. In some embodiments, the p26-binding DD comprises the amino acid sequence of SEQ ID NO: 73. In some embodiments, p26 comprises an amino acid sequence of SEQ ID NO: 37-43 or 44. In some embodiments, p26 comprises the amino acid sequence of SEQ ID NO: 39. In some embodiments, p26 comprises the amino acid sequence of SEQ ID NO: 40.

In some embodiments, a CAR disclosed herein comprises an extracellular domain comprising an ADBD. In several embodiments, the ADBD is made up of, at least in part, a target-binding polypeptide (e.g., D domain) as disclosed herein. In some embodiments, the ADBD can recognize an Antigenic Determinant (AD) (e.g., CD123) on a target cell or an AD (e.g., p26) comprised by an Adapter. In some embodiments, CARs comprising an ADBD capable of binding an AD on a target cell can be expressed on the surface of cells (e.g., immune cell or immune effector cell) and used, for example, to kill a target cell expressing the AD. In some embodiments, CARs comprising a first ADBD capable of binding a first AD (e.g., p26) can be expressed on the surface of cells (e.g., immune cell or immune effector cell) and used in combination with an Adapter comprising the first AD and a second ADBD (e.g., a D domain) that binds a second AD on a target cell, for example, to kill the target cell. In some embodiments, p26 comprises an amino acid sequence of SEQ ID NO: 37-43 or 44. In some embodiments, p26 comprises the amino acid sequence of SEQ ID NO: 39. In some embodiments, p26 comprises the amino acid sequence of SEQ ID NO: 40.

The present invention further provides a means by which to create cell-associated DDpp, comprised of at least one DDpp designed to impart binding specificity a membrane bound fusion protein. DDpp-receptors may be expressed by any cell type. In one embodiment, the DDpp-receptor fusion protein comprises a chimeric antigen receptor (CAR), or DDpp-CAR, that comprises: an extracellular targeting domain, a transmembrane domain, and an intracellular signaling domain. In another embodiment, the DDpp-CAR is composed of an extracellular targeting domain, a transmembrane domain, and a cytoplasmic domain wherein the cytoplasmic domain comprises the signaling domain. In a further embodiment the DDpp-CAR extracellular domain comprises one or more DDpp, in which each DDpp constitutes a specific binding domain with the same or different specificities. In some embodiments, the target-specific domain is directed to one (or more) of the cancer or tumor antigens disclosed herein, such as BCMA, CD123, and CS1, as non-limiting examples. In some embodiments, the target-specific domain is directed to AFP p26.

In several embodiments, the intracellular signaling domain or fragment thereof is selected from the group: a human CD3 zeta domain, 41BB domain, a CD28 domain and any combination thereof. In some embodiments, the intracellular signaling domain contains the sequence of SEQ ID NO: 115, 116 or combination thereof. In some embodiments, the intracellular signaling domain contains the sequence of SEQ ID NO: 117. Depending on the embodiment, the costimulatory signaling region comprises the intracellular domain of a costimulatory molecule selected from the group: CD27, CD28, 41BB, OX40, CD30, CD40, PD1, lymphocyte function-associated antigen-1 (LFA1), CD2, CD7, LIGHT, NKG2C, B7H3, a ligand that specifically binds with CD83, and any combination thereof.

In several embodiments, the CAR comprises a fusion protein that includes an additional target-binding polypeptide.

In some embodiments, the ADBD of a CAR comprises at least one alternative scaffold binding domain (e.g., a D domain or affibody) designed to impart binding specificity to a membrane bound CAR. A receptor comprising an alternative scaffold binding domain may be expressed by any cell type.

In one embodiment, the CAR is composed of the following elements: an extracellular domain, a transmembrane domain and a cytoplasmic domain wherein the cytoplasmic domain comprises a signaling domain. In another embodiment the CAR is composed of an extracellular domain and a transmembrane domain. In a further embodiment the CAR is comprised of an extracellular domain composed of one or more ADBDs (e.g., D domain) with the same or different specificities. In one embodiment, the intracellular domain (e.g., the cytoplasmic domain) of the CAR comprises the intracellular domain of CD3 zeta chain. In another embodiment the intracellular signaling domain of the CAR is comprised of part of the intracellular domain of CD3 zeta chain. In a further embodiment, the intracellular domain of the CAR comprises the intracellular domain of CD3 zeta chain and a costimulatory signaling region. The costimulatory signaling region refers to a portion of the CAR comprising all or part of the intracellular domain of a costimulatory molecule. Costimulatory molecules and portions of these molecules that are able to confer costimulatory properties to a CAR are known in the art and can routinely be incorporated into the CAR. In addition, truncations or mutation to these intracellular signaling and costimulatory domains may be incorporated to further enhance or reduce receptor signaling. In preferred embodiments, a T cell is genetically modified to stably express a CAR. In such embodiments the cytoplasmic domain of the CAR can be designed to comprise the CD28 and/or 41BB signaling domain by itself or be combined with any other desired cytoplasmic domain(s) useful in the context of the invention. In one embodiment, the cytoplasmic domain of the CAR can be designed to further comprise the signaling domain of CD3-zeta. In some embodiments, the cytoplasmic domain contains the sequence of SEQ ID NO: 115, 116 or combination thereof. In some embodiments, the cytoplasmic domain contains the sequence of SEQ ID NO: 117. In one embodiment, the CAR comprises an extracellular domain, an extracellular protein linker with a transmembrane domain that passes through the cellular membrane (such as found in T cells or NK cells), and a cytoplasmic domain, optionally comprising multiple signaling modules. In several embodiments, the CAR may also comprise an epitope tag. In several embodiments, the cytoplasmic domain of the CAR can include but is not limited to CD3-zeta, 41BB and CD28 signaling modules and combinations thereof. In some embodiments, the cytoplasmic domain contains the sequence of SEQ ID NO: 115, 116 or combination thereof. In some embodiments, the cytoplasmic domain contains the sequence of SEQ ID NO: 117.

Also provided for are isolated nucleic acid sequences encoding CARs that include the target-binding polypeptides as part (or all) of the targeting region.

In some embodiments, the targeting domain of the CAR comprises a plurality of binding domains (e.g., DDs, or one or more DD and a scFv) that includes an additional target-binding polypeptide The disclosure also provides cells comprising a nucleic acid sequence encoding a CAR, wherein the CAR comprises an antigen binding domain made up of, at least in part, a disclosed DDpp that binds a target of interest (e.g., CD123 and AFP p26), a transmembrane domain, and a signaling domain. In some embodiments, the CAR binds specifically to a tumor antigen (and thus functions to deliver the cell expressing the CAR to the tumor. In some embodiments, the tumor antigen is associated with a hematologic malignancy. In some embodiments, the tumor antigen is CD123. In some embodiments, the cell expressing the CAR is a T cell, a natural killer (NK) cell or other immune cell type. In some embodiments, the cell expressing the CAR (whether T cell, NK cell or other cell type) exhibits an anti-tumor immunity when the polypeptide binds to its corresponding tumor antigen.

i. Extracellular Domain

The CARs provided herein comprise one or more antigenic determinant binding domains (ADBDs) (e.g., D domains). The ADBD of the CAR can be any ADBD (e.g., D domain) described herein. An exemplary ADBD comprises a polypeptide, e.g., an antibody molecule (which includes an antibody, and antigen binding fragments thereof, e.g., an immunoglobulin, single domain antibody (sdAb), and a scFv), or a non-antibody scaffold (e.g., a D domain, or affibody).

Depending on the desired antigen(s) to be targeted, the extracellular domain of the CAR can be engineered to include one or more antigenic determinant binding domains (ADBDs) that specifically bind the desired antigen target(s). For example, in one embodiment, the CAR is engineered to target CD123 and a CD123-binding ADBD (e.g., D domain) is incorporated into the extracellular domain of the CAR. Alternatively, an extracellular domain of a CAR may include more than one ADBD, thereby imparting multi-specificity or multi-valency to the CAR.

The choice of ADBDs in the extracellular domain of the CAR depends upon the identity of the cell or cells to be targeted. For example, the extracellular domain of the CAR may be engineered to specifically bind to cell surface proteins, such as a receptor, on the same cell or another cell. In other embodiments, the extracellular domain of the CAR is engineered to specifically bind to a soluble molecule, such as an immunoglobulin.

In other embodiments, the extracellular domain of the CAR contains one or more ADBDs (e.g., D domain) that bind a ligand that acts as a cell surface marker on target cells associated with a cancer. In some embodiments, ADBD(s) target and bind a tumor or cancer antigen (e.g., a TAA, TSA, CAA, CSA or other tumor antigen described herein or otherwise known in the art). Accordingly, provided herein are methods for creating CAR, their use in creating chimeric cells such as, human T cells and natural killer cells, and the use of these chimeric T and NK cells in adoptive immunotherapy.

The choice of an ADBD (e.g., D domain) can depend upon the type and number of ligands or receptors that define the surface of a target cell. For example, the ADBD may be chosen to recognize a ligand or receptor that acts as a cell surface marker on target cells associated with a particular disease state. Examples of cell surface markers that may act as ligands or receptors include a cell surface marker associated with a particular disease state, e.g., cell surface makers for viral diseases, bacterial diseases parasitic infections, autoimmune diseases and disorders associated with unwanted cell proliferation, e.g., a cancer, such as, a cancer described herein.

In some embodiments, the ADBD binds to CD123 (e.g., a polypeptide comprising the sequence of SEQ ID NO: 1).

In some embodiments, the ADBD comprises a DD sequence selected from the group consisting of SEQ ID NO: 8-33, 99 and 100. In some embodiments, the CD123-specific DD comprises an amino acid sequence selected from the group consisting of SEQ ID NO: 8, 13, 14, 31, 32, and 33. In some embodiments, the CD123-specific DD comprises the amino acid sequence of SEQ ID NO: 14.

In some embodiments, the ADBD (e.g., D domain) binds to AFP (e.g., a polypeptide comprising the sequence of SEQ ID NO: 36) or a fragment thereof. In some embodiments, the ADBD (e.g., D domain) binds to AFP p26 (e.g., a polypeptide comprising the sequence of SEQ ID NO: 37-43 or 44). In some embodiments, the ADBD (e.g., D domain) binds to a polypeptide comprising the sequence of SEQ ID NO: 37. In some embodiments, the ADBD comprises a DD sequence selected from the group consisting of SEQ ID NO: 74-93 and 94. In some embodiments, the DD binds AFP p26 and comprises the amino acid sequence of SEQ ID NO: 70-73 or 92-94. In some embodiments, the DD binds AFP p26 and comprises the amino acid sequence of SEQ ID NO: 73.

In some embodiments, the CAR comprises an ADBD that is an antibody or an antigen-binding fragment thereof. In some embodiments, the CAR comprises an ADBD that is a scFv. In some embodiments, the CAR comprises an ADBD that is an alternative scaffold binding domain. In some embodiments, the CAR comprises an ADBD that is a D domain. In some embodiments, the CAR comprises a T cell receptor, or an antigen-binding fragment thereof.

Also provided herein are CAR wherein the CAR comprises a plurality of ADBDs. In some embodiments, the CAR comprises a plurality of the same ADBD. In some embodiments, the CAR comprises a plurality of different ADBDs. In some embodiments, the CAR comprises a plurality of ADBDs that bind the same antigenic determinant. In some embodiments, the CAR comprises a plurality of ADBDs, wherein the binding domains bind to different ADs. In some embodiments, the CAR comprises a plurality of ADBDs, wherein the binding domains bind to different ADs on the same cell. In some embodiments, the CAR comprises a plurality of ADBDs, wherein the binding domains bind to different ADs on different cells.

In some embodiments, a CAR comprises a plurality of, e.g., 2, 3, 4, 5, or more than 5, ADBDs (e.g., D domains, affibodies, or scFvs), wherein each ADBD(s) are able to bind to a target antigen. In one embodiment, two or more of the ADBDs of a CAR can bind to different ADs. In an additional embodiment, two or more of the ADBDs of the CAR can bind to the same antigen, e.g., the same or different epitopes on the same antigen. In one embodiment, a plurality of ADBDs of the CAR are linked to each other, e.g., the C-terminus of a first ADBD is linked to the N-terminus of a second ADBD. In an embodiment, the C-terminus of a first ADBD is linked to the N-terminus of a second ADBD by a covalent bond, e.g., a peptide bond.

In some embodiments, a linker or hinge region is contained between one or more of the ADBDs, e.g., a linker or hinge region is located between the C-terminus of a first ADBD and the N-terminus of a second ADBD. By way of example, an antigen binding member comprising two ADBDs (e.g., $ADBD_1$ and $ADBD_2$) can be arranged in the following configuration: $[ADBD_1]$-[linker/hinge]-$[ADBD_2]$. Additional ADBDs can be added in a similar manner, optionally with linker or hinge regions located between the C-terminus of an ADBD and the N-terminus of the next ADBD. Linkers or hinge regions suitable for use in linking a plurality of antigen binding members are flexible, non-cleavable, and allow near-free motion of each ADBD independent from the other ADBDs to encourage binding with multiple target ADs simultaneously. Any flexible linker or hinge region known in the art can be used. Examples of linkers include peptide linkers comprising glycine and serine residues, e.g., (GGGGS)n, where n is a positive integer equal to or greater than 1, e.g., n=1, 2, 3, 4, 5, 6, 7, 8, 9, or 10 (SEQ ID NO: 96). In some embodiments, the peptide linker contains the sequence of SEQ ID NO: 45-48, 118 or 119. In some embodiments, the peptide linker contains the sequence of SEQ ID NO: 45-48, 118 or 119.

In some embodiments, the CAR comprises a CD123-binding DD. In some embodiments, the CAR comprises a BCMA-binding DD and a CD123-binding DD.

In some embodiments, the antigen binding moiety portion of the CAR specifically binds CD123 and CD33. In some embodiments, the antigen binding moiety portion of the CAR specifically binds CD123 and LeY. In additional embodiments, the antigen binding moiety portion of the CAR further binds a target selected from: BCMA, CS1, HVEM, BTLA, DR3, CD19, CD20, and CD22.

In some embodiments, the antigen binding moiety portion of the CAR further binds a tumor antigen. In additional embodiments, the antigen binding moiety portion of the CAR further binds CD33 or LeY. In additional embodiments, the antigen binding moiety portion of the CAR further binds a target selected from: BCMA, CD123, CS1, HER2, HVEM, BTLA, DR3, CD19, CD20, and CD22.

In some embodiments, the CAR comprises 2, 3, 4, 5, or more than 5, DD and/or other binding domains (e.g., scFv) that specifically bind a target of interest (e.g., CD123) expressed on the surface of the cancer cell. In additional embodiments, the CAR comprises 2, 3, 4, 5, or more than 5, DD or other binding domains (e.g., scFv) that specifically bind a second, different target of interest, expressed on the surface of the cancer cell. In additional embodiments, the administered CAR further comprises 2, 3, 4, 5, or more than 5, DD or other binding domains (e.g., scFv) that specifically binds a second, different target of interest, expressed by a second, different cancer cell or a vascular endothelial cell. In some embodiments, the CAR comprises 2, 3, 4, 5, or more than 5, DD and/or other binding domains (e.g., scFv) that specifically bind AFP p26. In some embodiments, the CAR comprises 2, 3, 4, 5, or more than 5, DD and/or other binding domains (e.g., scFv) that specifically bind CD123. In some embodiments, the CD123-binding DD comprises an amino acid sequence selected from the group consisting of SEQ ID NO: 8, 13, 14, 31, 32, and 33. In some embodiments, the CD123-binding DD comprises the amino acid sequence of SEQ ID NO: 14.

ii. Extracellular Spacer Domain

In some embodiments, the CARs comprise an extracellular spacer domain. As used herein, the term "extracellular spacer domain" or "ESD" refers to a polypeptide sequence of a CAR positioned between the ADBD and the transmembrane domain. In an embodiment the extracellular spacer domain allows sufficient distance from the outer surface of the cell and the ADBD as well as flexibility to minimize steric hindrance between the cell and the ADBD.

In particular embodiments, the extracellular spacer domain is sufficiently short or flexible that it does not interfere with engagement of the cell that includes the CAR with a cell bearing an AD, e.g., a target cell. In an embodiment, the extracellular spacer domain is from 2 to 20, 5 to 15, 7 to 12, or 8 to 10 amino acids in length. In some embodiments, the ESD domain includes at least 50, 20, or 10 residues. In some embodiments the ESD is 10 to 300, 10 to 250, or 10 to 200 residues in length.

In some embodiments the distance from which the ESD extends from the cell is sufficiently short that the hinge does not hinder engagement of the CAR ADBD with the surface of a target cell. In some embodiment the ESD extends less than 20, 15, or 10 nanometers from the surface of the cytotoxic cell. Thus, suitability for an ESD can be influenced by both linear length, the number of amino acid residues and flexibility of the ESD. By way of example, an IgG4 ESD can be as long as 200 amino acids in length, but the distance it extends from the surface of the cytotoxic cell is smaller due to Ig-domain folding. A CD8 alpha ESD, which is ~43 amino acids at ~8 nm in length. In contrast, the IgG4 C2 & C3 ESD is ~200 amino acids in length, but has a distance from the cytotoxic cell surface that is comparable to that of the CD8 alpha ESD. While not wishing to be bound by theory, the similarity in extension is influenced by flexibility.

In some embodiments, the extracellular spacer domains include but are not limited to Fc fragments of antibodies or fragments or derivatives thereof, hinge regions of antibodies or fragments or derivatives thereof, CH2 regions of antibodies, CH3 regions of antibodies, artificial spacer sequences or combinations thereof. Additional examples of extracellular spacer domains include but are not limited to CD8a hinge, and artificial spacers made of polypeptides which may be as small as, for example, Gly3 or CH1 and CH3 domains of IgGs (such as human IgG4). In some embodiments, the extracellular spacer domain is any one or more of (i) a hinge, CH2 and CH3 regions of IgG4, (ii) a hinge region of IgG4, (iii) a hinge and CH2 of IgG4, (iv) a hinge region of CD8a, (v) a hinge, CH2 and CH3 regions of IgG1, (vi) a hinge region of IgG1 or (vi) a hinge and CH2 region of IgG1. Other extracellular spacer domains will be apparent to those of skill in the art and may be used in connection with alternate embodiments provided herein.

In some embodiments, the ESD is a naturally occurring sequence. In some embodiments, the ESD of the CAR corresponds to an ESD from a human protein, a fragment thereof, or a short oligo- or polypeptide linker. In some embodiments, the CAR ESD corresponds to a human Ig (immunoglobulin) ESD (hinge), or fragment thereof. In one embodiment, the ESD comprises (e.g., consists of) the amino acid sequence of the IgG4 ESD. In one embodiment, for example, the hinge comprises (e.g., consists of) the amino acid sequence of the IgD hinge. In some embodiments, the hinge can be a human CD8 hinge, or fragment thereof. In one embodiment, for example, the hinge comprises (e.g., consists of) the amino acid sequence of the CD8 hinge.

In some embodiments, the ESD is an artificial sequence. In one embodiment, the ESD is a short oligopeptide linker comprising a glycine-serine doublet.

In some embodiments, the CAR comprises the CD8a extracellular spacer domain.

In some embodiments, the CAR does not contain an extracellular spacer domain iii. Transmembrane Domain The term "transmembrane domain" (TMD) as used herein refers to the region of a cell surface expressed protein, such as a CAR, which spans the plasma membrane. In some embodiments, the TMD links an extracellular sequence (e.g., an extracellular ADBD or an extracellular AD), and an intracellular sequence, such as an intracellular signaling domain. In some embodiments, the transmembrane domain of the CAR is the transmembrane region of a transmembrane protein (for example Type I transmembrane proteins), an artificial hydrophobic sequence or a combination thereof. Other transmembrane domains will be apparent to those of skill in the art and may be used in connection with alternate embodiments of the invention. In some embodiments, the extracellular ADBD is a CD123-binding ADBD (e.g., D domain) In some embodiments, the extracellular ADBD comprises the amino acid sequence of SEQ ID NO 8, 13, 14, 31, 32, or 33. In some embodiments, the extracellular ADBD comprises the amino acid sequence of SEQ ID NO 14. In some embodiments, the extracellular ADBD is a p26-binding ADBD (e.g., D domain) In some embodiments, the extracellular ADBD comprises the amino acid sequence of SEQ ID NO: 70-73 or 92-94. In some embodiments, the extracellular ADBD comprises the amino acid sequence of SEQ ID NO 73. In some embodiments, the extracellular AD comprises p26. In some embodiments, the extracellular AD comprises the amino acid sequence of SEQ ID NO 37-43 or 44.

The CAR can be designed to contain a transmembrane domain that is fused to the extracellular domain of the receptor. As described above, the fusion of the extracellular and transmembrane domains can be accomplished with or without a linker. In one embodiment, the transmembrane domain that is naturally associated with one of the domains in the CAR is used. In a specific embodiment, the transmembrane domain in the CAR is the CD8a transmembrane domain. In some embodiments, the CD8a transmembrane domain comprises the amino acid sequence of SEQ ID NO: 113. In some embodiments, the CD8a transmembrane domain comprises the amino acid sequence of SEQ ID NO: 114. In some instances, the transmembrane domain of the CAR comprises the CD8a hinge domain. In some embodiments, the CD8a hinge domain, also referred to as extracellular spacer domain (ESD), comprises the amino acid sequence of SEQ ID NO: 112. In some embodiments, the transmembrane domain is selected or modified by amino acid substitution to promote or inhibit association with other surface membrane proteins.

The transmembrane domain can be derived either from a natural or from a synthetic source. Where the source is natural, the domain can be derived from any membrane-bound or transmembrane protein. Transmembrane regions of particular use for the purposes herein may be derived from (i.e., comprise at least the transmembrane region(s) of) a member selected from the group: the alpha, beta or zeta chain of the T cell receptor; CD28, CD3 epsilon, CD45, CD4, CD5, CD8a, CD8b, CD9, CD16, CD22, CD33, CD37, CD64, CD80, CD86, CD134, CD137, and CD154. In some embodiments, the transmembrane domain is derived from the transmembrane region(s) of a NKR. In some embodiments, the transmembrane domain is derived from the transmembrane region of CD8a. In some embodiments, the CD8a transmembrane domain comprises the amino acid sequence of SEQ ID NO: 113. In some embodiments, the CD8a transmembrane domain comprises the amino acid sequence of SEQ ID NO: 114. In further embodiments, the transmembrane domain is derived from the transmembrane region of a molecule selected from the group consisting of, KIRDS2, OX40, TNFR2, LFA1 (CD11a, CD18), ICOS, 41BB, GITR, LTBR, BAFFR, HVEM, NKp80 (KLRF1), IL2R beta, IL2R gamma, IL7R α, ITGA1, ITGA4, ITGA6, ITGAD, ITGAE, ITGAL, ITGAM, ITGB7, VLA1, VLA6, IA4, ITGAX, CD11c, ITGB1 CD27, CD29, ITGB2, CD2, CD11a, CD11b, CD11d, CD18, CD19, CD40, CD49a, CD49d, CD49f, CD84, CD96, CD100, CD103, CD160, CD162, CD229, CEACAM1, CRTAM, PSGL1, SLAM (SLAMF1), SLAMF4, SLAMF6 (NTB-A, Ly108), SLAMF7, SLAMF8, SELPLG, and PAG/Cbp. Alternatively, the transmembrane domain can be synthetic, and preferably predominantly comprises hydrophobic residues such as leucine and valine. In further embodiments, the transmembrane domain comprises the triplet of FWV (phenylalanine, tryptophan and valine) at each end of the transmembrane domain.

Exemplary NKR domains, e.g., transmembrane, hinge or stem, or intracellular (e.g., cytoplasmic) domains (identified by the NKR from which the domain is derived) Killer immunoglobulin KIR2DL1 receptors (KIRs) include KIR2DL2/L3, KIR2DL4, KIR2DL5A, KIR2DL5B, KIR2DS1, KIR2DS2, KIR2DS3, KIR2DS4, KIR2DS5, KIR3DL1/S1, KIR3DL2, KIR3DL3, KIR2DP1, KIR2DP1, NCRs:, NKp30, NKp44, NKp46, SLAM; Receptors SLAM, CD48, CD229, 2B4, CD84, NTB-A, CRACC, BLAME, CD2F-10, SLAMF6, SLAMF7; Fc-binding Receptors CD16, FcgRIII, CD64, Ly49; Receptors Ly49, Lectin-related NK Ly49A cell receptor, Ly49C; other NK receptors NKG2D, CD160 (TM containing splice variant(s)) DNAM1, CRTAM, CD27, PSGL1, CD96, CD100, NKp80, CEACAM1, and CD244.

iv. Intracellular Signaling Domain

Described herein are intracellular signaling domains that can be used in a chimeric antigen receptor (CAR) according to the present invention.

"Intracellular signaling domain" (ISD) or "cytoplasmic domain" as used herein refer to the portion of the CAR which transduces the effector function signal and directs the cell to perform its specialized function (e.g., cytolytic activity and helper activity, including cytokine secretion).

The cytoplasmic domain (i.e., intracellular signaling domain) of a CAR is responsible for activation of at least one of the normal effector functions of an immune cell engineered to express a CAR. The term "effector function" refers to a specialized function of a cell. The effector function of a T cell, for example, includes cytolytic activity and helper activity including the secretion of cytokines. Thus the term "intracellular signaling domain" refers to the portion of a CAR protein which transduces the effector function signal and directs the cell to perform a specialized function. While typically the entire intracellular signaling domain corresponding to a naturally occurring receptor can be employed, in many cases it is not necessary to use the entire chain. To the extent that a truncated portion of the intracellular signaling domain is used, such truncated portion can be used in place of the intact chain as long as it transduces the effector function signal. The term intracellular signaling domain is thus meant to include any truncated portion of the intracellular signaling domain sufficient to transduce the effector function signal. In one embodiment, an intracellular signaling domain in the CAR includes the cytoplasmic sequences of the T cell receptor (TCR) and also the sequence of co-receptors that act in concert to initiate signal transduction following antigen receptor engagement, or any derivative or variant of these sequences that has functional capability. Examples of domains that transduce an effector function signal include but are not limited to the ζ chain of the T cell receptor complex or any of its homologues (e.g., η chain, FcsRly and β chains, MB 1 (Iga) chain, B29 (Ig) chain, etc.), human CD3 zeta chain, CD3 polypeptides (Δ, δ and ε), syk family tyrosine kinases (Syk, ZAP 70, etc.), src family tyrosine kinases (Lck, Fyn, Lyn, etc.) and other molecules involved in T cell transduction, such as CD2, CD5 and CD28.

In some embodiments, the intracellular signaling domain of the CAR produces an intracellular signal when an extracellular domain (e.g., an ADBD) to which it is fused, binds a cognate AD. The Intracellular signaling domains of the CAR can include primary intracellular signaling domains and costimulatory signaling domains. In one embodiment, the CAR is constructed for expression in an immune cell (e.g., a T or NK cell), such that the expressed CAR comprises a domain such as a primary intracellular signaling domain and/or costimulatory signaling domain, that is derived from a polypeptide typically associated with the immune cell. For example, in some embodiments, the CAR is for expression in a T cell and comprises a 41BB domain and a CD3 zeta domain. In another embodiment, the CAR molecule is constructed for expression in an immune cell such that the expressed CAR comprises a domain that is derived from a polypeptide that is not typically associated with the immune cell. For example, in some embodiments the CAR for expression in a T cell comprises a KIR domain derived from a NK cell. In an alternative embodiment, the CAR for expression in an NK cell comprises a 41BB domain and a CD3 zeta domain derived from a T cell (See e.g. WO2013/033626, incorporated herein by reference).

The intracellular signaling domain of the CAR comprises sufficient primary stimulatory molecule sequence to produce an intracellular signal, e.g., when an ADBD to which it is fused binds a cognate AD. In particular embodiments, the intracellular signal of the CAR mediates a T cell response selected from the group: proliferation, cytokine secretion, killing, activation, and differentiation.

In one embodiment, the intracellular signaling region of the CAR comprises a domain that contains an immunoreceptor tyrosine-based activation motif (ITAM). In a further embodiment, the CAR intracellular signaling region comprises one or more ITAM containing domains from a molecule selected from: TCR zeta (CD3 zeta), FcR gamma (FCER1G), Fc gamma RIIa, FcR beta (FCER1B), CD3 gamma, CD3 delta, CD3 epsilon, CD3 gamma, CD5, CD22, CD79a, CD79b, DAP10, DAP12, CD32 (Fc gamma RIIa), CD79a, and CD79b. In a specific embodiment, the intracellular signaling domain of the CAR comprises a CD3 zeta signaling domain. In another specific embodiment, the intracellular signaling domain of the CAR comprises a DAP12 signaling domain. In some embodiments, the ITAM containing signaling domain has at least 70, 75, 80, 85, 90, 95, 98, or 99% sequence identity with, or differs by no more than 30, 25, 20, 15, 10, 5, 4, 3, 2, or 1 amino acid residues from the corresponding residues of a naturally occurring ITAM containing domain.

Examples of ITAM containing primary cytoplasmic signaling sequences that are of particular use in the invention include those derived from TCR zeta, FcR gamma, FcR beta, CD3 gamma, CD3 delta, CD3 epsilon, CD22, CD79a, CD79b, and CD66d. It is particularly preferred that a cytoplasmic signaling molecule in the CAR comprises a cytoplasmic signaling sequence derived from CD3 zeta.

In a preferred embodiment, the cytoplasmic domain of the CAR comprises the CD3-zeta signaling domain by itself or combined with any other desired cytoplasmic domain(s) useful in the context of the CAR. For example, the cytoplasmic domain of the CAR can comprise a CD3 zeta chain portion and a costimulatory signaling region. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such molecules include CD27, CD28, 41BB (CD 137), OX40, CD30, CD40, PD1, ICOS, lymphocyte function-associated antigen-1 (LFA1), CD2, CD7, LIGHT, NKG2C, B7H3, TIM1, and LAG3.

"Co-stimulatory domain" (CSD) as used herein refers to the portion of the CAR which enhances the proliferation, survival and/or development of memory cells. The CAR may comprise one or more co-stimulatory domains. Each co-stimulatory domain comprises the costimulatory domain of any one or more of, for example, a member of the TNFR superfamily, selected from CD28, CD137 (41BB), CD134 (OX40), Dap10, CD27, CD2, CD5, ICAM1, LFA1 (CD11a/CD18), Lck, TNFRI, TNFRII, Fas, CD30, and CD40 or a combination thereof. Other co-stimulatory domains (e.g., from other proteins) will be apparent to those of skill in the art and may be used in connection with alternate embodiments of the invention.

In some embodiments, the intracellular domain of the CAR comprises an ITAM containing domain and a costimulatory signaling domain that comprises a functional fragment or analog of a costimulatory molecule that is sufficient to produce an intracellular signal when an extracellular ADBD to which it is fused, binds cognate ligand. In some embodiments, the CAR comprises a costimulatory signaling domain corresponding to that found in a molecule selected from: CD137 (41BB), OX40, LIGHT, TNFR2, TRANCE/RANKL, GITR, BAFFR, HVEM, B7H3, CDS, IL2R beta, IL2R gamma, IL7R alpha, ITGA4, ITGA6, ITGAD, ITGAE, ITGAL, ITGAM, ITGAX, ITGB1, ITGB2, ITGB7, VLA1, VLA6, C49f, IA4, LFA1, CD2, CD4, CD7, CD8 alpha, CD8 beta, CD11A, CD11B, CD11C, CD11D, CD18, CD19, CD27, CD28, CD29, CD30, CD40, CD49A, CD49D, CD69, CD84, CD96, CD100, CD103, CD150, CD160, CD162, CD226, CD229, CD278, ICAM1, CEACAM1, CRTAM, PSGL1, SLAMF1, SLAMF4, SLAMF6, SLAMF7, SLAMF8, LTBR, LAT, GADS, PAG/Cbp, SLP76, NKG2C, NKp30, NKp44, NKp46 and NKp80.

In some embodiments, the CAR comprises a costimulatory domain corresponding to that found in a molecule selected from the group consisting 41BB, CD28, CD27, ICOS, and OX40.

In some embodiments, the CAR comprises a plurality of costimulatory domains. In particular embodiments, the CAR comprises the following costimulatory signaling domains, from the extracellular to intracellular direction: 41BB-CD27, CD27-41BB, 41BB-CD28, CD28-41BB, OX40-CD28, CD28-OX40, CD28-41BB; or 41BB-CD28.

In some embodiments the costimulatory signaling domain of the CAR has at least 70, 75, 80, 85, 90, 95, 96, 97, 98, or 99% identity with, or differs by no more than 30, 25, 20, 15, 10, 5, 4, 3, 2, or 1 amino acid residues from the corresponding residues of a naturally occurring costimulatory domain.

In some embodiments, the CAR contains an intracellular signaling domain having the sequence of SEQ ID NO: 115, 116 or combination thereof. In some embodiments, the CAR contains an intracellular signaling domain having the sequence of SEQ ID NO: 117. In some embodiments, the CAR contains an intracellular signaling domain having a sequence that has at least 70, 75, 80, 85, 90, 95, 96, 97, 98, or 99% identity with of SEQ ID NO: 115, 116 or 117. In some embodiments, the CAR contains an intracellular signaling domain having the sequence of SEQ ID NO: 115, 116 or 117 comprising 1, 2, 3, 4, 5, 7, 8, 9, 10, 15 or 20 insertions, deletions or substitutions. In some embodiments, the CAR contains an intracellular signaling domain having the sequence of SEQ ID NO: 115, 116 or 117 comprising 1, 2, 3, 4, 5, 7, 8, 9, or 10 insertions, deletions or substitutions. In some embodiments, the CAR contains an intracellular signaling domain having the sequence of SEQ ID NO: 115, 116 or 117 comprising 1, 2, 3, 4, 5, 7, 8, 9, or 10 substitutions.

Polypeptide linkers may be positioned between adjacent elements of the CAR. For example linkers may be positioned between adjacent ADBDs or between an ADBD and the transmembrane domain or between the transmembrane domain and the cytoplasmic domain or between adjacent cytoplasmic domains. The cytoplasmic signaling sequences within the cytoplasmic signaling portion of the CAR may be linked to each other in a random or specified order. Optionally, a short linker, preferably between 2 and 10 amino acids in length may form the linkage. A glycine-serine doublet provides a particularly suitable linker.

In some embodiments, the CAR comprises, a target binding domain, a transmembrane domain, and an intracellular signaling domain. In some embodiments, the CAR transmembrane domain comprises a CD8a, 41BB or CD28 transmembrane domain. In some embodiments, the CAR transmembrane domain comprises the CD8a transmembrane domain. In some embodiments, the CAR comprises the CD8a transmembrane domain and CD8a extracellular spacer domain. In some embodiments, the CD8a transmembrane domain comprises the amino acid sequence of SEQ ID NO: 113. In some embodiments, the CD8a transmembrane domain comprises the amino acid sequence of SEQ ID NO: 114. In some embodiments, the CD8a extracellular spacer domain (ESD), also referred to as hinge domain, comprises the amino acid sequence of SEQ ID NO: 112. In some embodiments the CAR comprises an intracellular signaling domain selected from the group consisting of a domain of a human T cell receptor alpha, beta, or zeta chain; a human 41BB domain; a human CD28 domain; and any combination thereof. In some embodiments, the CAR contains an intracellular signaling domain having the sequence of SEQ ID NO: 115, 116 or combination thereof. In some embodiments, the CAR contains an intracellular signaling domain having the sequence of SEQ ID NO: 117. In some embodiments, the CAR contains an intracellular signaling domain having a sequence that has at least 70, 75, 80, 85, 90, 95, 96, 97, 98, or 99% identity with of SEQ ID NO: 115, 116 or 117. In some embodiments, the CAR contains an intracellular signaling domain having the sequence of SEQ ID NO: 115, 116 or 117 comprising 1, 2, 3, 4, 5, 7, 8, 9, 10, 15 or 20 insertions, deletions or substitutions. In some embodiments, the CAR contains an intracellular signaling domain having the sequence of SEQ ID NO: 115, 116 or 117 comprising 1, 2, 3, 4, 5, 7, 8, 9, or 10 insertions, deletions or substitutions. In some embodiments, the CAR contains an intracellular signaling domain having the sequence of SEQ ID NO: 115, 116 or 117 comprising 1, 2, 3, 4, 5, 7, 8, 9, or 10 substitutions. In some embodiments, the CAR intracellular signaling domain comprises the intracellular domain of a costimulatory molecule selected from the group consisting of CD27, CD28, 41BB, OX40, CD30, CD40, PD1, lymphocyte function-associated antigen-1 (LFA-1), CD2, CD7, LIGHT, NKG2C, B7-H3, a ligand that specifically binds with CD83, and any combination thereof. In some embodiments the CAR further comprises a second target binding domain having the same or a different target than the DD target binding domain. In some embodiments, the CAR comprises a first target binding domain that binds CD123 and a second target binding domain that binds a different target. In some embodiments, the CAR comprises first and second target binding domains that bind CD123. In some embodiments, the CAR is expressed in an immune effector cell. In some embodiments, the immune effector cell is a T cell (CAR-T cell) or a natural killer (NK) cell (CAR-NK cell). In some embodiments, the immune effector cell is an autologous cell. In some embodiments, the immune effector cell is an allogenic cell. In some embodiments, the CAR is associated with a liposome. In some embodiments, the CAR comprises a target binding domain comprising a DD disclosed herein (e.g., a DD comprising the amino acid sequence of SEQ ID NO: 8-33 or 74-94). In some embodiments, the DD binds CD123 and comprises an amino acid sequence selected from the group consisting of SEQ ID NO: 8-33, 99 and 100. In some embodiments, the CD123-specific DD comprises an amino acid sequence selected from the group consisting of SEQ ID NO: 8, 13, 14, 31, 32, and 33. In some embodiments, the CD123-specific DD comprises the amino acid sequence of SEQ ID NO: 14. In some embodiments, the DD binds AFP p26 and comprises an amino acid sequence selected from the group consisting of SEQ ID NO: 74-93 and 94. In some embodiments, the DD binds AFP p26 and comprises the amino acid sequence of SEQ ID NO: 70-73 or 92-94. In some embodiments, the DD binds AFP p26 and comprises the amino acid sequence of SEQ ID NO: 73. In some embodiments, the CAR comprises an extracellular AD comprising p26. In some embodiments, the extracellular AD comprises the amino acid sequence of SEQ ID NO 37-43 or 44.

CARs suitable for use in connection with the DDpp (e.g., Adapter and CAR) disclosed herein have been disclosed in Int'l. Appl. Pub. Nos. WO 2016164305, WO 2016164308A1, WO 2019099440, and WO 2019099433, U.S. Pat. Nos. 10,662,248, and 10,647,775, and US Pat. Appl. Nos. 20200223934, and 20210002381, each of which is incorporated herein by reference for all purposes.

TABLE 3

Exemplary Chimeric antigen receptors

| SEQ ID NO: | CAR Sequence | Target |
|---|---|---|
| 62 | DEMGSWDEFGRRLYAIESQLYALGGTEAELAAFE KEIAAFESELQAYKGKGNPEVEKLREIAAVIREN LQAYRHNGGGDGGGGSGTTTPAPRPPTPAPTIA SQPLSLRPEACRPAAGGAVHTRGLDFACDIYIWA PLAGTCGVLLLSLVITLYCKRGRKKLLYIFKQPF MRPVQTTQEEDGCSCRFPEEEEGGCELRVKFSRS ADAPAYKQGQNQLYNELNLGRREEYDVLDKRRGR DPEMGGKPRRKNPQEGLYNELQKDKMAEAYSEIG MKGERRRGKGHDGLYQGLSTATKDTYDALHMQAL PPR | CD123 |
| 63 | DEMGSWDEFGRRLYAIEAQLYALGGTEAELAAFE KEIAAFESELQAYKGKGNPEVEKLREIAAVIREN LQAYRHNGGGDGGGGSGTTTPAPRPPTPAPTIA SQPLSLRPEACRPAAGGAVHTRGLDFACDIYIWA PLAGTCGVLLLSLVITLYCKRGRKKLLYIFKQPF MRPVQTTQEEDGCSCRFPEEEEGGCELRVKFSRS ADAPAYKQGQNQLYNELNLGRREEYDVLDKRRGR DPEMGGKPRRKNPQEGLYNELQKDKMAEAYSEIG MKGERRRGKGHDGLYQGLSTATKDTYDALHMQAL PPR | CD123 |
| 64 | DEMGSWDEFGRRLYAIEEQLYALGGTEAELAAFE KEIAAFESELQAYKGKGNPEVEKLREIAAVIREN LQAYRHNGGGDGGGGSGTTTPAPRPPTPAPTIA SQPLSLRPEACRPAAGGAVHTRGLDFACDIYIWA PLAGTCGVLLLSLVITLYCKRGRKKLLYIFKQPF MRPVQTTQEEDGCSCRFPEEEEGGCELRVKFSRS ADAPAYKQGQNQLYNELNLGRREEYDVLDKRRGR DPEMGGKPRRKNPQEGLYNELQKDKMAEAYSEIG MKGERRRGKGHDGLYQGLSTATKDTYDALHMQAL PPR | CD123 |
| 65 | DEMGSWDEFGRRLYAIEWQLYALGGTEAELAAFE KEIAAFESELQAYKGKGSPEVEKLREIAAVIREN LQAYRHNGGGDGGGGSGTTTPAPRPPTPAPTIA | CD123 |

TABLE 3-continued

Exemplary Chimeric antigen receptors

| SEQ ID NO: | CAR Sequence | Target |
|---|---|---|
|  | SQPLSLRPEACRPAAGGAVHTRGLDFACDIYIWA<br>PLAGTCGVLLLSLVITLYCKRGRKKLLYIFKQPF<br>MRPVQTTQEEDGCSCRFPEEEEGGCELRVKFSRS<br>ADAPAYKQGQNQLYNELNLGRREEYDVLDKRRGR<br>DPEMGGKPRRKNPQEGLYNELQKDKMAEAYSEIG<br>MKGERRRGKGHDGLYQGLSTATKDTYDALHMQAL<br>PPR |  |
| 66 | DEMGSWDEFSRRLYAIEWQLYALGGTEAELAAFE<br>KEIAAFESELQAYKGEGSPEVEKLRELAAVIREN<br>LQAYRHNGGGDGGGGSGTTTPAPRPPTPAPTIA<br>SQPLSLRPEACRPAAGGAVHTRGLDFACDIYIWA<br>PLAGTCGVLLLSLVITLYCKRGRKKLLYIFKQPF<br>MRPVQTTQEEDGCSCRFPEEEEGGCELRVKFSRS<br>ADAPAYKQGQNQLYNELNLGRREEYDVLDKRRGR<br>DPEMGGKPRRKNPQEGLYNELQKDKMAEAYSEIG<br>MKGERRRGKGHDGLYQGLSTATKDTYDALHMQAL<br>PPR | CD123 |
| 67 | DEMGSWDEFSRRLYAIEWQLYAQGGTEAELAAFE<br>KEIAAFESELQAYKGEGSPEVEKLRELAAVIREN<br>LQAYRHNGGGDGGGGSGTTTPAPRPPTPAPTIA<br>SQPLSLRPEACRPAAGGAVHTRGLDFACDIYIWA<br>PLAGTCGVLLLSLVITLYCKRGRKKLLYIFKQPF<br>MRPVQTTQEEDGCSCRFPEEEEGGCELRVKFSRS<br>ADAPAYKQGQNQLYNELNLGRREEYDVLDKRRGR<br>DPEMGGKPRRKNPQEGLYNELQKDKMAEAYSEIG<br>MKGERRRGKGHDGLYQGLSTATKDTYDALHMQAL<br>PPR | CD123 |
| 68 | DEMGSWSEFYDRLNAIDARLWALGGSEAELAAFE<br>KEIAAFESELQAYKGKGNPEVESLREHAAAIREW<br>LQAYRHNGGGDGGGGSGTTTPAPRPPTPAPTIA<br>SQPLSLRPEACRPAAGGAVHTRGLDFACDIYIWA<br>PLAGTCGVLLLSLVITLYCKRGRKKLLYIFKQPF<br>MRPVQTTQEEDGCSCRFPEEEEGGCELRVKFSRS<br>ADAPAYKQGQNQLYNELNLGRREEYDVLDKRRGR<br>DPEMGGKPRRKNPQEGLYNELQKDKMAEAYSEIG<br>MKGERRRGKGHDGLYQGLSTATKDTYDALHMQAL<br>PPR | AFP p26 |
| 69 | DEMGSWFEFYDRLNAIDARLWALGGSEAELAAFE<br>KEIAAFESELQAYKGKGNPEVESLRVHAAAIREW<br>LQAYRHNGGGDGGGGSGTTTPAPRPPTPAPTIA<br>SQPLSLRPEACRPAAGGAVHTRGLDFACDIYIWA<br>PLAGTCGVLLLSLVITLYCKRGRKKLLYIFKQPF<br>MRPVQTTQEEDGCSCRFPEEEEGGCELRVKFSRS<br>ADAPAYKQGQNQLYNELNLGRREEYDVLDKRRGR<br>DPEMGGKPRRKNPQEGLYNELQKDKMAEAYSEIG<br>MKGERRRGKGHDGLYQGLSTATKDTYDALHMQAL<br>PPR | AFP p26 |

D. Additional DDpp Fusion Proteins

In some embodiments, the DDpp contains a heterologous polypeptide comprising a fragment consisting of 5-500, 5-400, 5-300, 5-200, 5-100, 5-50, 10-500, 10-400, 10-300, 10-200, 10-100, or 10-50 amino acids of an extracellular domain, of a cell surface receptor. In some embodiments, the DDpp contains a heterologous polypeptide that comprises the extracellular domain, or a fragment of an extracellular domain of BCMA (SEQ ID NO: 34) or CD123 (SEQ ID NO: 1). In some embodiments, the DDpp contains a heterologous polypeptide that comprises the extracellular domain, or a fragment of an extracellular domain of BCMA (SEQ ID NO: 34), or CD123 (SEQ ID NO: 1), or CS1 (SEQ ID NO: 35). In some embodiments, the DDpp contains a heterologous polypeptide that comprises the extracellular domain, or a fragment of an extracellular domain, of a receptor selected from the group consisting of: CD19, CD20, CD22, HVEM, BTLA, DR3, CD37; TSLPR, IL7R, and gp96.

In some embodiments, the protein contains a heterologous polypeptide that comprises a serum protein or an antigenic fragment of a serum protein (e.g., AFP, and AFP p26). In some embodiments, the DDpp contains a heterologous polypeptide comprising a fragment consisting of 5-500, 5-400, 5-300, 5-200, 5-100, 5-50, 10-500, 10-400, 10-300, 10-200, 10-100, or 10-50 amino acids of a serum protein. In some embodiments, the protein contains a heterologous polypeptide that comprises an intracellular protein or an antigenic portion of an intracellular protein (e.g., a nuclear protein). In some embodiments, the DDpp contains a heterologous polypeptide comprising a fragment consisting of 5-500, 5-400, 5-300, 5-200, 5-100, 5-50, 10-500, 10-400, 10-300, 10-200, 10-100, or 10-50 amino acids of an intracellular protein. In some embodiments, the DDpp contains a heterologous polypeptide having the sequence of SEQ ID NO: 37-43 or 44.

In some embodiments, the DDpp fusion protein specifically binds CD123 and/or AFP p26, and further binds one or more additional targets of interest. The targets of interest specifically bound by a DDpp fusion protein can be any molecule for which it is desirable for a DDpp to bind. For example, the targets specifically bound by the DDpp fusion protein can be CD123 and/or AFP p26, and additionally any additional target of manufacturing, formulation, therapeutic, diagnostic, or prognostic relevance or value. A number of exemplary additional targets are provided herein, by way of example, and are intended to be illustrative and not limiting. The additional target of interest bound by the DDpp fusion protein can be naturally occurring or synthetic. The additional target of interest can be an extracellular component or an intracellular component, a soluble factor (e.g., an enzyme, hormone, cytokine, and growth factor, toxin, venom, pollutant, etc.), or a transmembrane protein (e.g., a cell surface receptor). In some embodiments, the target of interest bound by the DDpp fusion protein is a human protein. In one embodiment, a DDpp (e.g., a DDpp fusion protein) binds a human protein target of interest and its monkey (e.g., cynomolgous monkey), mouse, rabbit, hamster and/or a rabbit ortholog. In some embodiments, the additional target of interest is BCMA, CS1, or HER2

In one embodiment a DDpp fusion protein specifically binds CD123 and/or AFP p26, and a serum protein. In one embodiment, the DDpp fusion protein specifically binds a serum protein selected from: serum albumin (e.g., human serum albumin (HSA)), thyroxin-binding protein, transferrin, fibrinogen, and an immunoglobulin (e.g., IgG, IgE and IgM). Without being bound by theory, the binding of a DDpp to a carrier protein is believed to confer upon the DDpp (or a fusion thereof) an improved pharmacodynamic profile that includes, but is not limited to, improved tumor targeting, tumor penetration, diffusion within the tumor, and enhanced therapeutic activity compared to the DDpp fusion protein in which the carrier protein binding sequence is missing (see, e.g., WO01/45746, the contents of which is herein incorporated by reference in its entirety).

E. Antibody-Based DDpp Fusion Proteins

In some embodiments, the DDpp fusion protein comprises a full-length antibody or a fragment or subdomain of an antibody. In some embodiment, the DDpp fusion protein comprises a full length IgG antibody (e.g., IgG1, IgG2, IgG2, or IgG4). In further embodiments, the DDpp fusion protein comprises a full length antibody that specifically binds a cancer antigen. In further embodiments, the DDpp comprises a commercially approved therapeutic antibody (e.g., rituximab, ofatumumab, ocrelizumab, veltuzumab, MEDI-551, epratuzumab, belimumab, tabalumab, AMG-557, MEDI-570, and NN882). In further embodiments, the DDpp comprises an antibody or antigen-binding fragment thereof that binds to the T-cell receptor (TCR) complex on T cells (e.g., binds to the CD3 epsilon chain). In other embodiments, the DDpp is an Fc fusion protein. In further embodiments, the Fc protein comprises a variant human Fc domain.

In some embodiments, the DDpp fusion protein comprises a full-length antibody or an antibody fragment or subdomain (e.g., an IgG1 antibody, IgG3 antibody, antibody variable region, CDR3, scFv, Fc, FcRn binding subdomain, and other antibody subdomains). DDpp proteins can be operably linked to one another and/or to one or more termini of an antibody, antibody chain, antibody fragment, or antibody subdomain to form a DDpp fusion protein.

The antibody component of a DDpp fusion protein can be any suitable full-length immunoglobulin or antibody fragment (e.g., an antigen binding domain and/or effector domain) or a fragment thereof. In one embodiment, the DDpp-antibody fusion protein retains the structural and functional properties of a traditional monoclonal antibody. Thus, in some embodiments, the DDpp-antibody fusion protein retains the epitope binding properties, but advantageously also incorporate, via the DDpp fusion, one or more additional target-binding specificities. Antibodies that can be used in the DDpp fusions include, but are not limited to, monoclonal, multi-specific, human, humanized, primatized, and chimeric antibodies Immunoglobulin or antibody molecules provided herein can be of any type (e.g., IgG, IgE, IgM, IgD, IgA, and IgY), class (e.g., IgG1, IgG2, IgG3, IgG4, IgA1 and IgA2) or subclass of immunoglobulin molecule. In specific embodiments, the antibodies are Fc optimized antibodies. Antibodies can be from or derived from any animal origin including birds and mammals or generated synthetically. The antibody component of the DDpp-antibody fusion protein can be naturally derived or the result of recombinant engineering (e.g., phage display, xenomouse, and synthetic). In certain embodiments, the antibody component of the antibody-DDpp fusion enhances half-life, and increase or decrease antibody dependent cellular cytotoxicity (ADCC), and/or complement dependent cytotoxicity (CDC) activity. In some embodiments, the antibodies are human, murine, donkey, rabbit, goat, guinea pig, camel, llama, horse, or chicken antibodies. In specific embodiments, the antibodies are human.

It is generally understood that the constant region mediates several effector functions. For example, binding of the C1 component of complement to antibodies activates the complement system. Activation of complement is important in the opsonization and lysis of cell pathogens. The activation of complement also stimulates the inflammatory response and can also be involved in autoimmune hypersensitivity. Further, antibodies bind to cells via the Fc region, with an Fc receptor site on the antibody Fc region binding to an Fc receptor (FcR) on a cell. There are a number of Fc receptors that are specific for different classes of antibody, including IgG (gamma receptors), IgE (eta receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production.

In certain embodiments, the DDpp-Fc fusion protein has an altered effector function that, in turn, affects the biological profile of the administered DDpp-Fc fusion protein. For example, the deletion or inactivation (through point mutations or other means) of a constant region subdomain can reduce Fc receptor binding of the circulating modified antibody. In other cases the constant region modifications, can moderate complement binding and thus reduce the serum half-life and nonspecific association of a conjugated cytotoxin. Yet other modifications of the constant region can be used to eliminate disulfide linkages or oligosaccharide moieties that allow for enhanced localization due to increased antigen specificity or antibody flexibility. Similarly, modifications to the constant region in accordance with this disclosure can easily be made using biochemical or molecular engineering techniques known to those of ordinary skill in the art.

In some embodiments, the DDpp-Fc fusion protein does not have one or more effector functions. For instance, in some embodiments, the DDpp-Fc fusion protein has no antibody-dependent cellular cytoxicity (ADCC) activity and/or no complement-dependent cytoxicity (CDC) activity. In certain embodiments, the DDpp-Fc fusion protein does not bind to an Fc receptor and/or complement factors. In certain embodiments, the DDpp-Fc fusion protein has no effector function. Examples of Fc sequence engineering modifications that reduce or eliminate ADCC and/or CDC activity and Fc receptor and/or complement factor binding are described herein or otherwise know in the art, as are assays and procedures for testing the same.

In some embodiments, DDpp-Fc fusion protein is engineered to fuse the CH3 domain directly to the hinge region of the respective modified antibody. In other constructs a peptide spacer is inserted between the hinge region and the modified CH2 and/or CH3 domains. For example, compatible constructs can be expressed in which the CH2 domain has been deleted and the remaining CH3 domain (modified or unmodified) is joined to the hinge region with a 5-20 amino acid spacer. Such a spacer can be added, for instance, to ensure that the regulatory elements of the constant domain remain free and accessible or that the hinge region remains flexible. Amino acid spacers can, in some cases, prove to be immunogenic and elicit an unwanted immune response against the construct. Accordingly, in certain embodiments, any spacer added to the construct can be relatively non-immunogenic, or even omitted altogether, so as to maintain the desired biochemical qualities of the modified DDpp-Fc fusion protein.

In additional embodiments, the DDpp-Fc fusion protein is modified by the partial deletion or substitution of a few or even a single amino acid in a constant region. For example, the mutation of a single amino acid in selected areas of the CH2 domain can be enough to substantially reduce Fc binding and thereby. Similarly one or more constant region domains that control the effector function (e.g., complement C1Q binding) can be fully or partially deleted. Such partial deletions of the constant regions can improve selected characteristics of the DDpp-Fc fusion protein (e.g., serum half-life) while leaving other desirable functions associated with the corresponding constant region domain intact. In some embodiments, the constant region of the DDpp-Fc fusion protein is modified through the mutation or substitution of one or more amino acids that enhances the profile of the resulting construct. In this respect it is possible to disrupt the activity provided by a conserved binding site (e.g., Fc binding) while substantially maintaining the configuration and immunogenic profile of the modified DDpp-Fc fusion protein. The disclosure also provides an DDpp-Fc fusion protein that contains the addition of one or more amino acids to the constant region to enhance desirable characteristics such, as decreasing or increasing effector function or providing attachments sites for one or more cytotoxin, labeling or carbohydrate moieties. In such embodiments, it can be desirable to insert or replicate specific sequences derived from selected constant region domains.

In some embodiments, the DDpp is operably linked to an antibody fragment or subdomain (e.g., scFv, diabody, EP 404,097; WO93/111161; WO14/028776; and Holliger et al., PNAS 90: 6444-6448 (1993), the contents of each of which is herein incorporated by reference in its entirety). The antibody fragment or subdomain can be any fragment or domain of an antibody. See for example, WO04/058820, WO99/42077 and WO05/017148, the contents of each of which is herein incorporated by reference in its entirety. For example, a DDpp fusion protein can contain an antibody effector domain or derivative of an antibody effector domain that confers one or more effector functions to the DDpp and/or confers upon the DDpp fusion protein the ability to bind to one or more Fc receptors. In some embodiments, a DDpp-antibody fusion protein contains an antigen-binding fragment of an antibody or a fragment thereof. In additional embodiments, a DDpp-antibody fusion protein contains an immunoglobulin effector domain that comprises one or more CH2 and or CH3 domains of an antibody having effector function provided by the CH2 and CH3 domains. Other sequences in the DDpp fusion that provide an effector function and that are encompassed by the invention will be clear to those skilled in the art and can routinely be chosen and designed into a DDpp fusion protein encompassed herein on the basis of the desired effector function(s).

In one embodiment, the DDpp fusion contains a full-length antibody or an antibody fragment that is an antigen-binding fragment. In a further embodiment, the antibody or antibody fragment binds a disease-related antigen. In one embodiment the DDpp fusion protein comprises an antibody or an antibody fragment that specifically binds a cancer antigen. In another embodiment, the DDpp fusion protein comprises an antibody or an antibody fragment that specifically binds a particular pathogen (e.g., a bacterial cell (e.g., tuberculosis, smallpox, anthrax)), a virus (e.g., HIV), a parasite (e.g., malaria, leishmaniosis), a fungal infection, a mold, a mycoplasm, a prion antigen, In another embodiment, the DDpp fusion protein comprises an antibody or an antibody fragment that specifically binds a particular pathogen (e.g., a bacterial cell (e.g., tuberculosis, smallpox, anthrax)), a virus (e.g., HIV), a parasite (e.g., malaria, leishmaniosis), a fungal infection, a mold, a mycoplasm, or a prion antigen. In another embodiment, the DDpp fusion protein comprises an antibody or an antibody fragment that specifically binds an antigen associated with a disease or disorder of the immune system.

In preferred embodiments, the DDpp fusion protein containing an antibody fragment or domain retains activities of the parent antibody. Thus, in certain embodiments, the DDpp fusion protein containing an antibody fragment or domain is capable of inducing complement dependent cytotoxicity. In certain embodiments, the DDpp fusion protein containing an antibody fragment or domain is capable of inducing antibody dependent cell mediated cytotoxicity (ADCC).

Accordingly, in some embodiments, the DDpp fusion protein comprises an antibody fragment that confers upon the DDpp fusion protein a biological or biochemical characteristic of an immunoglobulin. In some embodiments, the antibody fragment confers a characteristic selected from: the ability to non-covalently dimerize, the ability to localize at the site of a tumor, and an increased serum half-life when compared to the DDpp fusion protein in which said one or more DDpp have been deleted. In certain embodiments, the DDpp fusion protein is at least as stable as the corresponding antibody without the attached DDpp. In certain embodiments, the DDpp fusion protein is more stable than the corresponding antibody without the attached DDpp. DDpp fusion protein stability can be measured using established methods, including, for example, ELISA techniques. In some embodiments, the DDpp fusion protein is stable in whole blood (in vivo or ex vivo) at 37° C. for at least about 10 hours, at least about 15 hours, at least about 20 hours, at least about 24 hours, at least about 25 hours, at least about 30 hours, at least about 35 hours, at least about 40 hours, at least about 45 hours, at least about 48 hours, at least about 50 hours, at least about 55 hours, at least about 60 hours, at least about 65 hours, at least about 70 hours, at least about 72 hours, at least about 75 hours, at least about 80 hours, at least about 85 hours, at least about 90 hours, at least about 95 hours, or at least about 100 hours (including any time between those listed). In one embodiment, a DDpp fusion contains an immunoglobulin effector domain or half-life influencing domain that corresponds to an immunoglobulin domain or fragment in which at least a fraction of one or more of the constant region domains has been altered so as to provide desired biochemical characteristics such as reduced or increased effector functions, the ability to non-covalently dimerize, increased ability to localize at the site of a tumor, reduced serum half-life, or increased serum half-life when compared with an immunoglobulin fragment having the corresponding unaltered immunoglobulin sequence. These alterations of the constant region domains can be amino acid substitutions, insertions, or deletions.

In one embodiment, a DDpp fusion protein comprises an amino acid sequence of an immunoglobulin effector domain or a derivative of an immunoglobulin effector domain that confers antibody dependent cellular cytotoxicity (ADCC) to the DDpp fusion protein. In additional embodiments, a DDpp fusion protein comprises a sequence of an immunoglobulin effector domain that has been modified to increase ADCC (see, e.g., Bruhns, Blood 113: 3716-3725 (2009); Shields, J. Biol. Chem. 276: 6591-6604 (2001); Lazar, PNAS 103: 4005-4010 (2006); Stavenhagen, Cancer Res. 67: 8882-8890 (2007); Horton, Cancer Res. 68: 8049-8057 (2008); Zalevsky, Blood 113: 3735-3743 (2009); Bruckheimer, Neoplasia 11: 509-517 (2009); WO06/020114; Strohl, Curr. Op. Biotechnol. 20: 685-691 (2009); and WO04/074455; the contents of each of which is herein incorporated by reference in its entirety). Examples of immunoglobulin fragment engineering modifications contained in an amino acid sequence in a DDpp fusion protein that increases ADCC include immunoglobulin effector domain sequences having one or more modifications corresponding to: IgG1-S298A, E333A, K334A; IgG1-S239D, 1332E; IgG1-S239D, A330L, 1332E; IgG1-P2471, A339D or Q; IgG1-D280H, K290S with or without S298D or V; IgG1-F243L, R292P, Y300L; IgG1-F243L, R292P, Y300L, P396L; and IgG1-F243L, R292P, Y300L, V3051, P396L; wherein the numbering of the residues in the Fc region is that of the EU index of Kabat et al. (Kabat et al., Sequences of proteins of Immunological Interest, 1991 Fifth edition, the contents of which is herein incorporated by reference in its entirety).

In other embodiments, a DDpp fusion protein comprises a sequence of an immunoglobulin effector domain that has been modified to decrease ADCC (see, e.g., Idusogie et al., J. Immunol. 166: 2571-2575 (2001); Sazinsky et al., PNAS 105: 20167-20172 (2008); Davis et al., J. Rheumatol. 34: 2204-2210 (2007); Bolt et al., Eur. J. Immunol. 23: 403-411 (1993); Alegre et al., Transplantation 57: 1537-1543 (1994); Xu et al., Cell Immunol. 200: 16-26 (2000); Cole et al., Transplantation 68: 563-571 (1999); Hutchins et al., PNAS 92: 11980-11984 (1995); Reddy et al., J. Immunol. 164: 1925-1933 (2000); WO97/11971; WO07/106585; US 2007/0148167A1; McEarchern et al., Blood 109: 1185-1192 (2007); Strohl, Curr. Op. Biotechnol. 20: 685-691 (2009); and Kumagai et al., J. Clin. Pharmacol. 47: 1489-1497 (2007), the contents of each of which is herein incorporated by reference in its entirety). Examples of immunoglobulin fragment sequence engineering modifications contained in an amino acid sequence in a DDpp fusion protein that decreases ADCC include immunoglobulin effector domain sequences having one or more modifications corresponding to: IgG1-K326W, E333S; IgG2-E333S; IgG1-N297A; IgG1-L234A, L235A; IgG2-V234A, G237A; IgG4-L235A, G237A, E318A; IgG4-S228P, L236E; IgG2-118-260; IgG4-261-447; IgG2-H268Q, V309L, A330S, A331S; IgG1-C220S, C226S, C229S, p268S; IgG1-C226S, C229S, E233P, L234V, L235A; or IgG1-L234F, L235E, P331S; wherein the numbering of the residues is that of the EU index of Kabat (Kabat et al., Sequences of Proteins of Immunological Interest, 1991 Fifth edition, the contents of which is herein incorporated by reference in its entirety).

In additional embodiments, a DDpp fusion protein comprises an amino acid sequence of an immunoglobulin effector domain, or a derivative of an immunoglobulin effector domain, that confers antibody-dependent cell phagocytosis (ADCP) to the DDpp fusion protein. In additional embodiments, a DDpp fusion protein comprises a sequence of an immunoglobulin effector domain that has been modified to increase antibody-dependent cell phagocytosis (ADCP); (see, e.g., Shields et al., J. Biol. Chem. 276: 6591-6604 (2001); Lazar et al., PNAS 103: 4005-4010 (2006); Stavenhagen et al., Cancer Res. 67: 8882-8890 (2007); Richards et al., Mol. Cancer Ther. 7: 2517-2527 (2008); Horton et al., Cancer Res. 68: 8049-8057 (2008), Zalevsky et al., Blood 113: 3735-3743 (2009); Bruckheimer et al., Neoplasia 11: 509-517 (2009); WO06/020114; Strohl, Curr. Op. Biotechnol. 20: 685-691 (2009); and WO04/074455, the contents of each of which is herein incorporated by reference in its entirety). Examples of immunoglobulin fragment engineering modifications contained in an amino acid sequence in a DDpp fusion protein that increases ADCP include immunoglobulin effector domain sequences having one or more modifications corresponding to: IgG1-S298A, E333A, K334A; IgG1-S239D, 1332E; IgG1-S239D, A330L, 1332E; IgG1-P2471, A339D or Q; IgG1-D280H, K290S with or without S298D or V; IgG1-F243L, R292P, Y300L; IgG1-F243L, R292P, Y300L, P396L; IgG1-F243L, R292P, Y300L, V3051, P396L; and IgG1-G236A, S239D, 1332E; wherein the numbering of the residues is that of the EU index of Kabat et al. (Kabat et al., Sequences of proteins of Immunological Interest, 1991 Fifth edition, the contents of which is herein incorporated by reference in its entirety).

In other embodiments, a DDpp fusion protein comprises a sequence of an immunoglobulin effector domain that has been modified to decrease ADCP (see, e.g., Sazinsky et al., PNAS 105: 20167-20172 (2008); Davis et al., J. Rheumatol. 34: 2204-2210 (2007); Bolt et al., Eur. J. Immunol. 23: 403-411 (1993); Alegre et al., Transplantation 57: 1537-1543 (1994); Xu et al., Cell Immunol. 200: 16-20 (2000); Cole et al., Transplantation 68: 563-571 (1999); Hutchins et al., PNAS 92: 11980-11984 (1995); Reddy et al., J. Immunol. 164: 1925-1933 (2000); WO97/11971; WO07/106585; US 2007/0148167A1; McEarchern et al., Blood 109: 1185-1192 (2007); Strohl, Curr. Op. Biotechnol. 20: 685-691 (2009); and Kumagai et al., J. Clin. Pharmacol. 47: 1489-1497 (2007), the contents of each of which is herein incorporated by reference in its entirety). By way of example, DDpp fusion proteins can contain an antibody fragment or domain that contains one or more of the following modifications that decrease ADCC: IgG1-N297A; IgG1-L234A, L235A; IgG2-V234A, G237A; IgG4-L235A, G237A, E318A; IgG4-S228P, L236E; IgG2 EU sequence 118-260; IgG4-EU sequence 261-447; IgG2-H268Q, V309L, A330S, A331S; IgG1-C220S, C226S, C229S, p268S; IgG1-C226S, C229S, E233P, L234V, L235A; and IgG1-L234F, L235E, P331S; wherein the numbering of the residues is that of the EU index of Kabat et al. (Kabat et al., Sequences of proteins of Immunological Interest, 1991 Fifth edition, the contents of which is herein incorporated by reference in its entirety).

In additional embodiments, a DDpp fusion protein comprises an amino acid sequence of an immunoglobulin effector domain, or a derivative of an immunoglobulin effector domain, that confers complement-dependent cytotoxicity (CDC) to the DDpp fusion protein. In additional embodiments, a DDpp fusion protein comprises a sequence of an immunoglobulin effector domain that has been modified to increase complement-dependent cytotoxicity (CDC) (see, e.g., Idusogie et al., J. Immunol. 166: 2571-2575 (2001); Strohl, Curr. Op. Biotechnol. 20: 685-691 (2009); and Natsume et al., Cancer Res. 68: 3863-3872 (2008), the contents of each of which is herein incorporated by reference in its entirety). By way of example, DDpp fusion proteins can contain an antibody fragment or domain that contains one or more of the following modifications that increase CDC: IgG1-K326A, E333A; IgG1-K326W, E333S, IgG2-E333S; wherein the numbering of the residues is that of the EU index of Kabat et al. (Kabat et al., Sequences of proteins of Immunological Interest, 1991 Fifth edition, the contents of which is herein incorporated by reference in its entirety).

In additional embodiments, a DDpp fusion protein comprises an amino acid sequence of an immunoglobulin effector domain, or a derivative of an immunoglobulin effector domain, that confers the ability to bind FcgammaRIIb receptor to the DDpp fusion. In additional embodiments, a DDpp fusion protein comprises a sequence of an immunoglobulin effector domain that has been modified to increase inhibitory binding to FcgammaRIIb receptor (see, e.g., Chu et al., Mol. Immunol. 45: 3926-3933 (2008)). An example of an immunoglobulin fragment engineering modification contained in an amino acid sequence in a DDpp fusion protein that increases binding to inhibitory FcgammaRIIb receptor is IgG1-S267E, L328F.

In other embodiments, a DDpp fusion protein comprises a sequence of an immunoglobulin effector domain that has been modified to decrease CDC (see, e.g., WO97/11971; WO07/106585; US 2007/0148167A1; McEarchern et al., Blood 109: 1185-1192 (2007); Hayden-Ledbetter et al., Clin. Cancer 15: 2739-2746 (2009); Lazar et al., PNAS 103: 4005-4010 (2006); Bruckheimer et al., Neoplasia 11: 509-517 (2009); Strohl, Curr. Op. Biotechnol. 20: 685-691 (2009); and Sazinsky et al., PNAS 105: 20167-20172 (2008); the contents of each of which is herein incorporated by reference in its entirety). By way of example, DDpp fusion proteins can contain an antibody fragment or domain that contains one or more of the following modifications that decrease CDC: IgG1-S239D, A330L, 1332E; IgG2-118-260; IgG4-261-447; IgG2-H268Q, V309L, A330S, A331S;

IgG1-C226S, C229S, E233P, L234V, L235A; IgG1-L234F, L235E, P331S; and IgG1-C226S, p260S; wherein the numbering of the residues is that of the EU index of Kabat et al. (Kabat et al., Sequences of proteins of Immunological Interest, 1991 Fifth edition, the contents of which is herein incorporated by reference in its entirety).

The half-life of an IgG is mediated by its pH-dependent binding to the neonatal receptor FcRn. In certain embodiments, a DDpp fusion protein comprises an amino acid sequence of an immunoglobulin effector domain, or a derivative of an immunoglobulin effector domain, that confers the ability to bind neonatal receptor FcRn to the to the DDpp fusion. In certain embodiments, a DDpp fusion protein comprises a sequence of an immunoglobulin FcRn binding domain that has been modified to enhance binding to FcRn (see, e.g., Petkova et al., Int. Immunol. 18: 1759-1769 (2006); Dall'Acqua et al., J. Immunol. 169: 5171-5180 (2002); Oganesyan et al., Mol. Immunol. 46: 1750-1755 (2009); Dall'Acqua et al., J. Biol. Chem. 281: 23514-23524 (2006); Hinton et al., J. Immunol. 176: 346-356 (2006); Datta-Mannan et al., Drug Metab. Dispos. 35: 86-94 (2007); Datta-Mannan et al., J. Biol. Chem. 282: 1709-1717 (2007); WO06/130834; Strohl, Curr. Op. Biotechnol. 20: 685-691 (2009); and Yeung et al., J. Immunol. 182: 7663-7671 (2009); the contents of each of which is herein incorporated by reference in its entirety).

In additional embodiments, a DDpp fusion protein comprises a sequence of an immunoglobulin effector domain that has been modified to have a selective affinity for FcRn at pH 6.0, but not pH 7.4. By way of example, DDpp fusion proteins can contain an antibody fragment or domain that contains one or more of the following modifications that increase half-life: IgG1-M252Y, S254T, T256E; IgG1-T250Q, M428L; IgG1-H433K, N434Y; IgG1-N434A; and IgG1-T307A, E380A, N434A; wherein the numbering of the residues is that of the EU index of Kabat et al. (Kabat et al., Sequences of Proteins of Immunological Interest, 1991 Fifth edition, the contents of which is herein incorporated by reference in its entirety).

In other embodiments, a DDpp fusion protein comprises a sequence of an immunoglobulin effector domain that has been modified to decrease binding to FcRn (see, e.g., Petkova et al., Int. Immunol. 18: 1759-1769 (2006); Datta-Mannan et al., Drug Metab. Dispos. 35: 86-94 (2007); Datta-Mannan et al., J. Biol. Chem. 282: 1709-1717 (2007); Strohl, Curr. Op. Biotechnol. 20: 685-691 (2009); and Vaccaro et al., Nat. Biotechnol. 23: 1283-1288 (2005); the contents of each of which is herein incorporated by reference in its entirety). By way of example, DDpp fusion proteins can contain an antibody fragment or domain that contains one or more of the following modifications that decrease half-life: IgG1-M252Y, S254T, T256E; H433K, N434F, 436H; IgG1-I253A; and IgG1-P257I, N434H and D376V, N434H; wherein the numbering of the residues is that of the EU index of Kabat et al. (Kabat et al., Sequences of proteins of Immunological Interest, 1991 Fifth edition, the contents of which is herein incorporated by reference in its entirety).

According to another embodiment, DDpp fusion protein comprises an amino acid sequence corresponding to a immunoglobulin effector domain that has been modified to contain at least one substitution in its sequence corresponding to the Fc region (e.g., FC gamma) position selected from the group consisting of: 238, 239, 246, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 332, 333, 334, 335, 337, 338, 340, 360, 373, 376, 378, 382, 388, 389, 398, 414, 416, 419, 430, 434, 435, 437, 438 and 439, wherein the numbering of the residues in the Fc region is according to the EU numbering system; of Kabat et al. (Kabat et al., Sequences of proteins of Immunological Interest, 1991 Fifth edition, the contents of which is herein incorporated by reference in its entirety). In a specific embodiment, the DDpp fusion protein comprises a sequence of an immunoglobulin effector domain derivative wherein at least one residue corresponding to position 434 is a residue selected from the group consisting of: A, W, Y, F and H. According to another embodiment, the DDpp fusion protein comprises a sequence of an immunoglobulin effector fragment derivative having the following respective substitutions S298A/E333A/K334A. In an additional embodiment, the DDpp fusion protein comprises an immunoglobulin effector domain derivative having a substitution corresponding to K322A. In another embodiment, the DDpp fusion protein comprises a sequence of an immunoglobulin effector domain derivative having one or any combination of the following substitutions K246H, H268D, E283L, S324G, S239D and I332E. According to yet another embodiment, a DDpp fusion protein comprises a sequence of an immunoglobulin effector domain derivative having substitutions corresponding to D265A/N297A.

In certain embodiments, a DDpp fusion protein comprises a sequence of an immunoglobulin effector domain that has been glycoengineered or mutated to increase effector function using techniques known in the art. For example, the inactivation (through point mutations or other means) of a constant region domain sequence contained in a DDpp may reduce Fc receptor binding of the circulating DDpp fusion protein thereby increasing tumor localization. In other cases it may be that constant region modifications consistent with certain provided embodiments, moderate complement binding and thus reduce the serum half-life and nonspecific association of a conjugated cytotoxin. Yet other modifications of the constant region may be used to modify disulfide linkages or oligosaccharide moieties that allow for enhanced localization due to increased antigen specificity or antibody flexibility. The resulting physiological profile, bioavailability and other biochemical effects of the modifications, such as tumor localization, biodistribution and serum half-life, can easily be measured and quantified using well know immunological techniques without undue experimentation.

In some embodiments, an immune effector cell comprises a cell surface receptor for an immunoglobulin or other peptide binding molecule, such as a receptor for an immunoglobulin constant region and including the class of receptors commonly referred to as "Fc receptors" ("FcR"s). A number of FcRs have been structurally and/or functionally characterized and are known in the art, including FcR having specific abilities to interact with a restricted subset of immunoglobulin heavy chain isotypes, or that interact with Fc domains with varying affinities, and/or which may be expressed on restricted subsets of immune effector cells under certain conditions (e.g., Kijimoto-Ochichai et al., Cell Mol. Life. Sci. 59: 648 (2002); Davis et al., Curr. Top. Microbiol. Immunol. 266: 85 (2002); Pawankar, Curr. Opin. Allerg. Clin. Immunol. 1: 3 (2001); Radaev et al., Mol. Immunol. 38: 1073 (2002); Wurzburg et al., Mol. Immunol. 38: 1063 (2002); Sulica et al., Int. Rev. Immunol. 20: 371 (2001); Underhill et al., Ann. Rev. Immunol. 20: 825 (2002); Coggeshall, Curr. Dir. Autoimm. 5: 1 (2002); Mimura et al., Adv. Exp. Med. Biol. 495: 49 (2001); Baumann et al., Adv. Exp. Med. Biol. 495: 219 (2001); Santoso et al., Ital. Heart J. 2: 811 (2001); Novak et al., Curr. Opin. Immunol. 13: 721

(2001); Fossati et al., Eur. J. Clin. Invest. 31: 821 (2001)); the contents of each of which is herein incorporated by reference in its entirety.

Cells that are capable of mediating ADCC are examples of immune effector cells. Other immune effector cells include Natural Killer cells, tumor-infiltrating T lymphocytes (TILs), cytotoxic T lymphocytes, and granulocytic cells such as cells that comprise allergic response mechanisms Immune effector cells thus include, but are not limited to, cells of hematopoietic origin including cells at various stages of differentiation within myeloid and lymphoid lineages and which may (but need not) express one or more types of functional cell surface FcR, such as T lymphocytes, B lymphocytes, NK cells, monocytes, macrophages, dendritic cells, neutrophils, basophils, eosinophils, mast cells, platelets, erythrocytes, and precursors, progenitors (e.g., hematopoietic stem cells), as well as quiescent, activated, and mature forms of such cells. Other immune effector cells may include cells of non-hematopoietic origin that are capable of mediating immune functions, for example, endothelial cells, keratinocytes, fibroblasts, osteoclasts, epithelial cells, and other cells Immune effector cells can also include cells that mediate cytotoxic or cytostatic events, or endocytic, phagocytic, or pinocytotic events, or that effect induction of apoptosis, or that effect microbial immunity or neutralization of microbial infection, or cells that mediate allergic, inflammatory, hypersensitivity and/or autoimmune reactions.

F. DDpp Fusion Proteins with Increased Half-Life

The disclosed DDpp can be fused or complexed to a second peptide domain increases the half-life or stability of the DDpp.

In one aspect, the DDpp further comprises one or more amino acids that facilitate synthesis, handling, or use of the peptide, including, but not limited to, one or two lysines at the N-terminus and/or C-terminus to increase solubility of the polypeptide. Suitable fusion proteins include, but are not limited to, proteins comprising a DDpp linked to one or more polypeptides, polypeptide fragments, or amino acids not generally recognized to be part of the protein sequence. In one aspect, a fusion peptide comprises the entire amino acid sequences of two or more peptides or, alternatively, comprises portions (fragments) of two or more peptides. In some aspects, a peptide (e.g., Protein S-binding peptide) is operably linked to, for instance, one or more of the following: a marker protein, a peptide that facilitates purification, a peptide sequence that promotes formation of multimeric proteins, or a fragment of any of the foregoing. Suitable fusion partners include, but are not limited to, a His tag, a FLAG tag, a strep tag, and a myc tag.

In some embodiments, the DDpp is fused to one or more moieties that enhance the half-life of the polypeptide. Half-life can be increased by for example, increasing the molecular weight of the DDpp to avoid renal clearance and/or incorporating a binding domain for FcRn-mediated recycling pathway. In one embodiment, the DDpp is fused to, or chemically conjugated to, an albumin polypeptide or a fragment thereof (e.g., human serum albumin (HSA)). In particular embodiments, the fused or chemically conjugated albumin fragment comprises 10%, 25%, 50%, or 75% of the full length albumin protein. In additional or alternative embodiments, the DDpp is fused to or complexed with an albumin binding domain or fatty acid that binds albumin when administered in vivo. An example of an albumin binding domain is "albu-tag," a moiety derived from on 4-(p-iodophenyl)-butanoic acid (Dumelin et al., Angew Chem. Int. Ed Engl. 47: 3196-3201 (2008)).

In one embodiment, the DDpp is fused to, or chemically conjugated to, a transferrin polypeptide or a fragment thereof (e.g., human transferrin). In particular embodiments, the fused or chemically conjugated transferrin fragment comprises 10%, 25%, 50%, or 75% of the full length transferrin protein. In additional or alternative embodiments, the DDpp is fused to or complexed with a transferrin binding domain that binds transferrin when administered in vivo.

In some embodiments, the DDpp is fused to, or chemically conjugated to a proline-alanine-serine multimer (PA-Sylation; XL-Protein GmbH), a non-exact repeat peptide sequence (XTENylation, rPEG), a homopolymer of glycine residues (HAPylation), elastin-like repeat(s) sequences (ELPylation; see for example, U.S. Pat. Appl. No. 61/442, 106, the contents of which is herein incorporated by reference in its entirety), an artificial GLK (GLK fusion; Huang et al., Eur. J. Pharm. Biopharm. 72: 435-41 (2010)), or a CTP peptide from human CG beta-subunit (CTP fusion).

G. Additional DDpp Fusion Proteins

In some embodiments, the DDpp fusion protein specifically binds CD123 and/or AFP p26, and further binds a disease-related antigen. The disease-related antigen can be an antigen characteristic of a cancer, and/or of a particular cell type (e.g., a hyperproliferative cell), and/or of a pathogen (e.g., a bacterial cell (e.g., tuberculosis, smallpox, and anthrax), a virus (e.g., HIV), a parasite (e.g., malaria and leishmaniosis), a fungal infection, a mold, a mycoplasm, a prion antigen, or an antigen associated with a disorder of the immune system. In further embodiments, the DDpp fusion protein is conjugated to a therapeutic or cytotoxic agent.

In an additional embodiment, a DDpp fusion protein is linked to one or more chemical moieties (e.g., labels) that facilitate detection, multimerization, binding with an interaction partner, or characterization of DDpp activity. An exemplary chemical moiety is biotin. Other moieties suitable for conjugation to the DDpp include, but are not limited to, a photosensitizer, a dye, a fluorescence dye, a radionuclide, a radionuclide-containing complex, an enzyme, a toxin, and a cytotoxic agent. Photosensitizers include, e.g., Photofrin, Visudyne, Levulan, Foscan, Metvix, Hexvix®, Cysview™, Laserphyrin, Antrin, Photochlor, Photosens, Photrex, Lumacan, Cevira, Visonac, BF-200 ALA, and Amphinex. In additional embodiments, a His tag, a FLAG tag, a strep tag, or a myc tag is conjugated to the DDpp.

In another embodiment, the DDpp fusion protein comprises a DD that binds CD123, AFP p26, or a fragment thereof, and further binds a peptide tag present on a target of interest. Such peptide tags provide a useful means by which to detect and/or attach targets of interest containing the peptide tags. In one embodiment, the DDpp fusion protein specifically binds a peptide tag selected from the group: a hexahistidyl (His6) tag, a myc tag or a FLAG tag. Other peptide tags are described herein or otherwise known in the art.

H. DDpp Fusion Proteins with an Epitope Tag

In some embodiments, the DDpp fusion protein comprises a peptide epitope tag. In some embodiments, the peptide tag is selected from the group consisting of a hexahistidyl (His6) tag, a myc tag and a FLAG tag. In additional embodiments, peptide tags include, but are not limited to, avitag (allows biotinylation of the tag and isolation with streptavidin), calmodulin, E-tag, hemagglutinin (HA), S-tag, SBP-tag, softag 1, streptavidin, tetra or polycysteine, V5, VSV, and Xpress tag. Additionally polyhistidyl tags (other than 6 residues) can be used. In additional embodiments, covalent peptide tags, protein tags, and the like can be used. Covalent peptide tags include, but are not limited to, isopeptag (covalently binds pilinC protein), Spytag (covalently binds to the SpyCatcher protein), and Snooptag (covalently binds to the SnoopCatcher protein). In still additional embodiments, protein tags, including but not limited to biotin carboxyl carrier protein (BCCP), glutathione-s-transferase, green fluorescent protein (or other fluorophore), Halo tag, Nus tag, thioredoxin, and Fc tags may optionally be used. In still additional embodiments, multiple types of tags may be used. In still additional embodiments, no tag is used. In still additional embodiments, the DDpp fusion protein comprises a removable tag. Any combination of extracellular, transmembrane and intracellular domains disclosed herein may be used, depending on the embodiment.

I. DDpp as Chemical Conjugates

DDpp fusion proteins (e.g., an Adapter) that promote specific binding to targets of interest can be chemically conjugated with a variety of compound such as fluorescent dyes, radioisotopes, chromatography compositions (e.g., beads, resins, gels, etc.) and chemotherapeutic agents. DDpp fusion protein conjugates have uses that include but are not limited to diagnostic, analytic, manufacturing and therapeutic applications.

The inherent lack of cysteines in the DD sequence provides the opportunity for introduction of unique cysteines for purposes of site-specific conjugation.

In some embodiments, the DDpp fusion protein (e.g., an Adapter) contains at least one reactive residue. Reactive residues are useful, for example, as sites for the attachment of conjugates such as chemotherapeutic drugs. The reactive residue can be, for example, a cysteine, a lysine, or another reactive residue. Thus, a cysteine can be added to a DDpp at either the N- or C-terminus, or within the DDpp sequence. A cysteine can be substituted for another amino acid in the sequence of a DDpp. In addition, a lysine can be added to a DDpp at either end or within the DDpp sequence and/or a lysine can be substituted for another amino acid in the sequence of a DDpp. In one embodiment, a reactive residue (e.g., cysteine, lysine, etc.) is located in a loop sequence of a DDpp (e.g., amino acid residues corresponding to residues 22-24 and 46-49 of SEQ ID NO: 2). In one embodiment, a reactive residue is located between components of a DDpp fusion, e.g., in a linker located between a DDpp and other component of a DDpp fusion protein. The reactive residue (e.g., cysteine, lysine, etc.) can also be located within the sequence of a DDpp, or other component of the DDpp fusion protein. In one embodiment, a DDpp or a DDpp fusion protein comprises at least one, at least two, at least three reactive residues. In one embodiment, a DDpp such as a DDpp fusion protein comprises at least one, at least two, or at least three, cysteine residues.

Expressions like "binding affinity for a target", "binding to a target" and the like refer to a property of a polypeptide which may be directly measured through the determination of the affinity constants, e.g., the amount of DDpp that associates and dissociates at a given antigen concentration. Different methods can be used to characterize the molecular interaction, including but not limited to, competition analysis, equilibrium analysis and microcalorimetric analysis, and real-time interaction analysis based on surface plasmon resonance interaction (for example using a Biacore® instrument). These methods are known to the skilled person and are described, for example, in Neri et al., Tibtech 14: 465-470 (1996) and Jansson et al., J Biol Chem 272: 8189-8197 (1997).

Affinity requirements for a given DDpp binding event are contingent on a variety of factors including, but not limited to: the composition and complexity of the binding matrix, the valency and density of both the DDpp and target molecules, and the functional application of the DDpp. In one embodiment, DDpp bind a target of interest (e.g., CD123 or AFP p26) with a dissociation constant (KD) of less than or equal to $5\times10^{-3}$ M, $10^{-3}$ M, $5\times10^{-4}$ M, $10^{-4}$ M, $5\times10^{-5}$ M, or $10^{-5}$ M. In an additional embodiment, a DDpp binds a target of interest with a KD of less than or equal to $5\times10^{-6}$ M, $10^{-6}$ M, $5\times10^{-7}$ M, $10^{-7}$ M, $5\times10^{-8}$ M, or $10^{-8}$ M. In additional embodiments, a DDpp binds a target of interest with a KD of less than or equal to $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M. In some embodiments, the provided DDpp has a dissociation constant selected from the group consisting of between $10^{-14}$ M and $10^{-5}$ M, between $10^{-5}$ M and $10^{-6}$ M, between $10^{-6}$ M and $10^{-17}$ M, between $10^{-7}$ M and $10^{-8}$ M, between $10^{-8}$ M and $10^{-9}$ M, between $10^{-9}$ M and $10^{-10}$ M, between $10^{-10}$ M and $10^{-11}$ M and between $10^{-11}$ M and $10^{-12}$ M.

In some embodiments, the DDpp binds a target of interest (e.g., CD123 or AFP p26) in active form. In one embodiment the DDpp reversibly binds the target of interest in active form and also releases the bound target in active form. In some embodiments, the DDpp binds a target of interest in the native form. In specific embodiments, DDpp binds a target of interest with an off-rates or $K_{off}$ of greater than or equal to $10^{-10}$ sec$^{-1}$, $5\times10^{-9}$ sec$^{-1}$, $10^{-9}$ sec$^{-1}$, $5\times10^{-8}$ sec$^{-1}$, $10^{-7}$, sec$^{-1}$, $5\times10^{-7}$ sec$^{-1}$, $10^{-7}$ sec$^{-1}$, $5\times10^{-6}$ sec$^{-1}$, $10^{-6}$ sec$^{-1}$, $5\times10^{-5}$ sec$^{-1}$, $10^{-5}$ sec$^{-1}$, $5\times10^{-4}$ sec$^{-1}$, $10^{-4}$ sec$^{-1}$, $5\times10^{-3}$ sec$^{-1}$, $10^{-3}$ sec$^{-1}$, $5\times10^{-2}$ sec$^{-1}$, $10^{-2}$ sec$^{-1}$, $5\times10^{-1}$ sec$^{-1}$, or $10^{-1}$ sec$^{-1}$.

Binding experiments to determine KD and off-rates can routinely be performed in a number of conditions including, but not limited to, [pH 6.0, 0.01% Tween 2, [pH 6.0, 0.1% gelatin], [p H5.0, 0.01% Tween 2, [pH 9.0, 0.1% Tween 2, [pH 6.0, 15% ethylene glycol, 0.01% Tween 2, [pH 5.0, 15% ethylene glycol, 0.01% Tween 2, and [pH 9.0, 15% ethylene glycol, 0.01% Tween 2. The buffers in which to make these solutions can routinely be determined by one skilled in the art, and depend largely on the desired pH of the final solution. Low pH solutions (<pH 5.5) can be made, for example, in citrate buffer, glycine-HCl buffer, or in succinic acid buffer. High pH solutions can be made, for example, in Tris-HCl, phosphate buffers, or sodium bicarbonate buffers. A number of conditions may routinely be used by those skilled in the art to determine KD and off-rates for the purpose of determining, for example, optimal pH and/or salt concentrations.

In one embodiment, the DDpp specifically binds a target of interest (e.g., CD123 or AFP p26) with a $K_{Off}$ ranging from 0.1 to 10 sec$^{-1}$, $10^{-2}$ to 10 sec$^{-1}$, or $0.5\times10^{-2}$ to 10 sec$^{-1}$. In a specific embodiment, the DDpp (e.g., a DDpp fusion protein) binds a target of interest with an off rate ($K_{Off}$) of less than $5\times10$ sec$^{-1}$, $10^{-2}$ sec$^{-1}$, $5\times10^{-3}$ sec$^{-1}$, or $10^{-3}$ sec$^{-1}$. In an additional embodiment, a DDpp, binds a target of interest with an off rate ($K_{Off}$) of less than $5\times10$ sec$^{-1}$, 10 sec$^{-1}$, $5\times10^{-5}$ sec$^{-1}$, or $10^{-5}$ sec$^{-1}$, $5\times10^{-6}$ sec$^{-1}$, $10^{-6}$ sec$^{-1}$, $5\times10$ sec$^{-1}$, or 10 sec$^{-1}$.

In one embodiment, the DDpp specifically binds a target of interest (e.g., CD123 or AFP p26) with a $K_{On}$ ranging from $10^3$ to $10^7$ M$^{-1}$ sec$^{-1}$, $10^3$ to $10^6$ M$^{-1}$ sec$^{-1}$, or $10^3$ to $10^5$ M$^{-1}$ sec$^{-1}$. In a specific embodiment, the DDpp (e.g., a DDpp fusion protein) binds the target of interest with an on rate ($K_{On}$) of greater than $10^3$ M$^{-1}$ sec$^{-1}$, $5\times10^3$ M$^{-1}$ sec$^{-1}$, $10^4$ M$^{-1}$ sec$^{-1}$, or $5\times10^4$ M$^{-1}$ sec$^{-1}$. In an additional embodiment, the DDpp, binds the target of interest with a $K_{On}$ of greater than $10^5$ M$^{-1}$ sec$^{-1}$, $5\times10^5$ M$^{-1}$ sec$^{-1}$, $10^6$ M$^{-1}$ sec$^{-1}$, or $5\times10^6$ M$^{-1}$ sec$^{-1}$, or $10^7$M$^{-1}$ sec$^{-1}$.

Nucleic acid molecules encoding the disclosed DDpp are encompassed herein, as are vectors containing these nucleic acids, host cells containing these nucleic acids vectors, and methods of making the DDpp-albumin fusion proteins and using these nucleic acids, vectors, and/or host cells. The invention also encompasses pharmaceutical formulations comprising a DDpp-albumin fusion protein and a pharmaceutically acceptable diluent or carrier. Such formulations can be used in methods of treating, preventing, ameliorating or diagnosing a disease or disease symptom in a patient, preferably a mammal, most preferably a human, comprising the step of administering the pharmaceutical formulation to the patient.

DDpp Drug Conjugates

In a further embodiment a DDpp fusion protein may be linked to other organic or inorganic molecules or substrates through the use of chemically conjugation. In one embodiment, DDpp-drug conjugates are intended to facilitate the local delivery of cytotoxic agents through the targeting specificity of the DDpp. This combination of targeting specificity and cytotoxic agent, allows targeted delivery of the drug to tumors, and intracellular accumulation therein, where systemic administration of these unconjugated drug agents may result in unacceptable levels of toxicity to normal cells as well as the tumor cells sought to be eliminated (Baldwin et al., Lancet pages 603-605 (1986); Thorpe, "Antibody Carriers Of Cytotoxic agents In Cancer Therapy: A Review," in Monoclonal Antibodies '84: Biological And Clinical Applications, A. Pinchera et al., (ed.$), pp. 475-506 (1985)).

Cytotoxic agents include chemotherapeutic agents, growth inhibitory agents, toxins (e.g., an enzymatically active toxin of bacterial, fungal, plant, or animal origin, or fragments thereof), radioactive isotopes (i.e., a radioconjugate), etc. Chemotherapeutic agents useful in the generation of such immunoconjugates include, for example, methotrexate, adriamicin, doxorubicin, melphalan, mitomycin C, chlorambucil, daunorubicin or other intercalating agents. Chemotherapeutic agents useful in the generation of such immunoconjugates also include antitubulin drugs, such as auristatins, including monomethyl auristatin E (MMAE) and monomethyl auristatin F (MMAF). Enzymatically active toxins and fragments thereof that can be used according to the disclosed methods include diphtheria A chain, nonbinding active fragments of diphtheria toxin, exotoxin A chain, ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In one embodiment, a DDpp (e.g., a DDpp fusion protein) is conjugated to a radioisotope. In a further embodiment, a DDpp is conjugated to an isotope selected from $^{90}$Y, $^{125}$I, $^{131}$I, $^{123}$I, $^{111}$In, $^{105}$Rh, $^{153}$Sm, $^{67}$Cu, $^{67}$Ga, $^{166}$Ho, $^{177}$Lu, $^{186}$Re and $^{188}$Re using anyone of a number of known chelators or direct labeling. In other embodiments, the DDpp is coupled to drugs, prodrugs or lymphokines such as interferon. Conjugates of the DDpp and cytotoxin can routinely be made using a variety of bifunctional protein-coupling agents such as N-succinimidyl-3-(2-pyridyidithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazo-niumbenzoyl)-ethylenediamine), diisocyanates (such as tolyene 2,6-diisocyanate), and bis-active fluorine compounds (such as 1,5-difluoro-2,4-dinitrobenzene). In a specific embodiment, the toxin is conjugated to a DDpp fusion protein through an enzyme-cleavable linker system (e.g., such as that present in SGN-35). Conjugates of a DDpp and one or more small molecule toxins, such as a calicheamicin, maytansinoids, a trichothene, and CC1065, and the derivatives of these toxins that have toxin activity, can also be used.

In some embodiments, the cytotoxic agent is covalently attached to a DDpp by a linker. In some embodiments, the linker attaching the DDpp and the cytotoxic agent is cleavable by a protease.

Affinity Maturation and De-Immunization of DD and DDpp

Affinity maturation strategies can be used to generate high affinity DD and DDpp that can be used in the DDpp fusion proteins described herein. An improved DD and DDpp that specifically binds a desired target (e.g., BCAM, CD123, CS1, HER2, AFP, and AFP p26) can also be prepared based on a known DDpp reference sequence. For example, at least one, two, three, four, five, or more amino acid mutations (e.g., conservative or non-conservative substitutions), deletions or insertions can be introduced into a DD sequence disclosed in Table 1 (i.e., a reference sequence) and the resulting DDpp can be screened for binding to the respective target and biological activity, such as the ability to antagonize the biological activity of the respective target or agonize the biological activity of the respective target.

The disclosed DDpp, particularly those administered to a subject, are preferably not antigenic with respect to the subject (e.g., human) In some embodiments, the sequence of the DDpp does not contain a human HLA-DR binding motif or cleavage sites for proteasomes and immune-proteasomes. In particular embodiments, the DDpp sequence does not contain an antigenic sequence as determined by a computer prediction model version existent on the filing date of this specification. In particular embodiments, the DDpp sequence does not contain an MHC (class I or class II) binding site sequence as predicted by an algorithm selected from ProPred (see, e.g., Singh, Bioinformatics 17(12): 1236-1237 (2001)), ProPred1 (Singh, Bioinformatics 19(8): 1009-14 (2003)), SYFPEITHI (see, e.g., Schuler, Immunoinf. Meth. in Mol. Biol. 409(1): 75-93 (2007)), SMM-align (see, e.g., Nielsen, BMC Bioinformatics 8: 238 (2007)), RANK-PEP (see, e.g., Reche, Hum Immunol 63: 701-709. (2004)), or TEPITOPE (see, Sturniolo, Nat Biotechnol 17: 555-561 (1999)), wherein the version of the algorithm and the applied database are in existence on the filing date of this application. In some embodiments, the DDpp does not contain a sequence that shares characteristics with a high affinity (binding threshold less than 6%) T cell epitope. (Singh, Bioinformatics 17: 1236-1237 (2001)). In some embodiments, the DDpp does not contain a sequence that shares characteristics with a promiscuous (present in greater than 50% of relevant alleles) T cell epitope (Singh, Bioinformatics 17: 1236-1237 (2001)). In some embodiments, the DDpp does not contain a sequence that shares characteristics with a high affinity or a promiscuous T cell epitope. In particular embodiments, the DDpp does not contain the sequence LAAIKTRLQ (SEQ ID NO: 49). Techniques for generating, screening, and identifying affinity matured DDpp variants and target-binding DDpp variants containing a sequence alteration that removes a predicted MHC (class I or class II) binding site sequence are known in the art.

Polynucleotides

Polynucleotides comprising a nucleotide sequence encoding a DDpp (e.g., an Adapter or CAR) are also provided. Such polynucleotides optionally further comprise, one or more expression control elements. For example, the polynucleotide can comprise one or more promoters or transcriptional enhancers, ribosomal binding sites, transcription termination signals, and polyadenylation signals, as expression control elements. The polynucleotide can be inserted within any suitable vector, which can be contained within any suitable host cell for expression.

In some embodiments, a polynucleotide disclosed herein encodes a polypeptide comprising a D domain that binds to CD123. In some embodiments, the D domain that binds to CD123 comprises an amino acid sequence selected from the group consisting of SEQ ID NO: 8-33, 99 and 100. In some embodiments, the D domain that binds to CD123 comprises an amino acid sequence selected from the group consisting of SEQ ID NO: 8, 13, 14, 31, 32, and 33. In some embodiments, the D domain that binds to CD123 comprises the amino acid sequence of SEQ ID NO: 14.

In some embodiments, a polynucleotide disclosed herein encodes a chimeric antigen receptor (CAR), wherein the CAR comprises a D domain that binds to CD123, (ii) a transmembrane domain, and (iii) an intracellular domain. In some embodiments, the D domain that binds to CD123 comprises an amino acid sequence selected from the group consisting of SEQ ID NO: 8-33, 99 and 100. In some embodiments, the D domain that binds to CD123 comprises an amino acid sequence selected from the group consisting of SEQ ID NO: 8, 13, 14, 31, 32, and 33. In some embodiments, the D domain that binds to CD123 comprises the amino acid sequence of SEQ ID NO: 14. In some embodiments, the CAR comprises the amino acid sequence of SEQ ID NO: 62-66 or 67. In some embodiments, the CAR comprises the amino acid sequence of SEQ ID NO: 67.

In some embodiments, a polynucleotide disclosed herein encodes a chimeric antigen receptor (CAR), wherein the CAR comprises (i) a D domain that binds to AFP p26 AD, (ii) a transmembrane domain, and (iii) an intracellular domain. In some embodiments, the DD that binds to an AFP p26 AD comprises an amino acid sequence selected from the group consisting of SEQ ID NO: 74-93 and 94. In some embodiments, the DD that binds to an AFP p26 AD comprises the amino acid sequence of SEQ ID NO: 70-73 or 92-94. In some embodiments, the DD that binds to an AFP p26 AD comprises the amino acid sequence of SEQ ID NO: 73. In some embodiments, the CAR comprises the amino acid sequence of SEQ ID NO: 68. In some embodiments, the CAR comprises the amino acid sequence of SEQ ID NO: 69.

In some embodiments, a polynucleotide disclosed herein encodes a chimeric antigen receptor (CAR), wherein the CAR comprises (i) an AFP p26 antigenic determinant (AD), (ii) a transmembrane domain, and (iii) an intracellular domain. In some embodiments, the AFP p26 AD comprises an amino acid sequence selected from the group consisting of SEQ ID NO: 37-43 and 44. In some embodiments, the AFP p26 AD comprises the amino acid sequence of SEQ ID NO: 37. In some embodiments, the AFP p26 AD comprises the amino acid sequence of SEQ ID NO: 39.

In some embodiments, a polynucleotide disclosed herein encodes an Adapter comprising (a) a D domain (DD) that binds to CD123 and (b) an antigenic determinant (AD). In some embodiments, the D domain that binds to CD123 comprises an amino acid sequence selected from the group consisting of SEQ ID NO: 8-33, 99 and 100. In some embodiments, the D domain that binds to CD123 comprises an amino acid sequence selected from the group consisting of SEQ ID NO: 8, 13, 14, 31, 32, and 33. In some embodiments, the D domain that binds to CD123 comprises the amino acid sequence of SEQ ID NO: 14. In some embodiments, the Adapter is a monovalent Adapter comprising a single D domain that binds CD123. In some embodiments, the Adapter is a bivalent Adapter comprising two D domains that bind CD123. In some embodiments, the two D domains that bind CD123 are the same. In some embodiments, the two D domains that bind CD123 are different. In some embodiments, the Adapter is a bivalent Adapter comprising a first D domain that binds CD123 and a second D domain that binds a second AD. In some embodiments, the second AD is CD33 or LeY. In some embodiments, a monovalent Adapter comprises a D domain comprising an amino acid sequence selected from the group consisting of SEQ ID NO: 8, 13, 14, 31, 32, and 33. In some embodiments, the monovalent Adapter comprises the D domain comprising the amino acid sequence of SEQ ID NO: 14. In some embodiments, a bivalent Adapter comprises a DD comprising an amino acid sequence selected from the group consisting of SEQ ID NO: 8, 13, 14, 31, 32, and 33. In some embodiments, the bivalent Adapter comprises the D domain comprising the amino acid sequence of SEQ ID NO: 14. In some embodiments, a bivalent Adapter comprises two identical D domains comprising an amino acid sequence selected from the group consisting of SEQ ID NO: 8, 13, 14, 31, 32, and 33. In some embodiments, the bivalent Adapter comprises two identical D domains comprising the amino acid sequence of SEQ ID NO: 14. In some embodiments, the Adapter comprises an AFP p26 antigenic determinant (AD). In some embodiments, the AFP p26 AD comprises an amino acid sequence selected from the group consisting of SEQ ID NO: 37-43 and 44. In some embodiments, the AFP p26 AD comprises the amino acid sequence of SEQ ID NO: 37. In some embodiments, the AFP p26 AD comprises the amino acid sequence of SEQ ID NO: 39. In some embodiments, the monovalent Adapter comprises the amino acid sequence of SEQ ID NO: 50-54 or 55. In some embodiments, the monovalent Adapter comprises the amino acid sequence of SEQ ID NO: 50. In some embodiments, the bivalent Adapter comprises the amino acid sequence of SEQ ID NO: 56-60 or 61. In some embodiments, the monovalent Adapter comprises the amino acid sequence of SEQ ID NO: 61. In some embodiments, the Adapter comprises one or more linkers.

In some embodiments, a polynucleotide disclosed herein encodes an Adapter comprising (a) a D domain that binds to CD123 and (b) an antigenic determinant binding domain (ADBD) that binds an AFP p26 AD. In some embodiments, the AFP p26 AD comprises an amino acid sequence selected from the group consisting of SEQ ID NO: 37-43 and 44. In some embodiments, the AFP p26 AD comprises the amino acid sequence of SEQ ID NO: 37. In some embodiments, the AFP p26 AD comprises the amino acid sequence of SEQ ID NO: 39. In some embodiments, the D domain that binds to CD123 comprises an amino acid sequence selected from the group consisting of SEQ ID NO: 8-33, 99 and 100. In some embodiments, the D domain that binds to CD123 comprises an amino acid sequence selected from the group consisting of SEQ ID NO: 8, 13, 14, 31, 32, and 33. In some embodiments, the D domain that binds to CD123 comprises the amino acid sequence of SEQ ID NO: 14. In some embodiments, the ADBD that binds to an AFP p26 AD comprises a D domain that binds to the AFP p26 AD. In some embodiments, the D domain that binds to an AFP p26 AD comprises an amino acid sequence selected from the group consisting of SEQ ID NO: 70-73 and 92-94. In some embodiments, the D domain that binds to an AFP p26 AD comprises the amino acid sequence of SEQ ID NO: 73. In some embodiments, the Adapter comprises one or more linkers.

In some embodiments, a polynucleotide disclosed herein encodes an Adapter comprising (a) a first antigenic determinant binding domain (ADBD) that binds to a target antigenic determinant (AD) on a target cell and (b) an antigenic determinant binding domain (ADBD) that binds to an AFP p26 AD. In some embodiments, the AFP p26 AD comprises an amino acid sequence selected from the group consisting of SEQ ID NO: 37-43 and 44. In some embodiments, the AFP p26 AD comprises the amino acid sequence of SEQ ID NO: 37. In some embodiments, the AFP p26 AD comprises the amino acid sequence of SEQ ID NO: 39. In some embodiments, the ADBD that binds to an AFP p26 AD comprises a D domain that binds to AFP p26. In some embodiments, the D domain that binds to an AFP p26 AD comprises an amino acid sequence selected from the group consisting of SEQ ID NO: 70-73 and 92-94. In some embodiments, the D domain that binds to an AFP p26 AD comprises the amino acid sequence of SEQ ID NO: 73. In some embodiments, the Adapter comprises one or more linkers.

In some embodiments, the polynucleotide is DNA.

In some embodiments, the polynucleotide is RNA. In some embodiments, the polynucleotide is mRNA. In some embodiment the RNA, e.g., mRNA comprises modified ribonucleotides.

In some embodiments, an mRNA disclosed herein comprises a coding region encoding a polypeptide disclosed herein, and additionally comprises one or more of a 5' untranslated region, 3' untranslated region, 5' cap, and polyadenylation signal. In some embodiments, an mRNA disclosed herein comprises a coding region encoding a polypeptide disclosed herein, a 5' untranslated region, a 3' untranslated region, a 5' cap, and a polyadenylation signal. In some embodiments, an mRNA disclosed herein comprises modified ribonucleotides. In some embodiments, the mRNA comprises N1-methylpseudouridine or N1-ethylpseudouridine. In some embodiments, the 5' terminal cap is 7mG(5')ppp(5')N1mpNp. See, e.g., US20200261572, US20190351040, and US20190211065, each of which is incorporated herein by reference in its entirety.

In some embodiments, the polynucleotide is a vector comprising a polynucleotide described herein. In some embodiments, the vector is a transfer vector suitable for use in the production of a recombinant lentivirus. In some embodiments, the vector is a lentiviral vector encoding a polypeptide disclosed herein (e.g., a CAR). In some embodiments, the lentiviral vector is suitable for transducing an immune cell (e.g., a T cell or NK cell) to produce a cell expressing the polypeptide (e.g., CAR).

In some embodiments, the polynucleotide is a recombinant virus comprising a polynucleotide described herein. In some embodiments, the polynucleotide is a recombinant lentivirus comprising a polynucleotide encoding a polypeptide (e.g., a CAR) described herein. In some embodiments, the polynucleotide is a recombinant adenovirus vectors or adeno-associated virus (AAV).

Production of DDpp

The disclosed DDpp (e.g., and Adapter) can routinely be made using commercially available reagents and techniques known in the art. In one embodiment, the DDpp are synthesized by solid phase synthesis techniques known in the art, such as, Merrifield, J. Am. Chem. Soc. 85: 2149 (1963); Davis et al., Biochem. Intl. 10: 394-414 (1985); Larsen et al., J. Am. Chem. Soc. 115: 6247 (1993); Smith et al., J. Peptide Protein Res. 44: 183 (1994); O'Donnell et al., J. Am. Chem. Soc. 118: 6070 (1996); Stewart and Young, Solid Phase Peptide Synthesis, Freeman (1969); Finn et al., The Proteins, 3.sup.rd ed., 2: 105-253 (1976); and Erickson et al., The Proteins, 3.sup.rd ed., 2: 257-527 (1976). The disclosure contemplates synthetic peptides. Alternatively, the peptide is expressed recombinantly by introducing a nucleic acid encoding the disclosed DDpp into host cells, which are cultured to express the peptide. Such peptides are purified from the culture media or cell pellets.

The production of the DDpp, useful in practicing the provided methods, may be carried out using a variety of standard techniques for chemical synthesis, semi-synthetic methods, and recombinant DNA methodologies known in the art. Also provided is a method for producing a DDpp, individually or as part of multi-domain fusion protein, as soluble agents and cell associated proteins.

Optionally, the reference sequence and/or the modified polypeptides (e.g., DDpp) can be de-immunized. For example, residues or motifs that are potentially immunogenic can be identified and modified in order to reduce or eliminate potential immune responses to the DDpp. Additional details regarding various embodiments, of the production, selection, and isolation of DDpp are provided in more detail below.

A. Recombinant Expression of DDpp

In some embodiments, a DDpp such as a DDpp fusion protein (e.g., an Adapter) is "recombinantly produced," (i.e., produced using recombinant DNA technology). Exemplary recombinant methods available for synthesizing DDpp fusion proteins, include, but are not limited to polymerase chain reaction (PCR) based synthesis, concatemerization, seamless cloning, and recursive directional ligation (RDL) (see, e.g., Meyer et al., Biomacromolecules 3: 357-367 (2002); Kurihara et al., Biotechnol. Lett. 27: 665-670 (2005); Haider et al., Mol. Pharm. 2: 139-150 (2005); and McMillan et al., 32: 3643-3646 (1999); the contents of each of which is herein incorporated by reference in its entirety).

Nucleic acids comprising a polynucleotide sequence encoding a DDpp (e.g., an Adapter or CAR) are also provided. Such polynucleotides optionally further comprise, one or more expression control elements. For example, the polynucleotide can comprise one or more promoters or transcriptional enhancers, ribosomal binding sites, transcription termination signals, and polyadenylation signals, as expression control elements. The polynucleotide can be inserted within any suitable vector, which can be contained within any suitable host cell for expression.

The expression of nucleic acids encoding DDpp (e.g., an Adapter or CAR) is typically achieved by operably linking a nucleic acid encoding the DDpp to a promoter in an expression vector. Typical expression vectors contain transcription and translation terminators, initiation sequences, and promoters useful for regulation of the expression of the desired nucleic acid sequence. Methods known in the art can be used to routinely construct expression vectors containing the nucleic acid sequence encoding a DDpp along with appropriate transcriptional/translational control signals. These methods include, but are not limited to in vitro recombinant DNA techniques, synthetic techniques and in vivo recombination/genetic recombination. The expression of the polynucleotide can be performed in any suitable expression host known in the art including, but not limited to bacterial cells, yeast cells, insect cells, plant cells or mammalian cells. In one embodiment, a nucleic acid sequence encoding a DDpp is operably linked to a suitable promoter sequence such that the nucleic acid sequence is transcribed and/or translated into DDpp in a host.

In one embodiment, a vector comprising a DDpp (e.g., an Adapter) encoding nucleic acid is introduced into a host cell for expression of the DDpp. The vector can remain episomal or become chromosomally integrated, as long as the insert encoding therapeutic agent can be transcribed. Vectors can be constructed by standard recombinant DNA technology. Vectors can be plasmids, phages, cosmids, phagemids, viruses, or any other types known in the art, which are used for replication and expression in prokaryotic or eukaryotic cells. It will be appreciated by one of skill in the art that a wide variety of components known in the art (such as expression control elements) can be included in such vectors, including a wide variety of transcription signals, such as promoters and other sequences that regulate the binding of RNA polymerase onto the promoter. Any promoter known or demonstrated to be effective in the cells in which the vector will be expressed can be used to initiate expression of the DDpp. Suitable promoters can be inducible (e.g., regulated) or constitutive. Non-limiting examples of suitable promoters include the SV40 early promoter region, the promoter contained in the 3' long terminal repeat of Rous sarcoma virus, the HSV-1 (herpes simplex virus-1) thymidine kinase promoter, the regulatory sequences of the metallothionein gene, etc., as well as the following animal transcriptional control regions, which exhibit tissue specificity and have been utilized in transgenic animals elastase I gene control region which is active in pancreatic acinar cells; insulin gene control region which is active in pancreatic beta cells, mouse mammary tumor virus control region which is active in testicular, breast, lymphoid and mast cells, albumin gene control region which is active in liver, alpha-fetoprotein gene control region which is active in liver, alpha 1-antitrypsin gene control region which is active in the liver, beta-globin gene control region which is active in erythroid cells, myelin basic protein gene control region which is active in oligodendrocyte cells in the brain, myosin light chain-2 gene control region which is active in skeletal muscle, and gonadotropin releasing hormone gene control region which is active in the hypothalamus. In a particular embodiment, the promoter is an immunoglobulin gene control region which is active in lymphoid cells.

In one embodiment, one or several nucleic acids encoding a DDpp (e.g., an Adapter) is expressed under the control of a constitutive promoter or, alternately, a regulated expression system. Suitable regulated expression systems include, but are not limited to, a tetracycline-regulated expression system, an ecdysone inducible expression system, a lac-switch expression system, a glucocorticoid-inducible expression system, a temperature-inducible promoter system, and a metallothionein metal-inducible expression system. If several different nucleic acids encoding a DDpp are contained within the host cell system, some of the nucleic acids may be expressed under the control of a constitutive promoter, while others may be expressed under the control of a regulated promoter. Expression levels may be determined by methods known in the art, including Western blot analysis and Northern blot analysis.

A variety of host-expression vector systems can be utilized to express a nucleic acid encoding a DDpp (e.g., an Adapter). Vectors containing the nucleic acids encoding the DDpp (e.g., individual DD subunits or DDpp fusions) or portions or fragments thereof, include plasmid vectors, a single and double-stranded phage vectors, as well as single and double-stranded RNA or DNA viral vectors. Phage and viral vectors may also be introduced into host cells in the form of packaged or encapsulated virus using known techniques for infection and transduction. Moreover, viral vectors may be replication competent or alternatively, replication defective. Alternatively, cell-free translation systems may also be used to produce the protein using RNAs derived from the DNA expression constructs (see, e.g., WO86/05807 and WO89/01036; and U.S. Pat. No. 5,122,464; the contents of each of which is herein incorporated by reference in its entirety).

Generally, any type of cells or cultured cell line can be used to express a DDpp (e.g., an Adapter) provided herein. In some embodiments, the background cell line used to generate an engineered host cells is a phage, a bacterial cell, a yeast cell or a mammalian cell. A variety of host-expression vector systems may be used to express the coding sequence a DDpp fusion protein. Mammalian cells can be used as host cell systems transfected with recombinant plasmid DNA or cosmid DNA expression vectors containing the coding sequence of the target of interest and the coding sequence of the fusion polypeptide.

The cells can be primary isolates from organisms (including human), cultures, or cell lines of transformed or transgenic nature. In some embodiments, the host cell is a human cell. In some embodiments, the host cell is human T cell. In some embodiments, the host cell is derived from a human patient.

Useful host cells include but are not limited to microorganisms such as, bacteria (e.g., *E. coli, B. subtilis, P. fluorescens*) transformed with recombinant bacteriophage DNA, plasmid DNA or cosmid DNA expression vectors containing DDpp (e.g., an Adapter) coding sequences; yeast (e.g., *Saccharomyces, Pichia*) transformed with recombinant yeast expression vectors containing DDpp coding sequences; insect cell systems infected with recombinant virus expression vectors (e.g., baculovirus) containing DDpp coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing DDpp coding sequences. In particular embodiments, the mammalian cell systems are used to produce the DDpp. Mammalian cell systems typically utilize recombinant expression constructs containing promoters derived from the genome of mammalian cells (e.g., metallothionein promoter) or from mammalian viruses (e.g., the adenovirus late promoter; the vaccinia virus 7.5K promoter).

Prokaryotes useful as host cells in producing a DDpp such as DDpp fusion protein (e.g., an Adapter), include gram negative or gram positive organisms such as, *E. coli* and *B. subtilis*. Expression vectors for use in prokaryotic host cells generally contain one or more phenotypic selectable marker genes (e.g., genes encoding proteins that confer antibiotic resistance or that supply an autotrophic requirement). Examples of useful prokaryotic host expression vectors include the pKK223-3 (Pharmacia, Uppsala, Sweden), pGEM1 (Promega, Wis., USA), pET (Novagen, Wis., USA) and pRSET (Invitrogen, Calif., USA) series of vectors (see, e.g., Studier, J. Mol. Biol. 219: 37 (1991) and Schoepfer, Gene 124: 83 (1993)). Exemplary promoter sequences frequently used in prokaryotic host cell expression vectors include T7, (Rosenberg et al., Gene 56: 125-135 (1987)), beta-lactamase (penicillinase), lactose promoter system (Chang et al., Nature 275: 615 (1978)); and Goeddel et al., Nature 281: 544 (1979)), tryptophan (trp) promoter system (Goeddel et al., Nucl. Acids Res. 8: 4057 (1980)), and tac promoter (Sambrook et al., 1990, Molecular Cloning, A Laboratory Manual, 2d Ed., Cold Spring Harbor Laboratory, Cold Spring Harbor, N.Y.).

In one embodiment, a eukaryotic host cell systems is be used, including yeast cells transformed with recombinant yeast expression vectors containing the coding sequence of a DDpp (e.g., an Adapter), such as, the expression systems taught in U.S. Appl. No. 60/344,169 and WO03/056914 (methods for producing humanlike glycoprotein in a non-human eukaryotic host cell) (the contents of each of which is herein incorporated by reference in its entirety). Exemplary yeast that can be used to produce the provided compositions, such as, DD, include yeast from the genus *Saccharomyces, Pichia*, Actinomycetes and *Kluyveromyces*. Yeast vectors typically contain an origin of replication sequence from a 2mu yeast plasmid, an autonomously replicating sequence (ARS), a promoter region, sequences for polyadenylation, sequences for transcription termination, and a selectable marker gene. Examples of promoter sequences in yeast expression constructs include, promoters from metallothionein, 3-phosphoglycerate kinase (Hitzeman, J. Biol. Chem. 255: 2073 (1980)) and other glycolytic enzymes, such as, enolase, glyceraldehyde-3-phosphate dehydrogenase, hexokinase, pyruvate decarboxylase, phosphofructokinase, glucose-6-phosphate isomerase, 3-phospho glycerate mutase, pyruvate kinase, triosephosphate isomerase, phosphoglucose isomerase, and glucokinase. Additional suitable vectors and promoters for use in yeast expression as well as yeast transformation protocols are known in the art. See, e.g., Fleer, Gene 107: 285-195 (1991) and Hinnen, PNAS 75: 1929 (1978).

Insect and plant host cell culture systems are also useful for producing the compositions encompassed by the disclosure. Such host cell systems include for example, insect cell systems infected with recombinant virus expression vectors (e.g., baculovirus) containing the coding sequence of a DD; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the coding sequence of a DD, including, but not limited to, the expression systems taught in U.S. Pat. No. 6,815,184; U.S. Publ. Nos. 60/365,769, and 60/368,047; and WO04/057002, WO04/024927, and WO03/078614; the contents of each of which is herein incorporated by reference in its entirety.

In an additional embodiment the host cell systems may be used, including animal cell systems infected with recombinant virus expression vectors (e.g., adenoviruses, retroviruses, adeno-associated viruses, herpes viruses, lentiviruses) including cell lines engineered to contain multiple copies of the DNA encoding a DDpp either stably amplified (CHO/dhfr) or unstably amplified in double-minute chromosomes (e.g., murine cell lines). In one embodiment, the vector comprising the polynucleotide(s) encoding the DDpp is polycistronic. Exemplary mammalian cells useful for producing these compositions include 293 cells (e.g., 293T and 293F), CHO cells, BHK cells, NS0 cells, SP2/0 cells, YO myeloma cells, P3X63 mouse myeloma cells, PER cells, PER.C6 (Crucell, Netherlands) cells VERY, Hela cells, COS cells, MDCK cells, 3T3 cells, W138 cells, BT483 cells, Hs578T cells, HTB2 cells, BT20 cells, T47D cells, CRL7O30 cells, HsS78Bst cells, hybridoma cells, and other mammalian cells. Additional exemplary mammalian host cells that are useful in practicing the the provided embodiments include but are not limited, to T cells. Some examples of expression systems and selection methods are described in the following references and references cited therein: Borth et al., Biotechnol. Bioen. 71(4): 266-73 (2000), in Werner et al., Arzneimittel-forschung/Drug Res. 48(8): 870-80 (1998), Andersen et al., Curr. Op. Biotechnol. 13: 117-123 (2002), Chadd et al., Curr. Op. Biotechnol. 12: 188-194 (2001), and Giddings, Curr. Op. Biotechnol. 12: 450-454 (2001). Additional examples of expression systems and selection methods are described in Logan et al., PNAS 81: 355-359 (1984), Birtner et al., Methods Enzymol. 153: 51-544 (1987)). Transcriptional and translational control sequences for mammalian host cell expression vectors are frequently derived from viral genomes. Commonly used promoter sequences and enhancer sequences in mammalian expression vectors include, sequences derived from Polyoma virus, Adenovirus 2, Simian Virus 40 (SV40), and human cytomegalovirus (CMV). Exemplary commercially available expression vectors for use in mammalian host cells include pCEP4 (Invitrogen) and pcDNA3 (Invitrogen).

Physical methods for introducing a nucleic acid into a host cell (e.g., a mammalian host cell) include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York).

Biological methods for introducing a polynucleotide of interest into a host cell include the use of DNA and RNA vectors. Viral vectors, and especially retroviral vectors, have become the most widely used method for inserting genes into mammalian (e.g., human) cells. Other viral vectors can be derived from lentivirus, poxviruses, herpes simplex virus I, adenoviruses and adeno-associated viruses, and the like. See, for example, U.S. Pat. Nos. 5,350,674 and 5,585,362, the contents of each of which is herein incorporated by reference in its entirety.

Methods for introducing a DNA and RNA polynucleotides of interest into a host cell include electroporation of cells, in which an electrical field is applied to cells in order to increase the permeability of the cell membrane, allowing chemicals, drugs, or polynucleotides to be introduced into the cell. DDpp containing DNA or RNA constructs may be introduced into mammalian or prokaryotic cells using electroporation.

Chemical means for introducing a polynucleotide into a host cell include colloidal dispersion systems, such as macromolecule complexes, nanocapsules, microspheres, beads, and lipid-based systems including olLin-water emulsions, micelles, mixed micelles, and liposomes. An exemplary colloidal system for use as a delivery vehicle in vitro and in vivo is a liposome (e.g., an artificial membrane vesicle). In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid can be associated with a lipid. The nucleic acid associated with a lipid can be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they can be present in a bilayer structure, as micelles, or with a "collapsed" structure. They can also simply be interspersed in a solution, possibly forming aggregates that are not uniform in size or shape. Lipids are fatty substances which can be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristoyl phosphatidylcholine ("DMPC") can be obtained from Sigma, St. Louis, MO; dicetyl phosphate ("DCP") can be obtained from K & K Laboratories (Plainview, NY); cholesterol ("Choi") can be obtained from Calbiochem-Behring; dimyristoyl phosphatidylglycerol ("DMPG") and other lipids may be obtained from Avanti Polar Lipids, Inc. (Birmingham, AL). Stock solutions of lipids in chloroform or chloroform/methanol can be stored at about −20° C. Chloroform may be used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., Glycobiology 5: 505-510 (1991)). However, compositions that have different structures in solution than the normal vesicular structure are also encompassed. For example, the lipids can assume a micellar structure or merely exist as non-uniform aggregates of lipid molecules. Also contemplated are lipofectamine-nucleic acid complexes.

Regardless of the method used to introduce exogenous nucleic acids into a host cell, or the presence of the recombinant nucleic acid sequence in the host cell can routinely be confirmed through a variety of assays known in the art. Such assays include, for example, "molecular biological" assays known in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the provided embodiments.

Reporter genes are used for identifying potentially transfected cells and for evaluating the functionality of regulatory sequences. In general, a reporter gene is a gene that is not present in or expressed by the recipient organism, tissue, or cell and that encodes a polypeptide whose expression is manifested by some easily detectable property, e.g., enzymatic activity. Expression of the reporter gene is assayed at a suitable time after the DNA has been introduced into the recipient cells. A non-limiting list of suitable reporter genes can include genes encoding luciferase, beta-galactosidase, chloramphenicol acetyl transferase, secreted alkaline phosphatase, or the green fluorescent protein gene (e.g., Ui-Tei et al., FEBS Lett. 479: 79-82 (2000)). Suitable expression systems are known in the art and can be prepared using known techniques or obtained commercially. In general, the construct with the minimal 5' flanking region showing the highest level of expression of reporter gene is identified as the promoter. Such promoter regions can routinely be linked to a reporter gene and used to evaluate agents for the ability to modulate promoter-driven transcription.

A number of selection systems can be used in mammalian host-vector expression systems, including, but not limited to, the herpes simplex virus thymidine kinase, hypoxanthine-guanine phosphoribosyltransferase and adenine phosphoribosyltransferase (Lowy et al., Cell 22: 817 (1980)) genes, which can be employed in tk$^-$, hgprt$^-$ or aprt$^-$ cells, respectively. Additionally, antimetabolite resistance can be used as the basis of selection for e.g., dhfr, gpt, neo, hygro, trpB, hisD, ODC (ornithine decarboxylase), and the glutamine synthase system.

Once a DDpp (e.g., an Adapter) has been produced by recombinant expression, it can be purified by any method known in the art for purification of a recombinant protein, for example, by chromatography (e.g., ion exchange, hydrophobic interaction, affinity, and sizing column chromatography), centrifugation, differential solubility, or by any other standard technique for the purification of proteins. In additional embodiments, the DDpp is optionally fused to a heterologous polypeptide sequences (e.g., FLAg tag or HIS tag) described herein or otherwise known in the art to facilitate purification. More particularly, it is envisioned that ligands (e.g., antibodies and other affinity matrices) for affinity purification are used and that optionally, the component of the DDpp fusion composition (e.g., an Adapter) that are bound by these ligands (e.g., FLAg tag or HIS tag) are removed from the composition prior to final preparation of the DDpp using techniques known in the art.

B. Expression of CARs

CARs (e.g., CARs comprising an extracellular D domain disclosed herein or an extracellular p26) are intentionally cell associated and used in the context of the cell in which they are expressed. One particular embodiment relates to a strategy of adoptive cell transfer of T cells which have been transduced to express a CAR. Preferably, the cell can be genetically modified to stably express a CAR on its surface, conferring novel target specificity that is MHC independent.

A variety of viral-derived vectors can be used in applications in which viruses are used for transfection and integration into a mammalian cell genome. Viruses, which are useful as vectors include, but are not limited to, retroviruses, adenoviruses, adeno-associated viruses, herpes viruses, and lentiviruses. Lentiviral vectors are particularly suitable to achieving long-term gene transfer (e.g., adoptive T cell immune therapy) since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity. In general, a suitable vector contains an origin of replication functional in at least one organism, a promoter sequence, convenient restriction endonuclease sites, and one or more selectable markers, (e.g., Intl. Appl. Publ. Nos. WO 01/96584 and WO 01/29058; and U.S. Pat. No. 6,326,193). Several vector promoter sequences are available for expression of the transgenes. One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is EF-1a. However, other constitutive promoter sequences can also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Inducible promoters include, but are not limited to a metallothionein promoter, a glucocorticoid promoter, a progesterone promoter, and a tetracycline promoter.

In order to assess the expression of a CAR polypeptide or portions thereof, the expression vector introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and are otherwise known in the art.

Prior to expansion and genetic modification of the T cells of the invention, a source of T cells is obtained from a subject. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments provided herein, any number of T cell lines available in the art, may be used.

A full discussion of T cell isolation, culturing, activation and expansion methods may be found in WO 2012079000, the contents of which is herein incorporated by reference in its entirety.

Additionally provided is a host cell comprising nucleic acids encoding a CAR described herein. Further provided is a composition comprising a nucleic acid sequence encoding the CAR.

In a preferred embodiment, electroporation of cells results in the expression of a DDpp-CAR on the surface of T cells, NK cells, and/or NKT cells. Such expression may be transient or stable over the life of the cell. Electroporation may be accomplished with methods known in the art including MaxCyte GT® and STX® Transfection Systems (MaxCyte, Gaithersburg, MD, USA).

In some embodiments, the expression of a CAR disclosed herein results in cell associated compositions. In some embodiments, the CAR comprises a target binding domain comprising a DD disclosed herein (e.g., a DD comprising the amino acid sequence of SEQ ID NO: 8-33 or 74-94). In some embodiments, the DD binds CD123 and comprises an amino acid sequence selected from the group consisting of SEQ ID NO: 8-33, 99 and 100. In some embodiments, the CD123-specific DD comprises an amino acid sequence selected from the group consisting of SEQ ID NO: 8, 13, 14, 31, 32, and 33. In some embodiments, the CD123-specific DD comprises the amino acid sequence of SEQ ID NO: 14. In some embodiments, the DD binds AFP p26 and comprises an amino acid sequence selected from the group consisting of SEQ ID NO: 74-93 and 94. In some embodiments, the DD binds AFP p26 and comprises the amino acid sequence of SEQ ID NO: 70-73 or 92-94. In some embodiments, the DD binds AFP p26 and comprises the amino acid sequence of SEQ ID NO: 73. In some embodiments, the CAR comprises an extracellular AD comprising p26. In some embodiments, the extracellular AD comprises the amino acid sequence of SEQ ID NO 37-43 or 44.

C. Chemical Synthesis of DDpp

In addition to recombinant methods, DDpp (e.g., an Adapter) production may also be carried out using organic chemical synthesis of the desired polypeptide using a variety of liquid and solid phase chemical processes known in the art. Various automatic synthesizers are commercially available and can be used in accordance with known protocols. See, for example, Tam et al., J. Am. Chem. Soc. 105: 6442 (1983); Merrifield, Science 232: 341-347 (1986); Barany and Merrifield, The Peptides, Gross and Meienhofer, eds, Academic Press, New York, 1-284; Barany et al., Int. J. Pep. Protein Res. 30: 705-739 (1987); Kelley et al. in Genetic Engineering Principles and Methods, Setlow, J. K., ed. Plenum Press, N.Y. 1990, vol. 12, pp. 1-19; Stewart et al., Solid-Phase Peptide Synthesis, W.H. Freeman Co., San Francisco, 1989. One advantage of these methodologies is that they allow for the incorporation of non-natural amino acid residues into the sequence of the DDpp.

The DDpp (e.g., an Adapter) that are used in the methods encompassed herein may be modified during or after synthesis or translation, e.g., by glycosylation, acetylation, benzylation, phosphorylation, amidation, pegylation, formylation, derivatization by known protecting/blocking groups, proteolytic cleavage, linkage to an antibody molecule, hydroxylation, iodination, methylation, myristoylation, oxidation, pegylation, proteolytic processing, phosphorylation, prenylation, racemization, selenoylation, sulfation, ubiquitination, etc. (See, e.g., Creighton, Proteins: Structures and Molecular Properties, 2d Ed. (W.H. Freeman and Co., N.Y., 1992); Postranslational Covalent Modification of Proteins, Johnson, ed. (Academic Press, New York, 1983), pp. 1-12; Seifter, Meth. Enzymol. 182: 626-646 (1990); Rattan, Ann. NY Acad. Sci. 663: 48-62 (1992).) In specific embodiments, the peptides are acetylated at the N-terminus and/or amidated at the C-terminus.

The disclosure also provides DDpp (e.g., an Adapter) derivatives and include polypeptides that have been chemically modified in some manner distinct from addition, deletion, or substitution of amino acids. In this regard, a DDpp is chemically bonded with polymers, lipids, other organic moieties, and/or inorganic moieties. Exemplary polypeptide modifications are provided in Hermanson, Bioconjugate Techniques, Academic Press, (1996). The DDpp optionally comprise a functional group that facilitates conjugation to another moiety (e.g., a peptide moiety). Exemplary functional groups include, but are not limited to, isothiocyanate, isocyanate, acyl azide, NHS ester, sulfonyl chloride, aldehyde, epoxide, oxirane, carbonate, arylating agent, imidoester, carbodiimide, anhydride, alkyl halide derivatives (e.g., haloacetyl derivatives), maleimide, aziridine, acryloyl derivatives, arylating agents, thiol-disulfide exchange reagents (e.g., pyridyl disulfides or TNB thiol), diazoalkane, carboyldiimadazole, N,N'-Disuccinyl carbonate, N-Hydroxysuccinimidyl chloroformate, and hydrazine derivatives. Maleimide is useful, for example, for generating a DDpp that binds albumin in vivo.

In some embodiments, the DDpp (e.g., an Adapter) is covalently modified to include one or more water soluble polymer attachments. The water soluble polymer (or other chemical moiety) is attached to any amino acid residue, although attachment to the N- or C-terminus is preferred in some embodiments. Useful polymers include, but are not limited to, PEG (e.g., PEG approximately 40 kD, 30 kD, 20 kD, 10 kD, 5 kD, or 1 kD in size), polyoxyethylene glycol, polypropylene glycol, monomethoxy-polyethylene glycol, dextran, hydroxyethyl starch, cellulose, poly-(N-vinyl pyrrolidone)-polyethylene glycol, propylene glycol homopolymers, a polypropylene oxide/ethylene oxide co-polymer, polysialic acid (PSA), polyoxyethylated polyols (e.g., glycerol) and polyvinyl alcohol, as well as mixtures of any of the foregoing. In one embodiment, the DDpp is PEGylated. PEG moieties are available in different shapes, e.g., linear or branched. For further discussion of water soluble polymer attachments, see U.S. Pat. Nos. 4,640,835; 4,496,689; 4,301,144; 4,670,417; 4,791,192; and 4,179,337. Other moieties useful for improving peptide half-life or stability are described herein and include, for instance, albumin (optionally modified to allow conjugation to the DDpp), fatty acid chains (e.g., C12-C18 fatty acid, such as a C14 fatty acid, or dicarboxylic acids, such as octadecane dicarboxylic acid (oddc)), an antibody or fragment thereof (e.g., an Fc portion of an antibody), and proline-alanine-serine multimers.

In some embodiments, the DDpp (e.g., an Adapter) is conjugated to a polyethylene glycol (PEG) moiety, human serum albumin (HSA), an antibody or antibody fragment, hydroxyethyl starch, a proline-alanine-serine multimer (PASylation), a C12-C18 fatty acid, or polysialic acid.

In some embodiments, the DDpp (e.g., an Adapter) are acylated at the N-terminal amino acid of the peptide. In another aspect, the DDpp are amidated at the C-terminal amino acid of the polypeptide. In a still further aspect, the peptides are acylated at the N-terminal amino acid of the peptide and are amidated at the C-terminal amino acid of the peptide.

In some embodiments, the DDpp (e.g., an Adapter) comprises one or more modified or non-proteinogenic amino acids or a modified linker group (see, e.g., Grant, Synthetic Peptides: A User's Guide, Oxford University Press (1992)). Modified amino acids include, for example, amino acids wherein the amino and/or carboxyl group is replaced by another group. Non-limiting examples include modified amino acids incorporating thioamides, ureas, thioureas, acylhydrazides, esters, olefines, sulfonamides, phosphoric acid amides, ketones, alcohols, boronic acid amides, benzodiazepines and other aromatic or non-aromatic heterocycles (see, Estiarte et al., Burgers Medicinal Chemistry, 6.sup.th edition, Volume 1, Part 4, John Wiley & Sons, New York (2002)). Non-proteinogenic amino acids include, but are not limited to, beta-alanine (Bal), norvaline (Nva), norleucine (Nle), 4-aminobutyric acid (gamma-Abu), 2-aminoisobutyric acid (Aib), 6-aminohexanoic acid (epsilon-Ahx), ornithine (Orn), hydroxyproline (Hyp), taurine, sarcosine, citrulline (Cit), cysteic acid (Coh), cyclohexylalanine (Cha), methioninesulfoxide (Meo), methioninesulfone (Moo), homoserine-methylester (Hsm), propargylglycine (Eag), 5-fluorotryptophan (5Fw), 6-fluorotryptophan (6Fw), 3',4'-dimethoxyphenyl-alanine (Ear), 3',4'-difluorophenylalanine (Dff), 4'-fluorophenyl-alanine (Pff), 1-naphthyl-alanine (1Ni), 2-Naphthylalanine (2Ni), 1-methyltryptophan (1Mw), penicillamine (Pen), homoserine (Hse), t-butylglycine, t-butylalanine, phenylglycine (Phg), benzothienylalanine (Bta), L-homo-cysteine (Hcy), N-methyl-phenylalanine (Nmf), 2-thienylalanine (Thi), 3,3-diphenylalanine (Ebw), L-alpha-t-Butylglycine (Tle), Bpa, homophenylalanine (Hfe), and S-benzyl-L-cysteine (Ece). These and other non-proteinogenic amino acids may exist as D- or L-isomers. Examples of modified linkers include but are not limited to the flexible linker 4,7,10-trioxa-1,13-tridecanediamine (Ttds), glycine, 6-aminohexanoic acid, beta-alanine (Bal), pentynoic acid (Pyn), and combinations of Ttds, glycine, 6-aminohexanoic acid and Bal.

Any of numerous chemical modifications may be carried out by known techniques, including, but not limited to acetylation, formylation, etc. Additionally, the derivative may contain one or more non-classical amino acids.

Chimeric Antigen Receptor Cells

The disclosure provides compositions and methods to regulate the specificity and activity of cells modified to express one or more different CAR(s).

In some embodiments, cells are engineered to express one or more of the CARs described herein. Such CAR-containing cells, referred to as "CAR cells" have uses in monotherapy and in combination therapies that include other therapeutic agents, such as the Adapters described herein, for example, to kill a target cell.

In some embodiments, a cell expressing a chimeric antigen receptor (CAR) is provided herein, wherein the CAR comprises a D domain that binds to CD123, (ii) a transmembrane domain, and (iii) an intracellular domain. In some embodiments, the D domain that binds to CD123 comprises an amino acid sequence selected from the group consisting of SEQ ID NO: 8-33, 99 and 100. In some embodiments, the D domain that binds to CD123 comprises an amino acid sequence selected from the group consisting of SEQ ID NO: 8, 13, 14, 31, 32, and 33. In some embodiments, the D domain that binds to CD123 comprises the amino acid sequence of SEQ ID NO: 14. In some embodiments, the CAR comprises the amino acid sequence of SEQ ID NO: 62-66 or 67. In some embodiments, the CAR comprises the amino acid sequence of SEQ ID NO: 67. In some embodiments, the cell is an immune cell. In some embodiments, the cell is an immune effector cell. In some embodiments, the cell is a T cell (CAR-T cell) or a natural killer (NK) cell (CAR-NK cell). In some embodiments, the cell is an autologous immune effector cell. In some embodiments the cell is an autologous T cell (CAR-T cell) or an autologous natural killer (NK) cell. In some embodiments, the cell is an allogenic immune effector cell. In some embodiments the cell is an allogenic T cell (CAR-T cell) or an allogenic natural killer (NK) cell. In some embodiments, an immune effector cell expressing the CAR is capable of directing an immune response to a cell expressing CD123 in an in vitro assay.

In some embodiments, a cell expressing a chimeric antigen receptor (CAR) is provided herein, wherein the CAR comprises an antigenic determinant binding domain (ADBD) that binds to an AFP p26 AD, (ii) a transmembrane domain, and (iii) an intracellular domain. In some embodiments, the ADBD that binds to AFP p26 AD comprises an scFv that binds to AFP p26 AD. In some embodiments, the ADBD that binds to AFP p26 AD comprises a D domain that binds to AFP p26 AD. In some embodiments, the AFP p26 AD comprises an amino acid sequence selected from the group consisting of SEQ ID NO: 37-43 and 44. In some embodiments, the AFP p26 AD comprises the amino acid sequence of SEQ ID NO: 37. In some embodiments, the AFP p26 AD comprises the amino acid sequence of SEQ ID NO: 39. In some embodiments, the DD that binds to an AFP p26 AD comprises an amino acid sequence selected from the group consisting of SEQ ID NO: 74-93 and 94. In some embodiments, the DD that binds to an AFP p26 AD comprises the amino acid sequence of SEQ ID NO: 70-73 or 92-94. In some embodiments, the DD that binds to an AFP p26 AD comprises the amino acid sequence of SEQ ID NO: 73. In some embodiments, the CAR comprises the amino acid sequence of SEQ ID NO: 68. In some embodiments, the CAR comprises the amino acid sequence of SEQ ID NO: 69. In some embodiments, the cell is an immune cell. In some embodiments, the cell is an immune effector cell. In some embodiments, the cell is a T cell (CAR-T cell) or a natural killer (NK) cell (CAR-NK cell). In some embodiments, the cell is an autologous immune effector cell. In some embodiments the cell is an autologous T cell (CAR-T cell) or an autologous natural killer (NK) cell. In some embodiments, the cell is an allogenic immune effector cell. In some embodiments the cell is an allogenic T cell (CAR-T cell) or an allogenic natural killer (NK) cell. In some embodiments, the cell is capable of directing an immune response to a cell expressing CD123 in an in vitro assay comprising the cell, a cell expressing CD123 and an Adapter comprising (1) a D domain that binds to CD123 and (b) an AFP p26 AD, e.g., an Adapter comprising the amino acid sequence of SEQ ID NO: 50.

In some embodiments, a cell expressing a chimeric antigen receptor (CAR) is provided herein, wherein the CAR comprises an AFP p26 antigenic determinant (AD), (ii) a transmembrane domain, and (iii) an intracellular domain. In some embodiments, the AFP p26 AD comprises an amino acid sequence selected from the group consisting of SEQ ID NO: 37-43 and 44. In some embodiments, the AFP p26 AD comprises the amino acid sequence of SEQ ID NO: 37. In some embodiments, the AFP p26 AD comprises the amino acid sequence of SEQ ID NO: 39. In some embodiments, the cell is an immune cell. In some embodiments, the cell is an immune effector cell. In some embodiments, the cell is a T cell (CAR-T cell) or a natural killer (NK) cell (CAR-NK cell). In some embodiments, the cell is an autologous immune effector cell. In some embodiments the cell is an autologous T cell (CAR-T cell) or an autologous natural killer (NK) cell. In some embodiments, the cell is an allogenic immune effector cell. In some embodiments the cell is an allogenic T cell (CAR-T cell) or an allogenic natural killer (NK) cell. In some embodiments, the cell is capable of directing an immune response to a cell expressing CD123 in an in vitro assay comprising the cell, a cell expressing CD123 and an Adapter comprising (1) a D domain that binds to CD123 and (b) a D domain that binds an AFP p26 AD.

In some embodiments, a CAR cell comprises a nucleic acid sequence encoding a CAR, wherein the CAR comprises an extracellular domain made up of, at least in part, an ADBD (e.g., D domain) that binds a target of interest, a transmembrane domain, and a signaling domain. In several embodiments, the encoded CAR polypeptide binds specifically to a tumor antigen (and thus functions to deliver the cell expressing the CAR to the tumor). In several embodiments, the tumor antigen bound by the CAR is associated with a hematologic malignancy. In additional embodiments, tumor antigen bound by the CAR is associated with a solid tumor. In further embodiments the CAR is engineered to bind both solid and hematologic tumors. Depending on the embodiment, the cell expressing the CAR can be an immune effector cell (e.g., a T cell or a natural killer (NK) cell) or another cell type. In some embodiments, the immune effector cell is an autologous cell. In some embodiments, the immune effector cell is an allogenic cell. In several embodiments, the cell (whether T cell, NK cell or other cell type) exhibits an anti-tumor immunity when the antigen-binding domain of the CAR binds to its targeted tumor antigen(s).

In some embodiments, prior to expansion and genetic modification or other modification, a source of cells (e.g., T cells or natural killer cells), can routinely be obtained from a subject using techniques known in the art. The term "subject" is intended to include living organisms in which an immune response can be elicited (e.g., mammals) T cells can be obtained from sources, including but not limited to peripheral blood mononuclear cells, bone marrow, lymph node tissue, cord blood, thymus tissue, tissue from a site of infection, ascites, pleural effusion, spleen tissue, and tumors.

In some embodiments, the CAR cell is capable of killing a target cell, e.g., when the ADBD (e.g., D domain) of the CAR interacts with an AD, which can be present on the surface of a target cell and/or in an Adapter. In some embodiments, the CAR cell is capable of degranulating, e.g., when the ADBD of the CAR interacts with an AD, which can be present on the surface of a target cell and/or in an Adapter. In some embodiments, the CAR cell is capable of secreting a cytokine or cytokines, e.g., when the ADBD of the CAR interacts with an AD, which can be present on the surface of a target cell and/or in an Adapter.

In some embodiments, the CAR-containing cell is an immune cell. In some embodiments, the CAR-containing cell is an immune effector cell. In further embodiments, the CAR-containing immune cell is a cytotoxic cell. In further embodiments, the cytotoxic cell is selected from a T cell, NK cell, or a cultured NK cell (e.g., a NK92 cell). In some embodiments, the CAR immune cell is an autologous immune cell. In some embodiments, the CAR immune cell is an allogenic immune cell.

In certain embodiments, an immune effector cell comprises a cell surface receptor for an immunoglobulin or other peptide binding molecule, such as a receptor for an immunoglobulin constant region and including the class of receptors commonly referred to as "Fc receptors" ("FcR"s). A number of FcRs have been structurally and/or functionally characterized and are known in the art, including FcR having specific abilities to interact with a restricted subset of immunoglobulin heavy chain isotypes, or that interact with Fc domains with varying affinities, and/or which may be expressed on restricted subsets of immune effector cells under certain conditions (e.g., Kijimoto-Ochichai et al., Cell Mol. Life. Sci. 59: 648 (2002); Davis et al., Curr. Top. Microbiol. Immunol. 266: 85 (2002); Pawankar, Curr. Opin. Allerg. Clin. Immunol. 1: 3 (2001); Radaev et al., Mol. Immunol. 38: 1073 (2002); Wurzburg et al., Mol. Immunol. 38: 1063 (2002); Sulica et al., Int. Rev. Immunol. 20: 371 (2001); Underhill et al., Ann. Rev. Immunol. 20: 825 (2002); Coggeshall, Curr. Dir. Autoimm. 5: 1 (2002); Mimura et al., Adv. Exp. Med. Biol. 495: 49 (2001); Baumann et al., Adv. Exp. Med. Biol. 495: 219 (2001); Santoso et al., Ital. Heart J. 2: 811 (2001); Novak et al., Curr. Opin. Immunol. 13: 721 (2001); Fossati et al., Eur. J. Clin. Invest. 31: 821 (2001)), the contents of each of which is herein incorporated by reference in its entirety.

Cells that are capable of mediating ADCC are examples of immune effector cells. Other immune effector cells include Natural Killer cells, tumor-infiltrating T lymphocytes (TILs), cytotoxic T lymphocytes, and granulocytic cells such as cells that comprise allergic response mechanisms Immune effector cells thus include, but are not limited to, cells of hematopoietic origin including cells at various stages of differentiation within myeloid and lymphoid lineages and which may (but need not) express one or more types of functional cell surface FcR, such as T lymphocytes, B lymphocytes, NK cells, monocytes, macrophages, dendritic cells, neutrophils, basophils, eosinophils, mast cells, platelets, erythrocytes, and precursors, progenitors (e.g., hematopoietic stem cells), as well as quiescent, activated, and mature forms of such cells. Other immune effector cells may include cells of non-hematopoietic origin that are capable of mediating immune functions, for example, endothelial cells, keratinocytes, fibroblasts, osteoclasts, epithelial cells, and other cells Immune effector cells can also include cells that mediate cytotoxic or cytostatic events, or endocytic, phagocytic, or pinocytotic events, or that effect induction of apoptosis, or that effect microbial immunity or neutralization of microbial infection, or cells that mediate allergic, inflammatory, hypersensitivity and/or autoimmune reactions.

In some embodiments, the CAR-containing cell is a T cell. In some embodiments, the CAR-containing cell is a NK cell. In additional embodiments, the CAR-containing cell is a B cell. Other immune cells, and/or combinations of different immune cell types can optionally be used. In some embodiments, the CAR immune cell is an autologous immune cell. In some embodiments, the CAR immune cell is an allogenic immune cell. In some embodiments, combinations of cell types (e.g., NK cells and T cells) are advantageous because they act synergistically to treat a disease or condition (e.g., a hyperproliferative disease such as cancer). When combinations are used, the various cell types can target the same, different, or overlapping tumor antigenic determinants.

In some embodiments, the CAR-containing immune cell is a T cell, and the binding of the ADBD of the CAR to a cognate ligand (i.e., target of interest) stimulates the T cell to initiate intracellular signaling. In further embodiments, binding of the ADBD of the CAR to a cognate ligand stimulates the T cell to produce cytokines and degranulate, leading to the cytotoxic effects on the cell expressing the target of interest on its surface (e.g., a cancer cell). In additional embodiments, the CAR-containing T cell proliferates in response to binding the target of interest. In some embodiments, the activity of the CAR-containing T cell does not result in the T cells exhibiting a phenotype associated with T cell exhaustion. In some embodiments where the CAR cell is a T cell, the transmembrane domain of the CAR comprises CD8a, 41BB or CD28, and the cytoplasmic domain comprises a T cell receptor alpha, beta, or zeta chain. In some embodiments, the CD8a transmembrane domain comprises the amino acid sequence of SEQ ID NO: 113. In some embodiments, the CD8a transmembrane domain comprises the amino acid sequence of SEQ ID NO: 114.

In some embodiments, the CAR-containing immune cell is a NK cell, the transmembrane domain comprises CD8a, CD28, or 41BB and the cytoplasmic domain comprises a zeta chain of a T cell receptor. In some embodiments, the cytoplasmic domain contains the sequence of SEQ ID NO: 115, 116 or combination thereof. In some embodiments, the cytoplasmic domain contains the sequence of SEQ ID NO: 117. In some embodiments, the CAR immune cell is an autologous NK cell. In some embodiments, the CAR immune cell is an allogenic NK cell.

In some embodiments, the CAR-containing immune cell has been engineered to bind to a target of interest expressed by a cancer cell. In further embodiments the CAR-containing cell binds a tumor antigen selected from the group: CD137, PDL1, CD123, CTLA4, CD47, KIR, DR5, TIM3, PD1, EGFR, TCR, CD19, CD20, CD22, ROR1, mesothelin, CD33, 1L3Ra, cMet, PSMA, Glycolipid F77, EGFRvIII, GD2, NY-ESO-1, and MAGE A3. In further embodiments the CAR-containing cell binds 2, 3, 4, 5 or more of the above tumor antigens.

In some embodiments, the CAR cell is engineered to express an Adapter disclosed herein.

In additional embodiments, the CAR cell is engineered to express a second CAR. In some embodiments, the second CAR comprises an extracellular domain comprising an ADBD (e.g., D domain), a transmembrane domain, and an intracellular signaling domain. In an additional embodiment the second CAR is comprised of an extracellular domain composed of one or more ADBDs with the same or different specificities. In some embodiments, the second CAR is able to transduce an effector function signal upon binding a target of interest. In further embodiments, the second CAR comprises an extracellular domain comprising an ADBD, and transmembrane or other cell-surface associating domain, but is unable to signal upon binding a target of interest.

In some embodiments the CAR cell is engineered such that the CAR coding sequence is site specifically introduced into a locus of a gene highly expressed in the corresponding host cell. In some embodiments the CAR coding sequence is introduced into a T cell receptor locus. In further embodiments, the CAR coding sequence is introduced into the T cell receptor a constant (TRAC) of the cell. Modified cells that lack expression of a functional TCR and/or HLA can routinely be obtained using any suitable means known in the art, including for example, siRNA, shRNA, CRISPR, TALEN, and/or ZFN.

In some embodiments, the immune effector cell can be an allogeneic immune effector cell, e.g., T cell or NK cell. In some embodiments, the immune effector cell can be an autologous immune effector cell, e.g., T cell or NK cell.

The production of CAR cells comprising a genetic modification useful in practicing the provided methods may be carried out using a variety of standard techniques for recombinant DNA methodologies, genetic manipulation, and genome editing known in the art. Genetically modified CAR cells described herein that lack expression of an AD can routinely be obtained using any suitable means known in the art, including for example, siRNA, shRNA, CRISPR, TALEN, and/or ZFN. Methods for genetic manipulation of CAR cells is described, for example, in U.S. Patent Appl. Pub. 20170204372, which is incorporated herein by reference in its entirety.

In some embodiments the CAR cell is engineered to eliminate or reduce the expression of a functional T cell receptor (TCR) and/or human leukocyte antigen (HLA), e.g., HLA class I and/or HLA class II. Modified cells that lack expression of a functional TCR and/or HLA can routinely be obtained using any suitable means known in the art, including for example, siRNA, shRNA, CRISPR, TALEN, and/or ZFN.

In some embodiments, the CAR cell is engineered to eliminate or reduce the expression of a molecule that may decrease the ability of a CAR cell to mount an immune effector response. In further embodiments, the CAR cell is engineered to eliminate or reduce the expression of a molecule selected from: PD1, PDL1, CTLA4, TIM3, LAG3, VISTA, BTLA, TIGIT, LAIR1, CD160, 2B4 and TGFR beta. In some embodiments, the CAR cell has been engineered to eliminate or reduce the expression of 2, 3, 4, 5 or more of the above molecules. Modified cells that lack expression of one or more of the above molecules can routinely be obtained using any suitable means known in the art, including for example, siRNA, shRNA, CRISPR, TALEN, and/or ZFN.

In further embodiments, the CAR cell is engineered to eliminate or reduce the expression of one or more of (a) a functional TCR and an HLA; and (b) a molecule selected from: PD1, PDL1, CTLA4, TIM3, LAG3, VISTA, BTLA, TIGIT, LAIR1, CD160, 2B4 and TGFR beta. In further embodiments, the CAR cell has been engineered to eliminate or reduce the expression of 2, 3, 4, 5, 6 or more of the above molecules.

CAR cells suitable for use in connection with the DDpp (e.g., Adapter and CAR) disclosed herein have been disclosed in Int'l. Appl. Pub. Nos. WO 2016164305, WO 2016164308A1, WO 2019099440, and WO 2019099433, U.S. Pat. Nos. 10,662,248, and 10,647,775, and US Pat. Appl. Nos. 20200223934, and 20210002381, each of which is incorporated herein by reference for all purposes.

Compositions

Provided herein are compositions comprising a D domain polypeptide, DDpp fusion protein (e.g., an Adapter) disclosed herein. Also provided are compositions comprising a cell expressing a chimeric antigen receptor (CAR) disclosed herein. Also provided herein are compositions comprising a polynucleotide encoding D domain polypeptide, DDpp fusion protein (e.g., an Adapter) or a CAR disclosed herein. In some embodiments, the compositions provided herein are pharmaceutical compositions. In some embodiments, the pharmaceutical compositions comprise a pharmaceutically acceptable excipient. In some embodiments, the pharmaceutical compositions comprise a physiologically tolerable carrier. In some embodiments, the compositions provided herein are suitable for administration to a patient, for example, via intravenous or subcutaneous administration.

In some embodiments, a composition provided herein comprises a cell expressing a chimeric antigen receptor (CAR), wherein the CAR comprises a D domain that binds to CD123, (ii) a transmembrane domain, and (iii) an intracellular domain. In some embodiments, the D domain that binds to CD123 comprises an amino acid sequence selected from the group consisting of SEQ ID NO: 8-33, 99 and 100. In some embodiments, the D domain that binds to CD123 comprises an amino acid sequence selected from the group consisting of SEQ ID NO: 8, 13, 14, 31, 32, and 33. In some embodiments, the D domain that binds to CD123 comprises the amino acid sequence of SEQ ID NO: 14. In some embodiments, the CAR comprises the amino acid sequence of SEQ ID NO: 62-66 or 67. In some embodiments, the CAR comprises the amino acid sequence of SEQ ID NO: 67. In some embodiments, the cell is an immune cell. In some embodiments, the cell is an immune effector cell. In some embodiments, the cell is a T cell (CAR-T cell) or a natural killer (NK) cell (CAR-NK cell). In some embodiments, the immune effector cell is an autologous cell. In some embodiments, the immune effector cell is an allogenic cell. In some embodiments, an immune effector cell expressing the CAR is capable of directing an immune response to a cell expressing CD123 in an in vitro assay.

In some embodiments, a composition provided herein comprises a cell expressing a chimeric antigen receptor (CAR), wherein the CAR comprises an antigenic determinant binding domain (ADBD) that binds to an AFP p26 AD, (ii) a transmembrane domain, and (iii) an intracellular domain. In some embodiments, the ADBD that binds to AFP p26 AD comprises an scFv that binds to AFP p26 AD. In some embodiments, the ADBD that binds to AFP p26 AD comprises a D domain that binds to AFP p26 AD. In some embodiments, the AFP p26 AD comprises an amino acid sequence selected from the group consisting of SEQ ID NO: 37-43 and 44. In some embodiments, the AFP p26 AD comprises the amino acid sequence of SEQ ID NO: 37. In some embodiments, the AFP p26 AD comprises the amino acid sequence of SEQ ID NO: 39. In some embodiments, the DD that binds to an AFP p26 AD comprises an amino acid sequence selected from the group consisting of SEQ ID NO: 74-93 and 94. In some embodiments, the DD that binds to an AFP p26 AD comprises the amino acid sequence of SEQ ID NO: 70-73 or 92-94. In some embodiments, the DD that binds to an AFP p26 AD comprises the amino acid sequence of SEQ ID NO: 73. In some embodiments, the CAR comprises the amino acid sequence of SEQ ID NO: 68. In some embodiments, the CAR comprises the amino acid sequence of SEQ ID NO: 69. In some embodiments, the cell is an immune cell. In some embodiments, the cell is an immune effector cell. In some embodiments, the cell is a T cell (CAR-T cell) or a natural killer (NK) cell (CAR-NK cell). In some embodiments, the immune cell is an autologous immune cell. In some embodiments, the immune cell is an allogenic immune cell. In some embodiments, the cell is capable of directing an immune response to a cell expressing CD123 in an in vitro assay comprising the cell, a cell expressing CD123 and an Adapter comprising (1) a D domain that binds to CD123 and (b) an AFP p26 AD, e.g., an Adapter comprising the amino acid sequence of SEQ ID NO: 50.

In some embodiments, a composition provided herein comprises a cell expressing a chimeric antigen receptor (CAR), wherein the CAR comprises an AFP p26 antigenic determinant (AD), (ii) a transmembrane domain, and (iii) an intracellular domain. In some embodiments, the AFP p26 AD comprises an amino acid sequence selected from the group consisting of SEQ ID NO: 37-43 and 44. In some embodiments, the AFP p26 AD comprises the amino acid sequence of SEQ ID NO: 37. In some embodiments, the AFP p26 AD comprises the amino acid sequence of SEQ ID NO: 39. In some embodiments, the cell is an immune cell. In some embodiments, the cell is an immune effector cell. In some embodiments, the cell is a T cell (CAR-T cell) or a natural killer (NK) cell (CAR-NK cell). In some embodiments, the immune cell is an autologous immune cell. In some embodiments, the immune cell is an allogenic immune cell. In some embodiments, the cell is capable of directing an immune response to a cell expressing CD123 in an in vitro assay comprising the cell, a cell expressing CD123 and an Adapter comprising (1) a D domain that binds to CD123 and (b) a D domain that binds an AFP p26 AD.

In some embodiments, a composition provided herein comprises an Adapter comprising (a) a D domain (DD) that binds to CD123 and (b) an antigenic determinant (AD). In some embodiments, the D domain that binds to CD123 comprises an amino acid sequence selected from the group consisting of SEQ ID NO: 8-33, 99 and 100. In some embodiments, the D domain that binds to CD123 comprises an amino acid sequence selected from the group consisting of SEQ ID NO: 8, 13, 14, 31, 32, and 33. In some embodiments, the D domain that binds to CD123 comprises the amino acid sequence of SEQ ID NO: 14. In some embodiments, the Adapter is a monovalent Adapter comprising a single D domain that binds CD123. In some embodiments, the Adapter is a bivalent Adapter comprising two D domains that bind CD123. In some embodiments, the two D domains that bind CD123 are the same. In some embodiments, the two D domains that bind CD123 are different. In some embodiments, the Adapter is a bivalent Adapter comprising a first D domain that binds CD123 and a second D domain that binds a second AD. In some embodiments, the second AD is CD33 or LeY. In some embodiments, a monovalent Adapter comprises a D domain comprising an amino acid sequence selected from the group consisting of SEQ ID NO: 8, 13, 14, 31, 32, and 33. In some embodiments, the monovalent Adapter comprises the D domain comprising the amino acid sequence of SEQ ID NO: 14. In some embodiments, a bivalent Adapter comprises a DD comprising an amino acid sequence selected from the group consisting of SEQ ID NO: 8, 13, 14, 31, 32, and 33. In some embodiments, the bivalent Adapter comprises the D domain comprising the amino acid sequence of SEQ ID NO: 14. In some embodiments, a bivalent Adapter comprises two identical D domains comprising an amino acid sequence selected from the group consisting of SEQ ID NO: 8, 13, 14, 31, 32, and 33. In some embodiments, the bivalent Adapter comprises two identical D domains comprising the amino acid sequence of SEQ ID NO: 14. In some embodiments, the Adapter comprises an AFP p26 antigenic determinant (AD). In some embodiments, the AFP p26 AD comprises an amino acid sequence selected from the group consisting of SEQ ID NO: 37-43 and 44. In some embodiments, the AFP p26 AD comprises the amino acid sequence of SEQ ID NO: 37. In some embodiments, the AFP p26 AD comprises the amino acid sequence of SEQ ID NO: 39. In some embodiments, the monovalent Adapter comprises the amino acid sequence of SEQ ID NO: 50-54 or 55. In some embodiments, the monovalent Adapter comprises the amino acid sequence of SEQ ID NO: 50. In some embodiments, the bivalent Adapter comprises the amino acid sequence of SEQ ID NO: 56-60 or 61. In some embodiments, the monovalent Adapter comprises the amino acid sequence of SEQ ID NO: 61. In some embodiments, the Adapter comprises one or more linkers. In some embodiments, the Adapter is capable of directing an immune response to a cell expressing CD123 in an in vitro assay comprising the Adapter, a cell expressing CD123 and an immune effector cell expressing a CAR comprising an ADBD that binds the AD comprised by the Adapter, e.g., a CAR comprising a D domain that binds AFP p26.

In some embodiments, a composition provided herein comprises an Adapter comprising (a) a D domain that binds to CD123 and (b) an antigenic determinant binding domain (ADBD) that binds an AFP p26 AD. In some embodiments, the AFP p26 AD comprises an amino acid sequence selected from the group consisting of SEQ ID NO: 37-43 and 44. In some embodiments, the AFP p26 AD comprises the amino acid sequence of SEQ ID NO: 37. In some embodiments, the AFP p26 AD comprises the amino acid sequence of SEQ ID NO: 39. In some embodiments, the D domain that binds to CD123 comprises an amino acid sequence selected from the group consisting of SEQ ID NO: 8-33, 99 and 100. In some embodiments, the D domain that binds to CD123 comprises an amino acid sequence selected from the group consisting of SEQ ID NO: 8, 13, 14, 31, 32, and 33. In some embodiments, the D domain that binds to CD123 comprises the amino acid sequence of SEQ ID NO: 14. In some embodiments, the ADBD that binds to an AFP p26 AD comprises a D domain that binds to the AFP p26 AD. In some embodiments, the D domain that binds to an AFP p26 AD comprises an amino acid sequence selected from the group consisting of SEQ ID NO: 70-73 and 92-94. In some embodiments, the D domain that binds to an AFP p26 AD comprises the amino acid sequence of SEQ ID NO: 73. In some embodiments, the Adapter comprises one or more linkers. In some embodiments, the Adapter is capable of directing an immune response to a cell expressing CD123 in an in vitro assay comprising the Adapter, a cell expressing CD123 and an immune effector cell expressing a CAR comprising an AFP p26 AD.

In some embodiments, a composition provided herein comprises an Adapter comprising (a) a first antigenic determinant binding domain (ADBD) that binds to a target antigenic determinant (AD) on a target cell and (b) an antigenic determinant binding domain (ADBD) that binds to an AFP p26 AD. In some embodiments, the AFP p26 AD comprises an amino acid sequence selected from the group consisting of SEQ ID NO: 37-43 and 44. In some embodiments, the AFP p26 AD comprises the amino acid sequence of SEQ ID NO: 37. In some embodiments, the AFP p26 AD comprises the amino acid sequence of SEQ ID NO: 39. In some embodiments, the ADBD that binds to an AFP p26 AD comprises a D domain that binds to AFP p26. In some embodiments, the D domain that binds to an AFP p26 AD comprises an amino acid sequence selected from the group consisting of SEQ ID NO: 70-73 and 92-94. In some embodiments, the D domain that binds to an AFP p26 AD comprises the amino acid sequence of SEQ ID NO: 73. In some embodiments, the Adapter comprises one or more linkers. In some embodiments, the Adapter is capable of directing an immune response to a cell expressing CD123 in an in vitro assay comprising the Adapter, a cell expressing CD123 and an immune effector cell expressing a CAR comprising an AFP p26 AD.

In certain embodiments, the CAR comprises a single-chain variable fragment (scFv) ADBD. In other embodiments, the CAR comprises an alternative scaffold binding domain (ASBD) ADBD. In further embodiments, the CAR comprises a D domain.

In some embodiments, the CAR comprises 2 ADBDs. In other embodiments, the CAR comprises an ASBD and a scFv. In further embodiments, the CAR comprises a D domain and a scFv. In some embodiments, the CAR comprises 2 ASBDs. In further embodiments, the CAR comprises 2 D domains.

In some embodiments, the CAR intracellular domain is a signaling domain. In further embodiments, the CAR intracellular domain comprises a primary signaling domain. In certain embodiments, the CAR intracellular domain comprises a CD3 primary signaling domain. In some embodiments, the CAR intracellular domain further comprises a costimulatory signaling domain. In further embodiments, the costimulatory signaling domain is selected from: CD28, 41BB, CD27, and CD134. In particular embodiments, the CAR intracellular signaling domain comprises a 41BB costimulatory signaling domain. In some embodiments, the intracellular signaling domain contains the sequence of SEQ ID NO: 115, 116 or combination thereof. In some embodiments, the intracellular signaling domain contains the sequence of SEQ ID NO: 117.

In some embodiments, the target AD is selected from: CD45, CD26, CD30, CD33, LeY and CD38. In some embodiments, the target AD is selected from: CD19, CD22, CD123, BCMA, CS1, HER2, TACI, BAFFR, and PDL1. In further embodiments, the target AD is BCMA. In further embodiments, the target AD is CS1. In other embodiments, the target AD is CD123. In other embodiments, the target AD is CD19. In other embodiments, the target AD is CD22. In other embodiments, the target AD is TACI. In other embodiments, the target AD is BAFFR. In other embodiments, the target AD is PDL1. In other embodiments, the target AD is HER2.

In some embodiments, the CAR comprises 2 ADBDs that bind to separate targets. In further embodiments, the CAR binds to CD123 and CD33. In further embodiments, the CAR binds to CD123 and CD38. In further embodiments, the CAR binds to CD123 and LeY. In further embodiments, the CAR binds to CD123 and BCMA. In further embodiments, the CAR binds to CD123 and CS1. In further embodiments, the CAR binds to CD19 and CD123. In other embodiments, the CAR binds to CD22 and CD123. In other embodiments, the CAR binds to PDL1 and CD123.

In some embodiments, the Adapter comprises an AD of a tumor antigen. In further embodiments, the tumor antigen is selected from the group: CD45, CD26, CD30, CD33, and CD38.

In some embodiments, the Adapter comprises an AD of a tumor antigen. In further embodiments, the tumor antigen is selected from the group: BCMA, CD19, CD22, CS1, TACI, BAFFR, and PDL1.

In some embodiments, the Adapter comprises an ADBD that is a scFv. In further embodiments, the Adapter comprises an ADBD that is an ASBD. In some embodiments, the Adapter comprises a D domain.

In some embodiments, the Adapter comprises two ADBDs. In further embodiments, the Adapter comprises two ADBDs that (a) are the same, (b) bind to the same antigenic determinant, (c) bind to different ADs of the same antigen, (d) bind to different antigens on the same cell, or (d) bind to different antigens on different cells. In further embodiments, the Adapter comprises two ASBDs. In certain embodiments, the Adapter comprises two D domains. In some embodiments, the Adapter comprises an ADBD that is a scFv and an ADBD that is an ASBD. In other embodiments, the Adapter comprises an ADBD that is a scFv and an ADBD that is a D domain.

In some embodiments, the Adapter comprises an ADBD that binds to a member selected from: CD45, CD26, CD30, CD33, and CD38. In certain embodiments, the Adapter comprises an ADBD binds to CD45. In other embodiments, the Adapter comprises an ADBD that binds to CD26. In some embodiments, the Adapter comprises an ADBD that binds to CD30. In other embodiments, the Adapter comprises an ADBD that binds to CD33. In other embodiments, the Adapter comprises an ADBD that binds to CD38. In some embodiments, the Adapter comprises an ADBD that binds to CD45.

In some embodiments, the Adapter comprises an ADBD that binds to a member selected from: BCMA, CD123, CD19, CD22, CS1, HER2, TACI, BAFFR, and PDL1. In certain embodiments, the Adapter comprises an ADBD binds to BCMA. In other embodiments, the Adapter comprises an ADBD that binds to CD123. In some embodiments, the Adapter comprises an ADBD that binds to CD19. In other embodiments, the Adapter comprises an ADBD that binds to CD22. In other embodiments, the Adapter comprises an ADBD that binds to CS1. In other embodiments, the Adapter comprises an ADBD that binds to HER2. In other embodiments, the Adapter comprises an ADBD that binds to TACI. In other embodiments, the Adapter comprises an ADBD that binds to BAFFR. In other embodiments, the Adapter comprises an ADBD that binds to PDL1.

In some embodiments, the Adapter is bispecific. In further embodiments, the Adapter comprises an ADBD that binds to CD123 and an ADBD that binds to CD33. In other embodiments, the Adapter comprises an ADBD that binds to CD123 and an ADBD that binds to CD38. In other embodiments, the Adapter comprises an ADBD that binds to CD123 and an ADBD that binds to LeY. In other embodiments, the Adapter comprises an ADBD that binds to PDL1 and an ADBD that binds to CD123.

In some embodiments, the target cell is a tumor cell. In further embodiments, the tumor cell is selected from the group of acute myeloid leukemia (AML) cell, B-cell acute lymphoblastic leukemia cell, hairy cell leukemia cell, Hodgkin's lymphoma cell, a myelodysplasia cell and blastic plasmacytoid dendritic neoplasm (BPDCN) cell. In some embodiments, the tumor cell is an AML tumor cell. In some embodiments, the tumor cell is a myelodysplasia cell. In some embodiments, the tumor cell is a B-cell acute lymphoblastic leukemia tumor cell. In some embodiments, the tumor cell is a hairy cell leukemia tumor cell. In some embodiments, the tumor cell is a Hodgkin's lymphoma tumor cell. In some embodiments, the tumor cell is a BPDCN tumor cell. In some embodiments, the tumor cell expresses CD123.

In the methods of killing a target cell provided herein, the target cell can be a cell of the immune system. In some embodiments, the target cell is a B cell. In some embodiments, the target cell is a T cell. In some embodiments, the target cell is a naïve T cell. In some embodiments, the target cell is a memory T cell.

In some embodiments, the cell expressing the CAR is an immune effector cell. In further embodiments, the immune effector cell is a T cell. In other embodiments, the immune effector cell is an NK cell. In some embodiments, the immune effector cell is not a T cell or an NK cell. In some embodiments, the immune effector cell is an autologous cell. In some embodiments, the immune effector cell is an allogenic cell. In some embodiments, the cell expressing the CAR kills the target cell. In some embodiments, binding of the Adapter to an AD blocks the activity of the antigen comprising the AD. In some embodiments, the cell expressing the CAR comprises a genetic modification that reduces or eliminates the expression of an AD described herein. In some embodiments, the cell expressing the CAR comprises a genetic modification that reduces or eliminates the expression of a human CD45 AD.

In some embodiments, the CAR cell binds to an AD that is present on both a target cell and an Adapter. In other embodiments, the CAR cell binds to an AD that is present on an Adapter, but is not present on a target cell. In some embodiments, the AD is a naturally occurring protein/molecule. In some embodiments, the AD is a human protein/molecule.

In one embodiment, therapeutic compositions provided herein contain a physiologically tolerable carrier together with at least one species of DDpp fusion protein (e.g., an Adapter) as described herein, dissolved or dispersed therein as an active ingredient. In another embodiment, therapeutic compositions provided herein contain a physiologically tolerable carrier together with at least one species of a DDpp as described herein, dissolved or dispersed therein as an active ingredient. In another embodiment, therapeutic compositions provided herein contain a physiologically tolerable carrier together with at least one species of a CAR cell as described herein, dissolved or dispersed therein as an active ingredient. In a preferred embodiment, therapeutic composition is not immunogenic when administered to a human patient for therapeutic purposes.

The preparation of a pharmacological composition that contains active ingredients dissolved or dispersed therein is well understood in the art. Typically such compositions are prepared as sterile injectables either as liquid solutions or suspensions, aqueous or non-aqueous. However, solid forms suitable for solution, or suspensions, in liquid prior to use can also be prepared. The preparation can also be emulsified. Thus, a DDpp-containing (e.g., Adapter-containing) composition can take the form of solutions, suspensions, tablets, capsules, sustained release formulations or powders, or other compositional forms. In some embodiments, the DDpp compositions (e.g., a DDpp fusion proteins, such as Adapters) are formulated to ensure or optimize distribution in vivo, For example, the blood-brain barrier (BBB) excludes many highly hydrophilic compounds and if so desired, the compositions are prepared so as to increase transfer across the BBB, by for example, formulation in liposomes. For methods of manufacturing liposomes, see, e.g., U.S. Pat. Nos. 4,522,811, 5,374,548, and 5,399,331. The liposomes can comprise one or more moieties that are selectively transported into specific cells or organs, thus enhance targeted drug delivery (see, e.g., Ranade, Clin. Pharmacol. 29: 685 (1989)).

The DDpp (e.g. DDpp fusion protein, such as an Adapter) and/or CAR cell can be mixed with other active ingredients and/or excipients that are pharmaceutically acceptable and compatible with the active ingredient and in amounts suitable for use in therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

Therapeutic DDpp (e.g., Adapter) formulations can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylarsine, 2-ethylamino ethanol, histidine, procaine and the like.

Physiologically tolerable carriers are known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, propylene glycol, polyethylene glycol, and other solutes.

Liquid compositions can also contain liquid phases in addition to, and to the exclusion of water. Exemplary of such additional liquid phases are glycerin, vegetable oils such as cottonseed oil, organic esters such as ethyl oleate, and water-oil emulsions.

In one embodiment, a therapeutic composition contains a DDpp fusion protein (e.g., Adapter), typically in an amount of at least 0.1 weight percent of DDpp fusion protein per weight of total therapeutic composition. A weight percent is a ratio by weight of DDpp fusion (e.g., Adapter) per total composition. Thus, for example, 0.1 weight percent is 0.1 grams of DDpp (e.g., Adapter) per 100 grams of total composition.

A DDpp fusion protein-containing (e.g., Adapter-containing) therapeutic composition typically contains about 10 micrograms (µg) per milliliter (ml) to about 100 milligrams (mg) per ml of DDpp fusion protein (e.g., Adapter) as active ingredient per volume of composition, and more preferably contains about 1 mg/ml to about 10 mg/ml (i.e., about 0.1 to 1 weight percent).

The dosage ranges for the administration of the DDpp (e.g., a DDpp fusion protein, such as an Adapter) are those large enough to produce the desired effect in which the disease symptoms mediated by the target molecule are ameliorated. The dosage should not be so large as to cause adverse side effects, such as hyperviscosity syndromes, pulmonary edema, congestive heart failure, and the like. Generally, the dosage will vary with the age, condition, sex and extent of the disease in the patient and can be determined by one of skill in the art. The dosage can be adjusted by the individual physician in the event of any complication.

The DDpp (e.g., a DDpp fusion protein, such as an Adapter) can be administered parenterally by injection or by gradual infusion over time. Although the target molecule can typically be accessed in the body by systemic administration and therefore most often treated by intravenous administration of therapeutic compositions, other tissues and delivery means are contemplated where there is a likelihood that the tissue targeted contains the target molecule. Thus, DDpp (e.g., Adapter) can be administered intravenously, intraperitoneally, intramuscularly, subcutaneously, intracavity, transdermally, and can be delivered by peristaltic means. DDpp fusion proteins (e.g., Adapter) can also be delivered by aerosol to airways and lungs.

Therapeutic compositions containing a DDpp (e.g., Adapter) can be conventionally administered intravenously, as by injection of a unit dose, for example. The term "unit dose" when used in reference to a therapeutic composition provided herein refers to physically discrete units suitable as unitary dosage for the subject, each unit containing a predetermined quantity of active material calculated to produce the desired therapeutic effect in association with the required diluent; e.g., carrier, or vehicle. In some embodiments, therapeutic compositions containing a DDpp (e.g., Adapter) are administered subcutaneously.

The DDpp (e.g., a DDpp fusion protein, such as an Adapter) is administered in a manner compatible with the dosage formulation, and in a therapeutically effective amount. The quantity to be administered depends on the subject to be treated, capacity of the subject's system to utilize the active ingredient of the administered composition, and degree of therapeutic effect desired. Precise amounts of active ingredient required to be administered depend on the judgment of the practitioner and are peculiar to each individual. However, suitable dosage ranges for systemic application are disclosed herein and depend on the route of administration. Suitable regimes for administration are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

The DDpp (e.g., Adapter) compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The dosage ranges for the administration of the DDpp (e.g., Adapter) are those large enough to produce the desired effect in which the disease symptoms mediated by the target molecule are ameliorated. The dosage should not be so large as to cause adverse side effects, such as, hyperviscosity syndromes, pulmonary edema, congestive heart failure, and the like. Generally, the dosage will vary with the age, condition, sex and extent of the disease in the patient and can be determined by one of skill in the art. The dosage can be adjusted by the individual physician in the event of any complication.

The dosage schedule and amounts effective for therapeutic and prophylactic uses, i.e., the "dosing regimen," will depend upon a variety of factors, including the cause, stage and severity of the disease or disorder, the health, physical status, age of the mammal being treated, and the site and mode of the delivery of the DDpp (e.g., Adapter). Therapeutic efficacy and toxicity of the complex and formation can be determined by standard pharmaceutical, pharmacological, and toxicological procedures in cell cultures or experimental animals Data obtained from these procedures can likewise be used in formulating a range of dosages for human use. Moreover, therapeutic index (i.e., the dose therapeutically effective in 50 percent of the population divided by the dose lethal to 50 percent of the population (ED50/LD50)) can readily be determined using known procedures. The dosage is preferably within a range of concentrations that includes the ED50 with little toxicity or none dose limiting toxicity, and may vary within this range depending on the dosage form employed, sensitivity of the patient, and the route of administration.

The dosage regimen also takes into consideration pharmacokinetic and pharmacodynamic parameters known in the art, such as, drug absorption rate, bioavailability, metabolism and clearance (see, e.g., Hidalgo-Aragones, J. Steroid Biochem. Mol. Biol. 58: 611-617 (1996); Groning et al., Pharmazie 51: 337-341 (1996); Fotherby, Contraception 54: 59-69 (1996); and Johnson et al., J. Pharm. Sci. 84: 1144-1146 (1995)). It is well within the state and level of skill of the clinician to determine the dosage regimen for each subject being treated. Moreover, single or multiple administrations of DDpp (e.g., Adapter) compositions can be administered depending on the dosage and frequency as required and tolerated by the subject. The duration of prophylactic and therapeutic treatment will vary depending on the particular disease or condition being treated. Some diseases are amenable to acute treatment whereas others require long-term, chronic therapy. DDpp (e.g., Adapter) can be administered serially, or simultaneously with the additional therapeutic agent.

In some embodiments, the DDpp (e.g., Adapter) is administered at about 0.1 mg/kg to about 50 mg/kg, about 0.1 mg/kg to about 25 mg/kg, about 0.1 mg/kg to about 20 mg/kg, about 0.1 mg/kg to about 15 mg/kg, about 0.1 mg/kg to about 10 mg/kg, or about 0.1 mg/kg to about 5 mg/kg.

In some embodiments, the DDpp (e.g., Adapter) is administered at about 0.1 mg/kg to about 50 mg/kg, about 0.1 mg/kg to about 25 mg/kg, about 0.1 mg/kg to about 20 mg/kg, about 0.1 mg/kg to about 15 mg/kg, about 0.1 mg/kg to about 10 mg/kg, or about 0.1 mg/kg to about 5 mg/kg. In some embodiments, the DDpp (e.g., Adapter) is administered at about 1 µg/kg to about 10 mg/kg, about 5 µg/kg to about 10 mg/kg, about 10 µg/kg to about 10 mg/kg, about 20 µg/kg to about 10 mg/kg, or about 50 µg/kg to about 10 mg/kg. In some embodiments, the DDpp (e.g., Adapter) is administered at about 10 µg/kg to about 10 mg/kg, about 50 µg/kg to about 10 mg/kg, about 100 µg/kg to about 10 mg/kg, about 200 µg/kg to about 10 mg/kg, or about 500 µg/kg to about 10 mg/kg. In some embodiments, the DDpp (e.g., Adapter) is administered at about 100 µg/kg to about 10 mg/kg, about 100 µg/kg to about 5 mg/kg, about 100 µg/kg to about 2 mg/kg, about 100 µg/kg to about 1 mg/kg, about 100 µg/kg to about 5 mg/kg, or about 100 µg/kg to about 2 mg/kg. In some embodiments, the DDpp (e.g., Adapter) is administered at about 1 µg/kg to about 10 mg/kg, about 5 µg/kg to about 5 mg/kg, about 10 µg/kg to about 2 mg/kg, about 20 µg/kg to about 1 mg/kg, or about 5 µg/kg to about 0.5 mg/kg. In some embodiments, the DDpp (e.g., Adapter) is administered at about 0.01 mg/kg, about 0.02 mg/kg, about 0.04 mg/kg, about 0.07 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 1 mg/kg, or about 2 mg/kg. In some embodiments, the DDpp (e.g., Adapter) is administered at about 0.07 mg/kg. In some embodiments, the DDpp (e.g., Adapter) is administered at about 0.01 mg/kg. In some embodiments, the DDpp (e.g., Adapter) is administered at about 0.1 mg/kg. In some embodiments, the DDpp (e.g., Adapter) is administered at about 0.2 mg/kg. In some embodiments, the DDpp (e.g., Adapter) is administered at about 0.3 mg/kg. In some embodiments, the DDpp (e.g., Adapter) is administered at about 0.4 mg/kg. In some embodiments, the DDpp (e.g., Adapter) is administered at about 0.5 mg/kg. In some embodiments, the DDpp (e.g., Adapter) is administered at about 0.6 mg/kg. In some embodiments, the DDpp (e.g., Adapter) is administered at about 0.7 mg/kg. In some embodiments, the DDpp (e.g., Adapter) is administered at about 0.8 mg/kg. In some embodiments, the DDpp (e.g., Adapter) is administered at about 0.9 mg/kg. In some embodiments, the DDpp (e.g., Adapter) is administered at about 1 mg/kg. In some embodiments, the DDpp (e.g., Adapter) is administered at about 2 mg/kg. In some embodiments, the DDpp (e.g., Adapter) is administered at about 3 mg/kg. In some embodiments, the DDpp (e.g., Adapter) is administered at about 4 mg/kg. In some embodiments, the DDpp (e.g., Adapter) is administered at about 5 mg/kg. In some embodiments, the DDpp (e.g., Adapter) is administered at about 6 mg/kg. In some embodiments, the DDpp (e.g., Adapter) is administered at about 7 mg/kg. In some embodiments, the DDpp (e.g., Adapter) is administered at about 8 mg/kg. In some embodiments, the DDpp (e.g., Adapter) is administered at about 9 mg/kg. In some embodiments, the DDpp (e.g., Adapter) is administered at about 10 mg/kg. In some embodiments, the DDpp (e.g., Adapter) is administered intravenously. In some embodiments, the DDpp (e.g., Adapter) is administered subcutaneously. In some embodiments, the DDpp (e.g., Adapter) comprises a D domain that binds to CD123 comprises an amino acid sequence selected from the group consisting of SEQ ID NO: 8-33, 99 and 100. In some embodiments, the DDpp (e.g., Adapter) comprises a D domain that binds to CD123 comprises an amino acid sequence selected from the group consisting of SEQ ID NO: 8, 13, 14, 31, 32, and 33. In some embodiments, the DDpp (e.g., Adapter) comprises a D domain that binds to CD123 comprises the amino acid sequence of SEQ ID NO: 14.

In some embodiments, the DDpp (e.g., Adapter) is administered at about 0.2 mg to about 200 mg, about 0.5 mg to about 100 mg, about 1 mg to about 50 mg, about 2 mg to about 25 mg, or about 2 mg to about 12 mg. In some embodiments, the DDpp (e.g., Adapter) is administered at about 0.4 mg, about 0.8 mg, about 1.6 mg, about 2.8 mg, about 3 mg, about 4 mg, about 8 mg, about 12 mg, about 16 mg, about 20 mg, about 24 mg, about 28 mg, about 40 mg, or about 80 mg. In some embodiments, the DDpp (e.g., Adapter) is administered at about 1.6 mg, about 2.8 mg, about 3 mg, about 4 mg, about 8 mg, about 12 mg, about 16 mg, or about 20 mg. In some embodiments, the DDpp (e.g., Adapter) is administered intravenously. In some embodiments, the DDpp (e.g., Adapter) is administered subcutaneously. In some embodiments, the DDpp (e.g., Adapter) comprises a D domain that binds to CD123 comprises an amino acid sequence selected from the group consisting of SEQ ID NO: 8-33, 99 and 100. In some embodiments, the DDpp (e.g., Adapter) comprises a D domain that binds to CD123 comprises an amino acid sequence selected from the group consisting of SEQ ID NO: 8, 13, 14, 31, 32, and 33. In some embodiments, the DDpp (e.g., Adapter) comprises a D domain that binds to CD123 comprises the amino acid sequence of SEQ ID NO: 14.

In some embodiments, more than one dose of the the DDpp (e.g., Adapter) is administered. In some embodiments, the more than one dose of the the DDpp (e.g., Adapter) is a constant dose. In some embodiments, the DDpp (e.g., Adapter) is administered at different doses. In some embodiments, the amount of DDpp (e.g., Adapter) administered is increased over time. In some embodiments, the amount of DDpp (e.g., Adapter) administered is decreased over time. In some embodiments, the DDpp (e.g., Adapter) is first administered at a low dose of between about 0.01 mg/kg and about 0.5 mg/kg, followed by administration at a high dose between about 0.1 mg/kg and about 5 mg/kg. In some embodiments, the DDpp (e.g., Adapter) is administered intravenously. In some embodiments, the DDpp (e.g., Adapter) is administered subcutaneously. In some embodiments, the DDpp (e.g., Adapter) comprises a D domain that binds to CD123 comprises an amino acid sequence selected from the group consisting of SEQ ID NO: 8-33, 99 and 100. In some embodiments, the DDpp (e.g., Adapter) comprises a D domain that binds to CD123 comprises an amino acid sequence selected from the group consisting of SEQ ID NO: 8, 13, 14, 31, 32, and 33. In some embodiments, the DDpp (e.g., Adapter) comprises a D domain that binds to CD123 comprises the amino acid sequence of SEQ ID NO: 14.

In some embodiments, the DDpp (e.g., Adapter) is administered daily. In some embodiments, the DDpp (e.g., Adapter) is administered twice a day. In some embodiments, the DDpp (e.g., Adapter) is administered three times a day. In some embodiments, the DDpp (e.g., Adapter) is administered four times a day. In some embodiments, the DDpp (e.g., Adapter) is administered every 12 hours. In some embodiments, the DDpp (e.g., Adapter) is administered every 8 hours. In some embodiments, the DDpp (e.g., Adapter) is administered every 6 hours. In some embodiments, the DDpp (e.g., Adapter) is administered every 4 hours. In some embodiments, the DDpp (e.g., Adapter) is administered every other day. In some embodiments, the DDpp (e.g., Adapter) is administered every three days. In some embodiments, the DDpp (e.g., Adapter) is administered twice a week. In some embodiments, the DDpp (e.g., Adapter) is administered twice a week, for example, on Monday, Wednesday and Friday. In some embodiments, the DDpp (e.g., Adapter) is administered weekly. In some embodiments, the DDpp (e.g., Adapter) is administered intravenously. In some embodiments, the DDpp (e.g., Adapter) is administered subcutaneously. In some embodiments, the DDpp (e.g., Adapter) comprises a D domain that binds to CD123 comprises an amino acid sequence selected from the group consisting of SEQ ID NO: 8-33, 99 and 100. In some embodiments, the DDpp (e.g., Adapter) comprises a D domain that binds to CD123 comprises an amino acid sequence selected from the group consisting of SEQ ID NO: 8, 13, 14, 31, 32, and 33. In some embodiments, the DDpp (e.g., Adapter) comprises a D domain that binds to CD123 comprises the amino acid sequence of SEQ ID NO: 14.

In some embodiments, the DDpp (e.g., Adapter) is administered for seven days. In some embodiments, the DDpp (e.g., Adapter) is administered for 2 weeks. In some embodiments, the DDpp (e.g., Adapter) is administered for 3 weeks. In some embodiments, the DDpp (e.g., Adapter) is administered for 4 weeks. In some embodiments, the DDpp (e.g., Adapter) is administered for 1 month. In some embodiments, the DDpp (e.g., Adapter) is administered for 2 months. In some embodiments, the DDpp (e.g., Adapter) is administered for 3 months. In some embodiments, the DDpp (e.g., Adapter) is administered intravenously. In some embodiments, the DDpp (e.g., Adapter) is administered subcutaneously. In some embodiments, the DDpp (e.g., Adapter) comprises a D domain that binds to CD123 comprises an amino acid sequence selected from the group consisting of SEQ ID NO: 8-33, 99 and 100. In some embodiments, the DDpp (e.g., Adapter) comprises a D domain that binds to CD123 comprises an amino acid sequence selected from the group consisting of SEQ ID NO: 8, 13, 14, 31, 32, and 33. In some embodiments, the DDpp (e.g., Adapter) comprises a D domain that binds to CD123 comprises the amino acid sequence of SEQ ID NO: 14.

In some embodiments, the DDpp (e.g., Adapter) is administered at the same frequency over the period of treatment. In some embodiments, the frequency of administration decreases over the period of treatment. In some embodiments, the DDpp (e.g., Adapter) is first administered daily for about a week followed by administration twice a week. In some embodiments, the DDpp (e.g., Adapter) is first administered between one and three times a day for about a week followed by daily administration. In some embodiments, the DDpp (e.g., Adapter) is first administered between one and three times a day for about a week followed by twice weekly or weekly administration. In some embodiments, the DDpp (e.g., Adapter) is administered as a continuous infusion. In some embodiments, the DDpp (e.g., Adapter) is first administered as a continuous infusion for about a week followed by daily administration. In some embodiments, the DDpp (e.g., Adapter) is first administered as a continuous infusion for about a week followed by twice weekly or weekly administration. In some embodiments, the DDpp (e.g., Adapter) is administered intravenously. In some embodiments, the DDpp (e.g., Adapter) is administered subcutaneously. In some embodiments, the DDpp (e.g., Adapter) comprises a D domain that binds to CD123 comprises an amino acid sequence selected from the group consisting of SEQ ID NO: 8-33, 99 and 100. In some embodiments, the DDpp (e.g., Adapter) comprises a D domain that binds to CD123 comprises an amino acid sequence selected from the group consisting of SEQ ID NO: 8, 13, 14, 31, 32, and 33. In some embodiments, the DDpp (e.g., Adapter) comprises a D domain that binds to CD123 comprises the amino acid sequence of SEQ ID NO: 14.

In some embodiments, between about $10 \times 10^6$ and about $300 \times 10^6$ cells expressing a CAR that specifically binds to a AFP p26 antigenic determinant has been administered to the subject receiving the DDpp (e.g., Adapter). In some embodiments, between about $50 \times 10^6$ and about $900 \times 10^6$ cells expressing a CAR that specifically binds to a AFP p26 antigenic determinant has been administered to the subject receiving the DDpp (e.g., Adapter). In some embodiments, between about $10 \times 10^6$ and about $500 \times 10^6$ cells expressing a CAR that specifically binds to a AFP p26 antigenic determinant has been administered to the subject receiving the DDpp (e.g., Adapter). In some embodiments, about $100 \times 10^6$ cells expressing a CAR that specifically binds to a AFP p26 antigenic determinant has been administered to the subject receiving the DDpp (e.g., Adapter). In some embodiments, about $50 \times 10^6$ cells expressing a CAR that specifically binds to a AFP p26 antigenic determinant has been administered to the subject receiving the DDpp (e.g., Adapter). In some embodiments, about $100 \times 10^6$ cells expressing a CAR that specifically binds to a AFP p26 antigenic determinant has been administered to the subject receiving the DDpp (e.g., Adapter). In some embodiments, about $150 \times 10^6$ cells expressing a CAR that specifically binds to a AFP p26 antigenic determinant has been administered to the subject receiving the DDpp (e.g., Adapter). In some embodiments, about $200 \times 10^6$ cells expressing a CAR that specifically binds to a AFP p26 antigenic determinant has been administered to the subject receiving the DDpp (e.g., Adapter). In some embodiments, about 250×10⁶ cells expressing a CAR that specifically binds to a AFP p26 antigenic determinant has been administered to the subject receiving the DDpp (e.g., Adapter). In some embodiments, about 300×10⁶ cells expressing a CAR that specifically binds to a AFP p26 antigenic determinant has been administered to the subject receiving the DDpp (e.g., Adapter). In some embodiments, about 400×10⁶ cells expressing a CAR that specifically binds to a AFP p26 antigenic determinant has been administered to the subject receiving the DDpp (e.g., Adapter). In some embodiments, about 500×10⁶ cells expressing a CAR that specifically binds to a AFP p26 antigenic determinant has been administered to the subject receiving the DDpp (e.g., Adapter). In some embodiments, about 600×10⁶ cells expressing a CAR that specifically binds to a AFP p26 antigenic determinant has been administered to the subject receiving the DDpp (e.g., Adapter). In some embodiments, about 700×10⁶ cells expressing a CAR that specifically binds to a AFP p26 antigenic determinant has been administered to the subject receiving the DDpp (e.g., Adapter). In some embodiments, more than one dose of cells expressing a CAR that specifically binds to a AFP p26 antigenic determinant has been administered to the subject receiving the DDpp (e.g., Adapter). In some embodiments, the CAR that specifically binds to a AFP p26 antigenic determinant has been administered to the subject at the same time as the first dose of the DDpp (e.g., Adapter). In some embodiments, the CAR that specifically binds to a AFP p26 antigenic determinant has been administered to the subject before the first dose of the DDpp (e.g., Adapter). In some embodiments, the AFP p26 antigenic determinant comprises the amino acid sequence of SEQ ID NO: 37-43 or 44. In some embodiments, the AFP p26 antigenic determinant comprises the amino acid sequence of SEQ ID NO: 37. In some embodiments, the AFP p26 antigenic determinant comprises the amino acid sequence of SEQ ID NO: 39. In some embodiments, the CAR that specifically binds to AFP p26 antigenic determinant comprises a D domain that specifically binds to AFP p26 antigenic determinant, optionally wherein the D domain comprises the amino acid sequence of SEQ ID NO: 70-73 or 92-94. In some embodiments, the D domain that specifically binds to AFP p26 antigenic determinant comprises the amino acid sequence of SEQ ID NO: 70 or 73. In some embodiments, the CAR that specifically binds to AFP p26 antigenic determinant comprises the amino acid sequence of SEQ ID NO: 68 or 69. In some embodiments, the cell expressing the CAR is an immune cell. In some embodiments, the cell expressing the CAR is an immune effector cell. In some embodiments, the cell expressing the CAR is a T cell (CAR-T cell) or a natural killer (NK) cell (CAR-NK cell). In some embodiments, the cell expressing the CAR is not a T cell or an NK cell. In some embodiments, the CAR immune cell is an autologous immune cell. In some embodiments, the CAR immune cell is an allogenic immune cell. The cells expressing a CAR provided herein can be administered either alone, or as a pharmaceutical composition in combination with diluents and/or with other components such as chemotherapeutics, antibodies, cytokines or cell populations. Compositions provided herein are preferably formulated for intravenous administration that can be administered one or more times. In some embodiments, the cells expressing the CAR are administered intravenously.

In another embodiment, the DDpp (e.g., Adapter) is administered in combination with one or more additional therapeutics.

A therapeutically effective amount of the DDpp (e.g., a DDpp fusion protein, such as an Adapter) can be an amount such that when administered in a physiologically tolerable composition is sufficient to achieve a plasma concentration of from about 0.1 microgram (μg) per milliliter (ml) to about 100 μg/ml, preferably from about 1 μg/ml to about 5 μg/ml, and usually about 5 μg/ml. Stated differently, the dosage can vary from about 0.1 mg/kg to about 300 mg/kg, preferably from about 0.2 mg/kg to about 200 mg/kg, most preferably from about 0.5 mg/kg to about 20 mg/kg, in one or more dose administrations daily, for one or several days. In some embodiments, the DDpp (e.g., Adapter) comprises a D domain that binds to CD123 comprises an amino acid sequence selected from the group consisting of SEQ ID NO: 8-33, 99 and 100. In some embodiments, the DDpp (e.g., Adapter) comprises a D domain that binds to CD123 comprises an amino acid sequence selected from the group consisting of SEQ ID NO: 8, 13, 14, 31, 32, and 33. In some embodiments, the DDpp (e.g., Adapter) comprises a D domain that binds to CD123 comprises the amino acid sequence of SEQ ID NO: 14.

Uses

The target binding DDpps, DDpp fusion proteins, polynucleotides and cells disclosed herein have uses that include diagnostic and therapeutic applications. In some embodiments, the DDpps, polynucleotides and cells are useful in a therapeutic context, e.g., for treatment and/or diagnosis of a disease or disorder. The therapeutic treatment methods can be in vitro, ex vivo, or in vivo methods. In some embodiments, the disease or disorder is cancer (e.g., a hematologic malignancy). In some embodiments, the disease or disorder is a disease or disorder of the immune system, such as inflammation or an autoimmune disease.

The application as a therapeutic entity is an attribute of the target binding specificity of the DDpp. The incorporation of DDpp within various molecular compositions, (e.g., a DD-antibody fusions, DD-drug conjugates and DD-chimeric receptors) affords application in a variety of therapeutic indications and modalities, which include, but not limited to soluble and cell-associated compositions.

In one embodiment, the DDpp is a soluble fusion protein made up of an optional epitope tag and a targeting domain that binds to a target that is associated with a disease or disorder of the immune system.

In some embodiments, the DDpp described herein are useful for treating cancer. Thus, in some embodiments, the disclosure provides a method of treating cancer that comprises administering a therapeutically effective amount of a DDpp (e.g. a DDpp fusion) to a patient.

In additional embodiments, the disclosure provides a chimeric antigen receptor (CAR), wherein the CAR includes a targeting domain, a transmembrane domain, and an intracellular signaling domain. In some embodiments, the targeting domain is made up of, at least in part, a target-binding DDpp disclosed herein.

The methods summarized above and/or set forth herein describe certain actions taken by a practitioner; however, it should be understood that they can also include the instruction of those actions by another party. Thus, actions such as "administering a T cell comprising a target specific binding polypeptide-CAR" include "instructing the administration of a T cell comprising a target specific binding polypeptide-CAR."

A. Methods Comprising Contacting a Target Cell with a CAR Cell.

In some embodiments, a method of delivering an immune response to one or more target cells comprises contacting a composition comprising the target cell with a cell expressing a chimeric antigen receptor (CAR) comprising (i) a D domain that binds to CD123, (ii) a transmembrane domain, and (iii) an intracellular domain. In some embodiments, the target cell expresses CD123.

In some embodiments, a method of killing a target cell comprises contacting a composition comprising the target cell with a cell expressing a chimeric antigen receptor (CAR) comprising (i) a D domain that binds to CD123, (ii) a transmembrane domain, and (iii) an intracellular domain. In some embodiments, the target cell expresses CD123.

In some embodiments, the D domain that binds to CD123 comprises an amino acid sequence selected from the group consisting of SEQ ID NO: 8-33, 99 and 100. In some embodiments, the D domain that binds to CD123 comprises an amino acid sequence selected from the group consisting of SEQ ID NO: 8, 13, 14, 31, 32, and 33. In some embodiments, the D domain that binds to CD123 comprises the amino acid sequence of SEQ ID NO: 8. In some embodiments, the D domain that binds to CD123 comprises the amino acid sequence of SEQ ID NO: 13. In some embodiments, the D domain that binds to CD123 comprises the amino acid sequence of SEQ ID NO: 14. In some embodiments, the D domain that binds to CD123 comprises the amino acid sequence of SEQ ID NO: 31. In some embodiments, the D domain that binds to CD123 comprises the amino acid sequence of SEQ ID NO: 32. In some embodiments, the D domain that binds to CD123 comprises the amino acid sequence of SEQ ID NO: 33.

In some embodiments, the transmembrane domain comprises a CD8a, 41BB or CD28 transmembrane domain. In some embodiments, the transmembrane domain comprises a CD8a transmembrane domain. In some embodiments, the CD8a transmembrane domain comprises the amino acid sequence of SEQ ID NO: 113. In some embodiments, the CD8a transmembrane domain comprises the amino acid sequence of SEQ ID NO: 114. In some embodiments, the intracellular signaling domain is selected from the group consisting of a domain of a human T cell receptor alpha, beta, or zeta chain; a human 41BB domain; a human CD28 domain; and any combination thereof. In some embodiments, the intracellular signaling domain comprises the intracellular domain of a costimulatory molecule selected from the group consisting of CD27, CD28, 41BB, OX40, CD30, CD40, PD1, lymphocyte function-associated antigen-1 (LFA-1), CD2, CD7, DAP12, LIGHT, NKG2C, NKG2D, B7-H3, a ligand that specifically binds with CD83, and any combination thereof. In some embodiments, the intracellular signaling domain contains the sequence of SEQ ID NO: 115, 116 or combination thereof. In some embodiments, the intracellular signaling domain contains the sequence of SEQ ID NO: 117.

In some embodiments, the CAR comprising a D domain that binds to CD123 comprises the amino acid sequence of SEQ ID NO: 62-66 or 67. In some embodiments, the CAR comprising a D domain that binds to CD123 comprises the amino acid sequence of SEQ ID NO: 62. In some embodiments, the CAR comprising a D domain that binds to CD123 comprises the amino acid sequence of SEQ ID NO: 63. In some embodiments, the CAR comprising a D domain that binds to CD123 comprises the amino acid sequence of SEQ ID NO: 64. In some embodiments, the CAR comprising a D domain that binds to CD123 comprises the amino acid sequence of SEQ ID NO: 65. In some embodiments, the CAR comprising a D domain that binds to CD123 comprises the amino acid sequence of SEQ ID NO: 66. In some embodiments, the CAR comprising a D domain that binds to CD123 comprises the amino acid sequence of SEQ ID NO: 67.

In some embodiments, the cell expressing the CAR is an immune cell. In some embodiments, the cell expressing the CAR is an immune effector cell. In some embodiments, the cell expressing the CAR is a T cell (CAR-T cell) or a natural killer (NK) cell (CAR-NK cell). In some embodiments, the cell expressing the CAR is not a T cell or an NK cell. In some embodiments, the CAR immune cell is an autologous immune cell. In some embodiments, the CAR immune cell is an allogenic immune cell.

In some embodiments, the target cell is a cancer cell, e.g., an acute myeloid leukemia (AML) cell. In some embodiments, the target cell is a myelodysplasia cell.

In some embodiments, the target cell is a tumor cell. In further embodiments, the tumor cell is selected from the group of acute myeloid leukemia (AML) cell, B-cell acute lymphoblastic leukemia cell, hairy cell leukemia cell, Hodgkin's lymphoma cell, myelodysplasia cell and blastic plasmacytoid dendritic neoplasm (BPDCN) cell. In some embodiments, the tumor cell is an AML tumor cell. In some embodiments, the tumor cell is a myelodysplasia cell. In some embodiments, the tumor cell is a B-cell acute lymphoblastic leukemia tumor cell. In some embodiments, the tumor cell is a hairy cell leukemia tumor cell. In some embodiments, the tumor cell is a Hodgkin's lymphoma tumor cell. In some embodiments, the tumor cell is a BPDCN tumor cell. In some embodiments, the tumor cell expresses CD123.

In the methods of killing a target cell provided herein, the target cell can be a cell of the immune system. In some embodiments, the target cell is a B cell. In some embodiments, the target cell is a T cell. In some embodiments, the target cell is a naïve T cell. In some embodiments, the target cell is a memory T cell.

The contacting can occur in vitro, ex vivo, or in vivo. In one embodiment, the contacting occurs in a patient, e.g. a human patient.

The contacting can occur in vitro, ex vivo, or in vivo. In some embodiments, the method comprises administering the CAR cell to a patient.

B. Methods Comprising Contacting a Target Cell with an Adapter and/or a CAR Cell.

In some embodiments, a method of delivering an immune response to a target cell comprises contacting a composition comprising the target cell with an Adapter, wherein (a) the composition comprising the target cell further comprises a cell expressing a CAR, wherein the CAR comprises (i) an antigenic determinant binding domain (ADBD) that binds to an AFP p26 antigenic determinant (AD), (ii) a transmembrane domain, and (iii) an intracellular domain; and (b) the Adapter comprises (i) a D domain that binds to CD123 and (ii) AFP p26 AD. In some embodiments, the target cell expresses CD123.

In some embodiments, a method of delivering an immune response to a target cell comprises contacting a composition comprising the target cell with an Adapter, wherein (a) the composition comprising the target cell further comprises a cell expressing a CAR, wherein the CAR comprises (i) AFP p26 antigenic determinant (AD), (ii) a transmembrane domain, and (iii) an intracellular domain; and (b) the Adapter comprises (i) a D domain that binds to CD123 and (ii) an antigenic determinant binding domain (ADBD) that binds to the AFP p26 antigenic determinant (AD). In some embodiments, the target cell expresses CD123.

In some embodiments, a method of delivering an immune response to a target cell comprises contacting a composition comprising the target cell with an Adapter, wherein (a) the composition comprising the target cell further comprises a cell expressing a CAR, wherein the CAR comprises (i) an antigenic determinant binding domain (ADBD) that binds to an antigenic determinant (AD) other than CD123, (ii) a transmembrane domain, and (iii) an intracellular domain; and (b) the Adapter comprises (i) a D domain that binds to CD123 and (ii) an the AD bound by the CAR. In some embodiments, the target cell expresses CD123.

In some embodiments, a method of delivering an immune response to a target cell comprises contacting a composition comprising the target cell with an Adapter, wherein (a) the composition comprising the target cell further comprises a cell expressing a CAR, wherein the CAR comprises (i) AFP p26 antigenic determinant (AD), (ii) a transmembrane domain, and (iii) an intracellular domain; and (b) the Adapter comprises (i) a first antigenic determinant binding domain (ADBD) that binds to a target AD and (ii) an second antigenic determinant binding domain (ADBD) that binds to the AFP p26 antigenic determinant (AD). In some embodiments, the target cell expresses the target AD.

In some embodiments, a method of delivering an immune response to a target cell comprises contacting a composition comprising the target cell with a cell expressing a CAR, wherein (a) the CAR comprises (i) an antigenic determinant binding domain (ADBD) that binds to an AFP p26 antigenic determinant (AD), (ii) a transmembrane domain, and (iii) an intracellular domain; and (b) the composition comprising the target cell further comprises an Adapter comprising (i) a D domain that binds to CD123 and (ii) an AFP p26 AD. In some embodiments, the target cell expresses CD123.

In some embodiments, a method of delivering an immune response to a target cell comprises contacting a composition comprising the target cell with a cell expressing a CAR, wherein (a) the CAR comprises (i) an AFP p26 antigenic determinant (AD), (ii) a transmembrane domain, and (iii) an intracellular domain; and (b) the composition comprising the target cell further comprises an Adapter comprising (i) a D domain that binds to CD123 and (ii) an antigenic determinant binding domain (ADBD) that binds to the AFP p26 antigenic determinant (AD). In some embodiments, the target cell expresses CD123.

In some embodiments, a method of delivering an immune response to a target cell comprises contacting a composition comprising the target cell with a cell expressing a CAR, wherein (a) the CAR comprises (i) an antigenic determinant binding domain (ADBD) that binds to an antigenic determinant (AD) other than CD123, (ii) a transmembrane domain, and (iii) an intracellular domain; and (b) the composition comprising the target cell further comprises an Adapter comprising (i) a D domain that binds to CD123 and (ii) the AD bound by the CAR. In some embodiments, the target cell expresses CD123.

In some embodiments, a method of delivering an immune response to a target cell comprises contacting a composition comprising the target cell with a cell expressing a CAR, wherein (a) the CAR comprises (i) an AFP p26 antigenic determinant (AD), (ii) a transmembrane domain, and (iii) an intracellular domain; and (b) the composition comprising the target cell further comprises an Adapter comprising (i) a first antigenic determinant binding domain (ADBD) that binds to a target AD and (ii) a second antigenic determinant binding domain (ADBD) that binds to the AFP p26 antigenic determinant (AD). In some embodiments, the target cell expresses the target AD.

In some embodiments, a method of killing a target cell comprises contacting a composition comprising the target cell with an Adapter, wherein (a) the composition comprising the target cell further comprises a cell expressing a CAR, wherein the CAR comprises (i) an antigenic determinant binding domain (ADBD) that binds to an AFP p26 antigenic determinant (AD), (ii) a transmembrane domain, and (iii) an intracellular domain; and (b) the Adapter comprises (i) a D domain that binds to CD123 and (ii) an AFP p26 AD. In some embodiments, the target cell expresses CD123.

In some embodiments, a method of killing a target cell comprises contacting a composition comprising the target cell with an Adapter, wherein (a) the composition comprising the target cell further comprises a cell expressing a CAR, wherein the CAR comprises (i) an AFP p26 antigenic determinant (AD), (ii) a transmembrane domain, and (iii) an intracellular domain; and (b) the Adapter comprises (i) a D domain that binds to CD123 and (ii) an antigenic determinant binding domain (ADBD) that binds to the AFP p26 antigenic determinant (AD). In some embodiments, the target cell expresses CD123.

In some embodiments, a method of killing a target cell comprises contacting a composition comprising the target cell with an Adapter, wherein (a) the composition comprising the target cell further comprises a cell expressing a CAR, wherein the CAR comprises (i) an antigenic determinant binding domain (ADBD) that binds to an antigenic determinant (AD) other than CD123, (ii) a transmembrane domain, and (iii) an intracellular domain; and (b) the Adapter comprises (i) a D domain that binds to CD123 and (ii) an the AD bound by the CAR. In some embodiments, the target cell expresses CD123.

In some embodiments, a method of killing a target cell comprises contacting a composition comprising the target cell with an Adapter, wherein (a) the composition comprising the target cell further comprises a cell expressing a CAR, wherein the CAR comprises (i) an AFP p26 antigenic determinant (AD), (ii) a transmembrane domain, and (iii) an intracellular domain; and (b) the Adapter comprises (i) a first antigenic determinant binding domain (ADBD) that binds to a target AD and (ii) an second antigenic determinant binding domain (ADBD) that binds to the AFP p26 antigenic determinant (AD). In some embodiments, the target cell expresses the target AD.

In some embodiments, a method of killing a target cell comprises contacting a composition comprising the target cell with a cell expressing a CAR, wherein (a) the CAR comprises (i) an antigenic determinant binding domain (ADBD) that binds to an AFP p26 antigenic determinant (AD), (ii) a transmembrane domain, and (iii) an intracellular domain; and (b) the composition comprising the target cell further comprises an Adapter comprising (i) a D domain that binds to CD123 and (ii) an AFP p26 AD. In some embodiments, the target cell expresses CD123.

In some embodiments, a method of killing a target cell comprises contacting a composition comprising the target cell with a cell expressing a CAR, wherein (a) the CAR comprises (i) an AFP p26 antigenic determinant (AD), (ii) a transmembrane domain, and (iii) an intracellular domain; and (b) the composition comprising the target cell further comprises an Adapter comprising (i) a D domain that binds to CD123 and (ii) an antigenic determinant binding domain (ADBD) that binds to the AFP p26 antigenic determinant (AD). In some embodiments, the target cell expresses CD123.

In some embodiments, a method of killing a target cell comprises contacting a composition comprising the target cell with a cell expressing a CAR, wherein (a) the CAR comprises (i) an antigenic determinant binding domain (ADBD) that binds to an antigenic determinant (AD) other than CD123, (ii) a transmembrane domain, and (iii) an intracellular domain; and (b) the composition comprising the target cell further comprises an Adapter comprising (i) a D domain that binds to CD123 and (ii) the AD bound by the CAR. In some embodiments, the target cell expresses CD123.

In some embodiments, a method of killing a target cell comprises contacting a composition comprising the target cell with a cell expressing a CAR, wherein (a) the CAR comprises (i) an AFP p26 antigenic determinant (AD), (ii) a transmembrane domain, and (iii) an intracellular domain; and (b) the composition comprising the target cell further comprises an Adapter comprising (i) a first antigenic determinant binding domain (ADBD) that binds to a target AD and (ii) a second antigenic determinant binding domain (ADBD) that binds to the AFP p26 antigenic determinant (AD). In some embodiments, the target cell expresses the target AD.

In some embodiments, the D domain that binds to CD123 comprises an amino acid sequence selected from the group consisting of SEQ ID NO: 8-33, 99 and 100. In some embodiments, the D domain that binds to CD123 comprises an amino acid sequence selected from the group consisting of SEQ ID NO: 8, 13, 14, 31, 32, and 33. In some embodiments, the D domain that binds to CD123 comprises the amino acid sequence of SEQ ID NO: 8. In some embodiments, the D domain that binds to CD123 comprises the amino acid sequence of SEQ ID NO: 13. In some embodiments, the D domain that binds to CD123 comprises the amino acid sequence of SEQ ID NO: 14. In some embodiments, the D domain that binds to CD123 comprises the amino acid sequence of SEQ ID NO: 31. In some embodiments, the D domain that binds to CD123 comprises the amino acid sequence of SEQ ID NO: 32. In some embodiments, the D domain that binds to CD123 comprises the amino acid sequence of SEQ ID NO: 33.

In some embodiments, the AFP p26 AD comprises an amino acid sequence selected from the group consisting of SEQ ID NO: 37-43 and 44. In some embodiments, the AFP p26 AD comprises the amino acid sequence of SEQ ID NO: 37. In some embodiments, the AFP p26 AD comprises the amino acid sequence of SEQ ID NO: 39.

In some embodiments, the ADBD that binds to AFP p26 AD comprises an scFv that binds to AFP p26 AD. In some embodiments, the ADBD that binds to AFP p26 AD comprises a D domain that binds to AFP p26 AD.

In some embodiments, the D domain that binds to AFP p26 AD comprises an amino acid sequence selected from the group consisting of SEQ ID NO: 74-93 and 94. In some embodiments, the D domain that binds to AFP p26 AD comprises the amino acid sequence of SEQ ID NO: 70-73 or 92-94. In some embodiments, the D domain that binds to AFP p26 AD comprises the amino acid sequence of SEQ ID NO: 73.

In some embodiments, the CAR comprising a D domain that binds to AFP p26 AD comprises the amino acid sequence of SEQ ID NO: 68. In some embodiments, the CAR comprising a D domain that binds to AFP p26 AD comprises the amino acid sequence of SEQ ID NO: 69.

In some embodiments, the Adapter comprising (i) a D domain that binds to CD123 and (ii) an AFP p26 AD comprises the amino acid sequence of SEQ ID NO: 50-54 or 55. In some embodiments, the Adapter comprising (i) a D domain that binds to CD123 and (ii) an AFP p26 AD comprises the amino acid sequence of SEQ ID NO: 50. In some embodiments, the Adapter comprising (i) a D domain that binds to CD123 and (ii) an AFP p26 AD comprises the amino acid sequence of SEQ ID NO: 51. In some embodiments, the Adapter comprising (i) a D domain that binds to CD123 and (ii) an AFP p26 AD comprises the amino acid sequence of SEQ ID NO: 52. In some embodiments, the Adapter comprising (i) a D domain that binds to CD123 and (ii) an AFP p26 AD comprises the amino acid sequence of SEQ ID NO: 53. In some embodiments, the Adapter comprising (i) a D domain that binds to CD123 and (ii) an AFP p26 AD comprises the amino acid sequence of SEQ ID NO: 54. In some embodiments, the Adapter comprising (i) a D domain that binds to CD123 and (ii) an AFP p26 AD comprises the amino acid sequence of SEQ ID NO: 55. In some embodiments, the Adapter comprising (i) a D domain that binds to CD123 and (ii) an AFP p26 AD comprises the amino acid sequence of SEQ ID NO: 56-60 or 61. In some embodiments, the Adapter comprising (i) a D domain that binds to CD123 and (ii) an AFP p26 AD comprises the amino acid sequence of SEQ ID NO: 56. In some embodiments, the Adapter comprising (i) a D domain that binds to CD123 and (ii) an AFP p26 AD comprises the amino acid sequence of SEQ ID NO: 57. In some embodiments, the Adapter comprising (i) a D domain that binds to CD123 and (ii) an AFP p26 AD comprises the amino acid sequence of SEQ ID NO: 58. In some embodiments, the Adapter comprising (i) a D domain that binds to CD123 and (ii) an AFP p26 AD comprises the amino acid sequence of SEQ ID NO: 59. In some embodiments, the Adapter comprising (i) a D domain that binds to CD123 and (ii) an AFP p26 AD comprises the amino acid sequence of SEQ ID NO: 60. In some embodiments, the Adapter comprising (i) a D domain that binds to CD123 and (ii) an AFP p26 AD comprises the amino acid sequence of SEQ ID NO: 61.

In some embodiments, the Adapter comprises (i) a D domain that binds to CD123 and comprises the amino acid sequence of SEQ ID NO: 8, 13, 14, 31, 32, or 33, and (ii) an AFP p26 AD comprising the amino acid sequence of SEQ ID NO: 37 or 39, and the CAR comprises a D domain that binds to AFP p26 AD and comprises the amino acid sequence of SEQ ID NO: 73. In some embodiments, the D domain that binds to CD123 comprises the amino acid sequence of SEQ ID NO: 8. In some embodiments, the D domain that binds to CD123 comprises the amino acid sequence of SEQ ID NO: 13. In some embodiments, the D domain that binds to CD123 comprises the amino acid sequence of SEQ ID NO: 14. In some embodiments, the D domain that binds to CD123 comprises the amino acid sequence of SEQ ID NO: 31. In some embodiments, the D domain that binds to CD123 comprises the amino acid sequence of SEQ ID NO: 32. In some embodiments, the D domain that binds to CD123 comprises the amino acid sequence of SEQ ID NO: 33.

In some embodiments, the Adapter comprising (i) a D domain that binds to CD123 and (ii) an AFP p26 AD comprises the amino acid sequence of SEQ ID NO: 50-54 or 55, and the CAR comprising a D domain that binds to AFP p26 AD comprises the amino acid sequence of SEQ ID NO: 68. In some embodiments, the Adapter comprising (i) a D domain that binds to CD123 and (ii) an AFP p26 AD comprises the amino acid sequence of SEQ ID NO: 50, and the CAR comprising a D domain that binds to AFP p26 AD comprises the amino acid sequence of SEQ ID NO: 68. In some embodiments, the Adapter comprising (i) a D domain that binds to CD123 and (ii) an AFP p26 AD comprises the amino acid sequence of SEQ ID NO: 56-60 or 61, and the CAR comprising a D domain that binds to AFP p26 AD comprises the amino acid sequence of SEQ ID NO: 68. In some embodiments, the Adapter comprising (i) a D domain that binds to CD123 and (ii) an AFP p26 AD comprises the amino acid sequence of SEQ ID NO: 61, and the CAR comprising a D domain that binds to AFP p26 AD comprises the amino acid sequence of SEQ ID NO: 68.

In some embodiments, the target AD is selected from: CD45, CD26, CD30, CD33, LeY and CD38. In some embodiments, the target AD is selected from: CD19, CD22, CD123, BCMA, CS1, HER2, TACI, BAFFR, and PDL1. In further embodiments, the target AD is BCMA. In further embodiments, the target AD is CD45. In other embodiments, the target AD is CS1. In other embodiments, the target AD is CD123. In other embodiments, the target AD is CD19. In other embodiments, the target AD is CD22. In other embodiments, the target AD is TACI. In other embodiments, the target AD is BAFFR. In other embodiments, the target AD is PDL1. In other embodiments, the target AD is HER2.

In some embodiments, wherein the CAR comprises an ADBD that binds to an AD other than CD123, the ADBD binds to a tumor antigen. In further embodiments, the tumor antigen is selected from the group: CD45, CD26, CD30, CD33, and CD38. In further embodiments, the tumor antigen is selected from the group: BCMA, CD19, CD22, CS1, HER2, TACI, BAFFR, and PDL1. In further embodiments, the tumor antigen is BCMA. In further embodiments, the tumor antigen is CD19.

In some embodiments, the cell expressing the CAR is an immune cell. In some embodiments, the cell expressing the CAR is an immune effector cell. In some embodiments, the cell expressing the CAR is a T cell (CAR-T cell) or a natural killer (NK) cell (CAR-NK cell). In some embodiments, the cell expressing the CAR is not a T cell or an NK cell. In some embodiments, the CAR immune cell is an autologous immune cell. In some embodiments, the CAR immune cell is an allogenic immune cell.

In some embodiments, the target cell is a cancer cell, e.g., an acute myeloid leukemia (AML) cell. In some embodiments, the target cell is an AML cell. In some embodiments, the target cell is a myelodysplasia cell. In some embodiments, the target cell is a B-cell acute lymphoblastic leukemia cell. In some embodiments, the target cell is a hairy cell leukemia cell. In some embodiments, the target cell is a Hodgkin's lymphoma cell. In some embodiments, the target cell is a blastic plasmacytoid dendritic neoplasm (BPDCN) cell. In some embodiments, the target cell expresses CD123.

The contacting can occur in vitro, ex vivo, or in vivo. In one embodiment, the contacting occurs in a patient, e.g. a human patient, for example after administration of an Adapter to a patient who has received a cell expressing a CAR or after administration of a cell expressing a CAR to a patient who has received an Adapter. In some embodiments, a method comprises administering the Adapter to a patient who has previously been administered the cell expressing the CAR.

In certain embodiments, the CAR comprises a single-chain variable fragment (scFv) ADBD. In other embodiments, the CAR comprises an alternative scaffold binding domain (ASBD) ADBD. In further embodiments, the CAR comprises a D domain.

In some embodiments, the CAR comprises 2 ADBDs. In other embodiments, the CAR comprises an ASBD and a scFv. In further embodiments, the CAR comprises a D domain and a scFv. In some embodiments, the CAR comprises 2 ASBDs. In further embodiments, the CAR comprises 2 D domains.

In some embodiments, the CAR intracellular domain is a signaling domain. In further embodiments, the CAR intracellular domain comprises a primary signaling domain. In certain embodiments, the CAR intracellular domain comprises a CD3 primary signaling domain. In some embodiments, the CAR intracellular domain further comprises a costimulatory signaling domain. In further embodiments, the costimulatory signaling domain is selected from: CD28, 41BB, CD27, and CD134. In particular embodiments, the CAR intracellular signaling domain comprises a 41BB costimulatory signaling domain. In some embodiments, the intracellular signaling domain contains the sequence of SEQ ID NO: 115, 116 or combination thereof. In some embodiments, the intracellular signaling domain contains the sequence of SEQ ID NO: 117.

In some embodiments, the target AD is selected from: CD45, CD26, CD30, CD33, and CD38. In some embodiments, the target AD is selected from: CD19, CD22, CD123, BCMA, CS1, HER2, TACI, BAFFR, and PDL1. In further embodiments, the target AD is BCMA. In other embodiments, the target AD is CS1. In other embodiments, the target AD is CD123. In other embodiments, the target AD is CD19. In other embodiments, the target AD is CD22. In other embodiments, the target AD is TACI. In other embodiments, the target AD is BAFFR. In other embodiments, the target AD is PDL1. In other embodiments, the target AD is HER2.

In some embodiments, the CAR comprises 2 ADBDs that bind to separate targets. In further embodiments, the CAR binds to CD19 and CD123. In other embodiments, the CAR binds to BCMA and CD123. In other embodiments, the CAR binds to CD22 and CD123. In other embodiments, the CAR binds to PDL1 and CD123. In further embodiments, the CAR binds to CD33 and CD123. In further embodiments, the CAR binds to CD38 and CD123. In further embodiments, the CAR binds to LeY and CD123.

In some embodiments, the Adapter comprises an AD of a tumor antigen. In further embodiments, the tumor antigen is selected from the group: CD45, CD26, CD30, CD33, and CD38.

In some embodiments, the Adapter comprises an AD of a tumor antigen. In further embodiments, the tumor antigen is selected from the group: BCMA, CD19, CD22, CS1, HER2, TACI, BAFFR, and PDL1.

In some embodiments, the Adapter comprises an ADBD that is a scFv. In further embodiments, the Adapter comprises an ADBD that is an ASBD. In some embodiments, the Adapter comprises a D domain.

In some embodiments, the Adapter comprises two ADBDs. In further embodiments, the Adapter comprises two ADBDs that (a) are the same, (b) bind to the same antigenic determinant, (c) bind to different ADs of the same antigen, (d) bind to different antigens on the same cell, or (e) bind to different antigens on different cells. In some embodiments, the Adapter comprises two ASBDs. In certain embodiments, the Adapter comprises two D domains. In some embodiments, the Adapter comprises an ADBD that is a scFv and an ADBD that is an ASBD. In other embodiments, the Adapter comprises an ADBD that is a scFv and an ADBD that is a D domain.

In some embodiments, the Adapter comprises an ADBD that binds to a member selected from: CD45, CD26, CD30, CD33, and CD38. In certain embodiments, the Adapter comprises an ADBD binds to CD45. In other embodiments, the Adapter comprises an ADBD that binds to CD26. In some embodiments, the Adapter comprises an ADBD that binds to CD30. In other embodiments, the Adapter comprises an ADBD that binds to CD33. In other embodiments, the Adapter comprises an ADBD that binds to CD38. In some embodiments, the Adapter comprises an ADBD that binds to CD45.

In some embodiments, the Adapter comprises an ADBD that binds to a member selected from: BCMA, CD123, CD19, CD22, CS1, HER2, TACI, BAFFR, and PDL1. In certain embodiments, the Adapter comprises an ADBD binds to BCMA. In other embodiments, the Adapter comprises an ADBD that binds to CD123. In some embodiments, the Adapter comprises an ADBD that binds to CD19. In other embodiments, the Adapter comprises an ADBD that binds to CD22. In other embodiments, the Adapter comprises an ADBD that binds to CS1. In other embodiments, the Adapter comprises an ADBD that binds to HER2. In other embodiments, the Adapter comprises an ADBD that binds to TACI. In other embodiments, the Adapter comprises an ADBD that binds to BAFFR. In other embodiments, the Adapter comprises an ADBD that binds to PDL1.

In some embodiments, the Adapter is bispecific. In further embodiments, the Adapter comprises an ADBD that binds to CD123 and an ADBD that binds to CD33. In other embodiments, the Adapter comprises an ADBD that binds to CD123 and an ADBD that binds to CD38. In other embodiments, the Adapter comprises an ADBD that binds to CD123 and an ADBD that binds to LeY. In other embodiments, the Adapter comprises an ADBD that binds to PDL1 and an ADBD that binds to CD123.

In some embodiments, the target cell is a tumor cell. In further embodiments, the tumor cell is selected from the group of acute myeloid leukemia (AML) cell, B-cell acute lymphoblastic leukemia cell, hairy cell leukemia cell, Hodgkin's lymphoma cell, myelodysplasia cell and blastic plasmacytoid dendritic neoplasm (BPDCN) cell. In some embodiments, the tumor cell is an AML tumor cell. In some embodiments, the tumor cell is a myelodysplasia cell. In some embodiments, the tumor cell is a B-cell acute lymphoblastic leukemia tumor cell. In some embodiments, the tumor cell is a hairy cell leukemia tumor cell. In some embodiments, the tumor cell is a Hodgkin's lymphoma tumor cell. In some embodiments, the tumor cell is a BPDCN tumor cell. In some embodiments, the tumor cell expresses CD123.

In the methods of killing a target cell provided herein, the target cell can be a cell of the immune system. In some embodiments, the target cell is a B cell. In some embodiments, the target cell is a T cell. In some embodiments, the target cell is a naïve T cell. In some embodiments, the target cell is a memory T cell.

In some embodiments, the cell expressing the CAR is an immune effector cell. An immune effector cell is a cell that is involved in an immune response, e.g., in the promotion of an immune effector response. Examples of immune effector cells include T cells (e.g., alpha/beta T cells and gamma/delta T cells), B cells, natural killer (NK) cells, natural killer T (NKT) cells, mast cells, and myeloid-derived phagocytes. An immune effector function or immune effector response is a function or response of for example, an immune effector cell that enhances or promotes an immune attack of a target cell. In some embodiments, the immune effector function or response refers a property of a T or NK cell that promotes killing, or the inhibition of growth or proliferation, of a target cell. For example, primary stimulation and costimulation are examples of immune effector function or response of a T cell. In particular embodiments, an immune effector function or response is promoted by the action of the disclosed CAR, Adapter, and/or CAR and Adapter compositions. Such function or response results in, for example, a CAR cell that is more effective at proliferation, cytokine production, cytotoxicity or upregulation of cell surface markers such as CD25, CD69, and CD107a.

In some embodiments, the immune effector cell is a T cell. In other embodiments, the immune effector cell is an NK cell. In some embodiments, the immune effector cell is not a T cell or an NK cell. In some embodiments, the immune effector cell is an autologous immune cell. In some embodiments, the immune effector cell is an allogenic cell. In some embodiments, the cell expressing the CAR kills the target cell. In some embodiments, binding of the Adapter to an AD blocks the activity of the antigen comprising the AD.

In some embodiments, the CAR cell kills the target cell upon direct binding to the target cell. In some embodiments, the CAR cell kills the target cell upon binding to the Adapter, wherein the Adapter is bound to the target cell.

In some embodiments, binding of CAR to the target cell and/or to the Adapter results in intracellular signaling in the cell expressing the CAR.

In some embodiments, binding of the CAR to the target cell and/or to the Adapter results in degranulation. Degranulation can result in the release of, depending on the cell type, antimicrobial, cytotoxic or other molecules from secretory granules in the immune cell. Molecules like perforin (a pore forming cytotoxin) or granzymes (serine proteases that induce apoptosis in the target cell) aid T cells and NK cells in killing tumor cells (or other cell types).

In some embodiments, binding of the CAR to the target cell and/or to the Adapter results in cytokine secretion by the cell expressing the CAR. The cytokine can be, for example, interferon gamma (IFNγ).

In some embodiments, binding of the CAR to the target cell and/or to the Adapter results in proliferation of the cell expressing the CAR.

C. Methods Comprising Administering a CAR Cell to a Patient

Described herein are methods of delivering an immune response to a target cell in a patient and/or killing a target cell in a patient comprising administering an Adapter and/or a CAR cell described herein to the patient. Also described herein are methods of depleting lymphocytes (e.g., B lymphocytes) comprising administering an Adapter and/or a CAR cell described herein to a patient in need thereof. In particular embodiments, provided herein are methods of treating cancer (e.g., hematological cancer) or an autoimmune disease or disorder comprising administering an Adapter and/or a CAR cell described herein to a patient in need thereof.

In some embodiments, a method of delivering an immune response to a target cell in a patient comprises administering to the patient a cell expressing a chimeric antigen receptor (CAR) comprising (i) a D domain that binds to CD123, (ii) a transmembrane domain, and (iii) an intracellular domain. In some embodiments, a method of killing a target cell in a patient in need thereof comprises administering to the patient a cell expressing a chimeric antigen receptor (CAR) comprising (i) a D domain that binds to CD123, (ii) a transmembrane domain, and (iii) an intracellular domain. In some embodiments, the target cell expresses CD123. In some embodiments, the target cell is a cancer cell. In some embodiments, the target cell is an acute myeloid leukemia (AML) cell. In some embodiments, the target cell is a myelodysplasia cell. In some embodiments, the target cell is a B-cell acute lymphoblastic leukemia cell. In some embodiments, the target cell is a hairy cell leukemia cell. In some embodiments, the target cell is a Hodgkin's lymphoma cell. In some embodiments, the target cell is a blastic plasmacytoid dendritic neoplasm (BPDCN) cell. In some embodiments, a method of depleting lymphocytes in a patient in need thereof comprises administering to the patient a cell expressing a chimeric antigen receptor (CAR) comprising (i) a D domain that binds to CD123, (ii) a transmembrane domain, and (iii) an intracellular domain. In some embodiments, the lymphoctes express CD123. In some embodiments, the lymphoctes are B lymphocytes. In some embodiments, a method of treating cancer comprises administering to a patient in need thereof a cell expressing a chimeric antigen receptor (CAR) comprising (i) a D domain that binds to CD123, (ii) a transmembrane domain, and (iii) an intracellular domain. In some embodiments, the cancer is hematological cancer. In some embodiments, the hematological cancer is acute myeloid leukemia (AML), myelodysplastic syndrome (e.g., high-risk myelodysplastic syndrome), B-cell acute lymphoblastic leukemia, hairy cell leukemia, Hodgkin's lymphoma or blastic plasmacytoid dendritic neoplasm (BPDCN). In some embodiments, the hematological cancer is AML. In some embodiments, the hematological cancer is myelodysplastic syndrome (e.g., high-risk myelodysplastic syndrome). In some embodiments, the hematological cancer is B-cell acute lymphoblastic leukemia. In some embodiments, the hematological cancer is hairy cell leukemia. In some embodiments, the hematological cancer is Hodgkin's lymphoma. In some embodiments, the hematological cancer is blastic plasmacytoid dendritic neoplasm (BPDCN). In some embodiments, a method of treating an autoimmune disease or disorder comprises administering to a patient in need thereof a cell expressing a chimeric antigen receptor (CAR) comprising (i) a D domain that binds to CD123, (ii) a transmembrane domain, and (iii) an intracellular domain. In some embodiments, the autoimmune disease or disorder is lupus erythematosus. In some embodiments, the D domain that binds to CD123 comprises an amino acid sequence selected from the group consisting of SEQ ID NO: 8-33, 99 and 100.

In some embodiments, the D domain that binds to CD123 comprises an amino acid sequence selected from the group consisting of SEQ ID NO: 8, 13, 14, 31, 32, and 33. In some embodiments, the D domain that binds to CD123 comprises the amino acid sequence of SEQ ID NO: 8. In some embodiments, the D domain that binds to CD123 comprises the amino acid sequence of SEQ ID NO: 13. In some embodiments, the D domain that binds to CD123 comprises the amino acid sequence of SEQ ID NO: 14. In some embodiments, the D domain that binds to CD123 comprises the amino acid sequence of SEQ ID NO: 31. In some embodiments, the D domain that binds to CD123 comprises the amino acid sequence of SEQ ID NO: 32. In some embodiments, the D domain that binds to CD123 comprises the amino acid sequence of SEQ ID NO: 33.

In some embodiments, the transmembrane domain comprises a CD8a, 41BB or CD28 transmembrane domain. In some embodiments, the transmembrane domain comprises a CD8a transmembrane domain. In some embodiments, the CD8a transmembrane domain comprises the amino acid sequence of SEQ ID NO: 113. In some embodiments, the CD8a transmembrane domain comprises the amino acid sequence of SEQ ID NO: 114. In some embodiments, the intracellular signaling domain is selected from the group consisting of a domain of a human T cell receptor alpha, beta, or zeta chain; a human 41BB domain; a human CD28 domain; and any combination thereof. In some embodiments, the intracellular signaling domain comprises the intracellular domain of a costimulatory molecule selected from the group consisting of CD27, CD28, 41BB, OX40, CD30, CD40, PD1, lymphocyte function-associated antigen-1 (LFA-1), CD2, CD7, LIGHT, NKG2C, NKG2D, B7-H3, a ligand that specifically binds with CD83, and any combination thereof. In some embodiments, the intracellular signaling domain contains the sequence of SEQ ID NO: 115, 116 or combination thereof. In some embodiments, the intracellular signaling domain contains the sequence of SEQ ID NO: 117.

In some embodiments, the CAR comprising a D domain that binds to CD123 comprises the amino acid sequence of SEQ ID NO: 62-66 or 67. In some embodiments, the CAR comprising a D domain that binds to CD123 comprises the amino acid sequence of SEQ ID NO: 62. In some embodiments, the CAR comprising a D domain that binds to CD123 comprises the amino acid sequence of SEQ ID NO: 63. In some embodiments, the CAR comprising a D domain that binds to CD123 comprises the amino acid sequence of SEQ ID NO: 64. In some embodiments, the CAR comprising a D domain that binds to CD123 comprises the amino acid sequence of SEQ ID NO: 65. In some embodiments, the CAR comprising a D domain that binds to CD123 comprises the amino acid sequence of SEQ ID NO: 66. In some embodiments, the CAR comprising a D domain that binds to CD123 comprises the amino acid sequence of SEQ ID NO: 67.

In some embodiments, the cell expressing the CAR is an immune cell. In some embodiments, the cell expressing the CAR is an immune effector cell. In some embodiments, the cell expressing the CAR is a T cell (CAR-T cell) or a natural killer (NK) cell (CAR-NK cell). In some embodiments, the immune cell is an autologous immune cell. In some embodiments, the immune cell is an allogenic cell. In some embodiments, the cell expressing the CAR is not a T cell or an NK cell.

In some embodiments, a method disclosed herein comprises administering to the patient between about $10 \times 10^6$ and about $300 \times 10^6$ cells expressing a CAR comprising a D domain that binds to CD123. In some embodiments, a method disclosed herein comprises administering to the patient between about $50 \times 10^6$ and about $900 \times 10^6$ cells expressing a CAR comprising a D domain that binds to CD123. In some embodiments, a method disclosed herein comprises administering to the patient between about $10 \times 10^6$ and about $500 \times 10^6$ cells expressing a CAR comprising a D domain that binds to CD123. In some embodiments, a method disclosed herein comprises administering to the patient about $100 \times 10^6$ cells expressing a CAR comprising a D domain that binds to CD123. In some embodiments, a method disclosed herein comprises administering to the patient about $50 \times 10^6$ cells expressing a CAR comprising a D domain that binds to CD123. In some embodiments, a method disclosed herein comprises administering to the patient about $100 \times 10^6$ cells expressing a CAR comprising a D domain that binds to CD123. In some embodiments, a method disclosed herein comprises administering to the patient about $150 \times 10^6$ cells expressing a CAR comprising a D domain that binds to CD123. In some embodiments, a method disclosed herein comprises administering to the patient about $200 \times 10^6$ cells expressing a CAR comprising a D domain that binds to CD123. In some embodiments, a method disclosed herein comprises administering to the patient about $250\times10^6$ cells expressing a CAR comprising a D domain that binds to CD123. In some embodiments, a method disclosed herein comprises administering to the patient about $300\times10^6$ cells expressing a CAR comprising a D domain that binds to CD123. In some embodiments, a method disclosed herein comprises administering to the patient about $400\times10^6$ cells expressing a CAR comprising a D domain that binds to CD123. In some embodiments, a method disclosed herein comprises administering to the patient about $500\times10^6$ cells expressing a CAR comprising a D domain that binds to CD123. In some embodiments, a method disclosed herein comprises administering to the patient about $600\times10^6$ cells expressing a CAR comprising a D domain that binds to CD123. In some embodiments, a method disclosed herein comprises administering to the patient about $700\times10^6$ cells expressing a CAR comprising a D domain that binds to CD123. In some embodiments, a method disclosed herein comprises administering to the patient more than one dose of the cells expressing a CAR comprising a D domain that binds to CD123, optionally wherein a single dose comprises between about $10\times10^6$ and about $300\times10^6$ cells, between about $50\times10^6$ and about $900\times10^6$ cells, between about $10\times10^6$ and about $500\times10^6$ cells, about $100\times10^6$ cells, about $50\times10^6$ cells, about $100\times10^6$ cells, about $150\times10^6$ cells, about $200\times10^6$ cells, about $250\times10^6$ cells, about $300\times10^6$ cells, about $400\times10^6$ cells, about $500\times10^6$ cells, about $600\times10^6$ cells, or about $700\times10^6$ cells. In some embodiments, a method disclosed herein comprises administering to the patient two doses of the cells expressing a CAR comprising a D domain that binds to CD123. In some embodiments, a method disclosed herein comprises administering to the patient three doses of the cells expressing a CAR comprising a D domain that binds to CD123. In some embodiments, a method disclosed herein comprises administering to the patient four doses of the cells expressing a CAR comprising a D domain that binds to CD123. In some embodiments, a method disclosed herein comprises administering to the patient five doses of the cells expressing a CAR comprising a D domain that binds to CD123. In some embodiments, the D domain that binds to CD123 comprises an amino acid sequence selected from the group consisting of SEQ ID NO: 8, 13, 14, 31, 32, and 33. In some embodiments, the cell expressing the CAR is an immune cell. In some embodiments, the cell expressing the CAR is an immune effector cell. In some embodiments, the cell expressing the CAR is a T cell (CAR-T cell) or a natural killer (NK) cell (CAR-NK cell). In some embodiments, the cell expressing the CAR is not a T cell or an NK cell. In some embodiments, the CAR immune cell is an autologous immune cell. In some embodiments, the CAR immune cell is an allogenic immune cell. The cells expressing a CAR provided herein can be administered either alone, or as a pharmaceutical composition in combination with diluents and/or with other components such as chemotherapeutics, antibodies, cytokines or cell populations. Compositions provided herein are preferably formulated for intravenous administration that can be administered one or more times. In some embodiments, the cells expressing the CAR are administered intravenously.

In some embodiments, the administering the cell expressing the CAR comprises administering a pharmaceutical composition comprising the cell expressing the CAR.

D. Methods Comprising Administering an Adapter and/or CAR Cell to a Patient

In some embodiments, a method of delivering an immune response to a target cell in a patient comprises administering to the patient an Adapter comprising (i) a D domain that binds to CD123 and (ii) an AFP p26 AD. In some embodiments, a method of killing a target cell in a patient in need thereof comprises administering to the patient an Adapter comprising (i) a D domain that binds to CD123 and (ii) an AFP p26 AD. In some embodiments, the target cell expresses CD123. In some embodiments, the target cell is a cancer cell. In some embodiments, the target cell is an acute myeloid leukemia (AML) cell. In some embodiments, the target cell is a myelodysplasia cell. In some embodiments, the target cell is a B-cell acute lymphoblastic leukemia cell. In some embodiments, the target cell is a hairy cell leukemia cell. In some embodiments, the target cell is a Hodgkin's lymphoma cell. In some embodiments, the target cell is a blastic plasmacytoid dendritic neoplasm (BPDCN) cell. In some embodiments, a method of depleting lymphocytes in a patient in need thereof comprises administering to the patient an Adapter comprising (i) a D domain that binds to CD123 and (ii) an AFP p26 AD. In some embodiments, the lymphocytes express CD123. In some embodiments, the lymphocytes are B lymphocytes. In some embodiments, a method of treating cancer comprises administering to a patient in need thereof an Adapter comprising (i) a D domain that binds to CD123 and (ii) an AFP p26 AD. In some embodiments, the cancer is hematological cancer. In some embodiments, the hematological cancer is acute myeloid leukemia (AML), myelodysplastic syndrome (e.g., high-risk myelodysplastic syndrome). B-cell acute lymphoblastic leukemia, hairy cell leukemia, Hodgkin's lymphoma or blastic plasmacytoid dendritic neoplasm (BPDCN). In some embodiments, the hematological cancer is AML. In some embodiments, the hematological cancer is myelodysplastic syndrome (e.g., high-risk myelodysplastic syndrome) In some embodiments, the hematological cancer is B-cell acute lymphoblastic leukemia. In some embodiments, the hematological cancer is hairy cell leukemia. In some embodiments, the hematological cancer is Hodgkin's lymphoma. In some embodiments, the hematological cancer is blastic plasmacytoid dendritic neoplasm (BPDCN). In some embodiments, a method of treating an autoimmune disease or disorder comprises administering to a patient in need thereof an Adapter comprising (i) a D domain that binds to CD123 and (ii) an AFP p26 AD. In some embodiments, the autoimmune disease or disorder is lupus erythematosus. In some embodiments, the patient has been administered a cell expressing a CAR, wherein the CAR comprises (i) an antigenic determinant binding domain (ADBD) that binds to an AFP p26 antigenic determinant (AD), (ii) a transmembrane domain, and (iii) an intracellular domain. In some embodiments, the patient comprises a cell expressing a CAR, wherein the CAR comprises (i) an antigenic determinant binding domain (ADBD) that binds to an AFP p26 antigenic determinant (AD), (ii) a transmembrane domain, and (iii) an intracellular domain. In some embodiments, the method further comprises administering a cell expressing a CAR, wherein the CAR comprises (i) an antigenic determinant binding domain (ADBD) that binds to an AFP p26 antigenic determinant (AD), (ii) a transmembrane domain, and (iii) an intracellular domain.

In some embodiments, a method of delivering an immune response to a target cell in a patient comprises administering to the patient an Adapter comprising (i) a D domain that binds to CD123 and (ii) an antigenic determinant binding domain (ADBD) that binds to the AFP p26 antigenic determinant (AD). In some embodiments, a method of killing a target cell in a patient in need thereof comprises administering to the patient an Adapter comprising (i) a D domain that binds to CD123 and (ii) an antigenic determinant binding domain (ADBD) that binds to the AFP p26 antigenic determinant (AD). In some embodiments, the target cell expresses CD123. In some embodiments, the target cell is a cancer cell. In some embodiments, the target cell is an AML cell. In some embodiments, the target cell is a myelodysplasia cell. In some embodiments, the target cell is a B-cell acute lymphoblastic leukemia cell. In some embodiments, the target cell is a hairy cell leukemia cell. In some embodiments, the target cell is a Hodgkin's lymphoma cell. In some embodiments, the target cell is a blastic plasmacytoid dendritic neoplasm (BPDCN) cell. In some embodiments, a method of depleting lymphocytes in a patient in need thereof comprises administering to the patient an Adapter comprising (i) a D domain that binds to CD123 and (ii) an antigenic determinant binding domain (ADBD) that binds to the AFP p26 antigenic determinant (AD). In some embodiments, the lymphocytes express CD123. In some embodiments, the lymphocytes are B lymphocytes. In some embodiments, a method of treating cancer comprises administering to a patient in need thereof an Adapter comprising (i) a D domain that binds to CD123 and (ii) an antigenic determinant binding domain (ADBD) that binds to the AFP p26 antigenic determinant (AD). In some embodiments, the cancer is hematological cancer. In some embodiments, the hematological cancer is acute myeloid leukemia (AML), myelodysplastic syndrome (e.g., high-risk myelodysplastic syndrome), B-cell acute lymphoblastic leukemia, hairy cell leukemia, Hodgkin's lymphoma or blastic plasmacytoid dendritic neoplasm (BPDCN). In some embodiments, the hematological cancer is AML. In some embodiments, the hematological cancer is myelodysplastic syndrome (e.g., high-risk myelodysplastic syndrome). In some embodiments, the hematological cancer is B-cell acute lymphoblastic leukemia. In some embodiments, the hematological cancer is hairy cell leukemia. In some embodiments, the hematological cancer is Hodgkin's lymphoma. In some embodiments, the hematological cancer is blastic plasmacytoid dendritic neoplasm (BPDCN). In some embodiments, a method of treating an autoimmune disease or disorder comprises administering to a patient in need thereof an Adapter comprising (i) a D domain that binds to CD123 and (ii) an antigenic determinant binding domain (ADBD) that binds to the AFP p26 antigenic determinant (AD). In some embodiments, the autoimmune disease or disorder is lupus erythematosus. In some embodiments, the patient has been administered a cell expressing a CAR, wherein (a) the CAR comprises (i) an AFP p26 antigenic determinant (AD), (ii) a transmembrane domain, and (iii) an intracellular domain. In some embodiments, the patient comprises a cell expressing a CAR, wherein (a) the CAR comprises (i) an AFP p26 antigenic determinant (AD), (ii) a transmembrane domain, and (iii) an intracellular domain. In some embodiments, the method further comprises administering a cell expressing a CAR, wherein (a) the CAR comprises (i) an AFP p26 antigenic determinant (AD), (ii) a transmembrane domain, and (iii) an intracellular domain.

In some embodiments, a method of delivering an immune response to a target cell in a patient comprises administering to the patient an Adapter comprising (i) a D domain that binds to CD123 and (ii) the AD bound by a CAR, wherein the patient has been administered a cell expressing the CAR, wherein (a) the CAR comprises (i) an antigenic determinant binding domain (ADBD) that binds to an antigenic determinant (AD) other than CD123, (ii) a transmembrane domain, and (iii) an intracellular domain. In some embodiments, a method of killing a target cell in a patient in need thereof comprises administering to the patient an Adapter comprising (i) a D domain that binds to CD123 and (ii) the AD bound by a CAR, wherein the patient has been administered a cell expressing the CAR, wherein (a) the CAR comprises (i) an antigenic determinant binding domain (ADBD) that binds to an antigenic determinant (AD) other than CD123, (ii) a transmembrane domain, and (iii) an intracellular domain, wherein the patient has been administered a cell expressing a CAR, wherein (a) the CAR comprises (i) an antigenic determinant binding domain (ADBD) that binds to an antigenic determinant (AD) other than CD123, (ii) a transmembrane domain, and (iii) an intracellular domain. In some embodiments, the target cell expresses CD123. In some embodiments, the target cell is an AML cell. In some embodiments, the target cell is a myelodysplasia cell. In some embodiments, the target cell is a B-cell acute lymphoblastic leukemia cell. In some embodiments, the target cell is a hairy cell leukemia cell. In some embodiments, the target cell is a Hodgkin's lymphoma cell. In some embodiments, the target cell is a blastic plasmacytoid dendritic neoplasm (BPDCN) cell. In some embodiments, a method of depleting lymphocytes in a patient in need thereof comprises administering to the patient an Adapter comprising (i) a D domain that binds to CD123 and (ii) the AD bound by a CAR, wherein the patient has been administered a cell expressing the CAR, wherein (a) the CAR comprises (i) an antigenic determinant binding domain (ADBD) that binds to an antigenic determinant (AD) other than CD123, (ii) a transmembrane domain, and (iii) an intracellular domain. In some embodiments, the lymphocytes express CD123. In some embodiments, the lymphocytes are B lymphocytes. In some embodiments, a method of treating cancer comprises administering to a patient in need thereof an Adapter comprising (i) a D domain that binds to CD123 and (ii) the AD bound by a CAR, wherein the patient has been administered a cell expressing the CAR, wherein (a) the CAR comprises (i) an antigenic determinant binding domain (ADBD) that binds to an antigenic determinant (AD) other than CD123, (ii) a transmembrane domain, and (iii) an intracellular domain. In some embodiments, the cancer is hematological cancer. In some embodiments, the hematological cancer is acute myeloid leukemia (AML), myelodysplastic syndrome (e.g., high-risk myelodysplastic syndrome), B-cell acute lymphoblastic leukemia, hairy cell leukemia, Hodgkin's lymphoma or blastic plasmacytoid dendritic neoplasm (BPDCN). In some embodiments, the hematological cancer is AML. In some embodiments, the hematological cancer is myelodysplastic syndrome (e.g., high-risk myelodysplastic syndrome). In some embodiments, the hematological cancer is B-cell acute lymphoblastic leukemia. In some embodiments, the hematological cancer is hairy cell leukemia. In some embodiments, the hematological cancer is Hodgkin's lymphoma. In some embodiments, the hematological cancer is blastic plasmacytoid dendritic neoplasm (BPDCN). In some embodiments, a method of treating an autoimmune disease or disorder comprises administering to a patient in need thereof an Adapter comprising (i) a D domain that binds to CD123 and (ii) the AD bound by a CAR, wherein the patient has been administered a cell expressing the CAR, wherein (a) the CAR comprises (i) an antigenic determinant binding domain (ADBD) that binds to an antigenic determinant (AD) other than CD123, (ii) a transmembrane domain, and (iii) an intracellular domain. In some embodiments, the autoimmune disease or disorder is lupus erythematosus.

In some embodiments, a method of delivering an immune response to a target cell in a patient comprises administering to the patient an Adapter comprising (i) a D domain that binds to CD123 and (ii) the AD bound by a CAR, wherein the patient comprise a cell expressing the CAR, wherein (a) the CAR comprises (i) an antigenic determinant binding domain (ADBD) that binds to an antigenic determinant (AD) other than CD123, (ii) a transmembrane domain, and (iii) an intracellular domain. In some embodiments, a method of killing a target cell in a patient in need thereof comprises administering to the patient an Adapter comprising (i) a D domain that binds to CD123 and (ii) the AD bound by a CAR, wherein the patient comprise a cell expressing the CAR, wherein (a) the CAR comprises (i) an antigenic determinant binding domain (ADBD) that binds to an antigenic determinant (AD) other than CD123, (ii) a transmembrane domain, and (iii) an intracellular domain. In some embodiments, the target cell expresses CD123. In some embodiments, the target cell is a cancer cell. In some embodiments, the target cell is an AML cell. In some embodiments, the target cell is a myelodysplasia cell. In some embodiments, the target cell is a B-cell acute lymphoblastic leukemia cell. In some embodiments, the target cell is a hairy cell leukemia cell. In some embodiments, the target cell is a Hodgkin's lymphoma cell. In some embodiments, the target cell is a blastic plasmacytoid dendritic neoplasm (BPDCN) cell. In some embodiments, a method of depleting lymphocytes in a patient in need thereof comprises administering to the patient an Adapter comprising (i) a D domain that binds to CD123 and (ii) the AD bound by a CAR, wherein the patient comprise a cell expressing the CAR, wherein (a) the CAR comprises (i) an antigenic determinant binding domain (ADBD) that binds to an antigenic determinant (AD) other than CD123, (ii) a transmembrane domain, and (iii) an intracellular domain. In some embodiments, the lymphocytes express CD123. In some embodiments, the lymphocytes are B lymphocytes. In some embodiments, a method of treating cancer comprises administering to a patient in need thereof an Adapter comprising (i) a D domain that binds to CD123 and (ii) the AD bound by a CAR, wherein the patient comprise a cell expressing the CAR, wherein (a) the CAR comprises (i) an antigenic determinant binding domain (ADBD) that binds to an antigenic determinant (AD) other than CD123, (ii) a transmembrane domain, and (iii) an intracellular domain. In some embodiments, the cancer is hematological cancer. In some embodiments, the hematological cancer is acute myeloid leukemia (AML), myelodysplastic syndrome (e.g., high-risk myelodysplastic syndrome), B-cell acute lymphoblastic leukemia, hairy cell leukemia, Hodgkin's lymphoma or blastic plasmacytoid dendritic neoplasm (BPDCN). In some embodiments, the hematological cancer is AML. In some embodiments, the hematological cancer is myelodysplastic syndrome (e.g., high-risk myelodysplastic syndrome). In some embodiments, the hematological cancer is B-cell acute lymphoblastic leukemia. In some embodiments, the hematological cancer is hairy cell leukemia. In some embodiments, the hematological cancer is Hodgkin's lymphoma. In some embodiments, the hematological cancer is blastic plasmacytoid dendritic neoplasm (BPDCN). In some embodiments, a method of treating an autoimmune disease or disorder comprises administering to a patient in need thereof an Adapter comprising (i) a D domain that binds to CD123 and (ii) the AD bound by a CAR, wherein the patient comprise a cell expressing the CAR, wherein (a) the CAR comprises (i) an antigenic determinant binding domain (ADBD) that binds to an antigenic determinant (AD) other than CD123, (ii) a transmembrane domain, and (iii) an intracellular domain. In some embodiments, the autoimmune disease or disorder is lupus erythematosus.

In some embodiments, a method of delivering an immune response to a target cell in a patient comprises administering to the patient an Adapter comprising (i) a first antigenic determinant binding domain (ADBD) that binds to a target AD and (ii) a second antigenic determinant binding domain (ADBD) that binds to the AFP p26 antigenic determinant (AD). In some embodiments, a method of killing a target cell in a patient in need thereof comprises administering to the patient an Adapter comprising (i) a first antigenic determinant binding domain (ADBD) that binds to a target AD and (ii) an second antigenic determinant binding domain (ADBD) that binds to the AFP p26 antigenic determinant (AD). In some embodiments, the target cell expresses the target AD. In some embodiments, the target cell is a cancer cell. In some embodiments, a method of depleting lymphocytes in a patient in need thereof comprises administering to the patient an Adapter comprising (i) a first antigenic determinant binding domain (ADBD) that binds to a target AD and (ii) an second antigenic determinant binding domain (ADBD) that binds to the AFP p26 antigenic determinant (AD). In some embodiments, the lymphocytes express the target AD. In some embodiments, the lymphocytes are B lymphocytes or T lymphocytes. In some embodiments, a method of treating cancer comprises administering to a patient in need thereof an Adapter comprising (i) a first antigenic determinant binding domain (ADBD) that binds to a target AD and (ii) an second antigenic determinant binding domain (ADBD) that binds to the AFP p26 antigenic determinant (AD). In some embodiments, the cancer is hematological cancer. In some embodiments, the hematological cancer is acute myeloid leukemia (AML), myelodysplastic syndrome (e.g., high-risk myelodysplastic syndrome), B-cell acute lymphoblastic leukemia, hairy cell leukemia, Hodgkin's lymphoma or blastic plasmacytoid dendritic neoplasm (BPDCN). In some embodiments, the hematological cancer is AML. In some embodiments, the hematological cancer is myelodysplastic syndrome (e.g., high-risk myelodysplastic syndrome). In some embodiments, the hematological cancer is B-cell acute lymphoblastic leukemia. In some embodiments, the hematological cancer is hairy cell leukemia. In some embodiments, the hematological cancer is Hodgkin's lymphoma. In some embodiments, the hematological cancer is blastic plasmacytoid dendritic neoplasm (BPDCN). In some embodiments, a method of treating an autoimmune disease or disorder comprises administering to a patient in need thereof an Adapter comprising (i) a first antigenic determinant binding domain (ADBD) that binds to a target AD and (ii) an second antigenic determinant binding domain (ADBD) that binds to the AFP p26 antigenic determinant (AD). In some embodiments, the autoimmune disease or disorder is rheumatoid arthritis. In some embodiments, the patient has been administered a cell expressing a CAR, wherein the CAR comprises (i) AFP p26 antigenic determinant (AD), (ii) a transmembrane domain, and (iii) an intracellular domain. In some embodiments, the patient comprises a cell expressing a CAR, wherein the CAR comprises (i) AFP p26 antigenic determinant (AD), (ii) a transmembrane domain, and (iii) an intracellular domain. In some embodiments, the method further comprises administering a cell expressing a CAR, wherein the CAR comprises (i) AFP p26 antigenic determinant (AD), (ii) a transmembrane domain, and (iii) an intracellular domain.

In some embodiments, a method described herein comprises administering to a subject in need thereof about $100 \times 10^6$ cells expressing a CAR that specifically binds to the AFP p26 antigenic determinant and more than one doses of about 0.1 mg/kg of an Adapter comprising a D domain that binds to CD123 and the p26 antigenic determinant. In some embodiments, a method described herein comprises administering to a subject in need thereof about $100 \times 10^6$ cells expressing a CAR that specifically binds to the AFP p26 antigenic determinant and more than one doses of about 0.3 mg/kg of an Adapter comprising a D domain that binds to CD123 and the p26 antigenic determinant. In some embodiments, a method described herein comprises administering to a subject in need thereof about $300 \times 10^6$ cells expressing a CAR that specifically binds to the AFP p26 antigenic determinant and more than one doses of about 0.1 mg/kg of an Adapter comprising a D domain that binds to CD123 and the p26 antigenic determinant. In some embodiments, a method described herein comprises administering to a subject in need thereof about $300 \times 10^6$ cells expressing a CAR that specifically binds to the AFP p26 antigenic determinant and more than one doses of about 0.3 mg/kg of an Adapter comprising a D domain that binds to CD123 and the p26 antigenic determinant. In some embodiments, a method described herein comprises administering to a subject in need thereof about $300 \times 10^6$ cells expressing a CAR that specifically binds to the AFP p26 antigenic determinant and more than one doses of about 0.9 mg/kg of an Adapter comprising a D domain that binds to CD123 and the p26 antigenic determinant. In some embodiments, a method described herein comprises administering to a subject in need thereof about $900 \times 10^6$ cells expressing a CAR that specifically binds to the AFP p26 antigenic determinant and more than one doses of about 0.1 mg/kg of an Adapter comprising a D domain that binds to CD123 and the p26 antigenic determinant. In some embodiments, a method described herein comprises administering to a subject in need thereof about $900 \times 10^6$ cells expressing a CAR that specifically binds to the AFP p26 antigenic determinant and more than one doses of about 0.3 mg/kg of an Adapter comprising a D domain that binds to CD123 and the p26 antigenic determinant. In some embodiments, a method described herein comprises administering to a subject in need thereof about $900 \times 10^6$ cells expressing a CAR that specifically binds to the AFP p26 antigenic determinant and more than one doses of about 0.9 mg/kg of an Adapter comprising a D domain that binds to CD123 and the p26 antigenic determinant. In some embodiments, the first dose of the Adapter is administered on the same day as the cells expressing the CAR. In some embodiments, the first dose of the Adapter is administered 1, 2, 3, 4, or 5 days after the administration of the cells expressing the CAR. In some embodiments, the method comprises administering a daily dose of the Adapter for 1 week. In some embodiments, the method comprises administering a daily dose of the Adapter for 2 weeks. In some embodiments, the method comprises administering a daily dose of the Adapter for 3 weeks. In some embodiments, the method comprises administering a daily dose of the Adapter for 4 weeks. In some embodiments, the daily dose of Adapter administered is the same. In some embodiments, the method further comprises administering 3 doses of the Adapter every week after the completion of the daily doses. In some embodiments, the three weekly doses of Adapter are administered on Monday, Wednesday and Friday. In some embodiments, the dose of Adapter administered on a single day is the same. In some embodiments, the administration of 3 doses of the Adapter every week continues for about 1, 2, 3, 4, 5, or 6 months. In some embodiments, the administration of 3 doses of the Adapter every week continues until the cells expressing the CAR are no longer measurable in peripheral blood. In some embodiments, the subject has a hematological cancer. In some embodiments, the subject has a hematological cancer, wherein the cancer cells express CD123. In some embodiments, the subject has Acute Myeloid Leukemia (AML). In some embodiments, the subject has Myelodysplastic Syndrome (MDS). In some embodiments, the subject has High-Risk Myelodysplastic Syndrome (MDS). In some embodiments, the CAR that specifically binds to the AFP p26 antigenic determinant comprises a D domain that specifically binds to the AFP p26 antigenic determinant, optionally wherein the D domain comprises the amino acid sequence of SEQ ID NO: 70-73 or 92-94. In some embodiments, the D domain that specifically binds to the AFP p26 antigenic determinant comprises the amino acid sequence of SEQ ID NO: 70 or 73. In some embodiments, the CAR that specifically binds to the AFP p26 antigenic determinant comprises the amino acid sequence of SEQ ID NO: 68 or 69. In some embodiments, the Adapter comprises a D domain that binds to CD123 comprises an amino acid sequence selected from the group consisting of SEQ ID NO: 8-33, 99 and 100. In some embodiments, the Adapter comprises a D domain that binds to CD123 comprises an amino acid sequence selected from the group consisting of SEQ ID NO: 8, 13, 14, 31, 32, and 33. In some embodiments, the Adapter comprises a D domain that binds to CD123 comprises the amino acid sequence of SEQ ID NO: 14. In some embodiments, the AFP p26 antigenic determinant comprises the amino acid sequence of SEQ ID NO: 37-43 or 44. In some embodiments, the AFP p26 antigenic determinant comprises the amino acid sequence of SEQ ID NO: 37. In some embodiments, the AFP p26 antigenic determinant comprises the amino acid sequence of SEQ ID NO: 39. In some embodiments, the cell expressing the CAR is an immune cell. In some embodiments, the cell expressing the CAR is an immune effector cell. In some embodiments, the cell expressing the CAR is a T cell (CAR-T cell) or a natural killer (NK) cell (CAR-NK cell). In some embodiments, the cell expressing the CAR is not a T cell or an NK cell. In some embodiments, the CAR immune cell is an autologous immune cell. In some embodiments, the CAR immune cell is an allogeneic immune cell.

In some embodiments of a method described herein, the Adapter is administered at about 0.1 mg/kg to about 50 mg/kg, about 0.1 mg/kg to about 25 mg/kg, about 0.1 mg/kg to about 20 mg/kg, about 0.1 mg/kg to about 15 mg/kg, about 0.1 mg/kg to about 10 mg/kg, or about 0.1 mg/kg to about 5 mg/kg. In some embodiments, the Adapter is administered at about 1 µg/kg to about 10 mg/kg, about 5 µg/kg to about 10 mg/kg, about 10 µg/kg to about 10 mg/kg, about 20 µg/kg to about 10 mg/kg, or about 50 µg/kg to about 10 mg/kg. In some embodiments, the Adapter is administered at about 10 µg/kg to about 10 mg/kg, about 50 µg/kg to about 10 mg/kg, about 100 µg/kg to about 10 mg/kg, about 200 µg/kg to about 10 mg/kg, or about 500 µg/kg to about 10 mg/kg. In some embodiments, the Adapter is administered at about 100 µg/kg to about 10 mg/kg, about 100 µg/kg to about 5 mg/kg, about 100 µg/kg to about 2 mg/kg, about 100 µg/kg to about 1 mg/kg, about 100 µg/kg to about 5 mg/kg, or about 100 µg/kg to about 2 mg/kg. In some embodiments, the Adapter is administered at about 1 µg/kg to about 10 mg/kg, about 5 µg/kg to about 5 mg/kg, about 10 µg/kg to about 2 mg/kg, about 20 µg/kg to about 1 mg/kg, or about 5 µg/kg to about 0.5 mg/kg. In some embodiments, the Adapter is administered at about 0.01 mg/kg, about 0.02 mg/kg, about 0.04 mg/kg, about 0.07 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 1 mg/kg, or about 2 mg/kg. In some embodiments, the Adapter is administered at about 0.07 mg/kg. In some embodiments, the Adapter is administered at about 0.01 mg/kg. In some embodiments, the Adapter is administered at about 0.1 mg/kg. In some embodiments, the Adapter is administered at about 0.2 mg/kg. In some embodiments, the Adapter is administered at about 0.3 mg/kg. In some embodiments, the Adapter is administered at about 0.4 mg/kg. In some embodiments, the Adapter is administered at about 0.5 mg/kg. In some embodiments, the Adapter is administered at about 0.6 mg/kg. In some embodiments, the Adapter is administered at about 0.7 mg/kg. In some embodiments, the Adapter is administered at about 0.8 mg/kg. In some embodiments, the Adapter is administered at about 0.9 mg/kg. In some embodiments, the Adapter is administered at about 1 mg/kg. In some embodiments, the Adapter is administered at about 2 mg/kg. In some embodiments, the Adapter is administered at about 3 mg/kg. In some embodiments, the Adapter is administered at about 4 mg/kg. In some embodiments, the Adapter is administered at about 5 mg/kg. In some embodiments, the Adapter is administered at about 6 mg/kg. In some embodiments, the Adapter is administered at about 7 mg/kg. In some embodiments, the Adapter is administered at about 8 mg/kg. In some embodiments, the Adapter is administered at about 9 mg/kg. In some embodiments, the Adapter is administered at about 10 mg/kg. In some embodiments, the Adapter is administered intravenously. In some embodiments, the Adapter is administered subcutaneously. In some embodiments, the Adapter comprises a D domain that binds to CD123 comprises an amino acid sequence selected from the group consisting of SEQ ID NO: 8-33, 99 and 100. In some embodiments, the Adapter comprises a D domain that binds to CD123 comprises an amino acid sequence selected from the group consisting of SEQ ID NO: 8, 13, 14, 31, 32, and 33. In some embodiments, the Adapter comprises a D domain that binds to CD123 comprises the amino acid sequence of SEQ ID NO: 14.

In some embodiments of a method described herein, the Adapter is administered at about 0.2 mg to about 200 mg, about 0.5 mg to about 100 mg, about 1 mg to about 50 mg, about 2 mg to about 25 mg, or about 2 mg to about 12 mg. In some embodiments, the Adapter is administered at about 0.4 mg, about 0.8 mg, about 1.6 mg, about 2.8 mg, about 3 mg, about 4 mg, about 8 mg, about 12 mg, about 16 mg, about 20 mg, about 24 mg, about 28 mg, about 40 mg, or about 80 mg. In some embodiments, the Adapter is administered at about 1.6 mg, about 2.8 mg, about 3 mg, about 4 mg, about 8 mg, about 12 mg, about 16 mg, or about 20 mg. In some embodiments, the Adapter is administered intravenously. In some embodiments, the Adapter is administered subcutaneously. In some embodiments, the Adapter comprises a D domain that binds to CD123 comprises an amino acid sequence selected from the group consisting of SEQ ID NO: 8-33, 99 and 100. In some embodiments, the Adapter comprises a D domain that binds to CD123 comprises an amino acid sequence selected from the group consisting of SEQ ID NO: 8, 13, 14, 31, 32, and 33. In some embodiments, the Adapter comprises a D domain that binds to CD123 comprises the amino acid sequence of SEQ ID NO: 14.

In some embodiments of a method described herein, more than one dose of the the Adapter is administered. In some embodiments, the more than one dose of the the Adapter is a constant dose. In some embodiments, the Adapter is administered at different doses. In some embodiments, the amount of Adapter administered is increased over time. In some embodiments, the amount of Adapter administered is decreased over time. In some embodiments, the Adapter is first administered at a low dose of between about 0.01 mg/kg and about 0.5 mg/kg, followed by administration at a high dose between about 0.1 mg/kg and about 5 mg/kg. In some embodiments, the Adapter is administered intravenously. In some embodiments, the Adapter is administered subcutaneously. In some embodiments, the Adapter comprises a D domain that binds to CD123 comprises an amino acid sequence selected from the group consisting of SEQ ID NO: 8-33, 99 and 100. In some embodiments, the Adapter comprises a D domain that binds to CD123 comprises an amino acid sequence selected from the group consisting of SEQ ID NO: 8, 13, 14, 31, 32, and 33. In some embodiments, the Adapter comprises a D domain that binds to CD123 comprises the amino acid sequence of SEQ ID NO: 14.

In some embodiments of a method described herein, the Adapter is administered daily. In some embodiments, the Adapter is administered twice a day. In some embodiments, the Adapter is administered three times a day. In some embodiments, the Adapter is administered four times a day. In some embodiments, the Adapter is administered every 12 hours. In some embodiments, the Adapter is administered every 8 hours. In some embodiments, the Adapter is administered every 6 hours. In some embodiments, the Adapter is administered every 4 hours. In some embodiments, the Adapter is administered as a continuous infusion. In some embodiments, the Adapter is administered every other day. In some embodiments, the Adapter is administered every three days. In some embodiments, the Adapter is administered twice a week. In some embodiments, the Adapter is administered twice a week, for example, on Monday, Wednesday and Friday. In some embodiments, the Adapter is administered weekly. In some embodiments, the Adapter is administered intravenously. In some embodiments, the Adapter is administered subcutaneously. In some embodiments, the Adapter comprises a D domain that binds to CD123 comprises an amino acid sequence selected from the group consisting of SEQ ID NO: 8-33, 99 and 100. In some embodiments, the Adapter comprises a D domain that binds to CD123 comprises an amino acid sequence selected from the group consisting of SEQ ID NO: 8, 13, 14, 31, 32, and 33. In some embodiments, the Adapter comprises a D domain that binds to CD123 comprises the amino acid sequence of SEQ ID NO: 14.

In some embodiments of a method described herein, the Adapter is administered for seven days. In some embodiments, the Adapter is administered for 2 weeks. In some embodiments, the Adapter is administered for 3 weeks. In some embodiments, the Adapter is administered for 4 weeks. In some embodiments, the Adapter is administered for 1 month. In some embodiments, the Adapter is administered for 2 months. In some embodiments, the Adapter is administered for 3 months. In some embodiments, the Adapter is administered intravenously. In some embodiments, the Adapter is administered subcutaneously. In some embodiments, the Adapter comprises a D domain that binds to CD123 comprises an amino acid sequence selected from the group consisting of SEQ ID NO: 8-33, 99 and 100. In some embodiments, the Adapter comprises a D domain that binds to CD123 comprises an amino acid sequence selected from the group consisting of SEQ ID NO: 8, 13, 14, 31, 32, and 33. In some embodiments, the Adapter comprises a D domain that binds to CD123 comprises the amino acid sequence of SEQ ID NO: 14.

In some embodiments of a method described herein, the Adapter is administered at the same frequency over the period of treatment. In some embodiments, the frequency of administration decreases over the period of treatment. In some embodiments, the Adapter is first administered daily for about a week followed by administration twice a week. In some embodiments, the Adapter is first administered between one and three times a day for about a week followed by daily administration. In some embodiments, the Adapter is first administered between one and three times a day for about a week followed by twice weekly or weekly administration. In some embodiments, the Adapter is first administered as a continuous infusion for about a week followed by daily administration. In some embodiments, the Adapter is first administered as a continuous infusion for about a week followed by twice weekly or weekly administration. In some embodiments, the Adapter is administered intravenously. In some embodiments, the Adapter is administered subcutaneously. In some embodiments, the Adapter comprises a D domain that binds to CD123 comprises an amino acid sequence selected from the group consisting of SEQ ID NO: 8-33, 99 and 100. In some embodiments, the Adapter comprises a D domain that binds to CD123 comprises an amino acid sequence selected from the group consisting of SEQ ID NO: 8, 13, 14, 31, 32, and 33. In some embodiments, the Adapter comprises a D domain that binds to CD123 comprises the amino acid sequence of SEQ ID NO: 14.

In some embodiments of a method described herein, cells expressing a CAR that specifically binds to the AFP p26 antigenic determinant has been administered to the subject receiving the Adapter. In some embodiments, between about $10 \times 10^6$ and about $300 \times 10^6$ cells expressing a CAR that specifically binds to the AFP p26 antigenic determinant has been administered to the subject receiving the Adapter. In some embodiments, between about $50 \times 10^6$ and about $900 \times 10^6$ cells expressing a CAR that specifically binds to the AFP p26 antigenic determinant has been administered to the subject receiving the Adapter. In some embodiments, between about $10 \times 10^6$ and about $500 \times 10^6$ cells expressing a CAR that specifically binds to the AFP p26 antigenic determinant has been administered to the subject receiving the Adapter. In some embodiments, about $100 \times 10^6$ cells expressing a CAR that specifically binds to the AFP p26 antigenic determinant has been administered to the subject receiving the Adapter. In some embodiments, about $50 \times 10^6$ cells expressing a CAR that specifically binds to the AFP p26 antigenic determinant has been administered to the subject receiving the Adapter. In some embodiments, more than one dose of the cells expressing a CAR that specifically binds to the AFP p26 antigenic determinant has been administered to the subject receiving the Adapter, optionally wherein a single dose comprises between about $10 \times 10^6$ and about $300 \times 10^6$ cells, between about $50 \times 10^6$ and about $900 \times 10^6$ cells, between about $10 \times 10^6$ and about $500 \times 10^6$ cells, about $100 \times 10^6$ cells, about $50 \times 10^6$ cells, about $100 \times 10^6$ cells, about $150 \times 10^6$ cells, about $200 \times 10^6$ cells, about $250 \times 10^6$ cells, about $300 \times 10^6$ cells, about $400 \times 10^6$ cells, about $500 \times 10^6$ cells, about $600 \times 10^6$ cells, or about $700 \times 10^6$ cells. In some embodiments, two doses of the cells expressing a CAR that specifically binds to the AFP p26 antigenic determinant have been administered to the subject receiving the Adapter. In some embodiments, three doses of the cells expressing a CAR that specifically binds to the AFP p26 antigenic determinant have been administered to the subject receiving the Adapter. In some embodiments, four doses of the cells expressing a CAR that specifically binds to the AFP p26 antigenic determinant have been administered to the subject receiving the Adapter. In some embodiments, five doses of the cells expressing a CAR that specifically binds to the AFP p26 antigenic determinant have been administered to the subject receiving the Adapter. In some embodiments, about $100 \times 10^6$ cells expressing a CAR that specifically binds to the AFP p26 antigenic determinant has been administered to the subject receiving the Adapter. In some embodiments, about $150 \times 10^6$ cells expressing a CAR that specifically binds to the AFP p26 antigenic determinant has been administered to the subject receiving the Adapter. In some embodiments, about $200 \times 10^6$ cells expressing a CAR that specifically binds to the AFP p26 antigenic determinant has been administered to the subject receiving the Adapter. In some embodiments, about $250 \times 10^6$ cells expressing a CAR that specifically binds to the AFP p26 antigenic determinant has been administered to the subject receiving the Adapter. In some embodiments, about $300 \times 10^6$ cells expressing a CAR that specifically binds to the AFP p26 antigenic determinant has been administered to the subject receiving the Adapter. In some embodiments, about $400 \times 10^6$ cells expressing a CAR that specifically binds to the AFP p26 antigenic determinant has been administered to the subject receiving the Adapter. In some embodiments, about $500 \times 10^6$ cells expressing a CAR that specifically binds to the AFP p26 antigenic determinant has been administered to the subject receiving the Adapter. In some embodiments, about $600 \times 10^6$ cells expressing a CAR that specifically binds to the AFP p26 antigenic determinant has been administered to the subject receiving the Adapter. In some embodiments, about $700 \times 10^6$ cells expressing a CAR that specifically binds to the AFP p26 antigenic determinant has been administered to the subject receiving the Adapter. In some embodiments, the CAR that specifically binds to the AFP p26 antigenic determinant has been administered to the subject at the same time as the first dose of the Adapter. In some embodiments, the CAR that specifically binds to the AFP p26 antigenic determinant has been administered to the subject before the first dose of the Adapter. In some embodiments, the AFP p26 antigenic determinant comprises the amino acid sequence of SEQ ID NO: 37-43 or 44. In some embodiments, the AFP p26 antigenic determinant comprises the amino acid sequence of SEQ ID NO: 37. In some embodiments, the AFP p26 antigenic determinant comprises the amino acid sequence of SEQ ID NO: 39. In some embodiments, the CAR that specifically binds to the AFP p26 antigenic determinant comprises a D domain that specifically binds to the AFP p26 antigenic determinant, optionally wherein the D domain comprises the amino acid sequence of SEQ ID NO: 70-73 or 92-94. In some embodiments, the D domain that specifically binds to the AFP p26 antigenic determinant comprises the amino acid sequence of SEQ ID NO: 70 or 73. In some embodiments, the CAR that specifically binds to the AFP p26 antigenic determinant comprises the amino acid sequence of SEQ ID NO: 68 or 69. In some embodiments, the cell expressing the CAR is an immune cell. In some embodiments, the cell expressing the CAR is an immune effector cell. In some embodiments, the cell expressing the CAR is a T cell (CAR-T cell) or a natural killer (NK) cell (CAR-NK cell). In some embodiments, the cell expressing the CAR is not a T cell or an NK cell. In some embodiments, the CAR immune cell is an autologous immune cell. In some embodiments, the CAR immune cell is an allogenic immune cell. The cells expressing a CAR provided herein can be administered either alone, or as a pharmaceutical composition in combination with diluents and/or with other components such as chemotherapeutics, antibodies, cytokines or cell populations. Compositions provided herein are preferably formulated for intravenous administration that can be administered one or more times. In some embodiments, the cells expressing the CAR are administered intravenously.

In some embodiments, a method described herein comprises administering a cell expressing a CAR, wherein the CAR comprises (i) an antigenic determinant binding domain (ADBD) that binds to an AFP p26 antigenic determinant (AD), (ii) a transmembrane domain, and (iii) an intracellular domain. In some embodiments, between about $10 \times 10^6$ and about $300 \times 10^6$ cells expressing a CAR that specifically binds to the AFP p26 antigenic determinant is administered to the subject. In some embodiments, between about $50 \times 10^6$ and about $900 \times 10^6$ cells expressing a CAR that specifically binds to the AFP p26 antigenic determinant is administered to the subject. In some embodiments, between about $10 \times 10^6$ and about $500 \times 10^6$ cells expressing a CAR that specifically binds to the AFP p26 antigenic determinant is administered to the subject. In some embodiments, about $100 \times 10^6$ cells expressing a CAR that specifically binds to the AFP p26 antigenic determinant is administered to the subject. In some embodiments, about $50 \times 10^6$ cells expressing a CAR that specifically binds to the AFP p26 antigenic determinant is administered to the subject. In some embodiments, about $100 \times 10^6$ cells expressing a CAR that specifically binds to the AFP p26 antigenic determinant is administered to the subject. In some embodiments, about $150 \times 10^6$ cells expressing a CAR that specifically binds to the AFP p26 antigenic determinant is administered to the subject. In some embodiments, about $200 \times 10^6$ cells expressing a CAR that specifically binds to the AFP p26 antigenic determinant is administered to the subject. In some embodiments, about $250 \times 10^6$ cells expressing a CAR that specifically binds to the AFP p26 antigenic determinant is administered to the subject. In some embodiments, about $300 \times 10^6$ cells expressing a CAR that specifically binds to the AFP p26 antigenic determinant is administered to the subject. In some embodiments, about $400 \times 10^6$ cells expressing a CAR that specifically binds to the AFP p26 antigenic determinant is administered to the subject. In some embodiments, about $500 \times 10^6$ cells expressing a CAR that specifically binds to the AFP p26 antigenic determinant is administered to the subject. In some embodiments, about $600 \times 10^6$ cells expressing a CAR that specifically binds to the AFP p26 antigenic determinant is administered to the subject. In some embodiments, about $700 \times 10^6$ cells expressing a CAR that specifically binds to the AFP p26 antigenic determinant is administered to the subject. In some embodiments, more than one dose of the cells expressing a CAR that specifically binds to the AFP p26 antigenic determinant is administered to the subject, optionally wherein a single dose comprises between about $10 \times 10^6$ and about $300 \times 10^6$ cells, between about $50 \times 10^6$ and about $900 \times 10^6$ cells, between about $10 \times 10^6$ and about $500 \times 10^6$ cells, about $100 \times 10^6$ cells, about $50 \times 10^6$ cells, about $100 \times 10^6$ cells, about $150 \times 10^6$ cells, about $200 \times 10^6$ cells, about $250 \times 10^6$ cells, about $300 \times 10^6$ cells, about $400 \times 10^6$ cells, about $500 \times 10^6$ cells, about $600 \times 10^6$ cells, or about $700 \times 10^6$ cells. In some embodiments, two doses of the cells expressing a CAR that specifically binds to the AFP p26 antigenic determinant is administered to the subject. In some embodiments, three doses of the cells expressing a CAR that specifically binds to the AFP p26 antigenic determinant is administered to the subject. In some embodiments, four doses of the cells expressing a CAR that specifically binds to the AFP p26 antigenic determinant is administered to the subject. In some embodiments, five doses of the cells expressing a CAR that specifically binds to the AFP p26 antigenic determinant is administered to the subject. In some embodiments, the CAR that specifically binds to the AFP p26 antigenic determinant is administered to the subject at the same time as the first dose of the Adapter. In some embodiments, the CAR that specifically binds to the AFP p26 antigenic determinant is administered to the subject before the first dose of the Adapter. In some embodiments, the AFP p26 antigenic determinant comprises the amino acid sequence of SEQ ID NO: 37-43 or 44. In some embodiments, the AFP p26 antigenic determinant comprises the amino acid sequence of SEQ ID NO: 37. In some embodiments, the AFP p26 antigenic determinant comprises the amino acid sequence of SEQ ID NO: 39. In some embodiments, the CAR that specifically binds to the AFP p26 antigenic determinant comprises a D domain that specifically binds to the AFP p26 antigenic determinant, optionally wherein the D domain comprises the amino acid sequence of SEQ ID NO: 70-73 or 92-94. In some embodiments, the D domain that specifically binds to the AFP p26 antigenic determinant comprises the amino acid sequence of SEQ ID NO: 70 or 73. In some embodiments, the CAR that specifically binds to the AFP p26 antigenic determinant comprises the amino acid sequence of SEQ ID NO: 68 or 69. In some embodiments, the cell expressing the CAR is an immune cell. In some embodiments, the cell expressing the CAR is an immune effector cell. In some embodiments, the cell expressing the CAR is a T cell (CAR-T cell) or a natural killer (NK) cell (CAR-NK cell). In some embodiments, the cell expressing the CAR is not a T cell or an NK cell. In some embodiments, the CAR immune cell is an autologous immune cell. In some embodiments, the CAR immune cell is an allogenic immune cell. The cells expressing a CAR provided herein can be administered either alone, or as a pharmaceutical composition in combination with diluents and/or with other components such as chemotherapeutics, antibodies, cytokines or cell populations. Compositions provided herein are preferably formulated for intravenous administration that can be administered one or more times. In some embodiments, the cells expressing the CAR are administered intravenously.

In some embodiments, the Adapter is administered at about 10 μg/kg to about 10 mg/kg, about 50 μg/kg to about 5 mg/kg, about 10 μg/kg to about 2 mg/kg, about 20 μg/kg to about 1 mg/kg, or about 50 μg/kg to about 0.5 mg/kg. In some embodiments, the Adapter is administered at about 0.01 mg/kg, about 0.02 mg/kg, about 0.04 mg/kg, about 0.07 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 1 mg/kg, or about 2 mg/kg. In some embodiments, the Adapter is administered at about 0.07 mg/kg. In some embodiments, the Adapter is administered at about 0.1 mg/kg. In some embodiments, the Adapter is administered at about 0.1 mg/kg. In some embodiments, the Adapter is administered at about 1.6 mg, about 2.8 mg, about 3 mg, about 4 mg, about 8 mg, about 12 mg, about 16 mg, or about 20 mg. In some embodiments, the Adapter is administered at about 0.1 mg/kg. In some embodiments, the Adapter is administered at about 0.2 mg to about 200 mg, about 0.5 mg to about 100 mg, about 1 mg to about 50 mg, about 2 mg to about 25 mg, or about 2 mg to about 12 mg. In some embodiments, the Adapter is administered subcutaneously. In some embodiments, the Adapter is administered daily. In some embodiments, the Adapter is administered twice a day, three times a day or four times a day. In some embodiments, the Adapter is administered every other day. In some embodiments, the Adapter is administered every three days. In some embodiments, the Adapter is administered twice a week. In some embodiments, the Adapter is administered weekly. In some embodiments, the Adapter is administered for seven days. In some embodiments, the Adapter is administered for between about a week and about 2 months. In some embodiments, the Adapter is administered at the same frequency over the period of treatment. In some embodiments, the frequency of administration decreases over the period of treatment. In some embodiments, the Adapter is first administered daily for about a week followed by administration twice a week. In one embodiment, between about $50 \times 10^6$ and about $300 \times 10^6$ cells expressing the CAR has been administered to the patient. In one embodiment, about $100 \times 10^6$ cells expressing the CAR has been administered to the patient.

In some embodiments, the D domain that binds to CD123 comprises an amino acid sequence selected from the group consisting of SEQ ID NO: 8-33, 99 and 100. In some embodiments, the D domain that binds to CD123 comprises an amino acid sequence selected from the group consisting of SEQ ID NO: 8, 13, 14, 31, 32, and 33. In some embodiments, the D domain that binds to CD123 comprises the amino acid sequence of SEQ ID NO: 8. In some embodiments, the D domain that binds to CD123 comprises the amino acid sequence of SEQ ID NO: 13. In some embodiments, the D domain that binds to CD123 comprises the amino acid sequence of SEQ ID NO: 14. In some embodiments, the D domain that binds to CD123 comprises the amino acid sequence of SEQ ID NO: 31. In some embodiments, the D domain that binds to CD123 comprises the amino acid sequence of SEQ ID NO: 32. In some embodiments, the D domain that binds to CD123 comprises the amino acid sequence of SEQ ID NO: 33.

In some embodiments, the transmembrane domain comprises a CD8a, 41BB or CD28 transmembrane domain. In some embodiments, the transmembrane domain comprises a CD8a transmembrane domain. In some embodiments, the CD8a transmembrane domain comprises the amino acid sequence of SEQ ID NO: 113. In some embodiments, the CD8a transmembrane domain comprises the amino acid sequence of SEQ ID NO: 114. In some embodiments, the intracellular signaling domain is selected from the group consisting of a domain of a human T cell receptor alpha, beta, or zeta chain; a human 41BB domain; a human CD28 domain; and any combination thereof. In some embodiments, the intracellular signaling domain comprises the intracellular domain of a costimulatory molecule selected from the group consisting of CD27, CD28, 41BB, OX40, CD30, CD40, PD1, lymphocyte function-associated antigen-1 (LFA-1), CD2, CD7, LIGHT, NKG2C, NKG2D, B7-H3, a ligand that specifically binds with CD83, and any combination thereof. In some embodiments, the intracellular signaling domain contains the sequence of SEQ ID NO: 115, 116 or combination thereof. In some embodiments, the intracellular signaling domain contains the sequence of SEQ ID NO: 117.

In some embodiments, the AFP p26 AD comprises an amino acid sequence selected from the group consisting of SEQ ID NO: 37-43 and 44. In some embodiments, the AFP p26 AD comprises the amino acid sequence of SEQ ID NO: 37. In some embodiments, the AFP p26 AD comprises the amino acid sequence of SEQ ID NO: 39.

In some embodiments, the ADBD that binds to AFP p26 AD comprises an scFv that binds to AFP p26 AD. In some embodiments, the ADBD that binds to AFP p26 AD comprises a D domain that binds to AFP p26 AD. In some embodiments, the D domain that binds to AFP p26 AD comprises an amino acid sequence selected from the group consisting of SEQ ID NO: 74-93 and 94. In some embodiments, the D domain that binds to AFP p26 AD comprises the amino acid sequence of SEQ ID NO: 70-73 or 92-94. In some embodiments, the D domain that binds to AFP p26 AD comprises the amino acid sequence of SEQ ID NO: 73.

In some embodiments, the CAR comprising a D domain that binds to AFP p26 AD comprises the amino acid sequence of SEQ ID NO: 68. In some embodiments, the CAR comprising a D domain that binds to AFP p26 AD comprises the amino acid sequence of SEQ ID NO: 69.

In some embodiments, the CAR comprises an ADBD that binds to an AD other than CD123, the ADBD binds to a tumor antigen. In some embodiments, the tumor antigen is selected from the group: BCMA, CD19, CD22, CS1, HER2, TACI, BAFFR, and PDL1. In some embodiments, the tumor antigen is BCMA. In some embodiments, the tumor antigen is CD19. In some embodiments, the tumor antigen is selected from the group: CD45, CD26, CD30, CD33, and CD38.

In some embodiments, the Adapter comprising (i) a D domain that binds to CD123 and (ii) an AFP p26 AD comprises the amino acid sequence of SEQ ID NO: 50-54 or 55. In some embodiments, the Adapter comprising (i) a D domain that binds to CD123 and (ii) an AFP p26 AD comprises the amino acid sequence of SEQ ID NO: 50. In some embodiments, the Adapter comprising (i) a D domain that binds to CD123 and (ii) an AFP p26 AD comprises the amino acid sequence of SEQ ID NO: 51. In some embodiments, the Adapter comprising (i) a D domain that binds to CD123 and (ii) an AFP p26 AD comprises the amino acid sequence of SEQ ID NO: 52. In some embodiments, the Adapter comprising (i) a D domain that binds to CD123 and (ii) an AFP p26 AD comprises the amino acid sequence of SEQ ID NO: 53. In some embodiments, the Adapter comprising (i) a D domain that binds to CD123 and (ii) an AFP p26 AD comprises the amino acid sequence of SEQ ID NO: 54. In some embodiments, the Adapter comprising (i) a D domain that binds to CD123 and (ii) an AFP p26 AD comprises the amino acid sequence of SEQ ID NO: 55. In some embodiments, the Adapter comprising (i) a D domain that binds to CD123 and (ii) an AFP p26 AD comprises the amino acid sequence of SEQ ID NO: 56-60 or 61. In some embodiments, the Adapter comprising (i) a D domain that binds to CD123 and (ii) an AFP p26 AD comprises the amino acid sequence of SEQ ID NO: 56. In some embodiments, the Adapter comprising (i) a D domain that binds to CD123 and (ii) an AFP p26 AD comprises the amino acid sequence of SEQ ID NO: 57. In some embodiments, the Adapter comprising (i) a D domain that binds to CD123 and (ii) an AFP p26 AD comprises the amino acid sequence of SEQ ID NO: 58. In some embodiments, the Adapter comprising (i) a D domain that binds to CD123 and (ii) an AFP p26 AD comprises the amino acid sequence of SEQ ID NO: 59. In some embodiments, the Adapter comprising (i) a D domain that binds to CD123 and (ii) an AFP p26 AD comprises the amino acid sequence of SEQ ID NO: 60. In some embodiments, the Adapter comprising (i) a D domain that binds to CD123 and (ii) an AFP p26 AD comprises the amino acid sequence of SEQ ID NO: 61.

In some embodiments, the Adapter comprises (i) a D domain that binds to CD123 and comprises the amino acid sequence of SEQ ID NO: 8, 13, 14, 31, 32, or 33, and (ii) an AFP p26 AD comprising the amino acid sequence of SEQ ID NO: 37 or 39, and the CAR comprises a D domain that binds to AFP p26 AD and comprises the amino acid sequence of SEQ ID NO: 73. In some embodiments, the D domain that binds to CD123 comprises the amino acid sequence of SEQ ID NO: 8. In some embodiments, the D domain that binds to CD123 comprises the amino acid sequence of SEQ ID NO: 13. In some embodiments, the D domain that binds to CD123 comprises the amino acid sequence of SEQ ID NO: 14. In some embodiments, the D domain that binds to CD123 comprises the amino acid sequence of SEQ ID NO: 31. In some embodiments, the D domain that binds to CD123 comprises the amino acid sequence of SEQ ID NO: 32. In some embodiments, the D domain that binds to CD123 comprises the amino acid sequence of SEQ ID NO: 33.

In some embodiments, the Adapter comprising (i) a D domain that binds to CD123 and (ii) an AFP p26 AD comprises the amino acid sequence of SEQ ID NO: 50-54 or 55, and the CAR comprising a D domain that binds to AFP p26 AD comprises the amino acid sequence of SEQ ID NO: 68. In some embodiments, the Adapter comprising (i) a D domain that binds to CD123 and (ii) an AFP p26 AD comprises the amino acid sequence of SEQ ID NO: 50, and the CAR comprising a D domain that binds to AFP p26 AD comprises the amino acid sequence of SEQ ID NO: 68. In some embodiments, the Adapter comprising (i) a D domain that binds to CD123 and (ii) an AFP p26 AD comprises the amino acid sequence of SEQ ID NO: 56-60 or 61, and the CAR comprising a D domain that binds to AFP p26 AD comprises the amino acid sequence of SEQ ID NO: 68. In some embodiments, the Adapter comprising (i) a D domain that binds to CD123 and (ii) an AFP p26 AD comprises the amino acid sequence of SEQ ID NO: 61, and the CAR comprising a D domain that binds to AFP p26 AD comprises the amino acid sequence of SEQ ID NO: 68.

In some embodiments, the target AD is selected from: CD45, CD26, CD30, CD33, and CD38. In some embodiments, the target AD is selected from: CD19, CD22, CD123, BCMA, CS1, HER2, TACI, BAFFR, and PDL1. In some embodiments, the target AD is BCMA. In some embodiments, the target AD is CD19. In some embodiments, the target AD is CD45. In some embodiments, the cell expressing the CAR is an immune cell.

In some embodiments, the cell expressing the CAR is an immune effector cell. In some embodiments, the cell expressing the CAR is a T cell. In some embodiments, the cell expressing the CAR is a natural killer (NK) cell.

In some embodiments, the target cell is a cancer cell. In some embodiments, the target cell is an AML cell. In some embodiments, the target cell is a myelodysplasia cell. In some embodiments, the target cell is a B-cell acute lymphoblastic leukemia cell. In some embodiments, the target cell is a hairy cell leukemia cell. In some embodiments, the target cell is a Hodgkin's lymphoma cell. In some embodiments, the target cell is a blastic plasmacytoid dendritic neoplasm (BPDCN) cell.

In some embodiments, the cell expressing the CAR and the Adapter is administered separately in any order. In some embodiments, the administering the Adapter comprises administering a pharmaceutical composition comprising the Adapter. In some embodiments, the administering the Adapter and cell expressing the CAR comprises administering a pharmaceutical composition comprising the Adapter and a pharmaceutical composition comprising the cell expressing the CAR.

In some embodiments, the patient has previously been treated with an Adapter (in addition to the cell expressing a CAR). In some embodiments, the Adapter that is administered to the patient and the Adapter that was previously administered to the patient bind to different ADs (e.g., on the same or different target cells).

In some embodiments, the target AD is selected from: CD45, CD26, CD30, CD33, and CD38. In some embodiments, the target AD is selected from: CD19, CD22, CD123, BCMA, CS1, HER2, TACI, BAFFR, and PDL1. In further embodiments, the target AD is BCMA. In further embodiments, the target AD is CD45. In other embodiments, the target AD is CS1. In other embodiments, the target AD is CD123. In other embodiments, the target AD is CD19. In other embodiments, the target AD is CD22. In other embodiments, the target AD is TACI. In other embodiments, the target AD is BAFFR. In other embodiments, the target AD is PDL1. In other embodiments, the target AD is HER2.

In some embodiments, wherein the CAR comprises an ADBD that binds to an AD other than CD123, the ADBD binds to a tumor antigen. In further embodiments, the tumor antigen is selected from the group: CD45, CD26, CD30, CD33, and CD38. In further embodiments, the tumor antigen is selected from the group: BCMA, CD19, CD22, CS1, HER2, TACI, BAFFR, and PDL1. In further embodiments, the tumor antigen is BCMA. In further embodiments, the tumor antigen is CD19.

In some embodiments, the cell expressing the CAR is an immune cell. In some embodiments, the cell expressing the CAR is an immune effector cell. In some embodiments, the cell expressing the CAR is a T cell (CAR-T cell) or a natural killer (NK) cell (CAR-NK cell). In some embodiments, the immune cell is an autologous immune cell. In some embodiments, the immune cell is an allogenic cell. In some embodiments, the cell expressing the CAR is not a T cell or an NK cell.

In some embodiments, the target cell is an AML cell. In some embodiments, the target cell is a myelodysplasia cell. In some embodiments, the target cell is a B-cell acute lymphoblastic leukemia cell. In some embodiments, the target cell is a hairy cell leukemia cell. In some embodiments, the target cell is a Hodgkin's lymphoma cell. In some embodiments, the target cell is a blastic plasmacytoid dendritic neoplasm (BPDCN) cell.

The contacting can occur in vitro, ex vivo, or in vivo. In one embodiment, the contacting occurs in a patient, e.g. a human patient, for example after administration of an Adapter to a patient who has received a cell expressing a CAR or after administration of a cell expressing a CAR to a patient who has received an Adapter. In some embodiments, a method comprises administering the Adapter to a patient who has previously been administered the cell expressing the CAR.

In certain embodiments, the CAR comprises a single-chain variable fragment (scFv) ADBD. In other embodiments, the CAR comprises an alternative scaffold binding domain (ASBD) ADBD. In further embodiments, the CAR comprises a D domain.

In some embodiments, the CAR comprises 2 ADBDs. In other embodiments, the CAR comprises an ASBD and a scFv. In further embodiments, the CAR comprises a D domain and a scFv. In some embodiments, the CAR comprises 2 ASBDs. In further embodiments, the CAR comprises 2 D domains.

In some embodiments, the CAR intracellular domain is a signaling domain. In further embodiments, the CAR intracellular domain comprises a primary signaling domain. In certain embodiments, the CAR intracellular domain comprises a CD3 primary signaling domain. In some embodiments, the CAR intracellular domain further comprises a costimulatory signaling domain. In further embodiments, the costimulatory signaling domain is selected from: CD28, 41BB, CD27, and CD134. In particular embodiments, the CAR intracellular signaling domain comprises a 41BB costimulatory signaling domain. In some embodiments, the intracellular signaling domain contains the sequence of SEQ ID NO: 115, 116 or combination thereof. In some embodiments, the intracellular signaling domain contains the sequence of SEQ ID NO: 117.

In some embodiments, the target AD is selected from: CD45, CD26, CD30, CD33, and CD38. In some embodiments, the target AD is selected from: CD19, CD22, CD123, BCMA, CS1, HER2, TACI, BAFFR, and PDL1. In further embodiments, the target AD is BCMA. In other embodiments, the target AD is CS1. In other embodiments, the target AD is CD123. In other embodiments, the target AD is CD19. In other embodiments, the target AD is CD22. In other embodiments, the target AD is TACI. In other embodiments, the target AD is BAFFR. In other embodiments, the target AD is PDL1. In other embodiments, the target AD is HER2.

In some embodiments, the CAR comprises 2 ADBDs that bind to separate targets. In further embodiments, the CAR binds to CD19 and CD123. In other embodiments, the CAR binds to BCMA and CD123. In other embodiments, the CAR binds to CD22 and CD123. In other embodiments, the CAR binds to PDL1 and CD123.

In some embodiments, the Adapter comprises an AD of a tumor antigen. In further embodiments, the tumor antigen is selected from the group: CD45, CD26, CD30, CD33, and CD38.

In some embodiments, the Adapter comprises an AD of a tumor antigen. In further embodiments, the tumor antigen is selected from the group: BCMA, CD19, CD22, CS1, HER2, TACI, BAFFR, and PDL1.

In some embodiments, the Adapter comprises an ADBD that is a scFv. In further embodiments, the Adapter comprises an ADBD that is an ASBD. In some embodiments, the Adapter comprises a D domain.

In some embodiments, the Adapter comprises two ADBDs. In further embodiments, the Adapter comprises two ADBDs that (a) are the same, (b) bind to the same antigenic determinant, (c) bind to different ADs of the same antigen, (d) bind to different antigens on the same cell, or (e) bind to different antigens on different cells. In some embodiments, the Adapter comprises two ASBDs. In certain embodiments, the Adapter comprises two D domains. In some embodiments, the Adapter comprises an ADBD that is a scFv and an ADBD that is an ASBD. In other embodiments, the Adapter comprises an ADBD that is a scFv and an ADBD that is a D domain.

In some embodiments, the Adapter comprises an ADBD that binds to a member selected from: CD45, CD26, CD30, CD33, and CD38. In certain embodiments, the Adapter comprises an ADBD binds to CD45. In other embodiments, the Adapter comprises an ADBD that binds to CD26. In some embodiments, the Adapter comprises an ADBD that binds to CD30. In other embodiments, the Adapter comprises an ADBD that binds to CD33. In other embodiments, the Adapter comprises an ADBD that binds to CD38. In some embodiments, the Adapter comprises an ADBD that binds to CD45.

In some embodiments, the Adapter comprises an ADBD that binds to a member selected from: BCMA, CD123, CD19, CD22, CS1, HER2, TACI, BAFFR, and PDL1. In certain embodiments, the Adapter comprises an ADBD binds to BCMA. In other embodiments, the Adapter comprises an ADBD that binds to CD123. In some embodiments, the Adapter comprises an ADBD that binds to CD19. In other embodiments, the Adapter comprises an ADBD that binds to CD22. In other embodiments, the Adapter comprises an ADBD that binds to CS1. In other embodiments, the Adapter comprises an ADBD that binds to HER2. In other embodiments, the Adapter comprises an ADBD that binds to TACI. In other embodiments, the Adapter comprises an ADBD that binds to BAFFR. In other embodiments, the Adapter comprises an ADBD that binds to PDL1.

In some embodiments, the Adapter is bispecific. In further embodiments, the Adapter comprises an ADBD that binds to CD123 and an ADBD that binds to CD33. In other embodiments, the Adapter comprises an ADBD that binds to CD123 and an ADBD that binds to CD38. In other embodiments, the Adapter comprises an ADBD that binds to CD123 and an ADBD that binds to LeY. In other embodiments, the Adapter comprises an ADBD that binds to PDL1 and an ADBD that binds to CD123.

In some embodiments, the target cell is a tumor cell. In further embodiments, the tumor cell is selected from the group: acute myeloid leukemia (AML), myelodysplasia cell, B-cell acute lymphoblastic leukemia, hairy cell leukemia, Hodgkin's lymphoma and blastic plasmacytoid dendritic neoplasm (BPDCN). In some embodiments, the tumor cell is an AML tumor cell. In some embodiments, the tumor cell is a myelodysplasia cell. In some embodiments, the tumor cell is a B-cell acute lymphoblastic leukemia tumor cell. In some embodiments, the tumor cell is a hairy cell leukemia tumor cell. In some embodiments, the tumor cell is a Hodgkin's lymphoma tumor cell. In some embodiments, the tumor cell is a BPDCN tumor cell. In some embodiments, the tumor cell expresses CD123.

In the methods of killing a target cell provided herein, the target cell can be a cell of the immune system. In some embodiments, the target cell is a B cell. In some embodiments, the target cell is a T cell. In some embodiments, the target cell is a naïve T cell. In some embodiments, the target cell is a memory T cell. In some embodiments, the target cell is an endothelial cell.

In some embodiments, the cell expressing the CAR is an immune effector cell. An immune effector cell is a cell that is involved in an immune response, e.g., in the promotion of an immune effector response. Examples of immune effector cells include T cells (e.g., alpha/beta T cells and gamma/delta T cells), B cells, natural killer (NK) cells, natural killer T (NKT) cells, mast cells, and myeloid-derived phagocytes. An immune effector function or immune effector response is a function or response of for example, an immune effector cell that enhances or promotes an immune attack of a target cell. In some embodiments, the immune effector function or response refers a property of a T or NK cell that promotes killing, or the inhibition of growth or proliferation, of a target cell. For example, primary stimulation and costimulation are examples of immune effector function or response of a T cell. In particular embodiments, an immune effector function or response is promoted by the action of the disclosed CAR, Adapter, and/or CAR and Adapter compositions. Such function or response results in, for example, a CAR cell that is more effective at proliferation, cytokine production, cytotoxicity or upregulation of cell surface markers such as CD25, CD69, and CD107a.

In some embodiments, the immune effector cell is a T cell. In other embodiments, the immune effector cell is an NK cell. In some embodiments, the immune effector cell is not a T cell or an NK cell. In some embodiments, the immune effector cell is an autologous immune cell. In some embodiments, the immune effector cell is an allogenic cell. In some embodiments, the cell expressing the CAR kills the target cell. In some embodiments, binding of the Adapter to an AD blocks the activity of the antigen comprising the AD.

In some embodiments, the CAR cell kills the target cell upon direct binding to the target cell. In some embodiments, the CAR cell kills the target cell upon binding to the Adapter, wherein the Adapter is bound to the target cell.

In some embodiments, binding of CAR to the target cell and/or to the Adapter results in intracellular signaling in the cell expressing the CAR.

In some embodiments, binding of the CAR to the target cell and/or to the Adapter results in degranulation. Degranulation can result in the release of, depending on the cell type, antimicrobial, cytotoxic or other molecules from secretory granules in the immune cell. Molecules like perforin (a pore forming cytotoxin) or granzymes (serine proteases that induce apoptosis in the target cell) aid T cells and NK cells in killing tumor cells (or other cell types).

In some embodiments, binding of the CAR to the target cell and/or to the Adapter results in cytokine secretion by the cell expressing the CAR. The cytokine can be, for example, interferon gamma (IFNγ).

In some embodiments, binding of the CAR to the target cell and/or to the Adapter results in proliferation of the cell expressing the CAR.

In some embodiments, a method disclosed herein comprises administering an Adapter and a cell expressing a CAR to the patient. The Adapter and the cell expressing the CAR can be administered in the same pharmaceutical composition or in different pharmaceutical compositions. The Adapter and the cell expressing the CAR can be administered in different pharmaceutical compositions. The Adapter and the cell expressing the CAR can be administered simultaneously or consecutively. In some embodiments, cell expressing the CAR and the Adapter are administered simulataneously. In some embodiments, the cell expressing the CAR and the Adapter are administered consecutively. In some embodiments, the Adapter is administered after administering the cell expressing the CAR. In some embodiments, the Adapter is administered to a subject that previously has been administered a CAR immune cell. In some embodiments, the the cell expressing the CAR is administered before the Adapter.

In some embodiments, the disclosure provides methods comprising administering to the subject a therapeutically effective amount of a CAR immune cell comprising a chimeric antigen receptor (CAR), wherein the CAR comprises a target binding domain that comprises a D domain that specifically binds AFP p26 (e.g., comprising an amino acid sequence selected from the group consisting of SEQ ID NO: 74-93 and 94), a transmembrane domain, and an intracellular domain (comprising a signaling domain) In some embodiments, the disclosure provides a method of treating a subject having cancer, comprising administering to the subject a therapeutically effective amount of a CAR immune cell comprising a chimeric antigen receptor (CAR), wherein the CAR comprises a target binding domain that comprises a D domain that specifically binds AFP p26 (e.g., comprising an amino acid sequence selected from the group consisting of SEQ ID NO: 70-73 and 92-94), a transmembrane domain, and an intracellular domain (comprising a signaling domain) In some embodiments, the p26-binding DD comprise the amino acid sequence of SEQ ID NO: 73. In some embodiments, the administered CAR immune cell is an immune effector cell. In some embodiments, the administered CAR immune cell is a T cell. In some embodiments, the administered CAR immune cell is a NK cell. In some embodiments, the administered CAR immune cell is not a T cell or an NK cell. In further embodiments, a combination of different CAR immune cell types (e.g., NK cells and T cells) is administered to the subject. In some embodiments, the CAR immune cell is an autologous immune cell. In some embodiments, the CAR immune cell is an allogenic immune cell. In some embodiments, the administration of a CAR immune cell that specifically binds p26 to a subject renders the subject receptive to treatment of cancer by the administration of an Adapter polypeptide comprising (i) a p26 antigenic determinant and (ii) a target binding domain that is expressed by a cancer cell of the subject (e.g., CD123), wherein the Adapte directs or redirects the CAR immune cell to generate a cytotoxic signal that results in cytotoxic effects on the cancer cell, thereby treating the cancer. The CAR immune cell and the Adapter can be administered simulataneously or consecutively in any order. In some embodiments, the CAR immune cell and the Adapter are administered simulataneously. In some embodiments, the CAR immune cell and the Adapter are administered consecutively. In some embodiments, the Adapter is administered after administering the CAR immune cell. In some embodiments, the Adapter is administered to a subject that previously has been administered a CAR immune cell.

In some embodiments, wherein CAR T cells are administered to the subject having cancer, the binding of the target of interest (e.g., CD123 or AFP p26) stimulates the CAR T cell to initiate intracellular signaling. In further embodiments, the binding of the CAR T cell to the target of interest stimulates the T cell to initiate intracellular signaling and produce cytokines. In further embodiments, the binding of the CAR T cell to the target of interest stimulates the T cell to initiate intracellular signaling, produce cytokines, and degranulate, leading to the cytotoxic effects on the cancer cell. In some embodiments, the CAR T cell proliferates in response to binding the target of interest. Advantageously, in some embodiments, the activity of the CAR T cell does not result in the T cell exhibiting a phenotype associated with T cell exhaustion. In some embodiments, the transmembrane domain of the CAR T cell comprises CD8a, 41BB or CD28, and the cytoplasmic domain comprises an alpha, beta, or zeta chain of the T cell receptor. In some embodiments, the cytoplasmic domain contains the sequence of SEQ ID NO: 115, 116 or combination thereof. In some embodiments, the cytoplasmic domain contains the sequence of SEQ ID NO: 117.

In some embodiments, wherein p26-binding CAR immune cells and Adapter polypeptide are administered to the subject having cancer, the directing or redirecting of the CAR immune cells by the Adapter polypeptide to the target of interest (e.g., CD123) stimulates the CAR immune cell to initiate intracellular signaling. In further embodiments, the directing or redirecting of the CAR immune cell via the Adapter polypeptide stimulates the immune cell to initiate intracellular signaling and produce cytokines. In further embodiments, the directing or redirecting of the CAR immune cell to the target of interest stimulates the immune cell to initiate intracellular signaling, produce cytokines, and degranulate, leading to the cytotoxic effects on the cancer cell. In some embodiments, the CAR immune cell proliferates in response to binding the target of interest. In some embodiments, the administered CAR immune cell is an immune effector cell. In some embodiments, the administered CAR immune cell is a T cell. In some embodiments, the administered CAR immune cell is a NK cell. In some embodiments, the administered CAR immune cell is not a T cell or an NK cell. In further embodiments, a combination of different CAR immune cell types (e.g., NK cells and T cells) is administered to the subject. In some embodiments, the CAR immune cell is an autologous immune cell. In some embodiments, the CAR immune cell is an allogenic immune cell. Advantageously, in some embodiments, immune cell is a T cell and the activity of the CAR T cell does not result in the T cell exhibiting a phenotype associated with T cell exhaustion. In some embodiments, the transmembrane domain of the CAR T cell comprises CD8a, 41BB or CD28, and the cytoplasmic domain comprises an alpha, beta, or zeta chain of the T cell receptor. The CAR immune cell and the Adapter can be administered simulataneously or consecutively in any order. In some embodiments, the CAR immune cell and the Adapter are administered simulataneously. In some embodiments, the CAR immune cell and the Adapter are administered consecutively. In some embodiments, the Adapter is administered after administering the CAR immune cell. In some embodiments, the Adapter is administered to a subject that previously has been administered a CAR immune cell. In some embodiments, the CAR comprises a p26-binding DD comprises an amino acid sequence selected from the group consisting of SEQ ID NO: 70-73 or 92-94. In some embodiments, the p26-binding DD comprise the amino acid sequence of SEQ ID NO: 73.

In some embodiments of a method disclosed herein, the patient has been diagnosed with cancer and the target cell is a cancer cell. In one embodiment, the cancer cell is a prostate cancer cell, a breast cancer cell, a colorectal cancer cell, a lung cancer cell, an osteosarcoma cell, or a glioblastoma cell. Thus, in some embodiments, the methods provided herein treat cancer. In some embodiments, the target cell is an endothelial cell.

Cancers that can be treated include tumors that are not vascularized, or not yet substantially vascularized, as well as vascularized tumors. The cancers can comprise non-solid tumors (such as hematological tumors, for example, leukemias and lymphomas) or can comprise solid tumors. Types of cancers to be treated include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

In another embodiment, the methods described herein are useful for treating a patient having a hematological cancer. Examples of hematological (or hematogenous) cancers include leukemias, including acute leukemias (such as acute lymphocytic leukemia, acute myelocytic leukemia, acute myelogenous leukemia and myeloblasts, promyeiocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome (e.g., high-risk myelodysplastic syndrome), hairy cell leukemia and myelodysplasia. In some embodiments, the hematological cancer is acute myeloid leukemia (AML), myelodysplastic syndrome (e.g., high-risk myelodysplastic syndrome), B-cell acute lymphoblastic leukemia, hairy cell leukemia, Hodgkin's lymphoma or blastic plasmacytoid dendritic neoplasm (BPDCN). In some embodiments, the hematological cancer is AML. In some embodiments, the hematological cancer is myelodysplastic syndrome (e.g., high-risk myelodysplastic syndrome). In some embodiments, the hematological cancer is B-cell acute lymphoblastic leukemia. In some embodiments, the hematological cancer is hairy cell leukemia. In some embodiments, the hematological cancer is Hodgkin's lymphoma. In some embodiments, the hematological cancer is blastic plasmacytoid dendritic neoplasm (BPDCN).

In some embodiments, the cancer is a relapsed of refractory cancer. In some embodiments, the cancer is a relapsed cancer. In some embodiments, the cancer has relapsed following chemotherapy. In some embodiments, the cancer has relapsed following treatment with a biological agent. In some embodiments, the biological agent is a therapeutic antibody or a CAR-T cell. In some embodiments, the cancer is a refractory cancer. In some embodiments, the cancer is refractory to chemotherapy. In some embodiments, the cancer is refractory to treatment with a biological agent. In some embodiments, the biological agent is a therapeutic antibody or a CAR-T cell.

In some embodiments, the cancer is a relapsed of refractory hematological cancer. In some embodiments, the cancer is a relapsed hematological cancer. In some embodiments, the cancer is a hematological cancer that has relapsed following chemotherapy. In some embodiments, the cancer is a hematological cancer that has relapsed following treatment with a biological agent. In some embodiments, the biological agent is a therapeutic antibody or a CAR-T cell. In some embodiments, the cancer is a hematological cancer that has relapsed following autologous bone marrow transplantation. In some embodiments, the cancer is a hematological cancer that has relapsed following allogeneic bone marrow transplantation. In some embodiments, the cancer is a hematological cancer that has relapsed following hematopoietic stem cell transplantation (HSCT). In some embodiments, the HSCT is autologous HSCT. In some embodiments, the cancer is a refractory hematological cancer. In some embodiments, the cancer is a hematological cancer that is refractory to chemotherapy. In some embodiments, the cancer is a hematological cancer that is refractory to treatment with a biological agent. In some embodiments, the biological agent is a therapeutic antibody or a CAR-T cell. In some embodiments, the hematological cancer is acute myeloid leukemia (AML), myelodysplastic syndrome (e.g., high-risk myelodysplastic syndrome), B-cell acute lymphoblastic leukemia, hairy cell leukemia, Hodgkin's lymphoma or blastic plasmacytoid dendritic neoplasm (BPDCN). In some embodiments, the hematological cancer is AML. In some embodiments, the hematological cancer is myelodysplastic syndrome (e.g., high-risk myelodysplastic syndrome). In some embodiments, the hematological cancer is B-cell acute lymphoblastic leukemia. In some embodiments, the hematological cancer is hairy cell leukemia. In some embodiments, the hematological cancer is Hodgkin's lymphoma. In some embodiments, the hematological cancer is blastic plasmacytoid dendritic neoplasm (BPDCN). In some embodiments, the target cell cell is a B cell. In some embodiments, the target cell is a T cell. In some embodiments, the target cell is a naïve T cell. In some embodiments, the target cell is a memory T cell. In some embodiments, the target cell is a myeloma cell. In some embodiments, the target cell is an AML cell. In some embodiments, the target cell is a myelodysplasia cell. In some embodiments, the target cell is a B-cell acute lymphoblastic leukemia cell. In some embodiments, the target cell is a hairy cell leukemia cell. In some embodiments, the target cell is a Hodgkin's lymphoma cell. In some embodiments, the target cell is a blastic plasmacytoid dendritic neoplasm (BPDCN) cell. In some embodiments, the target cell is an endothelial cell.

In some embodiments, cancers and disorders can be treated using the Adapters or CAR cells that target CD19, CD20, CD22, and ROR1. In one specific embodiment, the CAR, Adapter and/or CAR/Adapter combination targets CD22 and is used to treat B-cell lymphoma. In another embodiment the CAR, Adapter and/or CAR/Adapter combination targets CD19 and is used to treat cancers and disorders including but are not limited to pre-B ALL (pediatric indication), adult ALL, mantle cell lymphoma, diffuse large B-cell lymphoma, and salvage post allogenic bone marrow transplantation. In another embodiment the CAR, Adapter and/or CAR/Adapter combination targets CS1 and is used to treat multiple myeloma. In another embodiment the CAR, Adapter and/or CAR/Adapter combination targets BCMA and is used to treat multiple myeloma. In another embodiment the CAR, Adapter and/or CAR/Adapter combination targets CS1 and BCMA, and is used to treat multiple myeloma.

In some embodiments, the disclosure provides a method of treating a subject having cancer, comprising administering to the subject a therapeutically effective amount of a CAR immune cell comprising a chimeric antigen receptor (CAR), wherein the CAR comprises a target binding domain that comprises a D domain that specifically binds CD123 (e.g., comprising an amino acid sequence selected from the group consisting of SEQ ID NO: 8-33, 99 and 100), a transmembrane domain, and an intracellular domain (comprising a signaling domain) In some embodiments, the administered CAR immune cell is an immune effector cell. In some embodiments, the administered CAR immune cell is a T cell. In some embodiments, the administered CAR immune cell is a NK cell. In some embodiments, the administered CAR immune cell is not a T cell or an NK cell. In further embodiments, a combination of different CAR immune cell types (e.g., NK cells and T cells) is administered to the subject. In some embodiments, the CAR immune cell is an autologous immune cell. In some embodiments, the CAR immune cell is an allogenic immune cell. In some embodiments, the CD123-specific D domain comprises an amino acid sequence selected from the group consisting of SEQ ID NO: 8, 13, 14, 31, 32, and 33. In some embodiments, the CD123-specific DD comprise the amino acid sequence of SEQ ID NO: 8. In some embodiments, the CD123-specific DD comprise the amino acid sequence of SEQ ID NO: 13. In some embodiments, the CD123-specific DD comprise the amino acid sequence of SEQ ID NO: 14. In some embodiments, the CD123-specific DD comprise the amino acid sequence of SEQ ID NO: 31. In some embodiments, the CD123-specific DD comprise the amino acid sequence of SEQ ID NO: 32. In some embodiments, the CD123-specific DD comprise the amino acid sequence of SEQ ID NO: 33. In some embodiments, the target binding domain of the administered CAR immune cell specifically binds CD123 expressed by a cancer cell of the subject, and induces the CAR immune cell to generate a cytotoxic signal that results in cytotoxic effects on the cancer cell, thereby treating the cancer.

In some embodiments, wherein CAR T cells are administered to the subject having cancer, the binding of the target of interest (e.g., CD123 or AFP p26) stimulates the CAR T cell to initiate intracellular signaling. In further embodiments, the binding of the CAR T cell to the target of interest stimulates the T cell to initiate intracellular signaling and produce cytokines. In further embodiments, the binding of the CAR T cell to the target of interest stimulates the T cell to initiate intracellular signaling, produce cytokines, and degranulate, leading to the cytotoxic effects on the cancer cell. In some embodiments, the CAR T cell proliferates in response to binding the target of interest. Advantageously, in some embodiments, the activity of the CAR T cell does not result in the T cell exhibiting a phenotype associated with T cell exhaustion. In some embodiments, the transmembrane domain of the CAR T cell comprises CD8a, 41BB or CD28, and the cytoplasmic domain comprises an alpha, beta, or zeta chain of the T cell receptor.

In some embodiments, the administered CAR further comprises 2, 3, 4, 5, or more than 5, DD and/or other binding domains (e.g., scFv) that specifically bind the target of interest (e.g., CD123) expressed by the cancer cell. In additional embodiments, the administered CAR further comprises 2, 3, 4, 5, or more than 5, DD or other binding domains (e.g., scFv) that specifically binds a different target of interest expressed by the cancer cell. In additional embodiments, the administered CAR further comprises 2, 3, 4, 5, or more than 5, DD or other binding domains (e.g., scFv) that specifically binds a different target of interest expressed by a different cancer cell or a vascular endothelial cell.

In some embodiments, the administered immune cell further comprises a second CAR polypeptide having a DD or other binding domain (e.g., scFv) that specifically binds a second target of interest expressed by the cancer cell. In some embodiments, the administered immune cell further comprises a second CAR polypeptide having a DD or other binding domain (e.g., scFv) that specifically binds a second target of interest expressed by a different cancer cell or a vascular endothelial cell.

In some embodiments, the administration of the immune cells with a CAR is intravenous. In other embodiments, the immune cells with a CAR is administered through an intra-arterial, intramuscular, local, or other acceptable route for the given treatment scenario.

In additional embodiments, the DDpp fusion protein binds (1) a target on a cell or tissue of interest (e.g., a tumor antigen on a tumor cell) and (2) a target on an effector cell, such as, a T cell receptor molecule. According to one embodiment, the binding of one or more targets by the DDpp fusion protein is used to direct an immune response to a cell, tissue, or other location of interest in a patient. For example, in some embodiments, the DDpp fusion protein specifically binds a target on the surface of an effector cell. Thus, in some embodiments, the DDpp fusion protein specifically binds a target on the surface of a T cell. In specific embodiments, the DDpp fusion protein specifically binds CD3. In other embodiments, the DDpp fusion protein specifically binds CD2. In a further embodiment, the DDpp fusion protein specifically binds the T cell receptor (TCR). According to additional embodiments, the DDpp fusion protein specifically binds a target on the surface of a Natural Killer Cell. Thus, in some embodiments, the DDpp fusion protein specifically binds a NKG2D (Natural Killer Group 2D) receptor. In additional embodiments, the DDpp protein specifically binds CD16 (i.e., Fc gamma RIII) CD64 (i.e., Fc gamma RI), or CD32 (i.e., Fc gamma RII).

In one embodiment, a DDpp fusion protein binds a target on a leukocyte and a tumor antigen on a tumor cell. In some embodiments, the DDpp fusion protein binds NKG2D. In a further embodiment, a DDpp fusion protein binds NKG2D and a target selected from CD123, ErbB2, EGFR, IGF1R, CD19, CD20, CD80 and EPCAM. In one embodiment, a DDpp fusion protein binds CD3. In particular embodiments, the DDpp specifically binds CD3 epsilon. In one embodiment, a DDpp fusion protein binds CD4.

In one embodiment, the disclosed DDpp-CARs are used for the purpose of directing transduced immune cells (e.g., T cells and/or NK cells) to a tumor target defined by the binding specificity of the DDpp-CAR. In one embodiment, primary T cells are transduced with a lentiviral vector encoding a CAR that combines a DD target binding domain with a transmembrane domain and an intracellular domain of CD3-zeta, CD28, 41BB. The resultant population of transduced T cells may therefore elicit a DDpp-CAR-mediated T cell response. In some embodiments, T cells are genetically modified to express DDpp-CAR and the DDpp-CAR T cell is infused to a recipient in need thereof. In further embodiments, the infused cell is able to kill tumor cells in the recipient. Particularly advantageous properties of DDpp-CARs include one, several or all of the following benefits: (i) target-binding specificity, (ii) enhanced therapeutic efficacy, (iii) reduced off-target side effects, (iv) customizability for markers of a particular patient or patient population, (v) enhanced stability during production and processing, and (vi) ability to target one, two, or more specific targets to enhance target-directed therapy.

The DDpp-CAR-modified T cells provided herein can be administered either alone, or as a pharmaceutical composition in combination with diluents and/or with other components such as chemotherapeutics, antibodies, cytokines or cell populations. Compositions provided herein are preferably formulated for intravenous administration that can be administered one or more times.

In some embodiments, a method of delivering an immune response to a target cell in a patient in need thereof comprises administering to the patient a DDpp fusion protein (e.g., an antibody-based DDpp fusion protein) described herein comprising a D domain that specifically binds to CD123 and further comprising an antigenic determinant binding domain (ADBD) (e.g., an antibody or antigen-binding antibody fragment) that specifically binds to the T-cell receptor (TCR) complex on T cells (e.g., CD3 epsilon chain). In some embodiments, a method of killing a target cell in a patient in need thereof comprises administering to the patient comprises administering to the patient a DDpp fusion protein (e.g., an antibody-based DDpp fusion protein) described herein comprising a D domain that specifically binds to CD123 and further comprising an antigenic determinant binding domain (ADBD) (e.g., an antibody or antigen-binding antibody fragment) that specifically binds to the T-cell receptor (TCR) complex on T cells (e.g., CD3 epsilon chain). In some embodiments, the target cell expresses CD123. In some embodiments, the target cell is a cancer cell. In some embodiments, the target cell is an acute myeloid leukemia (AML) cell. In some embodiments, the target cell is a myelodysplasia cell. In some embodiments, the target cell is a B-cell acute lymphoblastic leukemia cell. In some embodiments, the target cell is a hairy cell leukemia cell. In some embodiments, the target cell is a Hodgkin's lymphoma cell. In some embodiments, the target cell is a blastic plasmacytoid dendritic neoplasm (BPDCN) cell. In some embodiments, a method of treating cancer comprises administering to a patient in need thereof an comprises administering to the patient a DDpp fusion protein (e.g., an antibody-based DDpp fusion protein) described herein comprising a D domain that specifically binds to CD123 and further comprising an antigenic determinant binding domain (ADBD) (e.g., an antibody or antigen-binding antibody fragment) that specifically binds to the T-cell receptor (TCR) complex on T cells (e.g., CD3 epsilon chain). In some embodiments, the cancer is hematological cancer. In some embodiments, the hematological cancer is acute myeloid leukemia (AML), myelodysplastic syndrome (e.g., high-risk myelodysplastic syndrome). B-cell acute lymphoblastic leukemia, hairy cell leukemia, Hodgkin's lymphoma or blastic plasmacytoid dendritic neoplasm (BPDCN). In some embodiments, the hematological cancer is AML. In some embodiments, the hematological cancer is myelodysplastic syndrome (e.g., high-risk myelodysplastic syndrome) In some embodiments, the hematological cancer is B-cell acute lymphoblastic leukemia. In some embodiments, the hematological cancer is hairy cell leukemia. In some embodiments, the hematological cancer is Hodgkin's lymphoma. In some embodiments, the hematological cancer is blastic plasmacytoid dendritic neoplasm (BPDCN). In some embodiments, the DDpp fusion protein is an antibody-based DDpp fusion protein. In some embodiments, the DDpp fusion protein is an antibody-based DDpp fusion protein capable of exerting cytotoxic effect on a target cell by via simultaneous binding to CD123 on the target cell and to the TCR complex (e.g., CD3 epsilon chain) on T cells. In some embodiments, the DDpp fusion protein comprises an antibody or antigen binding fragment thereof (e.g., scFv) that binds to the TCR complex. In some embodiments, the DDpp fusion protein comprises an antibody or antigen binding fragment thereof (e.g., scFv) that binds to CD3. In some embodiments, the DDpp fusion protein comprises an antibody or antigen binding fragment thereof (e.g., scFv) that binds to CD3 epsilon chain. In some embodiments, the D domain that specifically binds to CD123 comprises an amino acid sequence selected from the group consisting of SEQ ID NO: 8, 13, 14, 31, 32, and 33. In some embodiments, a D domain that specifically binds to CD123 comprises the amino acid sequence of SEQ ID NO: 8. In some embodiments, a D domain that specifically binds to CD123 comprises the amino acid sequence of SEQ ID NO: 13. In some embodiments, a D domain that specifically binds to CD123 comprises the amino acid sequence of SEQ ID NO: 14. In some embodiments, a D domain that specifically binds to CD123 comprises the amino acid sequence of SEQ ID NO: 31. In some embodiments, a D domain that specifically binds to CD123 comprises the amino acid sequence of SEQ ID NO: 32. In some embodiments, a D domain that specifically binds to CD123 comprises the amino acid sequence of SEQ ID NO: 33. The DDpp fusion protein (e.g., an antibody-based DDpp fusion protein) provided herein can be administered either alone, or as a pharmaceutical composition in combination with pharmaceutically acceptable excipients and/or with other components such as chemotherapeutics, antibodies, cytokines or cell populations. Compositions provided herein are preferably formulated for intravenous administration that can be administered one or more times.

E. Analytical and Diagnostic Applications

Whether alone, as fusion proteins, as chemical conjugates or as other embodiments, described herein, DDpp have a variety of applications. In some embodiments, DDpp are used as detection reagents, diagnostic reagents or analytical reagents. In some embodiments, DDpp are used as detection reagents of targets of interest in a variety of different sample types. Some embodiments have in vivo, in vitro and/or ex vivo applications. Methods that employ the DDpp in vitro can be performed in different formats, such as in microtiter plates, in protein arrays, on biosensor surfaces, on tissue sections, and in additional formats that would be apparent to a person skilled in the art.

In some embodiments, the DDpp is used to bind, detect, and/or quantitate, a target of interest (e.g., CD123) in a sample containing the target. In one embodiment, the disclosure provides a method for detecting a target of interest (e.g., CD123, or AFP p26) in a sample, comprising: (a) contacting the sample with a DDpp containing a DD that comprises an amino acid sequence selected from the group consisting of SEQ ID NO: 8-33, 99 and 100, that specifically binds the target, under conditions suitable for specific binding of the DDpp to the target, to form a target/DDpp complex, and (b) detecting the presence of the complex and/or captured target. In some embodiments, the DDpp is immobilized on a solid support. In some embodiments, the DD comprises an amino acid sequence selected from the group consisting of SEQ ID NO: 8-33, 99 and 100, and the DDpp is used to bind, detect, and/or quantitate, CD123 or a fusion protein comprising CD123 in a sample.

Also provided is a method for quantifying a target of interest (e.g., CD123) in a sample containing the target, comprising: (a) contacting the sample with a DDpp containing a DD that comprises an amino acid sequence selected from the group consisting of SEQ ID NO: 8-33 and 74-94, that specifically binds the target and that is immobilized on a solid support, under conditions suitable for specific binding of the DDpp to the target, to form a target/DDpp complex and (b) detecting the presence of the target/DDpp complex and/or captured target, wherein quantitative detection of the product indicates, or is otherwise able to be correlated with, the quantity of the target or a fusion protein containing the target in the sample.

In one embodiment a DDpp are used to detect targets of interest in solutions involved in manufacturing processes, such as protein expression. Samples may include, but are not limited to, water, buffers, in-process purification samples, bulk drug substance and final drug product. In still additional embodiments, the DDpp can be used to detect contaminants from a sample, such as a water supply source or water (or other fluid) used in manufacturing.

In another embodiment, DDpp are used to detect targets of interest in diagnostic samples. Samples may include, but are not limited to tissue homogenates, cell extracts, biopsy samples, sera, plasma, lymph, blood, blood fractions, urine, synovial fluid, spinal fluid, saliva, mucous, sputum, pleural fluid, nipple aspirates, fluid of the respiratory, intestinal, and genitourinary tracts, tear fluid, breast milk, fluid from the lymphatic system, semen, cerebrospinal fluid, intra-organ system fluid, ascitic fluid, tumor cyst fluid, amniotic fluid, and media or lysate from cultured cells.

In one embodiment, the DDpp are useful for detecting the presence of a factor or multiple factors (e.g., antigens or organisms) in a biological sample. The term "detecting" as used herein encompasses quantitative or qualitative detection. In certain embodiments, a biological sample comprises a cell, tissue or fluid. In certain embodiments, such tissues include normal and/or cancerous tissues.

Various formats and techniques for detection are known in the art and include but are not limited to Western Blot analysis, Immunohistochemistry, ELISA, FACS analysis, enzymatic assays, autoradiography and any of the binding assays mentioned herein.

In one embodiment, a method is provided for detecting a target of interest (e.g., CD123 or AFP p26) in a solution containing the target comprising: (a) contacting the solution with a DDpp that specifically binds the target of interest under conditions suitable for specific binding of the DDpp to the target and (b) detecting binding of the DDpp and target. The DDpp may be either free or immobilized. Sufficient time is allowed to permit binding between the target of interest and the DDpp, and non-binding components in the solution or mixture are removed or washed away. The formation of a binding complex between the DDpp and the target of interest can then be detected, for example, by detecting the signal from a label on the DDpp, which is one component of the binding complex. A label may be any label that generates a signal that can be detected by standard methods, such as a fluorescent label, a radioactive compound, or an enzyme that reacts with a substrate to generate a detectable signal. Examples of suitable labels for such purposes are described herein and/or otherwise known in the art.

DDpp that bind to a target of interest such as CD123 or AFP p26 can be detectably labeled through the use of radioisotopes, affinity labels (such as biotin, avidin, etc.), enzymatic labels (such as horseradish peroxidase, alkaline phosphatase, etc.) using methods known in the art, such as described in WO00/70023 and (Harlow and Lane (1989) Antibodies, Cold Spring Harbor Laboratory, pp. 1-726).

The detectable marker or label can be any which is capable of producing, either directly or indirectly, a measurable signal, such as a change in mass, radioactive, chromogenic, luminescence, or fluorescent signal, which can be used to quantitate the amount of bound detectable moiety or label in a sample. Detectable labels known in the art include heavy metals, radioisotopes, such as $^3H$, $^{14}C$, $^{32}P$, $^{35}S$, or $^{125}I$, electrochemiluminescent labels (such as Ruthenium (Ru)-based catalyst in conjunction with substrates, etc.), luminescent or bioluminescent labels (e.g., Europium, Vanadium), fluorescent or chemiluminescent compounds, such as fluorescein isothiocyanate, rhodamine, or luciferin, enzymes (e.g., enzyme, such as alkaline phosphatase, beta-galactosidase, or horseradish peroxidase), colorimetric labels such as colloidal gold, colored glass or plastic beads (e.g., polystyrene, polypropylene, latex, etc.), paramagnetic atoms or magnetic agents, electron-dense reagents, a nano- or microbead containing a fluorescent dye, nanocrystals, a quantum dot, a quantum bead, a nanotag, dendrimers with a fluorescent label, a micro-transponder, an electron donor molecule or molecular structure, or a light reflecting particle, the microparticles may be nanocrystals or quantum dots. Nanocrystals are substances that absorb photons of light, then re-emit photons at a different wavelength (fluorophores). In addition, additional fluorescent labels, or secondary antibodies may be conjugated to the nanocrystals. Nanocrystals are commercially available from sources such as Invitrogen and Evident Technologies (Troy, N.Y.). Other labels include E)-5-[2-(methoxycarbonyl) ethenyl]cytidine, which is a nonfluorescent molecule that when subjected to ultraviolet (UV) irradiation yields a product, 3 beta-D-ribofuranosyl-2,7-dioxopyrido[2,3-d]pyrimidine, which displays a strong fluorescence signal.

Competitive inhibition can be determined by any method known in the art, for example, competition ELISA assays. A DDpp, such as a DDpp fusion protein (e.g., a DDpp-Fc, DDpp-CAR, a DDpp-scFv), or other molecule is said to "competitively inhibit" binding of a reference molecule to a given epitope if it binds to that epitope to the extent that it blocks, to some degree, binding of the reference molecule to the epitope. As used herein, a DDpp (e.g., a DDpp fusion protein), or other molecule can be said to competitively inhibit binding of the reference molecule to a given epitope, for example, by at least 90%, at least 80%, at least 70%, at least 60%, at least 50%, by at least 40%, at least 30%, or at least 20%. The terms "compete," "ability to compete" and "competes with" are relative terms used to describe a DDpp, such as a DDpp fusion protein, that produce at least 20%, at least 30%, at least 40%, or at least 50% inhibition of binding of a reference molecule to a target by a DDpp such as a DDpp fusion protein (e.g., a DDpp-Fc, DDpp CAR, a DDpp-scFv, and an antibody-comprising a DDpp) as determined in a standard competition assay as described herein or otherwise known in the art, including, but not limited to, competitive assay systems using techniques such as radio-immunoassays (RIA), enzyme immunoassays (EIA), preferably the enzyme linked immunosorbent assay (ELISA), "sandwich" immunoassays, immunoradiometric assays, fluorescent immunoassays, luminescent, electrochemical luminescent, and immunoelectrophoresis assays. Methods for determining binding and affinity of candidate binding molecules are known in the art and include, but are not limited to, affinity chromatography, size exclusion chromatography, equilibrium dialysis, fluorescent probe displacement, and plasma resonance.

In additional embodiments, the provided DDpps are used in protein analytics. In some embodiments, the DDpps are conjugated to a detectable agent and/or tag. In some embodiments, the DDpp comprises an amino acid sequence selected from the group consisting of SEQ ID NO: 8-33 and 74-94. In other embodiments, the DDpp comprises a variant of an amino acid sequence selected from the group consisting of SEQ ID NO: 8-33 and 74-94. In some embodiments, the DDpp is conjugated to a detectable agent. In one embodiment, the detectable agent comprises a chromogen. In another embodiment, the detectable agent comprises a fluorescent dye. In and additional embodiment, the detectable agent comprises a radionuclide. In some embodiments, the DDpp is conjugated to the detectable agent by covalent binding. In some embodiments, the DDpp is a fusion protein. In additional embodiments, the DDpp is multimeric. In additional embodiments, the DDpp is conjugated to a tag. In some embodiments, the tag is a member selected from the group consisting of: a polyhistidyl tag, a myc tag, and a FLAG tag. In further embodiments, the DDpp is conjugated to a combination of tags (e.g., a polyhistidyl tag and a FLAG tag). In some embodiments, the DDpp is conjugated to the tag(s) by covalent binding. In some embodiments, the DDpp is a fusion protein. In some embodiments, the DDpp is multimeric.

Articles of Manufacture

Articles of manufacture, including, kits, are provided herein. The article of manufacture may comprise a container and a label or package insert on or associated with the container. Suitable containers include, for example, bottles, vials or syringes. The containers may be formed from a variety of materials such as glass or plastic. The container holds one or more DDpp, nucleic acids encoding DDpp and/or vectors or host cells of the present disclosure. The label or package insert may include directions for performing affinity based screening and/or detection.

Also provided are kits containing a DDpp. Such kits have uses including, but not limited to detecting the target of interest to which the DDpp specifically binds (e.g., CD123 or AFP p26)). Such assay kit may be useful in screening for the presence of a target of interest and/or quantitating the concentrations of a target of interest in a fluid, such as, a biological fluid (e.g., blood, serum, or synovial fluid).

In some embodiments, a kit provided herein comprises a cell expressing a chimeric antigen receptor (CAR), wherein the CAR comprises a D domain that binds to CD123, (ii) a transmembrane domain, and (iii) an intracellular domain. In some embodiments, the D domain that binds to CD123 comprises an amino acid sequence selected from the group consisting of SEQ ID NO: 8-33, 99 and 100. In some embodiments, the D domain that binds to CD123 comprises an amino acid sequence selected from the group consisting of SEQ ID NO: 8, 13, 14, 31, 32, and 33. In some embodiments, the D domain that binds to CD123 comprises the amino acid sequence of SEQ ID NO: 8. In some embodiments, the D domain that binds to CD123 comprises the amino acid sequence of SEQ ID NO: 13. In some embodiments, the D domain that binds to CD123 comprises the amino acid sequence of SEQ ID NO: 14. In some embodiments, the D domain that binds to CD123 comprises the amino acid sequence of SEQ ID NO: 31. In some embodiments, the D domain that binds to CD123 comprises the amino acid sequence of SEQ ID NO: 32. In some embodiments, the D domain that binds to CD123 comprises the amino acid sequence of SEQ ID NO: 33. In some embodiments, the CAR comprises the amino acid sequence of SEQ ID NO: 62-66 or 67. In some embodiments, the CAR comprises the amino acid sequence of SEQ ID NO: 67. In some embodiments, the cell is an immune cell. In some embodiments, the cell is an immune effector cell. In some embodiments, the cell is a T cell (CAR-T cell) or a natural killer (NK) cell (CAR-NK cell). In some embodiments, the CAR immune cell is an autologous immune cell. In some embodiments, the CAR immune cell is an allogenic immune cell.

In some embodiments, a kit provided herein comprises a cell expressing a chimeric antigen receptor (CAR), wherein the CAR comprises an antigenic determinant binding domain (ADBD) that binds to an AFP p26 AD, (ii) a transmembrane domain, and (iii) an intracellular domain. In some embodiments, the ADBD that binds to AFP p26 AD comprises an scFv that binds to AFP p26 AD. In some embodiments, the ADBD that binds to AFP p26 AD comprises a D domain that binds to AFP p26 AD. In some embodiments, the AFP p26 AD comprises an amino acid sequence selected from the group consisting of SEQ ID NO: 37-43 and 44. In some embodiments, the AFP p26 AD comprises the amino acid sequence of SEQ ID NO: 37. In some embodiments, the AFP p26 AD comprises the amino acid sequence of SEQ ID NO: 39. In some embodiments, the DD that binds to an AFP p26 AD comprises an amino acid sequence selected from the group consisting of SEQ ID NO: 74-93 and 94. In some embodiments, the DD that binds to an AFP p26 AD comprises the amino acid sequence of SEQ ID NO: 70-73 or 92-94. In some embodiments, the DD that binds to an AFP p26 AD comprises the amino acid sequence of SEQ ID NO: 73. In some embodiments, the CAR comprises the amino acid sequence of SEQ ID NO: 68. In some embodiments, the CAR comprises the amino acid sequence of SEQ ID NO: 69. In some embodiments, the cell is an immune cell. In some embodiments, the cell is an immune effector cell. In some embodiments, the cell is a T cell (CAR-T cell) or a natural killer (NK) cell (CAR-NK cell). In some embodiments, the immune cell is an autologous cell. In some embodiments, the immune cell is an allogenic immune cell.

In some embodiments, a kit provided herein comprises a cell expressing a chimeric antigen receptor (CAR), wherein the CAR comprises an AFP p26 antigenic determinant (AD), (ii) a transmembrane domain, and (iii) an intracellular domain. In some embodiments, the AFP p26 AD comprises an amino acid sequence selected from the group consisting of SEQ ID NO: 37-43 and 44. In some embodiments, the AFP p26 AD comprises the amino acid sequence of SEQ ID NO: 37. In some embodiments, the AFP p26 AD comprises the amino acid sequence of SEQ ID NO: 39. In some embodiments, the cell is an immune cell. In some embodiments, the cell is an immune effector cell. In some embodiments, the cell is a T cell (CAR-T cell) or a natural killer (NK) cell (CAR-NK cell). In some embodiments, the immune cell is an autologous cell. In some embodiments, the immune cell is an allogenic immune cell.

In some embodiments, a kit provided herein comprises an Adapter comprising (a) a D domain (DD) that binds to CD123 and (b) an antigenic determinant (AD). In some embodiments, the D domain that binds to CD123 comprises an amino acid sequence selected from the group consisting of SEQ ID NO: 8-33, 99 and 100. In some embodiments, the D domain that binds to CD123 comprises an amino acid sequence selected from the group consisting of SEQ ID NO: 8, 13, 14, 31, 32, and 33. In some embodiments, the D domain that binds to CD123 comprises the amino acid sequence of SEQ ID NO: 14. In some embodiments, the Adapter is a monovalent Adapter comprising a single D domain that binds CD123. In some embodiments, the Adapter is a bivalent Adapter comprising two D domains that bind CD123. In some embodiments, the two D domains that bind CD123 are the same. In some embodiments, the two D domains that bind CD123 are different. In some embodiments, the Adapter is a bivalent Adapter comprising a first D domain that binds CD123 and a second D domain that binds a second AD. In some embodiments, the second AD is CD33 or LeY. In some embodiments, a monovalent Adapter comprises a D domain comprising an amino acid sequence selected from the group consisting of SEQ ID NO: 8, 13, 14, 31, 32, and 33. In some embodiments, the monovalent Adapter comprises the D domain comprising the amino acid sequence of SEQ ID NO: 14. In some embodiments, a bivalent Adapter comprises a DD comprising an amino acid sequence selected from the group consisting of SEQ ID NO: 8, 13, 14, 31, 32, and 33. In some embodiments, the bivalent Adapter comprises the D domain comprising the amino acid sequence of SEQ ID NO: 14. In some embodiments, a bivalent Adapter comprises two identical D domains comprising an amino acid sequence selected from the group consisting of SEQ ID NO: 8, 13, 14, 31, 32, and 33. In some embodiments, the bivalent Adapter comprises two identical D domains comprising the amino acid sequence of SEQ ID NO: 14. In some embodiments, the Adapter comprises an AFP p26 antigenic determinant (AD). In some embodiments, the AFP p26 AD comprises an amino acid sequence selected from the group consisting of SEQ ID NO: 37-43 and 44. In some embodiments, the AFP p26 AD comprises the amino acid sequence of SEQ ID NO: 37. In some embodiments, the AFP p26 AD comprises the amino acid sequence of SEQ ID NO: 39. In some embodiments, the monovalent Adapter comprises the amino acid sequence of SEQ ID NO: 50-54 or 55. In some embodiments, the monovalent Adapter comprises the amino acid sequence of SEQ ID NO: 50. In some embodiments, the bivalent Adapter comprises the amino acid sequence of SEQ ID NO: 56-60 or 61. In some embodiments, the monovalent Adapter comprises the amino acid sequence of SEQ ID NO: 61. In some embodiments, the Adapter comprises one or more linkers.

In some embodiments, a kit provided herein comprises an Adapter comprising (a) a D domain that binds to CD123 and (b) an antigenic determinant binding domain (ADBD) that binds an AFP p26 AD. In some embodiments, the AFP p26 AD comprises an amino acid sequence selected from the group consisting of SEQ ID NO: 37-43 and 44. In some embodiments, the AFP p26 AD comprises the amino acid sequence of SEQ ID NO: 37. In some embodiments, the AFP p26 AD comprises the amino acid sequence of SEQ ID NO: 39. In some embodiments, the D domain that binds to CD123 comprises an amino acid sequence selected from the group consisting of SEQ ID NO: 8-33, 99 and 100. In some embodiments, the D domain that binds to CD123 comprises an amino acid sequence selected from the group consisting of SEQ ID NO: 8, 13, 14, 31, 32, and 33. In some embodiments, the D domain that binds to CD123 comprises the amino acid sequence of SEQ ID NO: 14. In some embodiments, the ADBD that binds to an AFP p26 AD comprises a D domain that binds to the AFP p26 AD. In some embodiments, the D domain that binds to an AFP p26 AD comprises an amino acid sequence selected from the group consisting of SEQ ID NO: 70-73 and 92-94. In some embodiments, the D domain that binds to an AFP p26 AD comprises the amino acid sequence of SEQ ID NO: 73. In some embodiments, the Adapter comprises one or more linkers.

In some embodiments, a kit provided herein comprises an Adapter comprising (a) a first antigenic determinant binding domain (ADBD) that binds to a target antigenic determinant (AD) on a target cell and (b) an antigenic determinant binding domain (ADBD) that binds to an AFP p26 AD. In some embodiments, the AFP p26 AD comprises an amino acid sequence selected from the group consisting of SEQ ID NO: 37-43 and 44. In some embodiments, the AFP p26 AD comprises the amino acid sequence of SEQ ID NO: 37. In some embodiments, the AFP p26 AD comprises the amino acid sequence of SEQ ID NO: 39. In some embodiments, the ADBD that binds to an AFP p26 AD comprises a D domain that binds to AFP p26. In some embodiments, the D domain that binds to an AFP p26 AD comprises an amino acid sequence selected from the group consisting of SEQ ID NO: 70-73 and 92-94. In some embodiments, the D domain that binds to an AFP p26 AD comprises the amino acid sequence of SEQ ID NO: 73. In some embodiments, the Adapter comprises one or more linkers.

In one embodiment a DDpp assay kit is contemplated which comprises one or more containers of a DDpp that specifically binds a target of interest and, optionally, a detection means for determining the presence or absence of a target/DDpp interaction or the absence thereof. The kit further optionally contains target of interest protein (e.g., BCMA, CD123, CD33, CD38, LeY, CS1, HER2, AFP, or AFP p26) that may be used, for example as a control or standard. The DDpp may be free or expressed on the surface of a host cell or on the surface of a bacteriophage. In a specific embodiment, the DDpp or target of interest provided in the kit is labeled. Any label known in the art can be used. In some embodiments, the label is selected from the group consisting of biotin, a fluorogen, an enzyme, an epitope, a chromogen, or a radionuclide. In some embodiments, the DDpp is immobilized on a solid support. The detection means employed to detect the label will depend on the nature of the label and can be any known in the art, e.g., film to detect a radionuclide; an enzyme substrate that gives rise to or amplifies a detectable signal to detect the presence of a target of interest.

Preferably, the kit further comprises a solid support for the DDpp, which may be provided as a separate element or on which a DDpp that specifically binds a target of interest (e.g., BCMA, CD123, CS1, HER2, AFP, or AFP p26) is immobilized. Hence, the DDpp that specifically binds the target of interest in the kit may be immobilized on a solid support, or they may be immobilized on such support that is included with the kit or provided separately from the kit. Preferably, DDpp is coated on a microtiter plate. In some embodiments, the detection involves a signal amplifying molecule. Where the signal amplifying molecule is an enzyme, the kit optionally further includes substrates and cofactors required by the enzyme, and where the amplifying molecule is a fluorophore. The kit optionally further includes a dye precursor that provides the detectable chromophore.

The kit may also contain instructions for carrying out the assay as well as other additives such as stabilizers, washing and incubation buffers, and the like. The components of the kit will be provided in predetermined ratios, with the relative amounts of the various reagents suitably varied to provide for concentrations in solution of the reagents that substantially maximize the sensitivity of the assay. Particularly, the reagents can be provided as dry powders, usually lyophilized, including excipients, which on dissolution will provide for a reagent solution having the appropriate concentration for combining with the sample to be tested.

Various formats and techniques for binding assays that can be used are known in the art and include but are not limited to, immobilization to filters such as nylon or nitrocellulose; two-dimensional arrays, enzyme linked immunosorbent assay (ELISA), radioimmuno-assay (RIA), competitive binding assays, direct and indirect sandwich assays, immunoprecipitation assays, fluorimetric microvolume assay technology (FMAT™), Luminex™ system assays, fluorescent resonance energy transfer (FRET), bioluminescence resonance energy transfer (BRET), electroimmunoassays, AlphaScreen™, nanoparticle-derived techniques, and surface plasmon resonance (SPR).

Binding assays can be homogeneous or semi-homogeneous. A homogeneous assay is an assay where all the components are mixed together, incubated, and then analyzed. A semi-homogeneous assay is one where the majority of the reaction takes place as a complex mixture, but a washing step is required prior to the addition of a final reagent and analysis, in contrast to a typical stepwise assembly sandwich assay where each component is added then washed off before the next component is added. In some embodiments, the assay is an immunoassay. In certain embodiments, the assay is a semi-homogeneous Enzyme Immuno-Assay (EIA).

Various embodiments, of the disclosure will now be illustrated through the description of experiments conducted in accordance therewith. The examples that follow are provided to facilitate the practice of the disclosed embodiments, and are not to be construed as limiting in any way the remainder of the disclosure. In the examples, reference is made to the appended figures.

EXAMPLES

Example 1. Isolation of Variant D Domains with Increased Affinity to CD123

Methods for isolating and characterizing D domains that bind exemplary targets of interest, producing and characterizing D domain fusion polypeptides comprising the D domains, producing and characterizing Adapters comprising the D domains, producing and characterizing CARs comprising the D domains, producing and characterizing immune cells expressing the CARs, and characterizing the cytotoxic activity of the cells expressing CARs with or without Adapters are disclosed, for example, in Intl. Appl. Pub. Nos. WO 2016164305, WO 2016164308A1, WO 2019099440, and WO 2019099433, U.S. Pat. Nos. 10,662,248, 10,647,775, and 11,008,397, each of which is incorporated herein by reference for all purposes.

Methods to improve affinity of D domain for a target antigen (e.g. CD123) can include mutagenesis of the existing amino acid sequence. These mutations can be directed towards specific amino acids or randomly distributed throughout the sequence. Mutated D domains can be subsequently assayed for changes in binding characteristics, protein expression or other biological activity associated with a particular application or function. One method of introducing random mutations is through error-prone PCR (EP-PCR). This approach was used to introduce mutations into the CD123 specific 8W9C D domain sequence (SEQ ID NO: 4). Briefly, the nucleotide sequence encoding the D domain and flanking regions, optionally including signal peptides, linker peptides and restriction enzyme sites was PCR amplified with an error-prone PCR enzyme (e.g. Mutazyme II, Agilent Technologies). After one or more sequential rounds of amplification, the PCR product was digested with the appropriate restriction enzymes and ligated into the corresponding sites of either 1) a maltose binding protein (MBP) fusion expression vector to generate an MBP library, or 2) a phage pIII protein fusion expression vector to generate a phage library.

Parent and mutated variant D domains were expressed as MBP fusions in $E.$ $coli$ (T7 Express, New England Biolabs) by either IPTG (isopropylthio-β-galactoside) induction for 4 hours at 37° C. in Luria broth containing antibiotics and 0.2% glucose or through auto-induction for 16 hours at 30° C. using MagicMedia (Life Technologies). Post induction, cells were pelleted, washed and resuspended in "leak-out buffer" comprising 200 mM Tris pH 7.5 and 20 mM EDTA. After incubation at 30° C. for 16 hours, supernatant containing MBP fusion proteins were assayed by ELISA for both target binding and expression. Supernatants were added to 96-well Immulon 4HBX microtiter plates coated with anti-MBP polyclonal antibody (Abcam) at 0.0032 ug/ml. Followed by washing, bound MBP fusion proteins were detected either with CD123-Fc (Sino Biological)+anti-human Fc HRP (Abcam) to assess CD123 binding, or with anti-MBP-HRP (New England Biolabs) to assess MBP fusion protein expression. As shown in FIG. 1, mutant variants of 8W9C (SEQ ID NO: 4) bind to CD123 with a range of affinities (y axis). 8W9C, 5S5W (SEQ ID NO: 97) and 5B7L (SEQ ID NO: 98) are parent, low affinity and high affinity control D domains, respectively. Mutations can also impact expression of the domain, as indicated by the variable anti-MBP detection signal (x axis).

Figure 2:
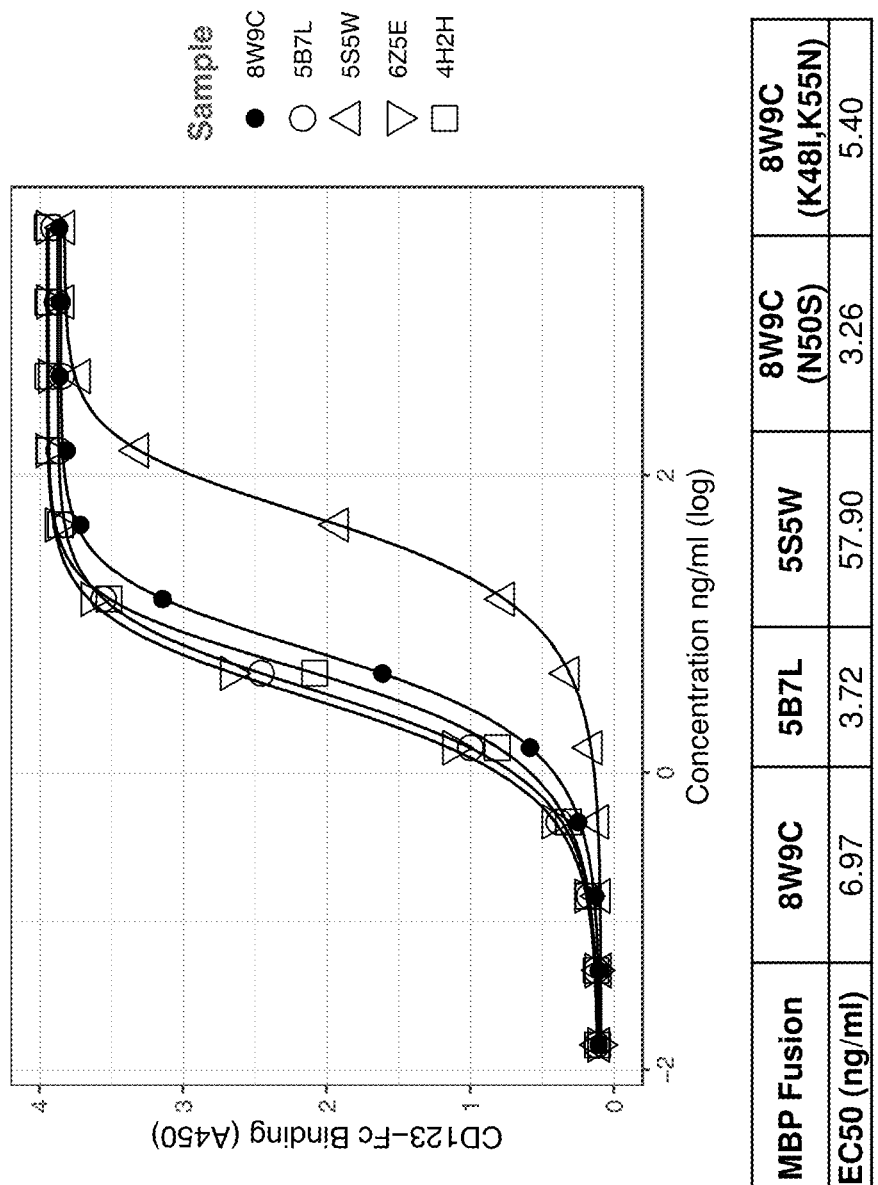
FIG. 2. CD123 binding of 8W9C mutants as MBP fusions. 8W9C mutants (6Z5E & 4H2H) were assayed by ELISA for binding to CD123 (CD123 Binding). Wild-type (8W9C), high-affinity (5B7L) and low-affinity (5S5W) controls were assayed for comparison.
Figure 3:
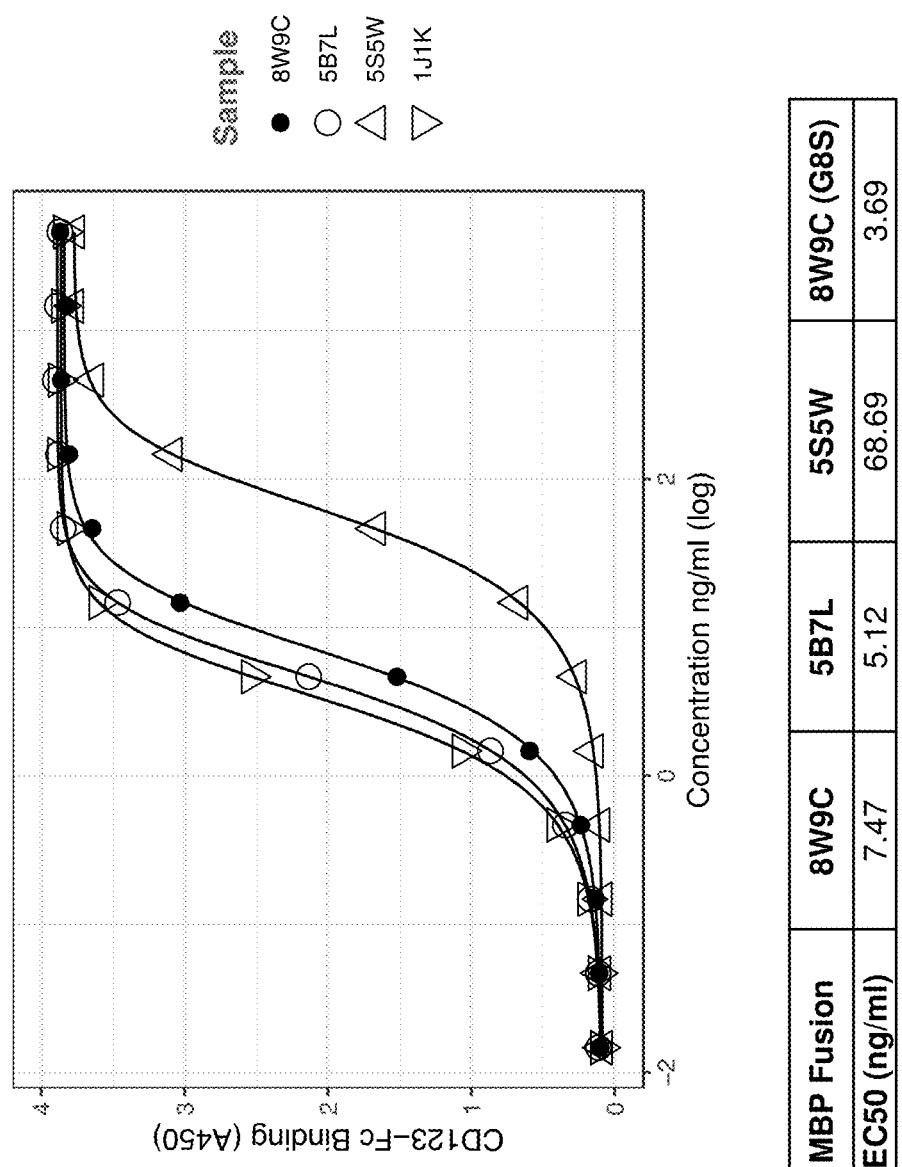
FIG. 3. CD123 binding of 8W9C mutants as MBP fusions. 8W9C mutant (1J1K) was assayed by ELISA for binding to CD123 (CD123 Binding). Wild-type (8W9C), high-affinity (5B7L) and low-affinity (5S5W) controls were assayed for comparison.
Figure 4:
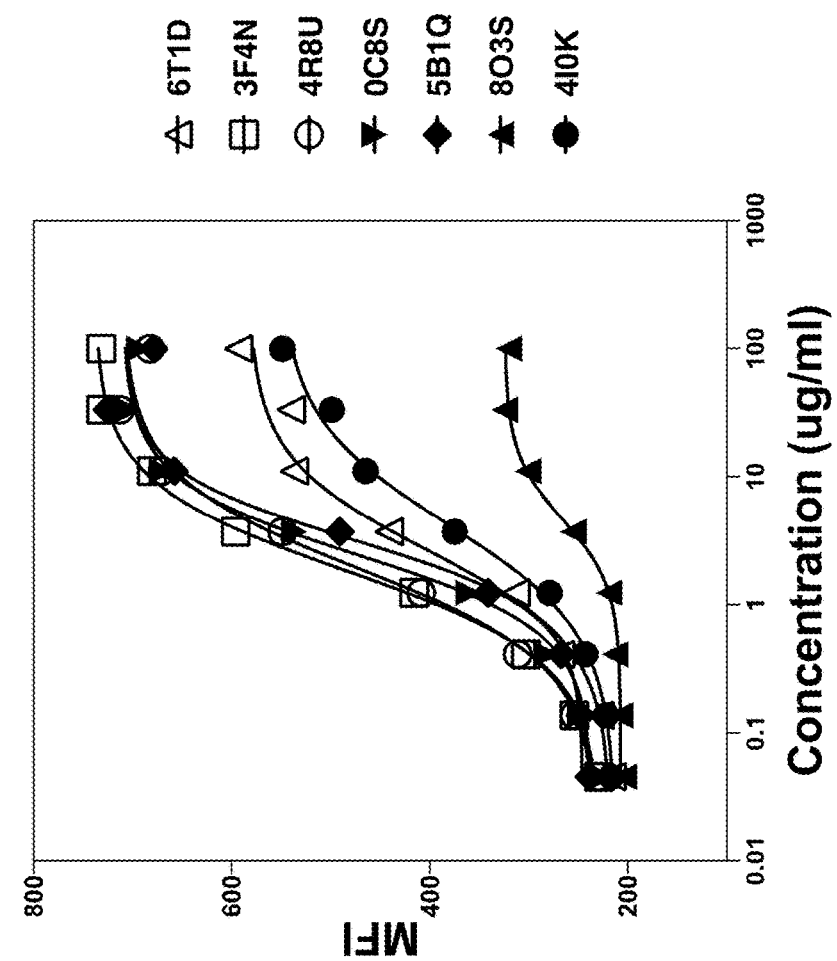
FIG. 4. Cell binding of 6T1D mutants as Adapters. Assorted variant 6T1D mutants were assayed at various concentrations by flow cytometry for binding to CD123-expressing OCI-AML2 cells. Binding was measured by mean fluorescent intensity (MFI).

Select clones of MBP fusions that exhibited enhanced CD123 binding in the screen were normalized for protein concentration and further assessed for binding to CD123 by serial dilution in ELISA. As shown in FIGS. 2 and 3, several mutants, including 6Z5E (SEQ ID NO: 6) (i.e. 8W9C (N50S)), 4H2H (SEQ ID NO: 30) (i.e. 8W9C (K48I, K55N)) and 1J1K (SEQ ID NO: 7) (i.e. 8W9C (G8S)) represent sequences that bind CD123 with greater affinity than the parental 8W9C sequence.

Alternatively, mutated variants of 8W9C (SEQ ID NO: 4) were subjected to further evolutionary selection prior to screening. To do so, mutated variants of 8W9C were cloned as an M13 phage display library encoding an N-terminal fusion of the D domain to truncated pIII. The resultant phage library was subjected to two rounds of binding selection with biotinylated recombinant human CD123-His (Sino Biological), first bound to BT-tris-NTA-biotin, followed by capture by M-280 Streptavidin Dynabeads (Invitrogen). Successive rounds of panning utilized 10 nM, and 5 nM of CD123-HIS antigen with 0.1% Tween 20. Bound phage were eluted by addition of 300 µl 500 mM imidazole in phosphate buffer, and propagated in TG1 cells (Lucigen) with VCSM13 helper phage (Agilent Technologies) Amplified output phage from each round was then precipitated with PEG/NaCl and resuspended in PBS to serve as the input library for the next round.

After two rounds of selection, the phage output was first subcloned as an MBP fusion library prior to screening. Individual MBP clones expressed as MBP fusions in BL21 (DE3) E. coli (New England Biolabs) through auto-induction for 16 hours at 30° C. using MagicMedia (Life Technologies). Post induction, cells were pelleted, washed and resuspended in 200 mM Tris ph7.5, 20 mM EDTA (leak-out buffer). After incubation at 30° C. for 16 hours supernatant containing MBP fusions were assayed for both binding and expression by ELISA. Supernatants were added to 96-well Immulon 4HBX microtiter plates coated with anti-MBP polyclonal antibody (Abcam) at 0.2 ug/ml. Followed by washing, bound MBP fusions were detected with CD123-HIS (Sino Biological)+anti-HIS-HRP (BioLegend) to assess CD123 binding. The mutations 0NSN (SEQ ID NO: 99) (i.e. 8W9C (I59L)) and 1H3C (SEQ ID NO: 100) (i.e. 8W9C (K46E)) were found to have higher affinity to CD123 than the parental domain, 8W9C (data not shown).

Figure 5:
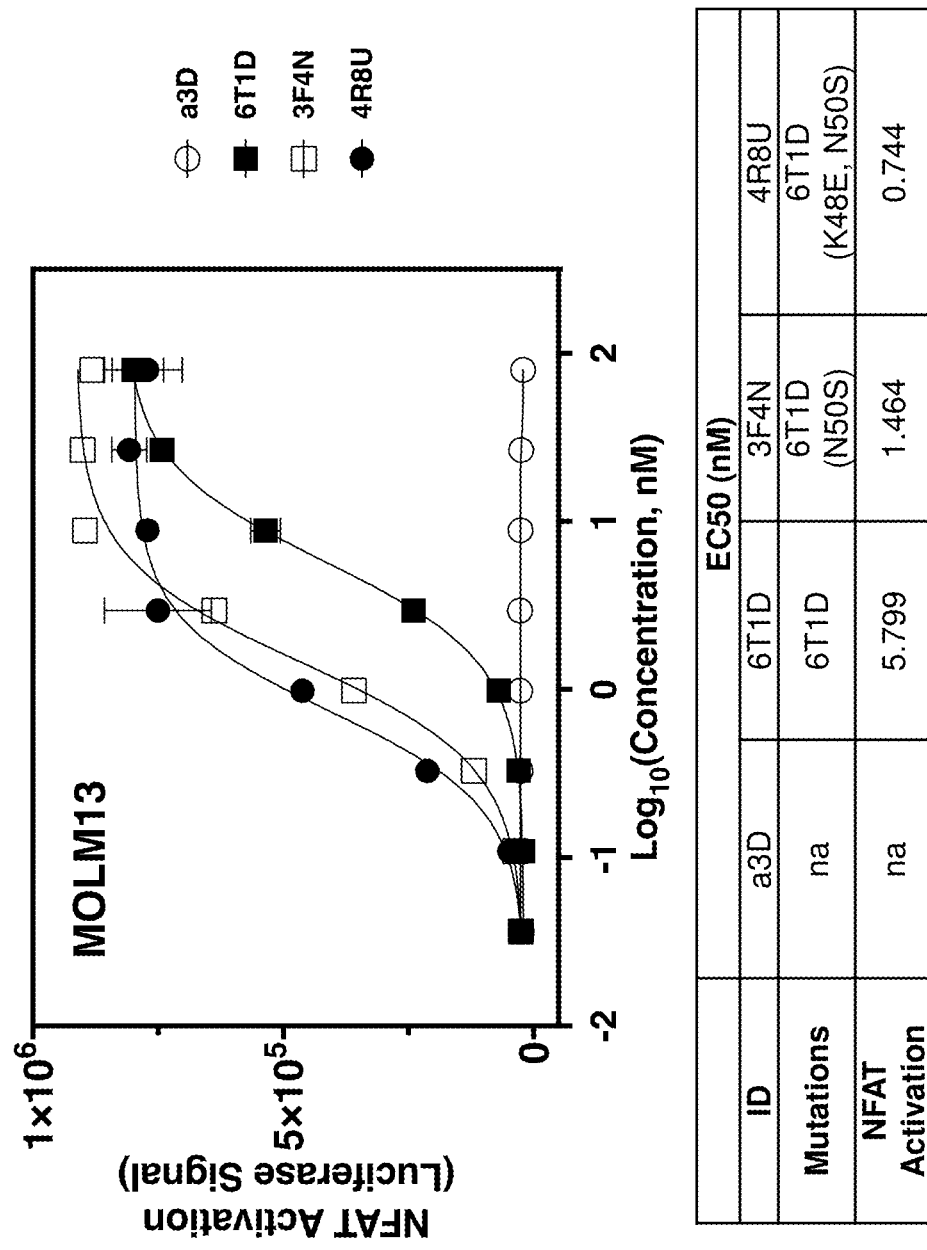
FIG. 5. NFAT activation of CAR T cells by sparX proteins. JNL10/8G8V-CAR are assayed for activation in the presence CD123 expressing MOLM13 target cells and various concentrations of CD123 specific Adapter proteins. Samples included affinity modified variants of 6T1D (e.g. 3F4N & 4R8U). The parental D domain (6T1D) and non-binding (a3D) controls are assayed for comparison.
Figure 6:
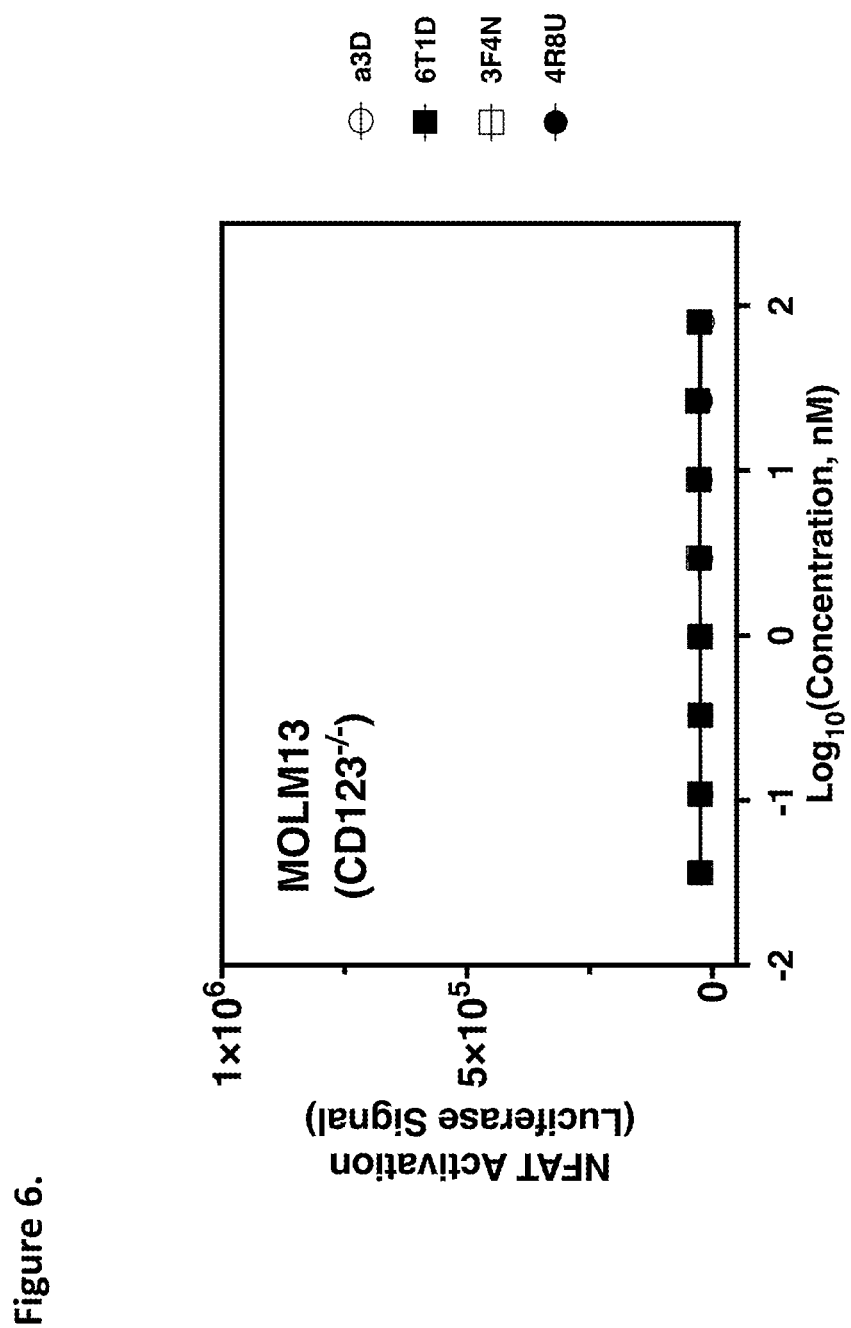
FIG. 6. NFAT activation of CAR T cells cultured with CD123-specific Adapter proteins. JNL10/8G8V-CAR are assayed for activation in the presence MOLM13 cells lacking CD123 expression (MOLM13 (CD123−/−)) and various concentrations of sparX proteins. Samples included affinity modified variants of 6T1D (e.g. 3F4N & 4R8U). The parental D domain (6T1D) and non-binding (a3D) controls were assayed for comparison.

Utilizing the methods described in Qin, et. al, (Mol Ther. 27(7):1262-1274 (2019)), the 8W9C (SEQ ID NO: 4) parent CD123-binding D domain was de-immunized to yield the 6T1D (SEQ ID NO: 5) D domain Briefly, the 8W9C sequence was screened for T cell epitopes using a virtual matrix-based prediction algorithm for identification of Class II epitopes (Singh and Raghava, Bioinformatics. 17(12): 1236-7 (2001)). High affinity epitopes were defined as those present at 6% threshold and below. A total of 51 MHC HLA-DR alleles were screened. Promiscuous epitopes were defined as those with 17 or greater hits. As defined, 8W9C has three high affinity, promiscuous epitopes, which are located at Y12, W16 and 163. The clone 6T1D was generated through the introduction of three mutations R17Q, S24T, S65E, which reduced the number of high affinity, promiscuous epitopes to zero. These mutations were intended to remove potential MHC type II T cell epitopes, but not to significantly impact the affinity of the domain for CD123.

Affinity enhancing mutations that were identified in the context of 8W9C (SEQ ID NO: 4) were combined with the de-immunizing mutations of 6T1D to produce a series of deimmunized variants with enhanced affinity. Consequently, the 3F4N (SEQ ID NO: 8), 6Y7D (SEQ ID NO: 9), 5M5U (SEQ ID NO: 10), 4R8U (SEQ ID NO: 11), 1F9I (SEQ ID NO: 12), 0C8S (SEQ ID NO: 13) and 5B1Q (SEQ ID NO: 14) D domains represent combinations of mutation that exhibit higher affinity binding to CD123 than 6T1D without increasing the predicted MHC type II mediated immunogenicity. For example 5B1Q (SEQ ID NO: 14), derived from 6T1D by replacing 5 residues (i.e., G8S, L21Q, K48E, N505, I59L), exhibits an approximately 10-fold enhancement of affinity over that of 6T1D while having a predicted immunogenicity comparable to 6T1D.

To assess the kinetics of CD123 binding, Adapter proteins comprising the D domains were analyzed using Bio-Layer Interferometry (BLI). Adapter proteins comprising a CD123-binding D domain and a P26 (Q26-V229) AFP polypeptide (SEQ ID NO: 39) were generated through transient transfection of HEK-293 cells, followed by Ni-Sepharose Excel (Cytiva) and SEC chromatography. BLI experiments were performed using an Octet RED386 (Sartorius). All experiments were performed at 25° C. in kinetic buffer (PBS, 0.1% BSA, 0.02% tween 20) under constant 1000 rpm agitation. CD123-Fc (20 nM) was captured on an AHC sensor (Sartorius) for 250 seconds to a loading density of −0.8 nm. To measure the binding affinities, sensors were dipped into Adapter proteins at concentration ranging from 500 nM to 0.69 nM (3-fold dilution series) for 300 seconds, then returned to kinetic buffer for 600 seconds. The surface was regenerated by 3 rounds of 10 seconds of 10 mM Glycine pH 1.5, followed by kinetic buffer. The data was analyzed using a global fit with a 1:1 interaction model from Sartorius Octet Analysis studio. Representative CD123 affinity measurements are shown below.

TABLE 3

CD123 binding affinities of representative mutant variants

| Clone | SEQ ID NO: | Mutations | KD (nM) | ka (1/Ms) | kdis (1/s) |
|---|---|---|---|---|---|
| 0C8S | 13 | 6T1D (G8S, K48E, N50S, I59L) | 1.0 | 1.46E+05 | 1.51E−04 |
| 1F9I | 12 | 6T1D (L21Q, I59L) | 7.6 | 8.52E+04 | 6.46E−04 |
| 3F4N | 8 | 6T1D (N50S) | 1.3 | 2.13E+05 | 2.75E−04 |
| 4I0K | 31 | 6T1D (W16S) | 14 | 1.77E+05 | 2.52E−03 |
| 4R8U | 11 | 6T1D (K48E, N50S) | 1.2 | 2.54E+05 | 3.04E−04 |
| 5B1Q | 14 | 6T1D(G8S, L21Q, K48E, N50S, I59L) | 0.73 | 1.87E+05 | 1.36E−04 |
| 6K4C | 111 | 6T1D (D5A) | 18 | 1.97E+05 | 3.53E−03 |
| 6T1D | 5 | 6T1D(R17Q, S24T, S65E) | 7.6 | 1.39E+05 | 1.05E−03 |
| 8O3S | 24 | 6T1D (W16T) | 28 | 2.35E+05 | 6.65E−03 |
| 8W9C | 4 | wild type | 5.2 | 1.77E+05 | 9.24E−04 |

Adapter proteins comprising variants of 8W9C (SEQ ID NO: 4) D domain were further assessed for binding to CD123-expressing target cells. All steps were performed in FCS buffer (FBS+3% BSA) on ice. CD123-expressing, OCI-AML2 cells (1e6/ml) were blocked in FCS buffer for 20 min then incubated with HIS-tagged Adapter proteins at concentrations of 100, 33, 11, 3.7, 1.2, 0.41, 0.14 and 0.046 ug/ml for 30 min. Cells were washed twice with FCS buffer then Fc receptors were blocked by incubation with Human TruStain FcX Fc Receptor Blocking Solution (Biolegend) for 10 min immediately followed by detection with AF647-anti-HIS antibody (Biolegend) for 30 min. Cells were washed twice with FCS buffer then immediately run on a FACSCelesta (BD) flow-cytometer. Flowcytometry data was analyzed using FlowJo software and the MFI defined as Mean Fluorescence Intensity. As shown in FIG. 4, mutations identified through screening for enhanced binding to recombinant CD123 binding (e.g. G8S, K48E, N50S and I59L) promote enhanced binding to native CD123 expressed on the surface of tumor cells.

Example 2. In Vitro Activity of Variant D Domains with Increased Affinity to CD123

To assess the impact of affinity increasing mutations identified in the context of 8W9C (SEQ ID NO: 4) to enhance the biological activity of Adapter proteins, a T cell reporter assay was performed. The Jurkat NFAT (Nuclear Factor of Activated T cells) reporter cell line (JNL10) was generated by transducing the Jurkat E6.1 cell line (Sigma) with the Cignal Lenti NFAT Reporter, containing the NFAT enhancer coupled to the luciferase reporter gene (Qiagen). To assess NFAT signaling activity, JNL10 reporter cells were transfected by electroporation with a construct encoding the 8G8V-CAR (SEQ ID NO: 69) comprising the 8G8V (SEQ ID NO: 70) p26 AFP-binding D domain and cultured at 37° C. overnight in a 12-well plate. The next day, electroporated JNL10 cells were co-cultured with either CD123+ or CD123− MOLM13 cells at an approximately 1:1 ratio in 100 µl culture medium in a 96-well plate for 5 hours at 37° C. along with titrated CD123 specific Adapter proteins comprising the p26 polypeptide and the 6T1D, 3F4N or 4R8U D domains, SEQ ID NO: 101, 102 and 103, respectively, diluted in 10 µl of culture media. After the 5-hour incubation, the activity of NFAT-mediated signaling was monitored by the addition of Bright-Glo luciferase substrate (Promega) and measuring relative luminescence units (RLU) using a plate reader. JNL10/8G8V-CAR cells are activated by the Adapter in a dose and target-specific manner (FIGS. 5 and 6). Furthermore, as compared to the parental D domain (6T1D), JNL10/8G8V-CAR T cells are activated at lower concentrations by the Adapter proteins comprising D domains that bind to CD123 with higher affinity such as 3F4N (SEQ ID NO: 8) and 4R8U (SEQ ID NO: 11). As shown in FIG. 6, no JNL10/8G8V-CAR T cell activation was observed in the absence of CD123 expression by the target cells.

Figure 7:
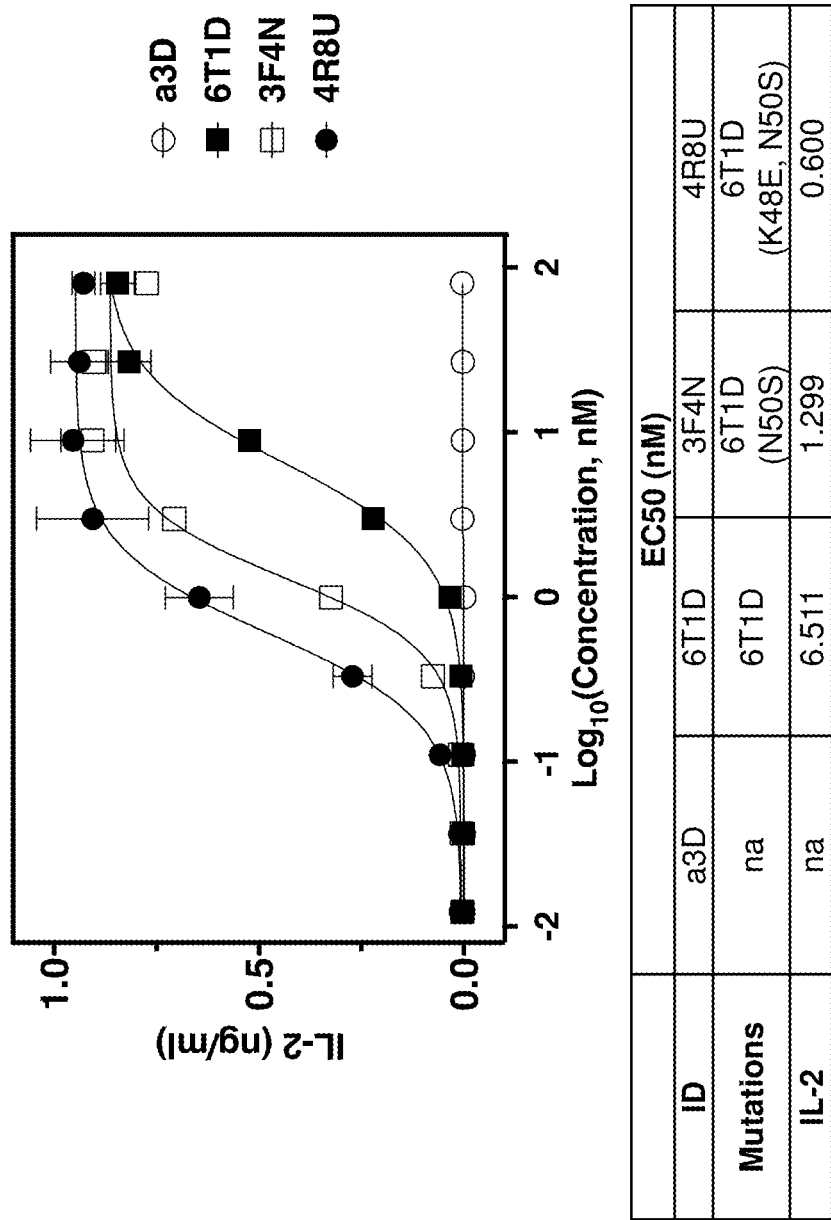
FIG. 7. IL-2 production of CAR T cells cultured with CD123-specific Adapter proteins. Primary T cells expressing 8G8V-CAR were assayed for IL-2 expression in the presence of MOLM13 target cells and various concentrations of Adapter proteins. Samples included affinity modified variants of 6T1D (e.g. 3F4N & 4R8U). The parental D domain (6T1D) and non-binding (a3D) controls were assayed for comparison.
Figure 8:
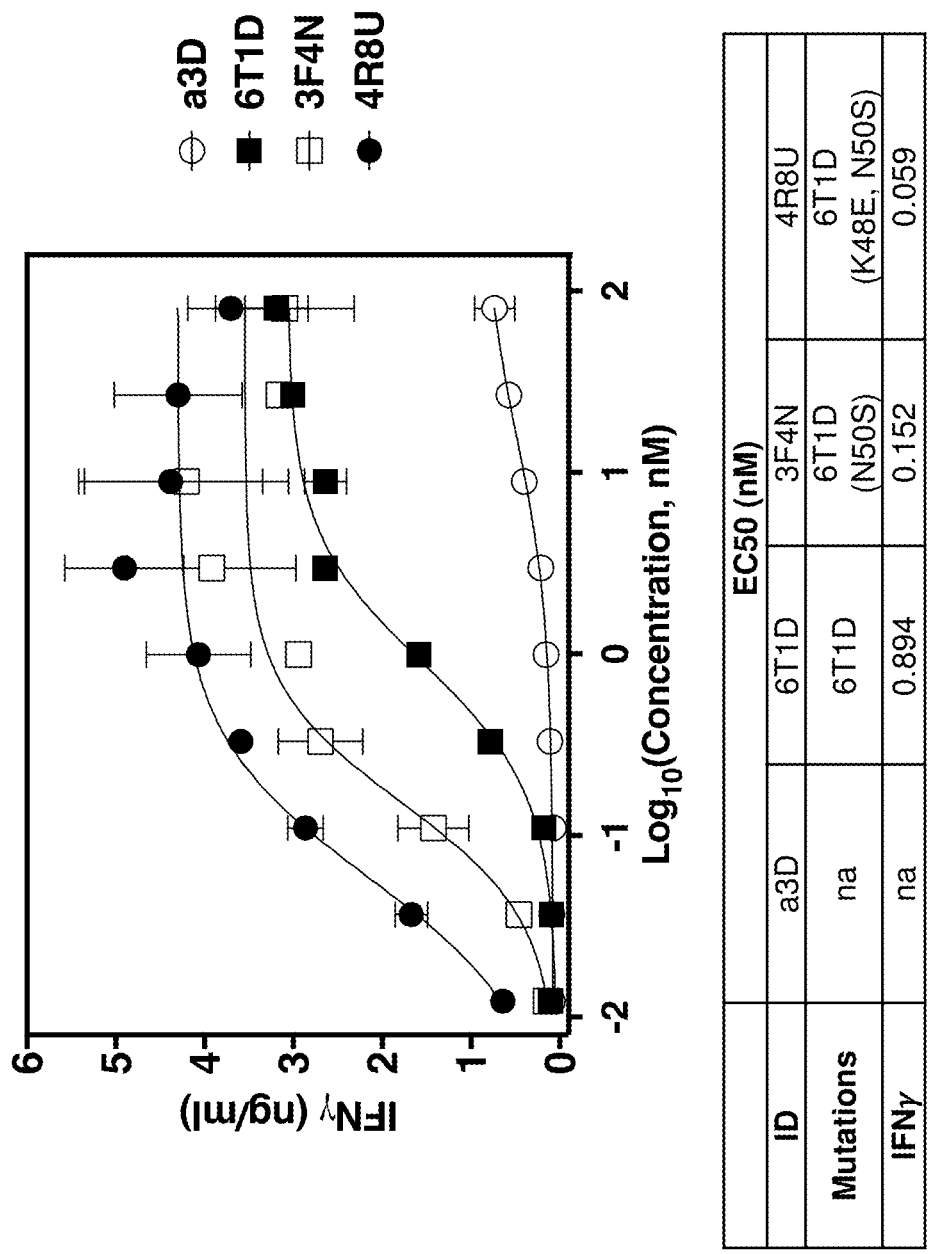
FIG. 8. IFNγ production of CAR T cells cultured with CD123-specific Adapter proteins. Primary T cells expressing 8G8V-CAR were assayed for IFNγ expression in the presence of MOLM13 target cells and various concentrations of Adapter proteins. Samples included affinity modified variants of 6T1D (e.g. 3F4N & 4R8U). The parental D domain (6T1D) and non-binding (a3D) controls were assayed for comparison.

Cytokine production can be an alternative measure of T cell activation. Cytokine production was assessed by culturing 8G8V-CAR (SEQ ID NO: 69) expressing T cells (7 days post-activation) with MOLM13-GFP/Luc target cells, in 96-well plates. After 24 hours culture supernatants were collected and cytokine production was assessed by Ready-Set-Go human IL2 and IFNγ uncoated ELISA kits, (eBioscience/ThermoFisher). Culture supernatants were diluted 1:5 prior to ELISA. In the presence of CD123 expressing MOLM13 target cells, CD123 specific Adapter proteins promote dose- and affinity-dependent production of IL-2 (FIG. 7) and IFNγ (FIG. 8) by primary T cells expressing 8G8V-CAR. Furthermore, as compared to Adapters comprising the parental D domain (6T1D), those that comprise D domains that bind to CD123 with higher affinity, such as 3F4N (SEQ ID NO: 8) and 4R8U (SEQ ID NO: 11), stimulated 8G8V-CAR T cells to produce more cytokine at lower Adapter concentrations.

Figure 9:
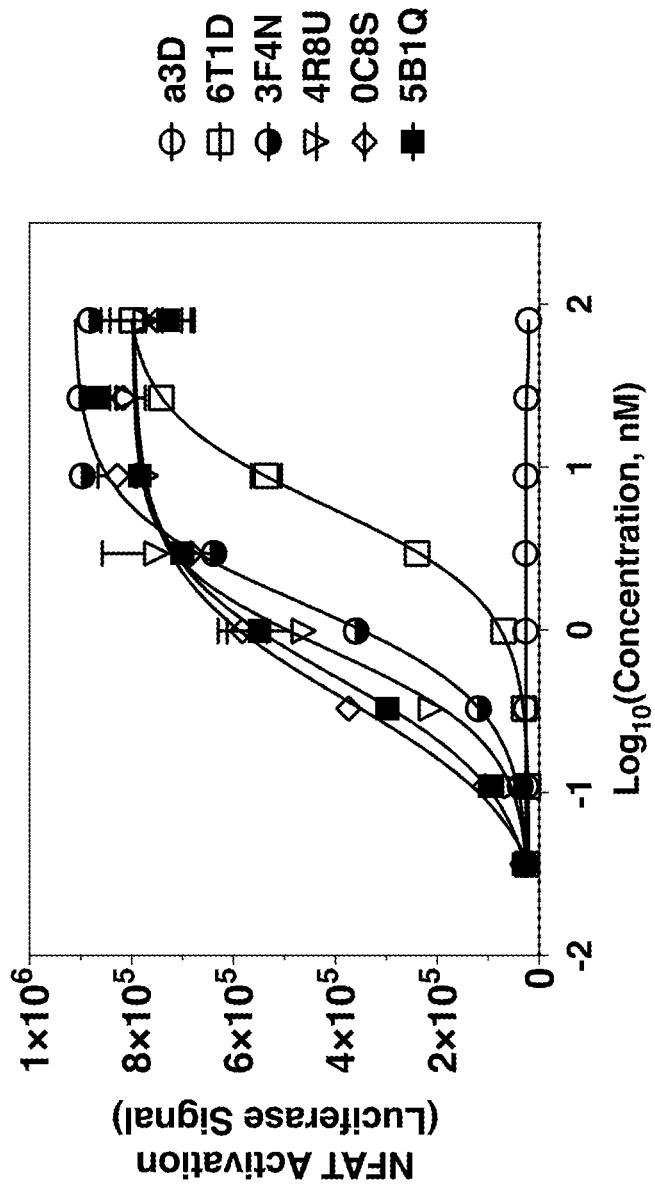
FIG. 9. NFAT activation of 8G8V-CAR T cells cultured with CD123-specific Adapter proteins and target cells. JNL10/8G8V-CAR were assayed for activation in the presence of MOLM13 target cells and various concentrations of Adapter proteins. Samples included affinity modified variants of 6T1D (e.g. 3F4N, 4R8U, 0C8S & 5B1Q). The parental D domain (6T1D) and non-binding (a3D) controls were assayed for comparison.
Figure 10:
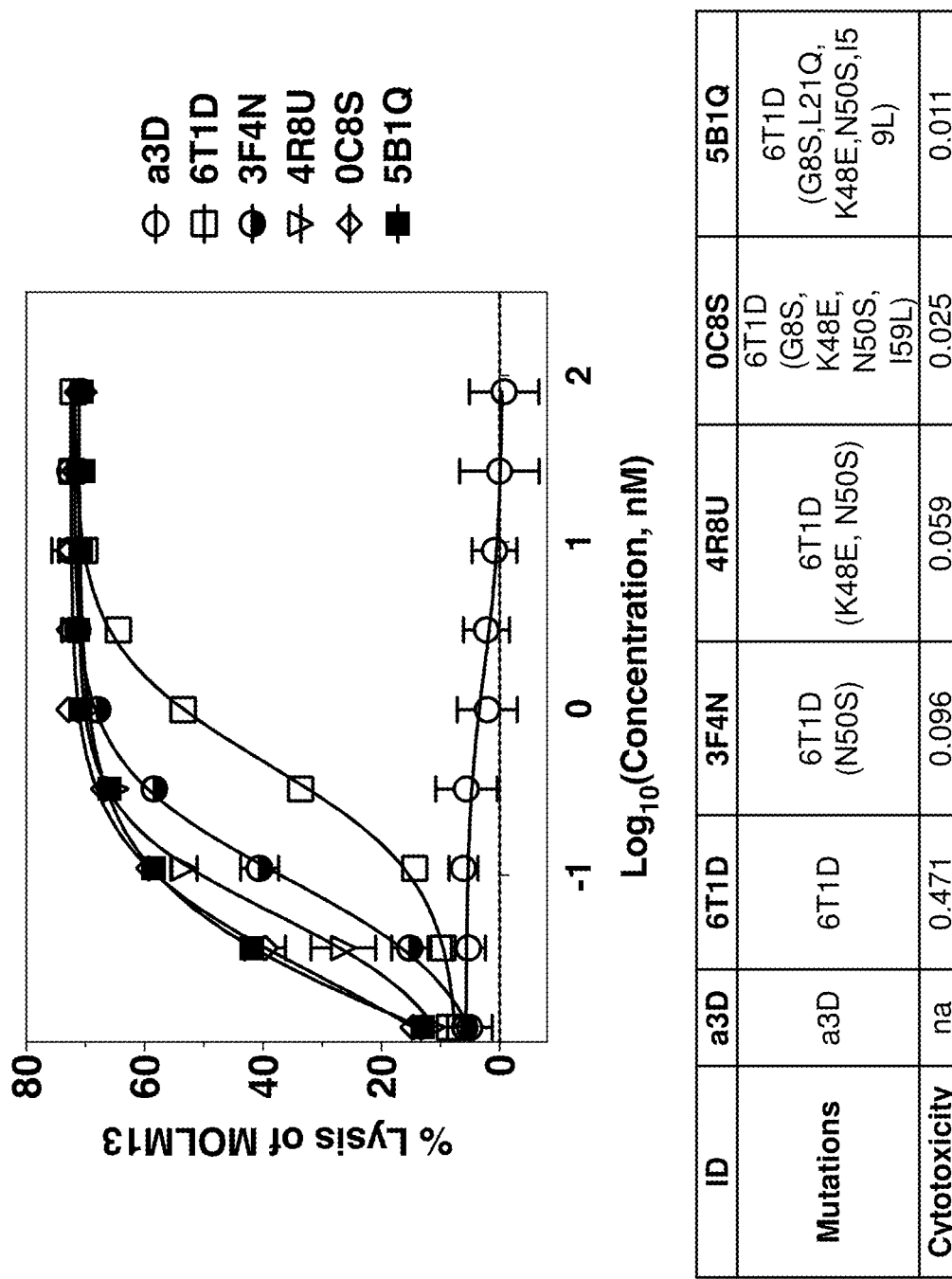
FIG. 10. Lysis of target cells by 8G8V-CAR T cells cultured with CD123-specific Adapter proteins. MOLM13 target cell lysis by primary 8G8V-CAR T cells in the presence of various concentrations of Adapter proteins were assayed. Samples included affinity modified variants of 6T1D (e.g. 3F4N, 4R8U, 0C8S & 5B1Q). The parental D domain (6T1D) and non-binding (a3D) controls were assayed for comparison.
Figure 11:
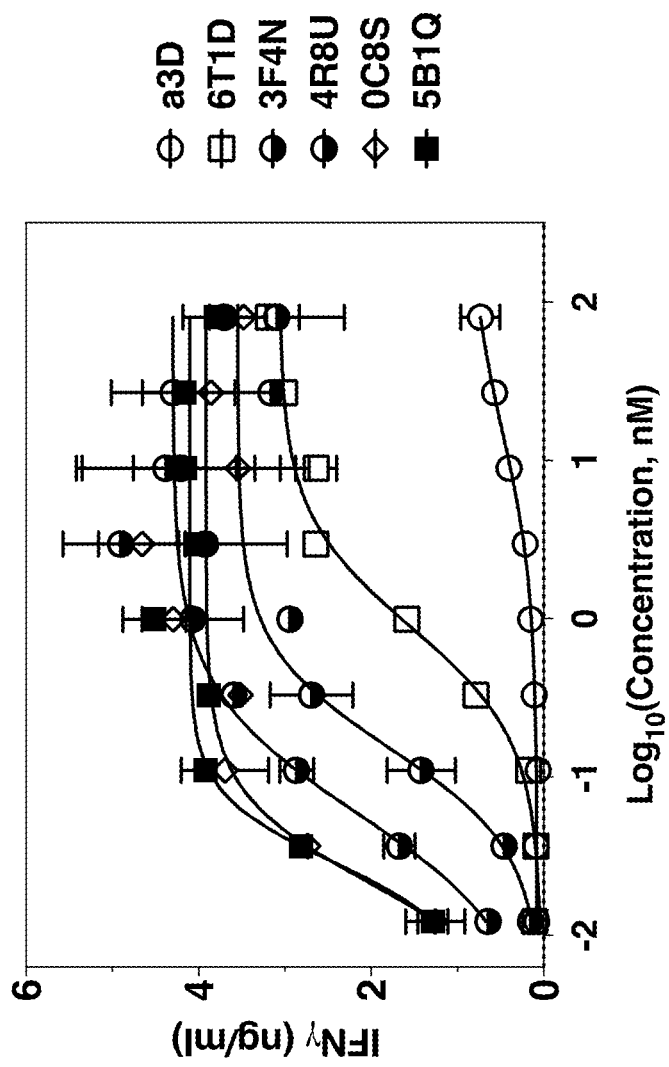
FIG. 11. IFNγ production by 8G8V-CAR T cells. Primary 8G8V-CAR T cells were assayed by ELISA for IFNγ production in the presence of MOLM13 target cells and various concentrations of CD123-specific Adapter protein. Samples included affinity modified variants of 6T1D (e.g. 3F4N, 4R8U, 0C8S & 5B1Q). The parental D domain (6T1D) and non-binding (a3D) controls were assayed for comparison.
Figure 12:
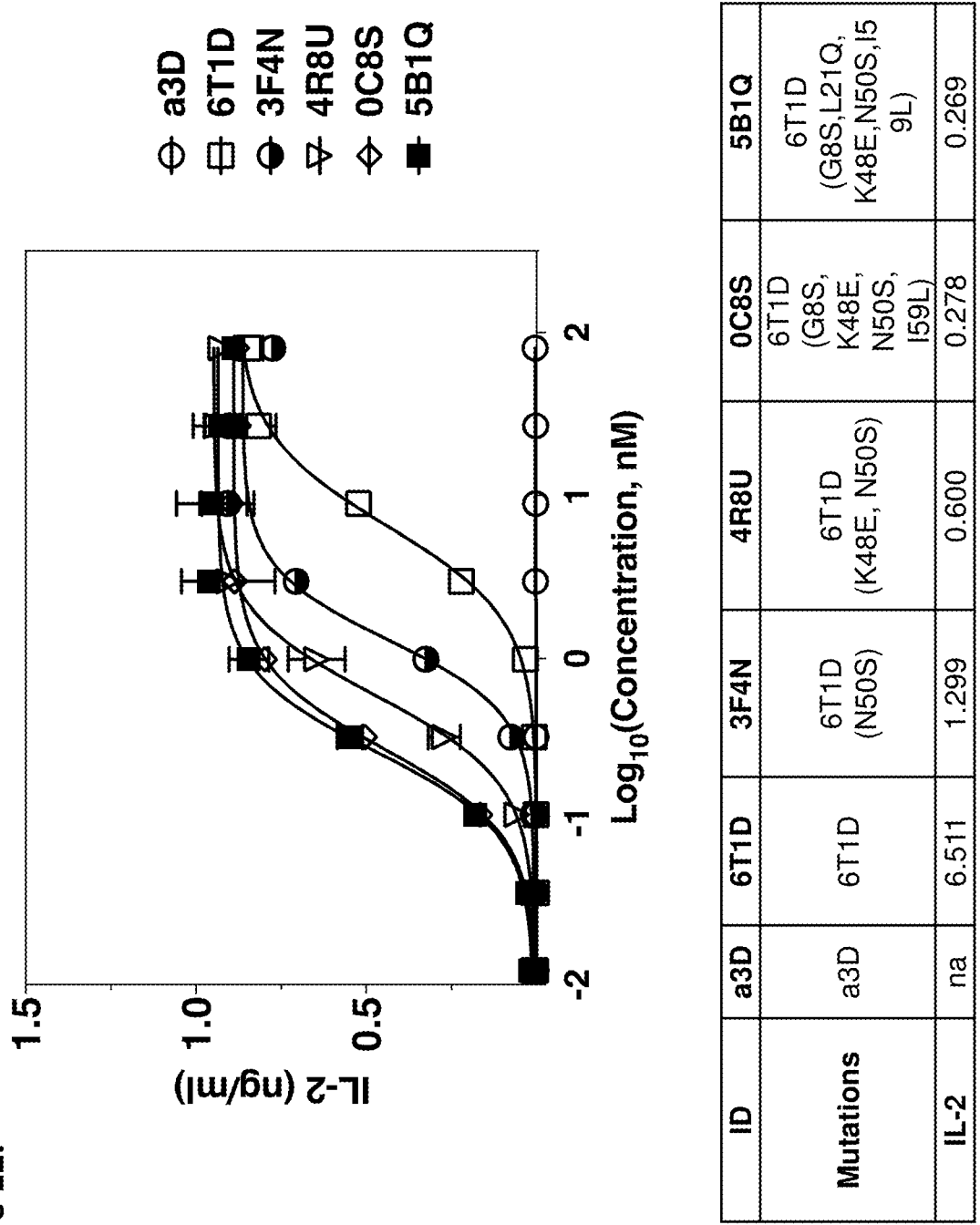
FIG. 12. IL-2 production by 8G8V-CAR T cells. Primary 8G8V-CAR T cells were assayed by ELISA for IL-2 production in the presence of MOLM13 target cells and various concentrations of CD123-specific Adapter protein. Samples included affinity modified variants of 6T1D (e.g. 3F4N, 4R8U, 0C8S & 5B1Q). The parental D domain (6T1D) and non-binding (a3D) controls are assayed for comparison.

Additional mutations (e.g. G8S, L21Q & I59L) identified through screens following phage library selection were combined with the ones presented above (6T1D(K48E, N50S)) to produce, the 0C8S (SEQ ID NO: 13) (i.e. 6T1D (G8S,K48E,N50S,I59L)) and 5B1Q (SEQ ID NO: 14) (i.e. 6T1D (G8S,L21Q,K48E,N50S,I59L)) D domains. When incorporated into an Adapter, these D domains are more potent than the parental variants, as measured by NFAT activation (FIG. 9), target cell lysis (FIG. 10) and production of IFNγ (FIG. 11) and IL-2 (FIG. 12).

Figure 13:
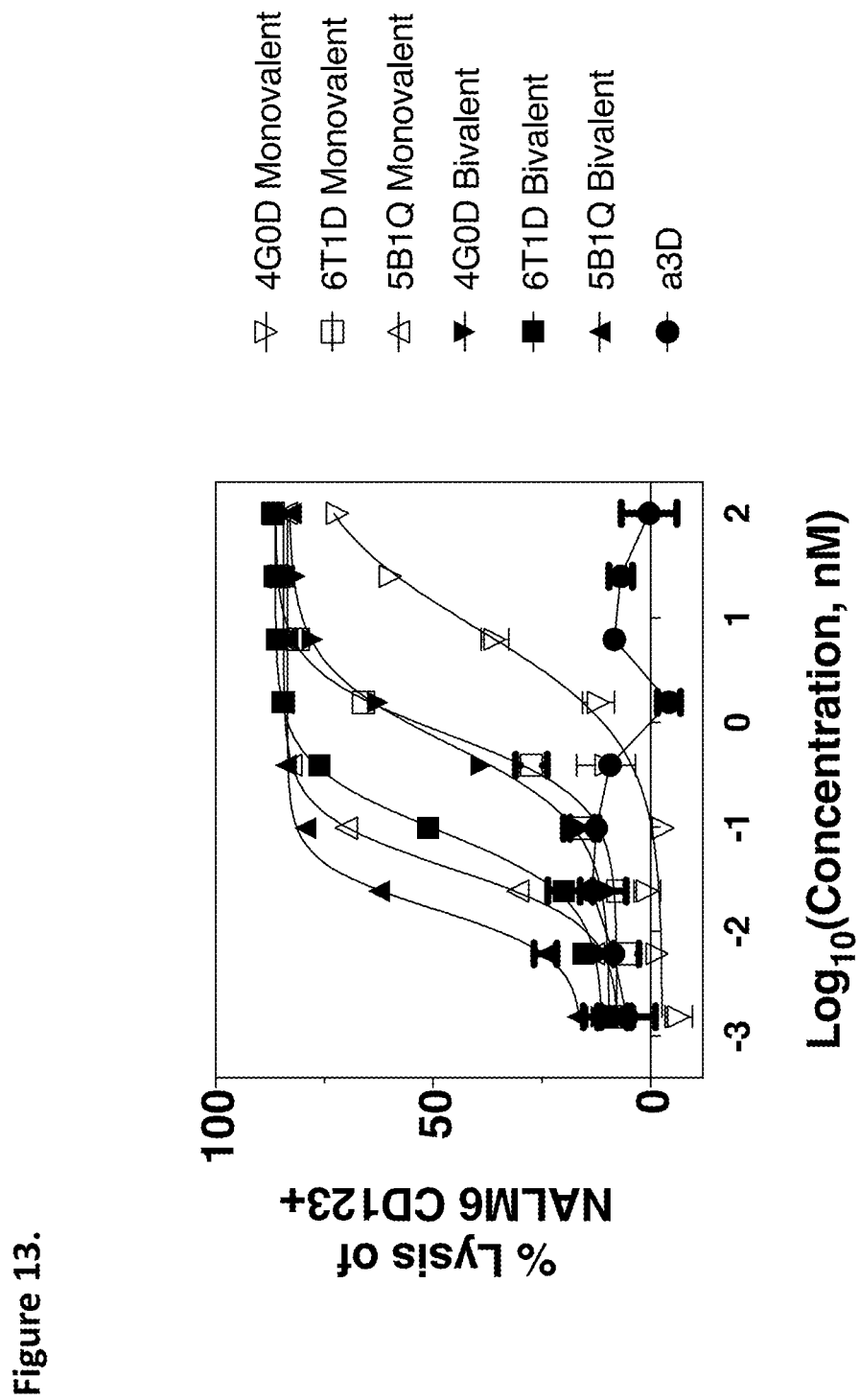
FIG. 13. Lysis of target cells by 8G8V-CAR T and CD123-specific Adapter proteins. NALM6-CD123+ cells were lysed by primary 8G8V-CAR T cells in the presence of various concentrations of Adapter proteins. Samples included both mono and bivalent formats of Adapter proteins comprised of low affinity (4G0D), high affinity (5B1Q) and parental D domain (6T1D). Non-binding (a3D) controls is assayed for comparison.

Combinations of affinity and valency of D domains can be used to further broaden the dynamic range of the CD123 specific Adapter proteins. Adapter proteins were generated in both mono and bivalent formats, utilizing the parent 6T1D (SEQ ID NO: 5) D domain or variants incorporating high affinity (e.g., 5B1Q (SEQ ID NO: 14)) or low affinity (e.g., 4G0D (SEQ ID NO: 32)) variants. These combinations were assessed using a clone of NALM6 cell line expressing elevated levels of CD123 (NALM6-CD123+). As shown in FIG. 13, the lysis of NALM6-CD123+ cells by primary 8G8V-CAR (SEQ ID NO: 69) expressing T cells can be modulated by the dose (concentration), valency (mono or bi-valent) and affinity (high, medium or low) of the CD123-binding Adapter proteins and collectively the EC50s span 3 logs. Low affinity (e.g., 4G0D) D domains exhibit the greatest gain in potency when incorporated into a bivalent Adapter format. However, a monovalent Adapter comprising the high affinity 5B1Q D domain is more potent than the bivalent Adapter comprising the 6T1D D domain.

Example 3. In Vivo Activity of Variant D Domains with Increased Affinity to CD123

Figure 14:
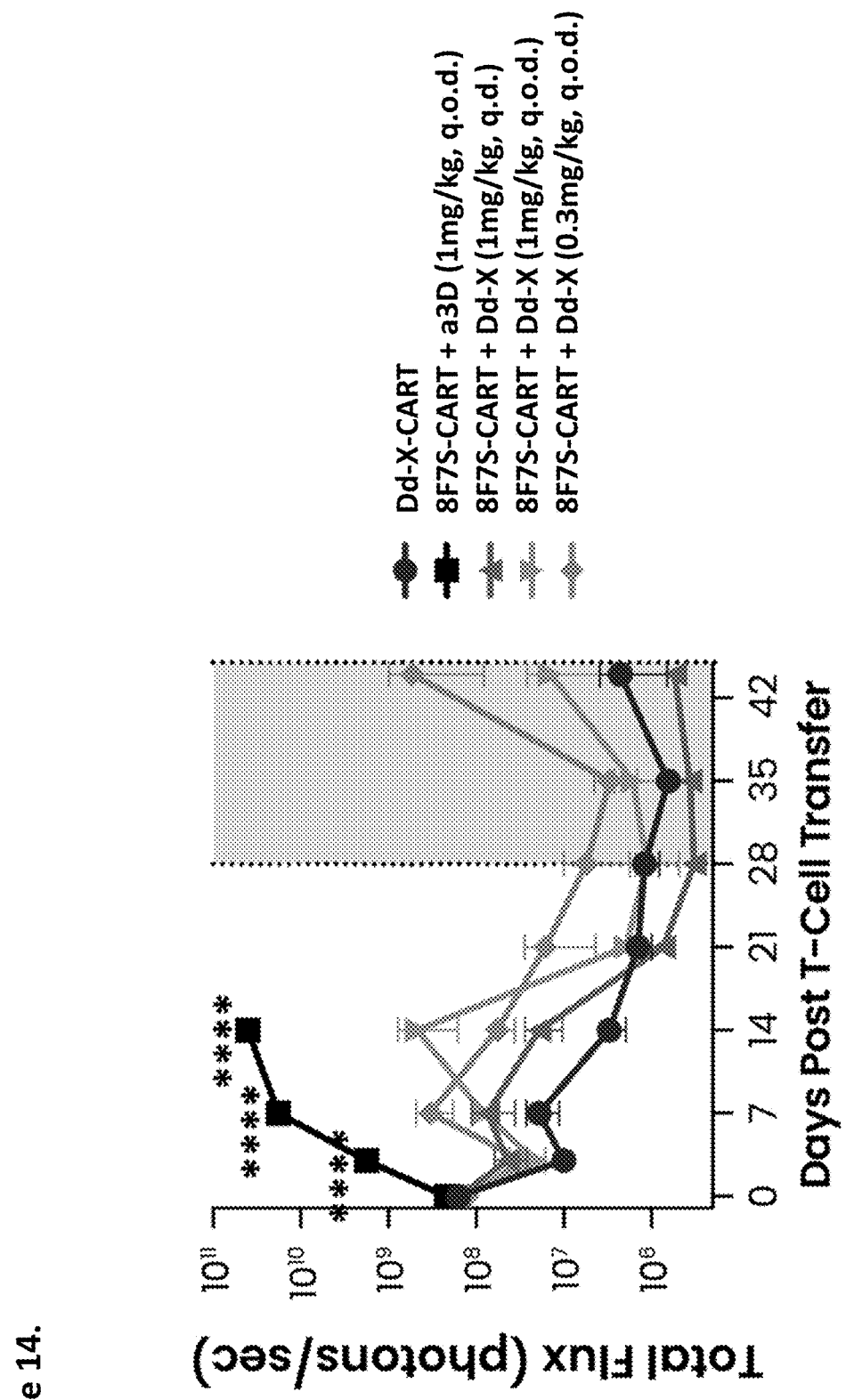
FIG. 14. In vivo efficacy of the Dd-X CD123 specific D domain were assessed using a MOLM14-GFP/Luciferase tumor model. Shaded area indicates Dd-X Adapter withdrawal. q.o.d. every other day; q.d. every day.

The in vivo efficacy of Adapters comprising the affinity enhanced variants of the 8W9C (SEQ ID NO: 4) D domain were assessed using a MOLM14-GFP/Luciferase tumor model. Tumor cells ($5×10^6$) were engrafted via intravenously tail vein injection of NOD.Cg-PrkdcscidIl2rgtm1Wjl/SzJ mice (Jackson Laboratories). Six days after tumor engraftment, mice were administered a single dose of either $5×10^6$ CD123 specific Dd-X-CAR expressing CD3 deficient T cells or $5×10^6$ universal 8F7S-CAR (SEQ ID NO: 107) expressing CD3 deficient T cells. Native T cells were transduced with lentiviral vectors encoding the Dd-X-CAR or 8F7S-CAR and a LentiCRISPRv2 construct encoding a gRNA targeting the constant region of the TCR β-chain. After 7 days of expansion, remaining CD3+/TCRαβ+ T cells were depleted and CD3− cells were expanded. Mice receiving the 8F7S-CAR-T cells were also administered for 28 days either the negative control a3D-Adapter (SEQ ID NO: 105) at 1 mg/kg i.p., q.o.d. or the CD123 specific Dd-X-Adapter at 1 mg/kg i.p., q.d., 1 mg/kg i.p., q.o.d., or 0.3 mg/kg i.p., q.o.d (FIG. 14) Animals were monitored for tumor burden during treatment and after Adapter withdrawal. Tumor burden was measured by intraperitoneal injection with 3 mg D-luciferin (Caliper Life Sciences), followed by florescence imaging 4 minutes later with a Xenogen IVIS Lumina (Caliper Life Sciences) and a 1 minute exposure time. Living Image Version 4.3.1 SP2 software (Caliper Life Sciences) was used to analyze the bioluminescent signal flux (photons/s/cm$^2$/sr, scaled at $10^5$-$10^7$) for each mouse. As measured by fluorescent flux, tumor control using the high-affinity monovalent CD123 specific Adapter protein in combination with universal 8F7S-CAR T cells, is comparable to that of the CD123 specific CAR T cell treatment group. The treatment resulted in complete regression of disseminated MOLM14 tumors in a schedule and dose-dependent manner without the aid of alloreactivity.

Figure 15:
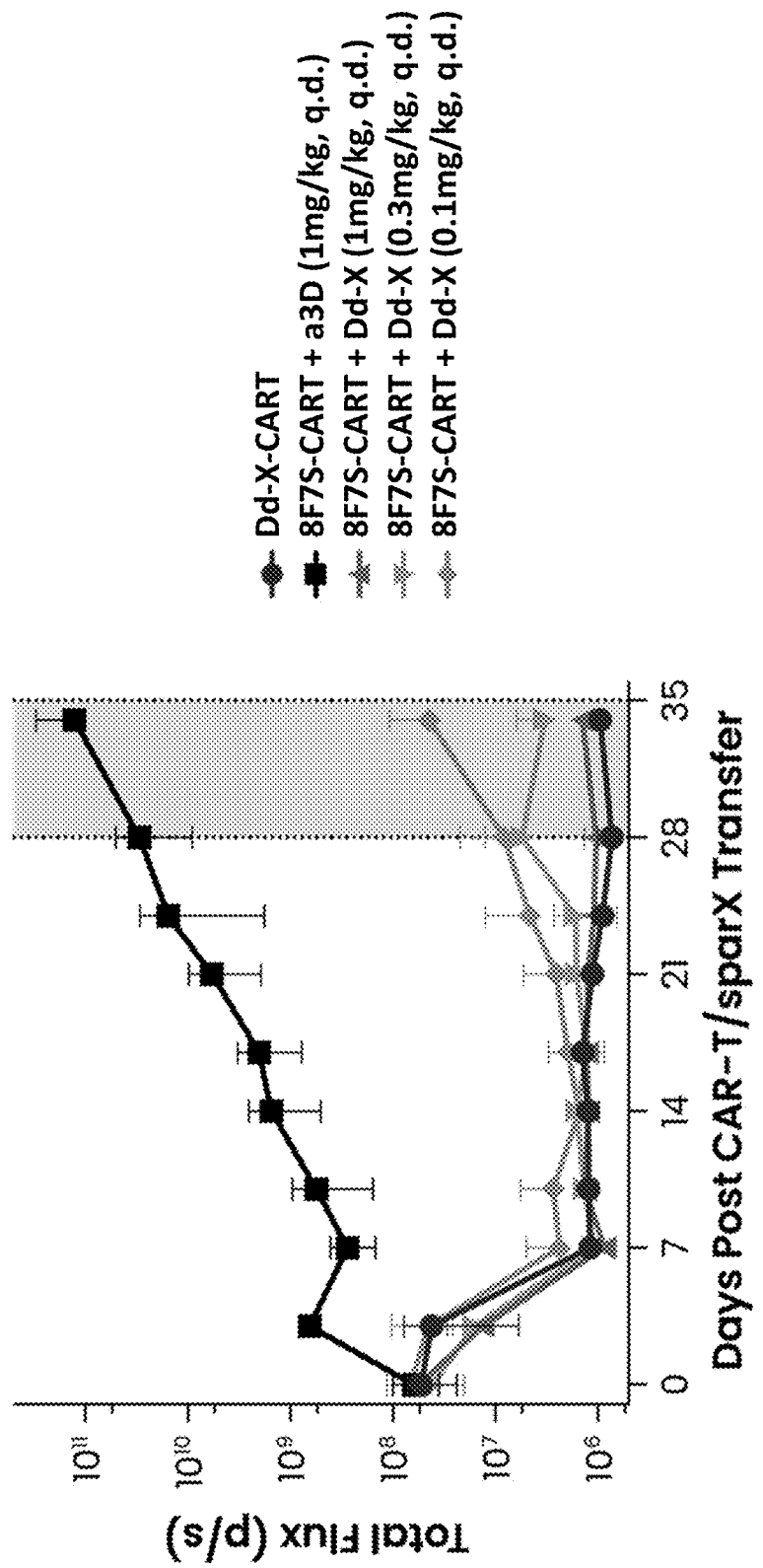
FIG. 15. In vivo efficacy of the Dd-X CD123 specific D domain were assessed using a disseminated MV4-11 tumor model. Shaded area indicates Dd-X Adapter withdrawal. q.d. every day.
Figure 17:
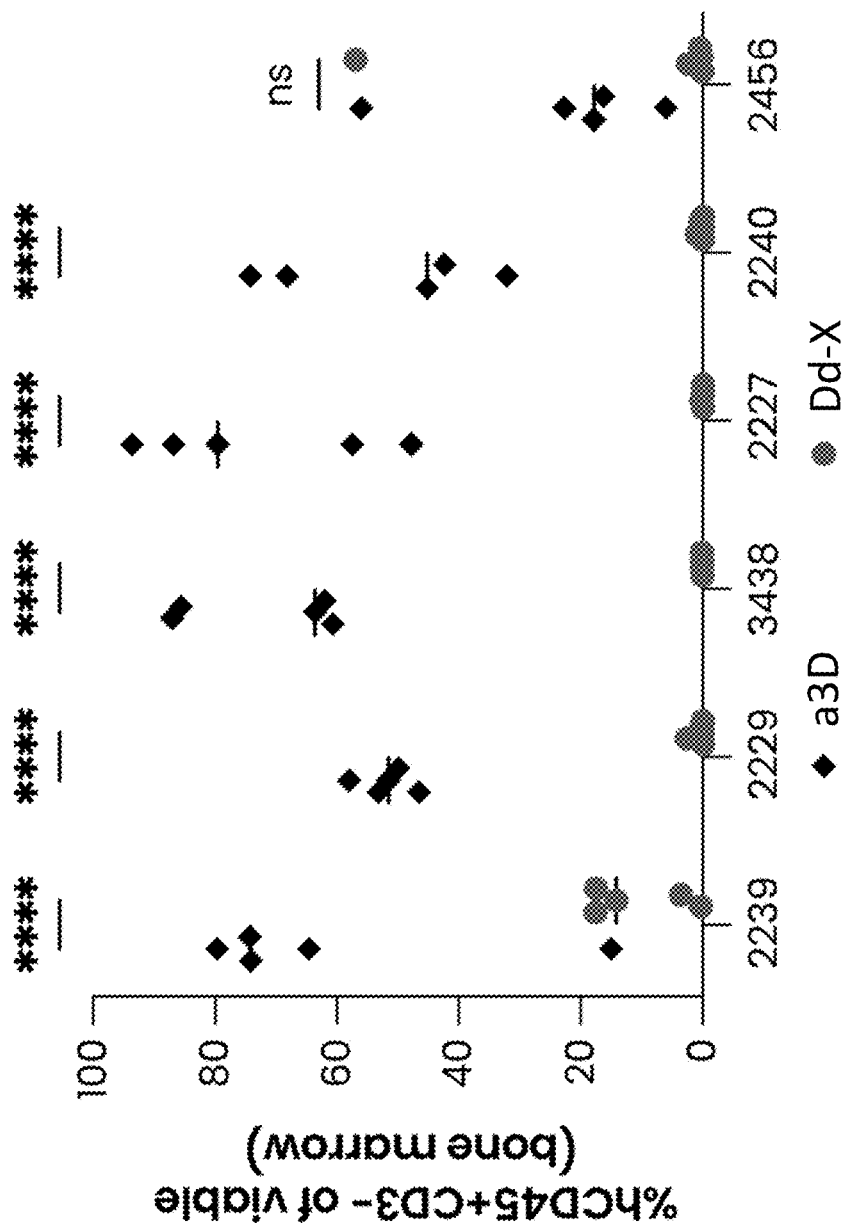
FIG. 17. The Dd-X CD123 specific D domain clears or controls multiple patient-derived AML xenografts. The proportion of the live cells within the bone marrow which represented engrafted AML cells (hCD45+CD3−) following treatment is shown.

T cell based treatments using an affinity enhanced variant of the 8W9C (SEQ ID NO: 4) D domain resulted in the complete regression of disseminated MV4-11 tumors in a dose-dependent manner in an animal model. NOD.Cg-PrkdcscidIl2rgtm1Wjl/SzJ mice (Jackson Laboratories) were engrafted with $5×10^6$ MV4-11 tumor cells. Fifteen days after tumor engraftment, mice were administered a single dose of either $5×10^6$ CD123 specific Dd-X-CAR expressing CD3 deficient T cells or $5×10^6$ universal 8F7S-CAR (SEQ ID NO: 107) expressing CD3 deficient T cells. Mice receiving the 8F7S-CAR-T cells were also administered for 28 days either the negative control a3D-Adapter (SEQ ID NO: 105) at 1 mg/kg i.p., q.d. or the CD123 specific Dd-X-Adapter at 1 mg/kg i.p., q.d., 0.3 mg/kg i.p., q.d., or 0.1 mg/kg i.p., q.d (FIG. 15) Animals were monitored for tumor burden during treatment and after Adapter withdrawal. As measured by fluorescent flux, tumor control using the high-affinity monovalent CD123 specific Adapter protein in combination with universal 8F7S-CAR T cells, is comparable to that of the CD123 specific CAR T cell treatment group. The treatment resulted in complete regression of disseminated MV4-11 tumors in a schedule and dose-dependent manner.

T cell based treatment using an affinity enhanced variant of the 8W9C (SEQ ID NO: 4) D domain cleared or controlled multiple patient-derived AML xenografts (PDX). Generation of AML-PDX models: Prior to inoculation with AML cells, animals were sub-lethally irradiated with 150 cGy whole body irradiation, followed by the transfer of $2\times10^6$ human T-cell depleted AML cells derived from cryo-preserved specimens of patient leukapheresis. The recipient strain (NOG, NOG-EXL, and NCG) was previously established and is indicated in the FIG. 16, along with patient and disease characteristics. Model engraftment kinetics were established to define a time window in which animals exhibited human tumor cell engraftment in the bone marrow of 20% or greater. For each model, a surrogate cohort of animals (n=3-5) were sacrificed at intermittent time points prior to the estimated engraftment window to collect bone marrow for AML burden analysis. Once surrogate animals had achieved engraftment criterion in bone marrow, defined as % hCD45+ of viable cells≥20% on average of animals sampled, the remainder of pre-study animals were randomized based on body weight for treatment initiation. All on-study animals received a single dose of 8F7S-CAR-T cells generated from healthy-donor T cells, followed by once daily IP injections of either the negative control a3D or CD123 specific Dd-X Adapter at 3 mg/kg for 14 days. On day 14 after treatment initiation, animals from all groups were euthanized to collect bone marrow for flow cytometry analysis. The proportion of the live cells within the bone marrow which represented engrafted AML cells (hCD45+ CD3−) was determined for all on-study animals.

All publications, patents, patent applications, internet sites, and accession numbers/database sequences (including both polynucleotide and polypeptide sequences) cited are herein incorporated by reference in their entirety for all purposes to the same extent as if each individual publication, patent, patent application, internet site, or accession number/database sequence were specifically and individually indicated to be so incorporated by reference.

It is contemplated that various combinations or subcombinations of the specific features and aspects disclosed above may be made and still fall within the embodiments, encompassed by the disclosure. Further, the disclosure of any particular feature, aspect, method, property, characteristic, quality, attribute, element, or the like in connection with an embodiment can be used in all other embodiments, set forth herein. Accordingly, it should be understood that various features and aspects of the disclosed embodiments, can be combined with or substituted for one another in order to form varying modes of the disclosed embodiments. Thus, it is intended that the scope of the embodiments, encompassed by the present disclosure should not be limited by the particular disclosed embodiments, described herein. Moreover, while the encompassed embodiments, are susceptible to various modifications, and alternative forms, specific examples thereof have been shown in the drawings and are herein described in detail. It should be understood, however, that the scope of the disclosure is not to be limited to the particular forms or methods disclosed, but to the contrary, the disclosure is to cover all modifications, equivalents, and alternatives falling within the spirit and scope of the various embodiments, described and the appended claims. Any methods disclosed herein need not be performed in the order recited. The methods disclosed herein include certain actions taken by a practitioner; however, they can also include any third-party instruction of those actions, either expressly or by implication. For example, actions such as "administering a T cell comprising a DDpp-CAR" include "instructing the administration of a T cell comprising a DDpp-CAR." In addition, where features or aspects of the disclosure are described in terms of Markush groups, those skilled in the art will recognize that the disclosure is also thereby described in terms of any individual member or subgroup of members of the Markush group.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 10 nanometers" includes "10 nanometers."

What is claimed is:

1. A D Domain target binding polypeptide that specifically binds CD123 and comprises the amino acid sequence of any one of SEQ ID NOs: 8, 13, or 14.

2. A polypeptide comprising the D domain of claim 1 fused to a heterologous polypeptide.

3. The polypeptide of claim 2, wherein the heterologous polypeptide comprises,
   (a) a full-length antibody or an antibody fragment;
   (b) an Fc domain;
   (c) a transmembrane domain;
   (d) a membrane associating domain;
   (e) human serum albumin or a fragment thereof;
   (f) AFP or a fragment thereof;
   (g) AFP p26 or a fragment thereof; or
   (h) the extracellular domain of a receptor or a fragment thereof.

4. The polypeptide of claim 2, which is labeled or conjugated to a therapeutic or cytotoxic agent.

5. An isolated polynucleotide encoding the polypeptide of claim 2.

6. A method of producing the polypeptide of claim 2, comprising culturing a host cell comprising a polynucleotide encoding the polypeptide under suitable conditions to produce the polypeptide.

7. A pharmaceutical composition comprising the polypeptide of claim 2 and a pharmaceutically acceptable excipient.

8. A chimeric antigen receptor (CAR) which comprises a target binding domain comprising the D domain that specifically binds CD123 of claim 1.

9. The CAR of claim 8 further comprising a transmembrane domain and an intracellular signaling domain.

10. The CAR of claim 9, wherein
    (a) the transmembrane domain comprises a CD8a, 41BB, or CD28 transmembrane domain;
    (b) the intracellular signaling domain is selected from the group consisting of a domain of a human T cell receptor alpha, beta, or zeta chain; a human 41BB domain; a human CD28 domain; and any combination thereof; and/or
    (c) the intracellular signaling domain comprises the intracellular domain of a costimulatory molecule selected from the group consisting of CD27, CD28, 41BB, OX40, CD30, CD40, PD1, lymphocyte function-associated antigen-1 (LFA-1), CD2, CD7, LIGHT, NKG2C, NKG2D, B7-H3, a ligand that specifically binds with CD83, and any combination thereof.

11. The CAR of claim 8, comprising the amino acid sequence of any one of SEQ ID NOs: 65, 66, or 67.

12. An isolated polynucleotide encoding the CAR of claim 8.

13. A lentiviral vector comprising the polynucleotide of claim 12.

14. A host cell comprising the polynucleotide of claim 12.

15. A cell engineered to express the CAR of claim 5.

16. The cell of claim 15, which is a T cell or a natural killer (NK) cell.

17. A pharmaceutical composition comprising a cell expressing the CAR of claim 8 and a pharmaceutically acceptable excipient.

18. The pharmaceutical composition of claim 17, wherein the cell is a T cell or a natural killer (NK) cell.

19. An adapter comprising (a) the D domain target binding domain that specifically binds CD123 of claim 1, and (b) an antigenic determinant (AD).

20. The adapter of claim 19, wherein the AD comprises an AFP p26 polypeptide.

21. The adapter of claim 20, wherein the AFP p26 polypeptide comprises an amino acid sequence selected from the group consisting of SEQ ID NO: 37-43 and 44.

22. The adapter of claim 10, wherein the adapter comprises two D domains that specifically bind CD123.

23. A method of delivering an immune response to a target cell or killing a target cell, the method comprising:
    (a) contacting a composition comprising the target cell with a cell expressing a chimeric antigen receptor (CAR) comprising (i) the D domain that binds to CD123 of claim 1, (ii) a transmembrane domain, and (iii) an intracellular domain;
    (b) contacting a composition comprising the target cell with an adapter, wherein (a) the composition comprising the target cell further comprises a cell expressing a CAR, wherein the CAR comprises (i) an antigenic determinant binding domain (ADBD) that binds to an AFP p26 antigenic determinant (AD), (ii) a transmembrane domain, and (iii) an intracellular domain; and (b) the adapter comprises (i) the D domain that binds to CD123 of claim 1 and (ii) AFP p26 AD;
    (c) contacting a composition comprising the target cell with a cell expressing a CAR, wherein (a) the CAR comprises (i) an antigenic determinant binding domain (ADBD) that binds to an AFP p26 antigenic determinant (AD), (ii) a transmembrane domain, and (iii) an intracellular domain; and (b) the composition comprising the target cell further comprises an adapter comprising (i) the D domain that binds to CD123 of claim 1 and (ii) an AFP p26 AD; or
    (d) contacting a composition comprising the target cell with a cell expressing a CAR and an adapter, wherein (a) the CAR comprises (i) an antigenic determinant binding domain (ADBD) that binds to an AFP p26 antigenic determinant binding domain (ADBD) that binds to an AFP p26 antigenic determinant (AD), (ii) a transmembrane domain, and (iii) an intracellular domain; and (b) the adapter comprises (i) the D domain that binds to CD123 of claim 1 and (ii) an AFP p26 AD.

24. The method of claim 23, wherein
    (a) the D domain that binds to CD123 comprises an amino acid sequence selected from the group consisting of SEQ ID NOs: 8, 13, and 14;
    (b) the D domain that binds to CD123 comprises the amino acid sequence of SEQ ID NO: 14;
    (c) the transmembrane domain comprises a CD8a, 41BB or CD28 transmembrane domain;
    (d) the intracellular signaling domain is selected from the group consisting of a domain of a human T cell receptor alpha, beta, or zeta chain; a human 41BB domain; a human CD28 domain; and any combination thereof;
    (e) the intracellular signaling domain comprises the intracellular domain of a costimulatory molecule selected from the group consisting of CD27, CD28, 41BB, OX40, CD30, CD40, PD1, lymphocyte function-associated antigen-1 (LFA-1), CD2, CD7, LIGHT, NKG2C, NKG2D, B7-H3, a ligand that specifically binds with CD83, and any combination thereof;
    (f) the AFP p26 AD comprises an amino acid sequence selected from the group consisting of SEQ ID NO: 37-43 and 44;
    (g) the ADBD that binds to AFP p26 AD comprises a D domain that binds to AFP p26 AD;
    (h) the ADBD that binds to AFP p26 AD comprises a D domain comprising the amino acid sequence of SEQ ID NO: 73, 70-72 or 92-94;

(i) the CAR comprising a D domain that binds to AFP p26 AD comprises the amino acid sequence of SEQ ID NO: 68 or 69;
the cell expressing the CAR is an immune cell,
(k) the cell expressing the CAR is a T cell or a natural killer (NK) cell;
(l) the contacting occurs in a human subject;
(m) the target cell is a cancer cell; and/or
(n) the target cell is an acute myeloid leukemia (AML) cell or a high-risk myelodysplastic syndrome cell.

25. A method of delivering an immune response to a target cell, killing a target cell or treating cancer in a patient, the method comprising:
(a) administering to the patient a cell expressing the chimeric antigen receptor (CAR) comprising (i) the D domain that binds to CD123 of claim 1, (ii) a transmembrane domain, and (iii) an intracellular domain; or
(b) administering to the patient an adapter comprising (i) the D domain that binds to CD123 of claim 1 and (ii) an AFP p26 AD.

26. The method of claim 25, wherein
(a) the patient receiving the adapter has been administered a cell expressing a CAR, wherein the CAR comprises (i) an antigenic determinant binding domain (ADBD) that binds to an AFP p26 antigenic determinant (AD), (ii) a transmembrane domain, and (iii) an intracellular domain;
(b) the patient receiving the adapter comprises a cell expressing a CAR, wherein the CAR comprises (i) an antigenic determinant binding domain (ADBD) that binds to an AFP p26 antigenic determinant (AD), (ii) a transmembrane domain, and (iii) an intracellular domain;
or
(c) the method of (b) further comprises administering a cell expressing a CAR, wherein the CAR comprises (i) an antigenic determinant binding domain (ADBD) that binds to an AFP p26 antigenic determinant (AD), (ii) a transmembrane domain, and (iii) an intracellular domain.

27. The method of claim 26, wherein
(a) the D domain that binds to CD123 comprises an amino acid sequence selected from the group consisting of SEQ ID NO: 8, 13, and 14;
(b) the D domain that binds to CD123 comprises the amino acid sequence of SEQ ID NO: 14;
(c) the transmembrane domain comprises a CD8a, 41BB or CD28 transmembrane domain;
(d) the intracellular signaling domain is selected from the group consisting of a domain of a human T cell receptor alpha, beta, or zeta chain, a human 41BB domain; a human CD28 domain; and any combination thereof;
(e) the intracellular signaling domain comprises the intracellular domain of a costimulatory molecule selected from the group consisting of CD27, CD28, 41BB, OX40, CD30, CD40, PD1, lymphocyte function-associated antigen-1 (LFA-1), CD2, CD7, LIGHT, NKG2C, NKG2D, B7-H3, a ligand that specifically binds with CD83, and any combination thereof;
(f) the ADBD that binds to AFP p26 AD comprises a D domain that binds to AFP p26 AD;
(g) the ADBD that binds to AFP p26 AD comprises a D domain comprising the amino acid sequence of SEQ ID NO: 73, 70-72 or 92-94;
(h) the CAR comprising a D domain that binds to AFP p26 AD comprises the amino acid sequence of SEQ ID NO: 68 or 69;
(i) the cell expressing the CAR is an immune cell;
(j) the cell expressing the CAR is a T cell or a natural killer (NK) cell;
(k) the cell expressing the CAR is an autologous immune cell;
(l) the cancer is a hematological cancer; and/or
(m) the cancer is acute myeloid leukemia (AML) or high-risk myelodysplastic syndrome.

* * * * *